US011535862B2

(12) United States Patent
Chae

(10) Patent No.: US 11,535,862 B2
(45) Date of Patent: Dec. 27, 2022

(54) ENGINEERED PESTICIDAL PROTEINS AND METHODS OF CONTROLLING PLANT PESTS

(71) Applicant: Syngenta Participations AG, Basel (CH)

(72) Inventor: Hyunsook Sarah Chae, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 401 days.

(21) Appl. No.: 16/468,528

(22) PCT Filed: Nov. 29, 2017

(86) PCT No.: PCT/US2017/063722
§ 371 (c)(1),
(2) Date: Jun. 11, 2019

(87) PCT Pub. No.: WO2018/111553
PCT Pub. Date: Jun. 21, 2018

(65) Prior Publication Data

US 2021/0274783 A1 Sep. 9, 2021

Related U.S. Application Data

(60) Provisional application No. 62/432,909, filed on Dec. 12, 2016.

(51) Int. Cl.

| | |
|---|---|
| *C12N 15/82* | (2006.01) |
| *A01N 63/50* | (2020.01) |
| *A01N 37/46* | (2006.01) |
| *C07K 14/325* | (2006.01) |

(52) U.S. Cl.
CPC ......... *C12N 15/8286* (2013.01); *A01N 37/46* (2013.01); *A01N 63/50* (2020.01); *C07K 14/325* (2013.01)

(58) Field of Classification Search

CPC ................................................. C12N 15/8286
USPC ......................................................... 800/302
See application file for complete search history.

(56) References Cited

U.S. PATENT DOCUMENTS

| | | | | |
|---|---|---|---|---|
| 7,799,971 B2 | 9/2010 | Frank et al. | | |
| 8,735,560 B1 | 5/2014 | English et al. | | |
| 2010/0017914 A1* | 1/2010 | Hart | C12N 15/8286 | 800/279 |
| 2011/0203015 A1* | 8/2011 | Sampson | C12N 15/8279 | 800/279 |
| 2015/0148288 A1* | 5/2015 | Kennedy | C07K 14/43518 | 514/4.5 |

FOREIGN PATENT DOCUMENTS

| | | | |
|---|---|---|---|
| JP | H06192295 A | 7/1994 | |
| WO | WO-9928477 A1 * | 6/1999 | C07K 14/325 |
| WO | 2003082910 A1 | 10/2003 | |
| WO | 2011075587 A1 | 6/2011 | |
| WO | 2011084631 A1 | 7/2011 | |
| WO | 2011103248 A2 | 8/2011 | |
| WO | 2016061197 A1 | 4/2016 | |
| WO | 2016061377 A2 | 4/2016 | |
| WO | 2016061391 A2 | 4/2016 | |
| WO | 2017003811 A1 | 5/2017 | |

OTHER PUBLICATIONS

GenBank Accession No. WP_033698688.1 (Year: 2014).*
Deist, Benjamin et al.: "Bt Toxin Modification for Enhanced Efficacy", TOXINS, vol. 6, No. 10, Oct. 22, 1994, pp. 3005-3027, XP055278078, DOI: 10.3390/toxins6103005.
Extended ESR for EP17880405.0, dated Oct. 1, 2020.
International Search Report cited in Internation Application No. PCT/US2017/063722 filed Nov. 29, 2019 dated Feb. 16, 2018.
Pesticidal protein, partial [Bacillus thuringiensis], NCBI Reference Sequence: WP_033698688.1, publication date: Nov. 26, 2014.

* cited by examiner

*Primary Examiner* — Li Zheng
(74) *Attorney, Agent, or Firm* — Katherine Seguin

(57) ABSTRACT

The invention provides nucleic acids, polypeptides, transgenic plants, compositions and methods for conferring pesticidal activity (e.g., insecticidal activity) to bacteria, plants, plant cells, tissues and seeds. Nucleic acids encoding the insecticidal proteins can be used to transform prokaryotic and eukaryotic organisms to express the insecticidal proteins. The recombinant organisms or compositions containing the recombinant organisms or insecticidal proteins or in combination with an appropriate agricultural carrier can be used to control an insect pest in various environments.

3 Claims, 8 Drawing Sheets

Specification includes a Sequence Listing.

```
BT-0029    1  ---MEINNQN-------Q--CVPYNCLNNPESEILNVAIFS---------------SEQVAEIHLKITRLILENFLPGGSFAFGLFDLIWGIFNEDQWSAF
BT-0022    1  ---MKSKNQN-MHQSLSNNATVDKNFTGSLENNTNELQNFNHEG----IEPFVSVSTIQTGIGIAGKILGNLGVPFAGQVASLYSFILGELWPKGKSQWEIF
CrylFa     1  ---MENNIQN-------Q--CVPYNCLNNPEVEILNEERST---------GRLPLDISLSLTREFLLSEFVPGVGVAFGLFDLIWGFITPSDWS

```
BT-0029    652  KRELSEKVKHAKRLCDERNLLQDPNFRGINRQPDRGWRGSTDITIQGGDDVFKENYVTLPGTFDECYPTYLYQKIDESKLKAYTRYELRGYIEDSQDLEI
BT-0022    692  TR------IYRWGYPSKKEYWYIWGYTSKY----------------------------------------------------------------------
Cry1Fa     657  KRELSEKVKHAKRLSDERNLLQDPNFKGINRQLDRGWRGSTDITIQRGDDVFKENYVTLPGTFDECYPTYLYQKIDESKLKPYTRYQLRGYIEDSQDLEI
Cry1Ka     693  KRELLEEVKYAKRLSDERNLLQDPTFTSISGQTDRGWIGSTGISIQGGDDIFKENYVRLPGTVDECYPTYLYQKIDESQLKSYTRYQLRGYIEDSQDLEI

BT-0029    752  YLIRYNAKHETVNVPGTGSLWPLSAQSPIGKCGEPNRCATHLEWNPDLDCSCRDGEKCAHHSHHFSLDIDVGCTDLNEDLGVWVIFKIKTQDGHARLGNL
BT-0022    716  ----------------------------------------------------------------------------------------------------
Cry1Fa     757  YLIRYNAKHETVNVLGTGSLWPLSVQSPIRKCGEPNRCAPHLEWNPDLDCSCRDGEKCAHHSHHFSLDIDVGCTDLNEDLDVWVIFKIKTQDGHARLGNL
Cry1Ka     793  YLIRYNAKHETLSVPGTESPWPSSGVYPSGRCGEPNRCAPRIEWNPDLDCSCRYGEKCVHHSHHFSLDIDVGCTDLNEDLGVWVIFKIKTQDGHAKLGNL

BT-0029    852  EFLEEKPLVGEALARVKRAEKKWRDKREKLELETNIVYKEAKKSVDALFVNSQYDRLQADTNIAIIHAADKRVHSIREAYLPELSVIPGVNAAIFEELEG
BT-0022    716
Cry1Fa     857  EFLEEKPLVGEALARVKRAEKKWRDKREKLELETNIVYKEAKESVDALFVNSQYDQLQADTNIAMIHAADKRVHRIREAYLPELSVIPGVNVDIFEELKG
Cry1Ka     893  EFIEEKPLLGKALSRVKRAEKKWRDKYEKLQLETKRVYTEAKESVDALFVDSQYDKLQANTNIGIIHGADKQVHRIREPYLSELPVIPSINAAIFEELEG

BT-0029    952  RIFTAYSLYDARNVIKNGDFNNGLSCWNVKGHVDVEEQNNHRSVLVVPEWEAEVSQEVRVCPGRGYILRVTAYKEGYGEGCVTIHEIEDNTDELKFSNCV
BT-0022    716  ----------------------------------------------------------------------------------------------------
Cry1Fa     957  RIFTAFFLYDARNVIKNGDFNNGLSCWNVKGHVDVEEQNNHRSVLVVPEWEAEVSQEVRVCPGRGYILRVTAYKEGYGEGCVTIHEIENNTDELKFSNCV
Cry1Ka     993  HIFKAYSLYDARNVIKNGDFNNGLSCWNVKGHVDVQQN-HHRSVLVLSEWEAEVSQKVRVCPDRGYILRVTAYKEGYGEGCVTIHEFEDNTDVLKFRNFV

BT-0029   1052  EEEIYPNNTVTCNDYTATQEEYEGTYTSRNR------GYDGAYESNSSVPADYASAYEEKAYTDGRRDNTCESNRGYGDYTPLPAGYVTKELEYFPETDK
BT-0022    710  ----------------------------------------------------------------------------------------------------
Cry1Fa    1057  EEEVYPNNTVTCNDYTANQEEYGGAYTSRNR------GYDETYGSNSSVPADYASVYEEKSYTDGRRDNPCESNRGYGDYTPLPAGYVTKELEYFPETDK
Cry1Ka    1092  EEEVYPNNTVTCNDYTTNQSAEGSTDACNSYNRGYEDGYENRYEPNPSAPVNYTPTYEEGMYTDTQGYNHCVSDRGYRNHTPLPAGYVTLELEYFPETEQ

BT-0029   1146  VWIEIGETEGTFIVDSVELLLMEE
BT-0022    716  ------------------------
Cry1Fa    1151  VWIEIGETEGTFIVDSVELLLMEE
Cry1Ka    1192  VWIEIGETEGTFIVGSVELLLMEE
```

Fig.1B

```
BT-0029      1  MEINNQNQCVPYNCLNNPESEILNVAIFSSEQVAEIHLKITRLILENFLPGGSFAFGLFDLIWGIFNEDQWSAFLRQVEELINQRITEFARGQAIQRLVG
BT29-BT22    1  MEINNQNQCVPYNCLNNPESEILNVAIFSSEQVAEIHLKITRLILENFLPGGSFAFGLFDLIWGIFNEDQWSAFLRQVEELINQRITEFARGQAIQRLVG
BT29-1Fa     1  MEINNQNQCVPYNCLNNPESEILNVAIFSSEQVAEIHLKITRLILENFLPGGSFAFGLFDLIWGIFNEDQWSAFLRQVEELINQRITEFARGQAIQRLVG
BT29-1Ka     1  MEINNQNQCVPYNCLNNPESEILNVAIFSSEQVAEIHLKITRLILENFLPGGSFAFGLFDLIWGIFNEDQWSAFLRQVEELINQRITEFARGQAIQRLVG

BT-0029    101  FGRSYDEYILALKEWENDPDNPASKERVRTRFRTTDDALLTGVPLMAIPGFELATLSVYAQSANLHLALLRDAVFFGERWGLTQTNINDLYSRLKNSIRD
BT29-BT22  101  FGRSYDEYILALKEWENDPDNPASKERVRTRFRTTDDALLTGVPLMAIPGFELATLSVYAQSANLHLALLRDAVFFGERWGLTQTNINDLYSRLKNSIRD
BT29-1Fa   101  FGRSYDEYILALKEWENDPDNPASKERVRTRFRTTDDALLTGVPLMAIPGFELATLSVYAQSANLHLALLRDAVFFGERWGLTQTNINDLYSRLKNSIRD
BT29-1Ka   101  FGRSYDEYILALKEWENDPDNPASKERVRTRFRTTDDALLTGVPLMAIPGFELATLSVYAQSANLHLALLRDAVFFGERWGLTQTNINDLYSRLKNSIRD

BT-0029    201  YTNHCVRFYNIGLGNLNVIRPEYYRFQRELTISVLDLVALFPNYDIRTYPIPTKSQLTREIYTDPIISPGAQAGYTLQDVLREPHLMDFLNRLIYTGEY
BT29-BT22  201  YTNHCVRFYNIGLGNLNVIRPEYYRFQRELTISVLDLVALFPNYDIRTYPIPTKSQLTREIYTDPIISPGAQAGYTLQDVLREPHLMDFLNRLIYTGEY
BT29-1Fa   201  YTNHCVRFYNIGLGNLNVIRPEYYRFQRELTISVLDLVALFPNYDIRTYPIPTKSQLTREIYTDPIISPGAQAGYTLQDVLREPHLMDFLNRLIYTGEY
BT29-1Ka   201  YTNHCVRFYNIGLGNLNVIRPEYYRFQRELTISVLDLVALFPNYDIRTYPIPTKSQLTREIYTDPIISPGAQAGYTLQDVLREPHLMDFLNRLIYTGEY

BT-0029    301  RGIRHWAGHEVESSRTGMMTNIRFPLYGTAATAEPTRFITPSTFPGLNLFYRTLSAPIFRDEPGANIIRYRTSLVEGVGFIQPNNGEQLYRVRGTLDSL
BT29-BT22  301  RGIRHWAGHEVESSRTGMMTNIRFPLYGTAATAEPTRFITPSTFPGLNLFYRTLSAPIFRDEPGANIIRYRTSLVEGVGFIQPNNGEQLYRVRGTLDSL
BT29-1Fa   301  RGIRHWAGHEVESSRTGMMTNIRFPLYGTAATAEPTRFITPSTFPGLNLFYRTLSAPIFRDEPGANIIRYRTSLVEGVGFIQPNNGEQLYRVRGTLDSL
BT29-1Ka   301  RGIRHWAGHEVESSRTGMMTNIRFPLYGTAATAEPTRFITPSTFPGLNLFYRTLSAPIFRDEPGANIIRYRTSLVEGVGFIQPNNGEQLYRVRGTLDSL

|--------------- CB3 ---------------|
BT-0029    401  DQLPLEGESSLTEYSHRLCHVRFAQSLRNAEPLDYARVPMFSWTHRSATPTNTIDPDVITQIPLVKAFNLHSGATIVKGPFTGGDILRRTNVGSFGDMR
BT29-BT22  401  DQLPLEGESSLTEYSHRLCHVRFAQSLRNAEPLDYARVPMFSWTHRSATPTNTIDPDVITQIPLVKAHTLQSGTTVVKGPFTGGDILRRTSGGPFAFSN
BT29-1Fa   401  DQLPLEGESSLTEYSHRLCHVRFAQSLRNAEPLDYARVPMFSWTHRSATPTNTIDPDVITQIPLVKAHTLQSGTTVVRGPFTGGDILRRTSGGPFAYTI
BT29-1Ka   401  DQLPLEGESSLTEYSHRLCHVRFAQSLRNAEPLDYARVPMFSWTHRSATPTNTIDPDVITQIPLVKAHTLQSGTTVVKGPFTGGDILRRTSGGPFAFSN
                |----------------------------- Domain III -----------------------------------------------------|

BT-0029    501  VNITTAPLSQRYRVRIRYASTTDLQFYTNINGTTNINGFSSTMDSGDDLQYGRFRVAGFTTPFTFSDAMSTFTIGAFSFSSNNEVYIDRIEFVPAEVTFE
BT29-BT22  501  VNLDWNLSQRYRARIRYASTTNLRMYVTIAGERIFAGQFNKTMNTGDPLTFQSFSYATIDTAFTFPTKASSLTVGADTFSSGNEVYVDRFELIPVTATFE
BT29-1Fa   501  VNINGQLPQRYRARIRYASTTNLRIYVTVAGERIFAGQFNKTMDTGDPLTFQSFSYATINTAFTFPMSQSSFTVGADTFSSGNEVYIDRFELIPVTATFE
BT29-1Ka   501  VNLDFNLSQRYRARIRYASTTNLRIYVTVAGERIFAGQFDKTMDAGAPLTFQSFSYATINTAFTFPERSSSLTIGADTFSSGNEVYVDRFELIQVTATFE

BT-0029    601  AEYDLEKAQKAVNALFTSSNQIGLKTDVTDYHIDKVSNLVECLSDEFCLDEKRELSEKVKHAKRLCDERNLLQDPNFRGINRQPDRGWRGSTDITIQGGD
BT29-BT22  601  AEYDLEKAQKAVNALFTSSNQIGLKTDVTDYHIDKVSNLVECLSDEFCLDEKRELSEKVKHAKRLCDERNLLQDPNFRGINRQPDRGWRGSTDITIQGGD
BT29-1Fa   601  AEYDLEKAQKAVNALFTSSNQIGLKTDVTDYHIDKVSNLVECLSDEFCLDEKRELSEKVKHAKRLCDERNLLQDPNFRGINRQPDRGWRGSTDITIQGGD
BT29-1Ka   601  AEYDLEKAQKAVNALFTSSNQIGLKTDVTDYHIDKVSNLVECLSDEFCLDEKRELSEKVKHAKRLCDERNLLQDPNFRGINRQPDRGWRGSTDITIQGGD
```

Fig.2A

```
BT-0029     701  DVFKENYVTLPGTFDECYPTYLYQKIDESKLKAYTRYELRGYIEDSQDLEIYLIRYNAKHETVNPGTGSLWPLSAQSPIGKCGEPNRCATHLEWNPDLD
BT29-BT22   701  DVFKENYVTLPGTFDECYPTYLYQKIDESKLKAYTRYELRGYIEDSQDLEIYLIRYNAKHETVNPGTGSLWPLSAQSPIGKCGEPNRCATHLEWNPDLD
BT29-1Fa    701  DVFKENYVTLPGTFDECYPTYLYQKIDESKLKAYTRYELRGYIEDSQDLEIYLIRYNAKHETVNPGTGSLWPLSAQSPIGKCGEPNRCATHLEWNPDLD
BT29-1Ka    701  DVFKENYVTLPGTFDECYPTYLYQKIDESKLKAYTRYELRGYIEDSQDLEIYLIRYNAKHETVNPGTGSLWPLSAQSPIGKCGEPNRCATHLEWNPDLD

BT-0029     801  CSCRDGEKCAHHSHHFSLDIDVGCTDLNEDLGVWVIFKIKTQDGHARLGNLEFLEEKPLVGEALARVKRAEKKWRDKREKLELETNIVYKEAKKSVDALF
BT29-BT22   801  CSCRDGEKCAHHSHHFSLDIDVGCTDLNEDLGVWVIFKIKTQDGHARLGNLEFLEEKPLVGEALARVKRAEKKWRDKREKLELETNIVYKEAKKSVDALF
BT29-1Fa    801  CSCRDGEKCAHHSHHFSLDIDVGCTDLNEDLGVWVIFKIKTQDGHARLGNLEFLEEKPLVGEALARVKRAEKKWRDKREKLELETNIVYKEAKKSVDALF
BT29-1Ka    801  CSCRDGEKCAHHSHHFSLDIDVGCTDLNEDLGVWVIFKIKTQDGHARLGNLEFLEEKPLVGEALARVKRAEKKWRDKREKLELETNIVYKEAKKSVDALF

BT-0029     901  VNSQYDRLQADTNIAIIHAADKRVHSIREAYLPELSVIPGVNAAIFEELEGRIFTAYSLYDARNVIKNGDFNNGLSCWNVKGHVDEEQNNHRSVLVVPE
BT29-BT22   901  VNSQYDRLQADTNIAIIHAADKRVHSIREAYLPELSVIPGVNAAIFEELEGRIFTAYSLYDARNVIKNGDFNNGLSCWNVKGHVDEEQNNHRSVLVVPE
BT29-1Fa    901  VNSQYDRLQADTNIAIIHAADKRVHSIREAYLPELSVIPGVNAAIFEELEGRIFTAYSLYDARNVIKNGDFNNGLSCWNVKGHVDEEQNNHRSVLVVPE
BT29-1Ka    901  VNSQYDRLQADTNIAIIHAADKRVHSIREAYLPELSVIPGVNAAIFEELEGRIFTAYSLYDARNVIKNGDFNNGLSCWNVKGHVDEEQNNHRSVLVVPE

BT-0029    1001  WEAEVSQEVRVCPGRGYILRVTAYKEGYGEGCVTIHEIEDNTDELKFSNCVEEEIYPNNTVTCNDYTATQEEYEGTYTSRNRGYDGAYESNSSVPADYAS
BT29-BT22  1001  WEAEVSQEVRVCPGRGYILRVTAYKEGYGEGCVTIHEIEDNTDELKFSNCVEEEIYPNNTVTCNDYTATQEEYEGTYTSRNRGYDGAYESNSSVPADYAS
BT29-1Fa   1001  WEAEVSQEVRVCPGRGYILRVTAYKEGYGEGCVTIHEIEDNTDELKFSNCVEEEIYPNNTVTCNDYTATQEEYEGTYTSRNRGYDGAYESNSSVPADYAS
BT29-1Ka   1001  WEAEVSQEVRVCPGRGYILRVTAYKEGYGEGCVTIHEIEDNTDELKFSNCVEEEIYPNNTVTCNDYTATQEEYEGTYTSRNRGYDGAYESNSSVPADYAS

BT-0029    1101  AYEEKAYTDGRRDNTCESNRGYGDYTPLPAGYVTKELEYFPETDKVWIEIGETEGTFIVDSVELLMEE
BT29-BT22  1101  AYEEKAYTDGRRDNTCESNRGYGDYTPLPAGYVTKELEYFPETDKVWIEIGETEGTFIVDSVELLMEE
BT29-1Fa   1101  AYEEKAYTDGRRDNTCESNRGYGDYTPLPAGYVTKELEYFPETDKVWIEIGETEGTFIVDSVELLMEE
BT29-1Ka   1101  AYEEKAYTDGRRDNTCESNRGYGDYTPLPAGYVTKELEYFPETDKVWIEIGETEGTFIVDSVELLMEE
```

Fig. 2B

```
SEQ ID NO:3       1 MEINNQNQCVPYNCLNNPESEILNVAIFSSEQVAEIHLKITRLILENFLPGGSFAFGLFDLIWGIFNEDQWSAFLRQVEE
SEQ ID NO:20      1 MEINNQNQCVPYNCLNNPESEILNVAIFSSEQVAEIHLKITRLILENFLPGGSFAFGLFDLIWGIFNEDQWSAFLRQVEE
SEQ ID NO:21      1 MEINNQNQCVPYNCLNNPESEILNVAIFSSEQVAEIHLKITRLILENFLPGGSFAFGLFDLIWGIFNEDQWSAFLRQVEE
SEQ ID NO:22      1 MEINNQNQCVPYNCLNNPESEILNVAIFSSEQVAEIHLKITRLILENFLPGGSFAFGLFDLIWGIFNEDQWSAFLRQVEE
SEQ ID NO:23      1 MEINNQNQCVPYNCLNNPESEILNVAIFSSEQVAEIHLKITRLILENFLPGGSFAFGLFDLIWGIFNEDQWSAFLRQVEE
SEQ ID NO:24      1 MEINNQNQCVPYNCLNNPESEILNVAIFSSEQVAEIHLKITRLILENFLPGGSFAFGLFDLIWGIFNEDQWSAFLRQVEE
SEQ ID NO:25      1 MEINNQNQCVPYNCLNNPESEILNVAIFSSEQVAEIHLKITRLILENFLPGGSFAFGLFDLIWGIFNEDQWSAFLRQVEE

Bt29-Bt22        81 LINQRITEFARGQAIQRLVGFGRSYDEYILALKEWENDPDNPASKERVRTRFRTTDDALLTGVPLMAIPGFELATLSVYA
SEQ ID NO:20     81 LINQRITEFARGQAIQRLVGFGRSYDEYILALKEWENDPDNPASKERVRTRFRTTDDALLTGVPLMAIPGFELATLSVYA
SEQ ID NO:21     81 LINQRITEFARGQAIQRLVGFGRSYDEYILALKEWENDPDNPASKERVRTRFRTTDDALLTGVPLMAIPGFELATLSVYA
SEQ ID NO:22     81 LINQRITEFARGQAIQRLVGFGRSYDEYILALKEWENDPDNPASKERVRTRFRTTDDALLTGVPLMAIPGFELATLSVYA
SEQ ID NO:23     81 LINQRITEFARGQAIQRLVGFGRSYDEYILALKEWENDPDNPASKERVRTRFRTTDDALLTGVPLMAIPGFELATLSVYA
SEQ ID NO:24     81 LINQRITEFARGQAIQRLVGFGRSYDEYILALKEWENDPDNPASKERVRTRFRTTDDALLTGVPLMAIPGFELATLSVYA
SEQ ID NO:25     81 LINQRITEFARGQAIQRLVGFGRSYDEYILALKEWENDPDNPASKERVRTRFRTTDDALLTGVPLMAIPGFELATLSVYA

SEQ ID NO:3     161 QSANLHLALLRDAVFFGERWGLTQTNINDLYSRLKNSIRDYTNHCVRFYNIGLGNLNVIRPEYYRFQRELTISVLDLVAL
SEQ ID NO:20    161 QSANLHLALLRDAVFFGERWGLTQTNINDLYSRLKNSIRDYTNHCVRFYNIGLGNLNVIRPEYYRFQRELTISVLDLVAL
SEQ ID NO:21    161 QSANLHLALLRDAVFFGERWGLTQTNINDLYSRLKNSIRDYTNHCVRFYNIGLGNLNVIRPEYYRFQRELTISVLDLVAL
SEQ ID NO:22    161 QSANLHLALLRDAVFFGERWGLTQTNINDLYSRLKNSIRDYTNHCVRFYNIGLGNLNVIRPEYYRFQRELTISVLDLVAL
SEQ ID NO:23    161 QSANLHLALLRDAVFFGERWGLTQTNINDLYSRLKNSIRDYTNHCVRFYNIGLGNLNVIRPEYYRFQRELTISVLDLVAL
SEQ ID NO:24    161 QSANLHLALLRDAVFFGERWGLTQTNINDLYSRLKNSIRDYTNHCVRFYNIGLGNLNVIRPEYYRFQRELTISVLDLVAL
SEQ ID NO:25    161 QSANLHLALLRDAVFFGERWGLTQTNINDLYSRLKNSIRDYTNHCVRFYNIGLGNLNVIRPEYYRFQRELTISVLDLVAL

SEQ ID NO:3     241 FPNYDIRTYPIPTKSQLTREIYTDPIISPGAQAGYTLQDVLREPHLMDFLNRLIIYTGEYRGIRHWAGHEVESSRTGMMT
SEQ ID NO:20    241 FPNYDIRTYPIPTKSQLTREIYTDPIISPGAQAGYTLQDVLREPHLMDFLNRLIIYTGEYRGIRHWAGHEVESSRTGMMT
SEQ ID NO:21    241 FPNYDIRTYPIPTKSQLTREIYTDPIISPGAQAGYTLQDVLREPHLMDFLNRLIIYTGEYRGIRHWAGHEVESSRTGMMT
SEQ ID NO:22    241 FPNYDIRTYPIPTKSQLTREIYTDPIISPGAQAGYTLQDVLREPHLMDFLNRLIIYTGEYRGIRHWAGHEVESSRTGMMT
SEQ ID NO:23    241 FPNYDIRTYPIPTKSQLTREIYTDPIISPGAQAGYTLQDVLREPHLMDFLNRLIIYTGEYRGIRHWAGHEVESSRTGMMT
SEQ ID NO:24    241 FPNYDIRTYPIPTKSQLTREIYTDPIISPGAQAGYTLQDVLREPHLMDFLNRLIIYTGEYRGIRHWAGHEVESSRTGMMT
SEQ ID NO:25    241 FPNYDIRTYPIPTKSQLTREIYTDPIISPGAQAGYTLQDVLREPHLMDFLNRLIIYTGEYRGIRHWAGHEVESSRTGMMT
```

Fig. 3A

```
SEQ ID NO:3   321 NIRFPLYGTAATAEPTRFITPSTFPGLNLFYRTLSAPIFRDEPGANIIIRYRTSLVEGVGFIQPNNGEQLYRVRGTLDSL
SEQ ID NO:20  321 NIRFPLYGTAATAEPTRFITPSTFPGLNLFYRTLSAPIFRDEPGANIIIRYRTSLVEGVGFIQPNNGEQLYRVRGTLDSL
SEQ ID NO:21  321 NIRFPLYGTAATAEPTRFITPSTFPGLNLFYRTLSAPIFRDEPGANIIIRYRTSLVEGVGFIQPNNGEQLYRVRGTLDSL
SEQ ID NO:22  321 NIRFPLYGTAATAEPTRFITPSTFPGLNLFYRTLSAPIFRDEPGANIIIRYRTSLVEGVGFIQPNNGEQLYRVRGTLDSL
SEQ ID NO:23  321 NIRFPLYGTAATAEPTRFITPSTFPGLNLFYRTLSAPIFRDEPGANIIIRYRTSLVEGVGFIQPNNGEQLYRVRGTLDSL
SEQ ID NO:24  321 NIRFPLYGTAATAEPTRFITPSTFPGLNLFYRTLSAPIFRDEPGANIIIRYRTSLVEGVGFIQPNNGEQLYRVRGTLDSL
SEQ ID NO:25  321 NIRFPLYGTAATAEPTRFITPSTFPGLNLFYRTLSAPIFRDEPGANIIIRYRTSLVEGVGFIQPNNGEQLYRVRGTLDSL

SEQ ID NO:3   401 DQLPLEGESSLTEYSHRLCHVRFAQSLRNAEPLDYARVPMFSWTHRSATPTNTIDPDVITQIPLVKAHTLQSGTTVVKGP
SEQ ID NO:20  401 DQLPLEGESSLTEYSHRLCHVRFAQSLRNAEPLDYARVPMFSWTHRSATPTNTIDPDVITQIPLVKAHTLQSGTTVVKGP
SEQ ID NO:21  401 DQLPLEGESSLTEYSHRLCHVRFAQSLRNAEPLDYARVPMFSWTHRSATPTNTIDPDVITQIPLVKAHTLQSGTTVVKGP
SEQ ID NO:22  401 DQLPLEGESSLTEYSHRLCHVRFAQSLRNAEPLDYARVPMFSWTHRSATPTNTIDPDVITQIPLVKAHTLQSGTTVVKGP
SEQ ID NO:23  401 DQLPLEGESSLTEYSHRLCHVRFAQSLRNAEPLDYARVPMFSWTHRSATPTNTIDPDVITQIPLVKAHTLQSGTTVVKGP
SEQ ID NO:24  401 DQLPLEGESSLTEYSHRLCHVRFAQSLRNAEPLDYARVPMFSWTHRSATPTNTIDPDVITQIPLVKAHTLQSGTTVVKGP
SEQ ID NO:25  401 DQLPLEGESSLTEYSHRLCHVRFAQSLRNAEPLDYARVPMFSWTHRSATPTNTIDPDVITQIPLVKAHTLQSGTTVVKGP

SEQ ID NO:3   481 GFTGGDILRRTSGGPFAFSNVNLDWNLSQRYRARIRYASTTNLRMYVTIAGERIFAGQFNKTMNTGDPLTFQSFSYATID
SEQ ID NO:20  481 GFTGGDILRRTSGGPFAFSNVNLDWNLSQRYRARIRYASTTNLRMYVTIAGERIFAGQFNKTMNTGDPLTFQSFSYATID
SEQ ID NO:21  481 GFTGGDILRRTSGGPFAFSNVNLDWNLSQRYRARIRYASTTNLRMYVTIAGERIFAGQFNKTMNTGDPLTFQSFSYATID
SEQ ID NO:22  481 GFTGGDILRRTSGGPFAFSNVNLDWNLSQRYRARIRYASTTNLRMYVTIAGERIFAGQFNKTMNTGDPLTFQSFSYATID
SEQ ID NO:23  481 GFTGGDILRRTSGGPFAFSNVNLDWNLSQRYRARIRYASTTNLRMYVTIAGERIFAGQFNKTMNTGDPLTFQSFSYATID
SEQ ID NO:24  481 GFTGGDILRRTSGGPFAFSNVNLDWNLSQRYRARIRYASTTNLRMYVTIAGERIFAGQFNKTMNTGDPLTFQSFSYATID
SEQ ID NO:25  481 GFTGGDILRRTSGGPFAFSNVNLDWNLSQRYRARIRYASTTNLRMYVTIAGERIFAGQFNKTMNTGDPLTFQSFSYATID

SEQ ID NO:3   561 TAFTFPTKASSLTVGADTFSSGNEVYVDRFELIPVTATFEAEYDLEKAQKAVNALFTSSNQIGLKTDVTDYHIDKVSNLV
SEQ ID NO:20  561 TAFTFPTKASSLTVGADTFSSGNEVYVDRFELIPVTATFEAEYDLEKAQKAVNALFTSSNQIGLKTDVTDYHIDKVSNLV
SEQ ID NO:21  561 TAFTFPTKASSLTVGADTFSSGNEVYVDRFELIPVTATFEAEYDLEKAQKAVNALFTSSNQIGLKTDVTDYHIDKV----
SEQ ID NO:22  561 TAFTFPTKASSLTVGADTFSSGNEVYVDRFELIPVTATFEAEYDLEKAQKAVNALFTSSNQI------------------
SEQ ID NO:23  561 TAFTFPTKASSLTVGADTFSSGNEVYVDRFELIPVTATFEAEYDLEKAQK-----------------------------
SEQ ID NO:24  561 TAFTFPTKASSLTVGADTFSSGNEVYVDRFELIPVTATFEAEYDLEK-------------------------------
SEQ ID NO:25  561 TAFTFPTKASSLTVGADTFSSGNEVYVDRFELIPVTATFEAEY-----------------------------------
```

Fig. 3B

| SEQ ID NO:3 | 641 | ECLSDEFCLDEKRELSEKVKHAKRLCDERNLLQDPNFRGINRQPDRGWRGSTDITIQGGDDVFKENYVTLPGTFDECYPT |
| SEQ ID NO:20 | 641 | ECLSDEFCLDEK |
| SEQ ID NO:21 | 637 | --- |
| SEQ ID NO:22 | 623 | --- |
| SEQ ID NO:23 | 611 | --- |
| SEQ ID NO:24 | 608 | --- |
| SEQ ID NO:25 | 604 | --- |

| SEQ ID NO:3 | 721 | YLYQKIDESKLKAYTRYELRGYIEDSQDLETYLIRYNAKHETVNVPGTGSLWPLSAQSPIGKCGEPNRCATHLEWNPDLD |
| SEQ ID NO:20 | 653 | --- |
| SEQ ID NO:21 | 637 | --- |
| SEQ ID NO:22 | 623 | --- |
| SEQ ID NO:23 | 611 | --- |
| SEQ ID NO:24 | 608 | --- |
| SEQ ID NO:25 | 604 | --- |

| SEQ ID NO:3 | 801 | CSCRDGEKCAHHSHHFSLDIDVGCTDLNEDLGVWVIFKIKTQDGHARLGNLEFLEEKPLVGEALARVKRAEKKWRDKREK |
| SEQ ID NO:20 | 653 | --- |
| SEQ ID NO:21 | 637 | --- |
| SEQ ID NO:22 | 623 | --- |
| SEQ ID NO:23 | 611 | --- |
| SEQ ID NO:24 | 608 | --- |
| SEQ ID NO:25 | 604 | --- |

| SEQ ID NO:3 | 881 | LELETNIVYKEAKKSVDALFVNSQYDRLQADTNIAIIHAADKRVHSIREAYLPELSVIPGVNAAIFEELEGRIFTAYSLY |
| SEQ ID NO:20 | 653 | --- |
| SEQ ID NO:21 | 637 | --- |
| SEQ ID NO:22 | 623 | --- |
| SEQ ID NO:23 | 611 | --- |
| SEQ ID NO:24 | 608 | --- |
| SEQ ID NO:25 | 604 | --- |

Fig. 3C

```
Bt29-Bt22    961  DARNVIKNGDFNNGLSCWNVKGHVDVEEQNNHRSVLVVPEWEAEVSQEVRVCPGRGYILRVTAYKEGYGEGCVTIHEIED
SEQ ID NO:20 653  --------------------------------------------------------------------------------
SEQ ID NO:21 637  --------------------------------------------------------------------------------
SEQ ID NO:22 623  --------------------------------------------------------------------------------
SEQ ID NO:23 611  --------------------------------------------------------------------------------
SEQ ID NO:24 608  --------------------------------------------------------------------------------
SEQ ID NO:25 604  --------------------------------------------------------------------------------

Bt29-Bt22   1041  NTDELKFSNCVEEEIYPNNTVTCNDYTATQEEYEGTYTSRNRGYDGAYESNSSVPADYASAYEEKAYTDGRRDNTCESNR
SEQ ID NO:20 653  --------------------------------------------------------------------------------
SEQ ID NO:21 637  --------------------------------------------------------------------------------
SEQ ID NO:22 623  --------------------------------------------------------------------------------
SEQ ID NO:23 611  --------------------------------------------------------------------------------
SEQ ID NO:24 608  --------------------------------------------------------------------------------
SEQ ID NO:25 604  --------------------------------------------------------------------------------

Bt29-Bt22   1121  GYGDYTPLPAGYVTKELEYFPETDKVWIEIGETEGTFIVDSVELLMEE
SEQ ID NO:20 653  ------------------------------------------------
SEQ ID NO:21 637  ------------------------------------------------
SEQ ID NO:22 623  ------------------------------------------------
SEQ ID NO:23 611  ------------------------------------------------
SEQ ID NO:24 608  ------------------------------------------------
SEQ ID NO:25 604  ------------------------------------------------
```

Fig. 3D

ENGINEERED PESTICIDAL PROTEINS AND METHODS OF CONTROLLING PLANT PESTS

RELATED APPLICATION INFORMATION

This application is a 371 of International Application No. PCT/US2017/063722, filed Nov. 29, 2017, which claims priority to U.S. Provisional Application No. 62/432,909, filed Dec. 12, 2016, the contents of which are incorporated herein by reference herein.

STATEMENT REGARDING ELECTRONIC SUBMISSION OF A SEQUENCE LISTING

A Sequence Listing in ASCII text format, submitted under 37 C.F.R. § 1.821, entitled 81090-WO-REG-ORG-P-1_SEQ_LISTING_ST25, 228 bytes in size, generated on May 8, 2019 and filed via EFS-Web is provided in lieu of a paper copy. This Sequence Listing is hereby incorporated by reference into the specification for its disclosures.

FIELD OF THE INVENTION

This invention relates to engineered pesticidal proteins and the nucleic acid molecules that encode them, as well as compositions and methods for controlling plant pests.

BACKGROUND

*Bacillus thuringiensis* (Bt) is a gram-positive spore forming soil bacterium characterized by its ability to produce crystalline inclusions that are specifically toxic to certain orders and species of plant pests, including insects, but are harmless to plants and other non-target organisms. For this reason, compositions comprising *Bacillus thuringiensis* strains or their insecticidal proteins can be used as environmentally-acceptable insecticides to control agricultural insect pests or insect vectors of a variety of human or animal diseases.

Crystal (Cry) proteins from *Bacillus thuringiensis* have potent insecticidal activity against predominantly lepidopteran, dipteran, and coleopteran pest insects. These proteins also have shown activity against pests in the Orders Hymenoptera, Homoptera, Phthiraptera, Mallophaga, and Acari pest orders, as well as other invertebrate orders such as Nemathelminthes, Platyhelminthes, and Sarcomastigorphora (Feitelson, J. 1993. The *Bacillus thuringiensis* family tree. In Advanced Engineered Pesticides. Marcel Dekker, Inc., New York, N.Y.). These proteins were originally classified as CryI to CryVI based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as CryIA, CryIB, CryIC, etc. Even more closely related proteins within each division were given names such as CryIC(a), CryIC(b), etc.

The terms "Cry toxin" and "delta-endotoxin" have been used interchangeably with the term "Cry protein." Current nomenclature for Cry proteins and genes is based upon amino acid sequence homology rather than insect target specificity (Crickmore et al. (1998) Microbiol. Mol. Biol. Rev. 62:807-813). In this more accepted classification, each toxin is assigned a unique name incorporating a primary rank (an Arabic number), a secondary rank (an uppercase letter), a tertiary rank (a lowercase letter), and a quaternary rank (another Arabic number). In the current classification, Roman numerals have been exchanged for Arabic numerals in the primary rank. For example, "CryIA(a)" under the older nomenclature is now "Cry1Aa" under the current nomenclature. According to Ibrahim et al. (2010, Bioeng. Bugs, 1:31-50), the Cry toxins can still be separated into six major classes according to their insect host specificities and include: Group 1—lepidopteran (e.g., Cry1, Cry9 and Cry15); group 2—lepidopteran and dipteran (e.g., Cry2); group 3—coleopteran (Cry3, Cry7 and Cry8); group 4—dipteran (Cry4, Cry10, Cry11, Cry16, Cry17, Cry19 and Cry20); group 5—lepidopteran and coleopteran (Cry1I); and group 6—nematodes (Cry6). The Cry1I, Cry2, Cry3, Cry10 and Cry11 toxins (73-82 kDa) are unique because they appear to be natural truncations of the larger Cry1 and Cry4 proteins (130-140 kDa).

Cry proteins are globular protein molecules which accumulate as protoxins in crystalline form during the sporulation stage of Bt. After ingestion by a pest, the crystals are typically solubilized to release protoxins, which can range in size, for example, from 130-140 kDa for many of the lepidopteran-active Cry proteins, such as Cry1 and Cry9, and 60-80 kDa for the coleopteran-active Cry3 proteins and the lepidopteran/dipteran-active Cry2 proteins. After the crystals are solubilized by a susceptible insect the released protoxins are processed by proteases in the insect gut, for example trypsin and chymotrypsin, to produce a protease-resistant core Cry protein toxin. This proteolytic processing involves the removal of amino acids from different regions of the various Cry protoxins. For example, Cry protoxins that are 130-140 kDa are typically activated through the proteolytic removal of an N-terminal peptide of 25-30 amino acids and approximately half of the remaining protein from the C-terminus resulting in an approximately 60-70 kDa mature Cry toxin. The protoxins that are 60-80 kDa, e.g. Cry2 and Cry3, are also processed but not to the same extent as the larger protoxins. The smaller protoxins typically have equal or more amino acids removed from the N-terminus than the larger protoxins but less amino acids removed from the C-terminus. For example, proteolytic activation of Cry2 family members typically involves the removal of approximately 40-50 N-terminal amino acids. Many of the Cry proteins are quite toxic to specific target insects, but many have narrow spectrums of activity.

The toxin portions of Cry proteins generally have five conserved sequence blocks, and three conserved structural domains (see, for example, de Maagd et al. (2001) Trends Genetics 17:193-199). The first conserved structural domain, called Domain I, typically consists of seven alpha helices and is involved in membrane insertion and pore formation. Domain II typically consists of three beta-sheets arranged in a Greek key configuration, and domain III typically consists of two antiparallel beta-sheets in 'jelly-roll' formation (de Maagd et al., 2001, supra). Domains II and III are involved in receptor recognition and binding, and are therefore considered determinants of toxin specificity.

The five conserved sequence blocks are numbered CB1 to CB5 from N-terminus to C-terminus of the Cry protein (Hofte & Whitely, 1989, Microbiol. Rev. 53:242-255). Conserved block 1 (CB1) comprises approximately 29 amino acids, conserved block 2 (CB2) comprises approximately 67 amino acids, conserved block 3 (CB3) comprises approximately 48 amino acids, conserved block 4 (CB4) comprises approximately 10 amino acids and conserved block 5 (CB5) comprises approximately 12 amino acids. The sequences before and after these five conserved blocks are highly variable and thus are designated the "variable regions," V1-V6. Domain I of a Bt delta-endotoxin typically comprises variable region 1, conserved block 1, variable region 2, and the N-terminal 52 amino acids of conserved block 2. Domain II typically comprises approximately the C-terminal 15 amino acids of conserved block 2, variable region 3, and approximately the N-terminal 10 amino acids of conserved block 3. Domain III typically comprises approximately the C-terminal 38 amino acids of conserved block 3, variable region 4, conserved block 4, variable region 5, and conserved block 5. The Cry1 lepidopteran active toxins, among other delta-endotoxins, have a variable region 6 with approximately 1-3 amino acids lying within domain III.

Numerous commercially valuable plants, including common agricultural crops, are susceptible to attack by plant pests including insect and nematode pests, causing substantial reductions in crop yield and quality. For example, plant pests are a major factor in the loss of the world's important agricultural crops. About $8 billion are lost every year in the United States alone due to infestations of invertebrate pests including insects. Insect pests are also a burden to vegetable and fruit growers, to producers of ornamental flowers, and to home gardeners.

Insect pests are mainly controlled by intensive applications of chemical pesticides, which are active through inhibition of insect growth, prevention of insect feeding or reproduction, or cause death. Biological pest control agents, such as *Bacillus thuringiensis* strains expressing pesticidal toxins such as Cry proteins, have also been applied to crop plants with satisfactory results, offering an alternative or complement to chemical pesticides. The genes coding for some of these Cry proteins have been isolated and their expression in heterologous hosts such as transgenic plants have been shown to provide another tool for the control of economically important insect pests.

Good insect control can thus be reached, but the continued use of certain chemical and biological control methods heightens the chance for insect pests to develop resistance to such control measures. This has been partially alleviated by various resistance management practices, but there remains a need to develop new and effective pest control agents. Particularly needed are control agents that can target to a wider spectrum of economically important insect pests and/or that efficiently control insect strains that are or could become resistant to existing insect control agents.

SUMMARY

The invention provides nucleic acids, polypeptides, compositions and methods for conferring pesticidal activity (e.g., insecticidal activity) to bacteria, plants, plant cells, tissues and seeds. In particular, the invention provides novel chimeric pesticidal proteins (e.g., chimeric insecticidal proteins), optionally with altered or enhanced activity as compared with the parent molecule.

In embodiments, the chimeric proteins of the invention are toxic to economically important insect pests (e.g., by inhibiting the ability of the insect pest to survive, grow and/or reproduce), particularly insect pests that infest plants. For example, in embodiments, the chimeric insecticidal proteins of the invention can be used to control one or more economically important lepidopteran pests including without limitation black cutworm (*Agrotis ipsilon*), European corn borer (*Ostrinia nubilalis*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia fumacalis*), cotton bollworm (*Helicoverpa armigera*), striped stem borer (*Chilo suppressalis*), pink stem borer (*Sesamia calamistis*), rice leaffolder (*Cnaphalocrocis medinalis*), and the like. In embodiments, the chimeric insecticidal protein has activity against a fall armyworm insect pest that is resistant to a Vip3A protein and/or a Cry1F protein.

Accordingly, as one aspect, the invention provides a chimeric insecticidal protein that is toxic to a lepidopteran insect pest comprising in an N-terminal to C-terminal direction: (a) an N-terminal region of a first Cry1 protein, which is optionally an N-terminal region of a BT-0029 protein of SEQ ID NO:2 or an amino acid sequence that is substantially identical thereto, fused to (b) a C-terminal region of a different Cry1 protein; wherein a crossover position between the first Cry1 protein and the different Cry1 protein is located in conserved block 3. In representative embodiments, the different Cry1 protein is a Cry1F (e.g., a Cry1Fa), a Cry1G, a Cry1I (e.g., a Cry1Ia or a Cry1If, such as BT-0022), a Cry1C (e.g. a Cry1Ca) or a Cry1K protein.

In embodiments, the chimeric insecticidal protein according to the invention has insecticidal activity against a *Spodoptera frugiperda* insect pest or an insect pest population with resistance to a Vip3A protein and/or a Cry1F protein.

As a further aspect, the invention provides a nucleotide sequence encoding the chimeric insecticidal proteins of the invention, and expression cassettes and vectors comprising the same. In embodiments, the polynucleotide is codon optimized for expression in a plant (e.g., a monocot plant such as maize or a dicot plant such as soybean).

As a further aspect, the invention provides a transgenic cell (e.g., a transgenic plant cell such as a dicot cell or monocot cell, or a transgenic bacterial cell), transgenic plant part, transgenic plant culture, and transgenic plant seed that comprises a nucleotide sequence, expression cassette, vector and/or chimeric insecticidal protein of the invention.

As still a further aspect, the invention encompasses transgenic plants comprising a plant cell, plant part, nucleotide sequence, expression cassette, vector and/or chimeric insecticidal protein of the invention.

As a further aspect are seeds that produce the transgenic plants of the invention and seeds produced by the transgenic plants of the invention.

Also provided are harvested products derived from the transgenic plants of the invention, wherein the harvested product optionally comprises a nucleotide sequence, expression cassette, vector and/or chimeric insecticidal protein of the invention. Further provided are processed products derived from the harvested products of the invention, wherein the harvested product optionally comprises a nucleotide sequence, expression cassette, vector and/or chimeric insecticidal protein of the invention. In embodiments, the harvested product or processed product comprises an chimeric insecticidal protein of the invention and has increased resistance to an insect pest (e.g., a lepidopteran insect pest).

As still a further aspect, the invention provides an insecticidal composition comprising a chimeric insecticidal protein of the invention and an agriculturally acceptable carrier.

Still further, the invention provides as an additional aspect a method of producing a transgenic plant with increased resistance to an insect pest (e.g., a lepidopteran insect pest). In embodiments, the method comprises introducing into a plant a polynucleotide, expression cassette, or vector of the invention, wherein the chimeric insecticidal protein is expressed in the plant, thereby producing a transgenic plant with increased resistance to an insect pest. Optionally, the introducing step comprises: (i) transforming a plant cell with the polynucleotide, expression cassette or vector and regenerating a transgenic plant; or (ii) crossing a first plant comprising the polynucleotide, expression cassette or vector with a second plant. In embodiments, the method further comprises producing a seed from the transgenic plant. In embodiments, the method further comprises obtaining a progeny plant from the transgenic plant, wherein the progeny plant comprises the polynucleotide, the expression cassette or the vector, expresses the chimeric insecticidal protein and has increased resistance to an insect pest.

As yet another aspect, the invention provides a method of producing a transgenic plant with increased resistance to an insect pest (e.g., a lepidopteran insect pest), the method comprising: (a) planting a seed comprising a polynucleotide, expression cassette or vector of the invention; and (b) growing a transgenic plant from the seed, wherein the transgenic plant comprises the polynucleotide, expression cassette or vector and produces the chimeric insecticidal protein and has increased resistance to an insect pest. In embodiments, the method further comprises: (c) harvesting a seed from the transgenic plant of (b), wherein the harvested seed comprises the polynucleotide, expression cassette, vector and/or the chimeric insecticidal protein. Optionally, the seed has increased resistance against an insect pest (e.g., a lepidopteran insect pest).

Still further, as another aspect, the invention provides a method of producing a seed. In embodiments, the method comprises: (a) providing a transgenic plant that comprises a polynucleotide, expression cassette or vector of the invention; and (b) harvesting a seed from the transgenic plant of (a), wherein the harvested seed comprises the polynucleotide, expression cassette or vector and/or a chimeric insecticidal protein of the invention. Optionally, the seed has increased resistance against an insect pest (e.g., a lepidopteran insect pest).

The invention further contemplates a method of producing a hybrid plant seed. In representative embodiments, the method comprises: (a) crossing a first inbred plant, which is a transgenic plant comprising a polynucleotide, expression cassette or vector of the invention with a different inbred plant, which may or may not comprise a polynucleotide, expression cassette or vector of the invention; and (b) allowing a hybrid seed to form. In embodiments, the hybrid seed comprises a polynucleotide, expression cassette or vector and/or a chimeric insecticidal protein of the invention. Optionally, the seed has increased resistance against an insect pest (e.g., a lepidopteran insect pest).

As another aspect, the invention provides a method of controlling an insect pest (e.g., a lepidopteran insect pest, such as fall armyworm), the method comprising delivering to the insect pest or an environment thereof a composition comprising an effective amount of a chimeric insecticidal protein or insecticidal composition of the invention. In embodiments, the method is a method of controlling a lepidopteran insect pest (e.g., fall armyworm) that is resistant to a Vip3A protein and/or a Cry1F protein.

Accordingly, as another aspect, the invention provides methods of reducing the development of resistance to a Vip3A protein and/or a Cry1F protein in a population of a target lepidopteran insect pest (e.g., fall armyworm). In embodiments, the method comprises delivering to the target population or an environment thereof a transgenic plant comprising: (i) a polynucleotide, expression cassette, or vector according to the invention; and (ii) a polynucleotide comprising a nucleotide sequence encoding a Vip3A protein and/or a nucleotide sequence encoding a Cry1F protein; wherein the chimeric insecticidal protein and the Vip3A protein and/or the Cry1F protein are produced in the transgenic plant.

The invention is also drawn to methods of using the polynucleotides of the invention, for example, in DNA constructs or expression cassettes or vectors for transformation and expression in organisms, including plants and microorganisms, such as bacteria. The nucleotide or amino acid sequences may be native or synthetic sequences that have been designed for expression in an organism such as a plant or bacteria. The invention is further drawn to methods of making the insecticidal proteins of the invention and to methods of using the polynucleotide sequences and insecticidal proteins, for example in microorganisms to control insects or in transgenic plants to confer protection from insect damage.

Another aspect of the invention includes insecticidal compositions and formulations comprising the chimeric insecticidal proteins of the invention, and methods of using the compositions or formulations to control insect populations, for example by applying the compositions or formulations to insect-infested areas, or to prophylactically treat insect-susceptible areas or plants to confer protection against the insect pests. Optionally, the compositions or formulations of the invention may, in addition to the chimeric insecticidal protein of the invention, comprise other pesticidal agents such as chemical pesticides, other pesticidal proteins, or dsRNA, e.g., in order to augment or enhance the insect-controlling capability of the composition or formulation and/or for insect resistance management.

The compositions and methods of the invention are useful for controlling insect pests that attack plants, particularly crop plants. The compositions of the invention are also useful for detecting the presence of a chimeric insecticidal protein or a nucleic acid encoding the same in commercial products or transgenic organisms.

The invention also provides for uses of the chimeric insecticidal proteins, nucleic acids, transgenic plants, plant parts, seed and insecticidal compositions of the invention, for example, to control an insect pest, such as a lepidopteran pest.

In embodiments, the invention provides a method of using a polynucleotide, expression cassette, vector or host cell of the invention to produce an insecticidal composition for controlling an insect pest (e.g., a lepidopteran insect pest).

In embodiments, the invention provides a method of using a polynucleotide, expression cassette or vector of the invention to produce a transgenic seed, where the transgenic seed grows a transgenic plant with increased resistance to an insect pest.

As another aspect, the invention also contemplates the use of a transgenic plant of the invention to produce a transgenic seed, which is optionally a hybrid seed.

In embodiments, the invention provides a method of using a chimeric insecticidal protein, polynucleotide, expression cassette, vector, transgenic plant or insecticidal composition of the invention to prevent the development of resistance in a population of a target lepidopteran insect pest to a Vip3A protein and/or Cry1F protein.

These and other features, aspects, and advantages of the invention will become better understood with reference to the following detailed description and claims.

BRIEF DESCRIPTION OF THE DRAWINGS

FIGS. 1A and 1B show an alignment of the amino acid sequences of full-length BT-0029 (SEQ ID NO: 2), BT-0022

(SEQ ID NO: 1), Cry1Fa (SEQ ID NO: 8) and Cry1Ka (SEQ ID NO: 12). The Domain III core and Conserved Block 3 (CB3) are indicated. Identical amino acids in the aligned sequences are shaded.

FIGS. 2A and 2B show an alignment of the amino acid sequences of full-length BT-0029 (SEQ ID NO: 2) with exemplary BT-0029 chimeras: Bt29-Bt22 (SEQ ID NO: 3), Bt29-1Fa (SEQ ID NO: 9), and Bt29-1Ka (SEQ ID NO: 13). The Domain III core and Conserved Block 3 (CB3) are indicated. The Domain III core indicated in the figure is derived from the second Cry protein. Identical amino acids in the aligned sequences are shaded.

FIGS. 3A, 3B, 3C and 3D show a full-length Bt29-Bt22 chimera (SEQ ID NO:3) aligned with a series of Bt29-Bt22 chimeras, Bt29-Bt22Tr1 (SEQ ID NO:20), Bt29-Bt22Tr2 (SEQ ID NO:21), Bt29-Bt22Tr3 (SEQ ID NO:22), Bt29-Bt22Tr4 (SEQ ID NO:23), Bt29-Bt22Tr5 (SEQ ID NO:24) and Bt29-Bt22Tr6 (SEQ ID NO:25), with C-terminal truncations within the BT-0029 protoxin tail.

BRIEF DESCRIPTION OF THE SEQUENCES IN THE SEQUENCE LISTING

SEQ ID NO: 1 is the amino acid sequence of a BT-0022 protein.

SEQ ID NO: 2 is the amino acid sequence of a BT-0029 protein.

SEQ ID NO: 3 is the amino acid sequence of a Bt29-Bt22 chimera. The BT-0022 sequence is amino acid 459-597.

SEQ ID NO: 4 is a nucleotide sequence encoding the Bt29-Bt22 chimera of SEQ ID NO: 3.

SEQ ID NO: 5 is an exemplary maize-optimized sequence encoding the Bt29-Bt22 chimera of SEQ ID NO: 3.

SEQ ID NO: 6 is an exemplary maize-optimized sequence encoding the Bt29-Bt22 chimera of SEQ ID NO: 3.

SEQ ID NO: 7 is an exemplary maize-optimized sequence encoding the Bt29-Bt22 chimera of SEQ ID NO: 3.

SEQ ID NO: 8 is the amino acid sequence of a full-length Cry1Fa.

SEQ ID NO: 9 is the amino acid sequence of a Bt29-1Fa chimera. The Cry1Fa sequence is amino acids 459-597.

SEQ ID NO: 10 is a nucleotide sequence encoding the Bt29-1Fa chimera of SEQ ID NO: 9.

SEQ ID NO: 11 is an exemplary maize-optimized sequence encoding the Bt29-1Fa chimera of SEQ ID NO: 9.

SEQ ID NO: 12 is the amino acid sequence of a full-length Cry1Ka.

SEQ ID NO: 13 is the amino acid sequence of a Bt29-1Ka chimera. The Cry1Ka sequence is amino acids 459-597.

SEQ ID NO: 14 is a nucleotide sequence encoding the Bt29-1Ka chimera of SEQ ID NO: 13.

SEQ ID NO: 15 is the amino acid sequence of a Bt29-1Kav2 chimera.

SEQ ID NO: 16 is the nucleotide sequence encoding the Bt29-1Ka chimera of SEQ ID NO: 15.

SEQ ID NO: 17 is the amino acid sequence of a full-length Cry1Ca.

SEQ ID NO: 18 is the amino acid sequence of a Bt29-1Ca chimera. The Cry1Ca sequence is amino acids 459-597.

SEQ ID NO: 19 is a nucleotide sequence encoding the Bt29-1Ca chimera of SEQ ID NO: 18.

SEQ ID NO: 20 is the amino acid sequence of Bt29-Bt22Tr1 protein.

SEQ ID NO: 21 is the amino acid sequence of Bt29-Bt22Tr2 protein.

SEQ ID NO: 22 is the amino acid sequence of Bt29-Bt22Tr3 protein.

SEQ ID NO: 23 is the amino acid sequence of Bt29-Bt22Tr4 protein.

SEQ ID NO: 24 is the amino acid sequence of Bt29-Bt22Tr5 protein.

SEQ ID NO: 25 is the amino acid sequence of Bt29-Bt22Tr6 protein.

SEQ ID NO: 26 is the amino acid sequence of BT29BT22-TL22v1 protein.

SEQ ID NO: 27 is the amino acid sequence of BT29BT22-TL22v2 protein.

SEQ ID NO: 28 is the amino acid sequence of BT29BT22-TL22v3 protein.

SEQ ID NO: 29 is the amino acid sequence of BT29BT22-TL22v4 protein.

SEQ ID NO: 30 is the amino acid sequence of BT29BT22-TL22v5 protein.

SEQ ID NO: 31 is the amino acid sequence of BT29BT22-TL22v6 protein.

SEQ ID NO: 32 is the amino acid sequence of BT291 FaTr1 protein.

SEQ ID NO: 33 is the amino acid sequence of BT291 FaTr2 protein.

SEQ ID NO: 34 is the amino acid sequence of BT291 FaTr3 protein.

SEQ ID NO: 35 is the amino acid sequence of BT291 FaTr4 protein.

DETAILED DESCRIPTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Nucleotide sequences provided herein are presented in the 5' to 3' direction, from left to right and are presented using the standard code for representing nucleotide bases as set forth in 37 CFR §§ 1.821-1.825 and the World Intellectual Property Organization (WIPO) Standard ST.25, for example: adenine (A), cytosine (C), thymine (T), and guanine (G).

Amino acids are likewise indicated using the WIPO Standard ST.25, for example: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount. As used herein, phrases such as "between about X and Y" mean "between about X and about Y" and phrases such as "from about X to Y" mean "from about X to about Y."

As used herein, phrases such as "from X to Y" should be interpreted to include X and Y, unless the context indicates otherwise.

By "activity" of an insecticidal protein of the invention is meant that the insecticidal protein functions as an orally active insect control agent, has a toxic effect, for example, by inhibiting the ability of the insect pest to survive, grow, and/or reproduce (e.g., causing morbidity and/or mortality) and/or is able to disrupt and/or deter insect feeding, which may or may not cause death of the insect. Thus, when an insecticidal protein of the invention is delivered to the insect, the result is typically morbidity and/or mortality of the insect and/or the insect reduces or stops feeding upon the source that makes the insecticidal protein available to the insect.

In the context of the present invention, a "chimeric" protein is a protein created by fusing all or a portion of at least two different proteins. In embodiments of the present invention, the chimeric protein is a chimeric Cry protein comprising all or a portion of two different Cry proteins fused together into a single polypeptide. A "chimeric insecticidal protein" is a chimeric protein that has insecticidal activity (as described herein).

A "coding sequence" is a nucleic acid sequence that is transcribed into RNA such as mRNA, rRNA, tRNA, snRNA, sense RNA or antisense RNA. In embodiments, the RNA is then translated to produce a protein.

As used herein, a "codon optimized" nucleotide sequence means a nucleotide sequence of a recombinant, transgenic, or synthetic polynucleotide wherein the codons are chosen to reflect the particular codon bias that a host cell or organism may have. This is typically done in such a way so as to preserve the amino acid sequence of the polypeptide encoded by the codon optimized nucleotide sequence. In certain embodiments, a nucleotide sequence is codon optimized for the cell (e.g., an animal, plant, fungal or bacterial cell) in which the construct is to be expressed. For example, a construct to be expressed in a plant cell can have all or parts of its sequence codon optimized for expression in a plant. See, for example, U.S. Pat. No. 6,121,014. In embodiments, the polynucleotides of the invention are codon-optimized for expression in a plant cell (e.g., a dicot cell or a monocot cell) or bacterial cell.

To "control" an insect pest means to inhibit, through a toxic effect, the ability of the insect pest to survive, grow, feed and/or reproduce and/or to limit insect-related damage or loss in a crop plant caused by the insect pest and/or to protect the yield potential of a crop caused by the pest when grown in the presence of an insect pest. To "control" an insect pest may or may not mean killing the insect, although in embodiments of the invention, "control" of the insect means killing the insect.

The term "comprise", "comprises" or "comprising," when used in this specification, indicates the presence of the stated features, integers, steps, operations, elements, or components, but does not preclude the presence or addition of one or more other features, integers, steps, operations, elements, components, and/or groups thereof.

As used herein, the transitional phrase "consisting essentially of" (and grammatical variants) means that the scope of a claim is to be interpreted to encompass the specified materials or steps recited in the claim "and those that do not materially alter the basic and novel characteristic(s)" of the claimed invention. Thus, the term "consisting essentially of" when used in a claim of this invention is not intended to be interpreted to be equivalent to "comprising."

In the context of the invention, "corresponding to" or "corresponds to" means that when the amino acid sequences of modified or homolog proteins are aligned with each other, the amino acids that "correspond to" certain enumerated positions in the modified or homolog protein are those that align with these positions in a reference protein, but are not necessarily in the same exact numerical positions relative to the particular reference amino acid sequence of the invention. For example, if SEQ ID NO: 2 (BT-0029) is the reference sequence and is aligned with SEQ ID NO: 1 (BT-0022) as in FIG. 1, the sequence TLEAVT immediately following Domain III in SEQ ID NO: 1 (BT-0022) "corresponds" to the sequence TFEAEY immediately following Domain III of SEQ ID NO: 2 (BT-0029).

As used herein, the term "Cry protein" means an insecticidal protein of a *Bacillus thuringiensis* crystal delta-endotoxin type. The term "Cry protein" can refer to the protoxin form or any insecticidally active fragment or toxin thereof including partially processed and the mature toxin form (e.g., without the N-terminal peptidyl fragment and/or the C-terminal protoxin tail).

As used herein, to "deliver" or "delivering" (and grammatical variations) a composition or insecticidal protein means that the composition or insecticidal protein comes in contact with an insect, which facilitates the oral ingestion of the composition or insecticidal protein, resulting in a toxic effect and control of the insect. The composition or insecticidal protein can be delivered in many recognized ways, including but not limited to, by transgenic plant expression, a formulated protein composition(s), a sprayable protein composition(s), a bait matrix, or any other art-recognized protein delivery system.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide group.

"Effective insect-controlling amount" means that concentration of an insecticidal protein that inhibits, through a toxic effect, the ability of an insect to survive, grow, feed and/or reproduce and/or that limits insect-related damage or loss in a crop plant. An "effective insect-controlling amount" may or may not mean killing the insect, although in embodiments it indicates killing the insect.

"Expression cassette" as used herein means a nucleic acid molecule capable of directing expression of at least one polynucleotide of interest, such as a polynucleotide that encodes an insecticidal protein of the invention, in an appropriate host cell, comprising a promoter operably linked to the polynucleotide of interest which is operably linked to a termination signal. An "expression cassette" also typically comprises additional polynucleotides to facilitate proper translation of the polynucleotide of interest. The expression cassette may also comprise other polynucleotides not related to the expression of a polynucleotide of interest but which are present due to convenient restriction sites for removal of the cassette from an expression vector. In embodiments, at least one of the components in the expression cassette may be heterologous (i.e., foreign) with respect to at least one of the other components (e.g., a heterologous promoter operatively associated with a polynucleotide of interest). The expression cassette may also be one that is naturally occurring but has been obtained in a recombinant form useful for heterologous expression. Typically, however, the expression cassette is heterologous with respect to the host, i.e., the expression cassette (or even the polynucleotide of interest) does not occur naturally in the host cell and has been introduced into the host cell or an ancestor cell thereof by a transformation process or a breeding process. The expression of the polynucleotide(s) of interest in the expression cassette is generally under the control of a promoter. In the case of a multicellular organism, such as a plant, the promoter can also be specific or preferential to a particular tissue, or organ, or stage of development (as described in more detail herein). An expression cassette, or fragment thereof, can also be referred to as "inserted polynucleotide" or "insertion polynucleotide" when transformed into a plant.

A "gene" is defined herein as a hereditary unit comprising one or more polynucleotides that occupies a specific location on a chromosome or plasmid and that contains the genetic instruction for a particular characteristic or trait in an organism.

As used herein, a "gut protease" refers to a protease naturally found in the digestive tract of an insect. This protease is usually involved in the digestion of ingested proteins. Examples of gut proteases include trypsin, which typically cleaves peptides on the C-terminal side of lysine (K) or arginine (R) residues, and chymotrypsin, which typically cleaves peptides on the C-terminal side of phenylalanine (F), tryptophan (W) or tyrosine (Y).

As used herein, the term "heterologous" means foreign, exogenous, non-native and/or non-naturally occurring. In embodiments, a "heterologous" polynucleotide or polypeptide is a polynucleotide or polypeptide that is not naturally associated with a host cell into which it is introduced, including non-naturally occurring multiple copies of a naturally occurring nucleotide sequence or polypeptide. In embodiments, a nucleotide sequence is heterologous to another sequence with which it is operatively associated, e.g., a promoter may be heterologous (i.e., foreign) to an operatively associated coding sequence.

As used here, "homologous" means native. For example, a homologous nucleotide sequence or amino acid sequence is a nucleotide sequence or amino acid sequence naturally associated with a host cell into which it is introduced, a homologous promoter sequence is the promoter sequence that is naturally associated with a coding sequence, and the like.

The terms "increase," "increasing," "increased," "enhance," "enhanced," "enhancing," and "enhancement" (and grammatical variations thereof) and similar terms, as used herein, describe an elevation in the control of a plant pest, e.g., by contacting a plant with a polypeptide of the invention (such as, for example, by transgenic expression or by topical application methods). This increase in control can be in reference to the level of control of the plant pest in the absence of the polypeptide of the invention (e.g., a plant that is not transgenically expressing the polypeptide or is not topically treated with the polypeptide). Thus, in embodiments, the terms "increase," "increasing," "increased," "enhance," "enhanced," "enhancing," and "enhancement" (and grammatical variations thereof), and similar terms can indicate an elevation of at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500% or more as compared to a suitable control (e.g., a plant, plant part, plant cell that is not contacted with a polypeptide of the invention).

"Insecticidal" as used herein is defined as a toxic biological activity capable of controlling an insect pest, optionally but preferably by killing them.

A nucleic acid sequence is "isocoding" with a reference nucleic acid sequence when the nucleic acid sequence encodes a polypeptide having the same amino acid sequence as the polypeptide encoded by the reference nucleic acid sequence.

In representative embodiments, the nucleic acids molecules, polynucleotides or proteins of the invention are "isolated." An "isolated" nucleic acid molecule, polynucleotide or protein, and the like, is a nucleic acid molecule, polynucleotide or protein, and the like that no longer exists in its natural environment. An isolated nucleic acid molecule, polynucleotide or protein of the invention may exist in a purified form or may exist in a recombinant host such as in a transgenic bacteria or a transgenic plant. In embodiments, an isolated nucleic acid molecule, nucleotide sequence or polypeptide exists in a purified form that is at least partially separated from at least some of the other components of the naturally occurring organism or virus, for example, the cell or viral structural components or other polypeptides or nucleic acids commonly found associated with the polynucleotide. In other embodiments, an "isolated" nucleic acid molecule, nucleotide sequence or polypeptide may exist in a non-native environment such as, for example, a recombinant host cell. Thus, for example, with respect to nucleotide sequences, the term "isolated" can mean that the nucleotide sequence is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, recombinant nucleic acid molecules, nucleotide sequences and their encoded polypeptides are "isolated" in that, by the hand of man, they exist apart from their native environment and therefore are not products of nature, however, in some embodiments, they can be introduced into and exist in a recombinant host cell. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism.

The terms "nucleic acid," "nucleic acid molecule," "nucleotide sequence," "oligonucleotide" and "polynucleotide" are used interchangeably herein, unless the context indicates otherwise, and refer to a heteropolymer of nucleotides. These terms include without limitation DNA and RNA molecules, including cDNA, genomic DNA, synthetic (e.g., chemically synthesized) DNA and RNA, plasmid DNA, mRNA, anti-sense RNA, and RNA/DNA hybrids, any of which can be linear or branched, single stranded or double stranded, or a combination thereof. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. In embodiments, the "nucleic acid," "nucleic acid molecule,", "nucleotide sequence,", "oligonucleotide" or "polynucleotide" refer to DNA.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence, means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to or "operatively associated" with the nucleotide sequence.

A "plant" as used herein, refers to any plant at any stage of development.

Any plant (or groupings of plants, for example, into a genus or higher order classification) can be employed in practicing the present invention including angiosperms or gymnosperms, monocots or dicots.

Exemplary plants include, but are not limited to corn (*Zea mays*), canola (*Brassica napus, Brassica rapa* ssp.), alfalfa (*Medicago saliva*), rice (*Oryza sativa*, including without limitation Indica and/or *Japonica* varieties), rape (*Brassica napus*), rye (*Secale cereale*), sorghum (*Sorghum bicolor, Sorghum vulgare*), sunflower (*Helianthus annus*), wheat (*Triticum aestivum*), soybean (*Glycine max*), tobacco (*Nicotiana tobacum*), potato (*Solanum tuberosum*), peanut (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus* vulgaris). duckweed (*Lemna* spp.), oats (*Avena sativa*), barley (*Hordium vulgare*), vegetables, ornamentals, conifers, and turfgrasses (e.g., for ornamental, recreational or forage purposes), and biomass grasses (e.g., switchgrass and miscanthus).

Vegetables include without limitation Solanaceous species (e.g., tomatoes; *Lycopersicon esculentum*), lettuce (e.g., *Lactuca sativa*), carrots (*Caucus carota*), cauliflower (*Brassica oleracea*), celery (*Apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* such as hubbard squash (*C. hubbard*), butternut squash (*C. moschata*), zucchini (*C. pepo*), crookneck squash (*C. crookneck*), *C. argyrosperma*, *C. argyrosperma* ssp *sororia*, *C. digitata*, *C. ecuadorensis*, *C. foetidissima*, *C. lundelliana*, and *C. martinezii*, and members of the genus *Cucumis* such as cucumber (*Cucumis sativus*), cantaloupe (*C. cantalupensis*), and musk melon (*C. melo*).

Ornamentals include without limitation azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherima*), and chrysanthemum.

Conifers, which may be employed in practicing the present invention, include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Turfgrass include but are not limited to zoysiagrasses, bentgrasses, fescue grasses, bluegrasses, St. Augustine-grasses, bermudagrasses, bufallograsses, ryegrasses, and orchardgrasses.

Also included are plants that serve primarily as laboratory models, e.g., *Arabidopsis*.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

A "plant cell culture" means a culture of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

As used herein, the term "plant part" includes but is not limited to embryos, pollen, ovules, seeds, leaves, flowers, branches, fruit, stalks, roots, root tips, anthers, and/or plant cells including plant cells that are intact in plants and/or parts of plants, plant protoplasts, plant tissues, plant cell tissue cultures, plant calli, plant clumps, and the like.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural or functional units. The use of this term in conjunction with, or in the absence of, any specific type of plant tissue as listed above or otherwise embraced by this definition is not intended to be exclusive of any other type of plant tissue.

A "polynucleotide of interest" refers to any polynucleotide which, when transferred to an organism, e.g., a plant, confers upon the organism a desired characteristic such as insect resistance, disease resistance, herbicide tolerance, antibiotic resistance, improved nutritional value, improved performance in an industrial process, production of a commercially valuable enzyme or metabolite, an altered reproductive capability, and the like.

A "portion" or "fragment" of a polypeptide of the invention will be understood to mean an amino acid sequence of reduced length relative to a reference amino acid sequence of a polypeptide of the invention. Such a portion or fragment according to the invention may be, where appropriate, included in a larger polypeptide of which it is a constituent (e.g., a tagged or fusion protein). In embodiments, the "portion" or "fragment" substantially retains insecticidal activity (e.g., at least 40%, 50%, 60%, 70%, 80%, 85%, 90%, 95% or even 100% of the activity of the full-length protein, or has even greater insecticidal activity than the full-length protein).

The terms "protein," "peptide" and "polypeptide" are used interchangeably herein.

The term "promoter" as used herein refers to a polynucleotide, typically upstream (5') of a coding polynucleotide, which controls the expression of the coding polynucleotide by providing the recognition for RNA polymerase and other transcriptional machinery.

A "protoplast" as used herein, refers to an isolated plant cell without a cell wall or with only parts of the cell wall.

As used herein, the term "recombinant" refers to a form of nucleic acid (e.g., DNA or RNA) or protein or an organism that would not normally be found in nature and as such was created by human intervention. As used herein, a "recombinant nucleic acid molecule" (and similar terms) is a nucleic acid molecule comprising a combination of polynucleotides that would not naturally occur together and is the result of human intervention, e.g., a nucleic acid molecule that is comprised of a combination of at least two polynucleotides heterologous to each other, or a nucleic acid molecule that is artificially synthesized and comprises a polynucleotide that deviates from the polynucleotide that would normally exist in nature, or a nucleic acid molecule that comprises a transgene artificially incorporated into a host cell's genomic DNA and the associated flanking DNA of the host cell's genome. An example of a recombinant nucleic acid molecule is a DNA molecule resulting from the insertion of a transgene into a plant's genomic DNA, which may ultimately result in the expression of a recombinant RNA or protein molecule in that organism. In embodiments, a "recombinant" protein is a protein that does not normally exist in nature or is present in a non-naturally occurring context, and is expressed from a recombinant nucleic acid molecule. As used herein, a "recombinant plant" is a plant that would not normally exist in nature, is the result of human intervention, and contains a recombinant polynucleotide (e.g., a transgene or heterologous nucleic acid molecule incorporated into its genome). As a result of such genomic alteration, the recombinant plant is distinctly different from the related wild-type plant.

The terms "reduce," "reduced," "reducing," "reduction," "diminish," and "suppress" (and grammatical variations thereof) and similar terms, as used herein, refer to a decrease in the survival, growth and/or reproduction of a plant pest, e.g., by contacting a plant with a polypeptide of the invention (such as, for example, by transgenic expression or by topical application methods). This decrease in survival, growth and/or reproduction can be in reference to the level observed in the absence of the polypeptide of the invention (e.g., a plant that is not transgenically expressing the polypeptide or is not topically treated with the polypeptide). Thus, in embodiments, the terms "reduce," "reduced," "reducing," "reduction," "diminish," and "suppress" (and grammatical variations thereof) and similar terms mean a decrease of at least about 5%, 10%, 15%, 20%, 25%, 30%, 35%, 40%, 45%, 50%, 55%, 60%, 65%, 70%, 75%, 80%, 85%, 90%, 95% or more as compared with a plant that is not contacted with a polypeptide of the invention (e.g., a plant that is not transgenically expressing the polypeptide or is not topically treated with the polypeptide). In representative embodiments, the reduction results in no or essentially no (i.e., an insignificant amount, e.g., less than about 10%, less than about 5% or even less than about 1%) detectable survival, growth and/or reproduction of the plant pest.

A "regulatory element" refers to a nucleotide sequence involved in controlling the expression of a polynucleotide. Examples of regulatory elements include promoters, termination signals, and nucleotide sequences that facilitate proper translation of a polynucleotide.

As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait).

As used herein, "specific activity" refers to the amount of protein required to have an insecticidal effect. Therefore, when a first protein has a higher specific activity than a second protein means that it takes a lesser amount of the first protein compared the second protein to have an insecticidal effect on the same percentage of insects.

The phrase "substantially identical," in the context of two nucleic acids or two amino acid sequences, refers to two or more sequences or subsequences that have at least about 50% nucleotide or amino acid residue identity when compared and aligned for maximum correspondence as measured using one of the following sequence comparison algorithms or by visual inspection. In certain embodiments, substantially identical sequences have at least about 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more nucleotide or amino acid residue identity. In certain embodiments, substantial identity exists over a region of the sequences that is at least about 50 residues, 100 residues, 150 residues, 200 residues, 250 residues, 300 residues, 350 residues, 400 residues or more in length. In further embodiments, the sequences are substantially identical when they are identical over the entire length of the coding regions.

"Identity" or "percent identity" refers to the degree of identity between two nucleic acid or amino acid sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., J. Mol. Biol. 215: 403 410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Two nucleotide sequences can also be considered to be substantially identical when the two sequences hybridize to each other under stringent conditions. In representative embodiments, two nucleotide sequences considered to be substantially identical hybridize to each other under highly stringent conditions.

The terms "stringent conditions" or "stringent hybridization conditions" include reference to conditions under which a nucleic acid will selectively hybridize to a target sequence to a detectably greater degree than other sequences (e.g., at least 2-fold over a non-target sequence), and optionally may substantially exclude binding to non-target sequences. Stringent conditions are sequence-dependent and will vary under different circumstances. By controlling the stringency of the hybridization and/or washing conditions, target sequences can be identified that can be up to 100% complementary to the reference nucleotide sequence. Alternatively, conditions of moderate or even low stringency can be used to allow some mismatching in sequences so that lower degrees of sequence similarity are detected. For example, those skilled in the art will appreciate that to function as a primer or probe, a nucleic acid sequence only needs to be sufficiently complementary to the target sequence to substantially bind thereto so as to form a stable double-stranded structure under the conditions employed. Thus, primers or probes can be used under conditions of high, moderate or even low stringency. Likewise, conditions of low or moderate stringency can be advantageous to detect homolog, ortholog and/or paralog sequences having lower degrees of sequence identity than would be identified under highly stringent conditions.

The terms "complementary" or "complementarity" (and similar terms), as used herein, refer to the natural binding of polynucleotides under permissive salt and temperature conditions by base-pairing. For example, the sequence "A-G-T" binds to the complementary sequence "T-C-A." Complementarity between two single-stranded molecules may be partial, in which only some of the nucleotides bind, or it may be complete when total complementarity exists between the single stranded molecules. The degree of complementarity between nucleic acid strands has significant effects on the efficiency and strength of hybridization between the molecules. As used herein, the term "substantially complementary" (and similar terms) means that two nucleic acid sequences are at least about 50%, 60%, 70%, 75%, 80%, 85%, 90%, 95%, 96%, 97%, 98%, 99% or more complementary. Alternatively, the term "substantially complementary" (and similar terms) can mean that two nucleic acid sequences can hybridize together under high stringency conditions (as described herein).

As used herein, "specifically" or "selectively" hybridizing (and similar terms) refers to the binding, duplexing, or hybridizing of a molecule to a particular nucleic acid target sequence under stringent conditions when that sequence is present in a complex mixture (e.g., total cellular DNA or RNA) to the substantial exclusion of non-target nucleic acids, or even with no detectable binding, duplexing or hybridizing to non-target sequences. Specifically or selectively hybridizing sequences typically are at least about 40% complementary and are optionally substantially complementary or even completely complementary (i.e., 100% identical).

For DNA-DNA hybrids, the $T_m$ can be approximated from the equation of Meinkoth and Wahl, Anal. Biochem., 138: 267-84 (1984): $T_m$=81.5° C.+16.6 (log M)+0.41 (% GC)−0.61 (% formamide)−500/L; where M is the molarity of monovalent cations, % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired degree of identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, highly stringent conditions can utilize a hybridization and/or wash at the thermal melting point ($T_m$) or 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). If the desired degree of mismatching results in a $T_m$ of less than 45° C. (aqueous solution) or 32° C. (formamide solution), optionally the SSC concentration can be increased so that a higher temperature can be used. An extensive guide to the hybridization of nucleic acids is found in Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier, New York (1993); Current Protocols in Molecular Biology, chapter 2, Ausubel, et al., eds, Greene Publishing and Wiley-Interscience, New York (1995); and Green & Sambrook, In: Molecular Cloning, A Laboratory Manual, 4th Edition, Cold Spring Harbor Press, Cold Spring Harbor, N.Y. (2012).

Typically, stringent conditions are those in which the salt concentration is less than about 1.5 M Na ion, typically about 0.01 to 1.0 M Na ion concentration (or other salts) at about pH 7.0 to pH 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide or Denhardt's (5 g Ficoll, 5 g polyvinylpyrrolidone, 5 g bovine serum albumin in 500 ml of water). Exemplary low stringency conditions include hybridization with a buffer solution of 30% to 35% formamide, 1 M NaCl, 1% SDS (sodium dodecyl sulfate) at 3TC and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 3TC and a wash in 0.1×SSC at 60° C. to 65° C. A further non-limiting example of high stringency conditions include hybridization in 4×SSC, 5×Denhardt's, 0.1 mg/ml boiled salmon sperm DNA, and 25 mM Na phosphate at 65° C. and a wash in 0.1×SSC, 0.1% SDS at 65° C. Another illustration of high stringency hybridization conditions includes hybridization in 7% SDS, 0.5 M NaPO₄, 1 mM EDTA at 50° C. with washing in 2×SSC, 0.1% SDS at 50° C., alternatively with washing in 1×SSC, 0.1% SDS at 50° C., alternatively with washing in 0.5×SSC, 0.1% SDS at 50° C., or alternatively with washing in 0.1×SSC, 0.1% SDS at 50° C., or even with washing in 0.1×SSC, 0.1% SDS at 65° C. Those skilled in the art will appreciate that specificity is typically a function of post-hybridization washes, the relevant factors being the ionic strength and temperature of the final wash solution.

Nucleic acids that do not hybridize to each other under stringent conditions are still substantially identical if the proteins that they encode are substantially identical (e.g., due to the degeneracy of the genetic code).

A further indication that two nucleic acids or proteins are substantially identical is that the protein encoded by the first nucleic acid is immunologically cross reactive with the protein encoded by the second nucleic acid. Thus, a protein is typically substantially identical to a second protein, for example, where the two proteins differ only by conservative substitutions.

As used herein, if a modified polypeptide or fragment (and the like) "substantially retains" insecticidal activity, it is meant that the modified polypeptide or fragment retains at least about 40%, 50%, 60%, 70%, 80%, 85%, 90%, 95% or even 100% of the insecticidal activity of the reference protein, or has even greater insecticidal activity.

"Synthetic" refers to a nucleotide sequence comprising bases or a structural feature(s) that is not present in the natural sequence. For example, an artificial sequence encoding a protein of the invention that resembles more closely the G+C content and the normal codon distribution of dicot or monocot plant genes is said to be synthetic.

As used herein, a protein that is "toxic" to an insect pest is an orally-active insect control agent that kills the insect pest, causes a reduction in growth and/or reproduction of the insect pest and/or is able to disrupt or deter insect feeding, the latter two of which may or may not cause death of the insect. When a protein of the invention is delivered to an insect or an insect comes into contact with the protein, the result is typically death of the insect, the insect's growth and/or reproduction is slowed and/or the insect reduces or stops feeding upon the source that makes the toxic protein available to the insect.

The terms "toxin fragment" and "toxin portion" are used interchangeably herein to refer to a fragment or portion of a longer (e.g., full-length) chimeric insecticidal protein of the invention, where the "toxin fragment" or "toxin portion" retains insecticidal activity. For example, it is known in the art that native Cry proteins are expressed as protoxins that are processed at the N-terminal and C-terminal ends to produce a mature toxin. In embodiments, the "toxin fragment" or "toxin portion" of a chimeric insecticidal protein of the invention is truncated at the N-terminus and/or C-terminus. In embodiments, the "toxin fragment" or "toxin portion" is truncated at the N-terminus to remove part or all of the N-terminal peptidyl fragment, and optionally comprises at least about 400, 425, 450, 475, 500, 510, 520, 530, 540, 550, 560, 570, 580 or 590 contiguous amino acids of chimeric insecticidal protein specifically described herein or an amino acid sequence that is substantially identical thereto. Thus, in embodiments, a "toxin fragment" or "toxin portion" of a chimeric insecticidal protein is truncated at the N-terminus (e.g., to omit part or all of the peptidyl fragment), for example, an N-terminal truncation of one amino acid or more than one amino acid, e.g., up to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more amino acids. In embodiments, a "toxin fragment" or "toxin portion" of a chimeric insecticidal protein is truncated at the C-terminus (e.g., to omit part or all of the protoxin tail), for example, a C-terminal truncation of one amino acid or more than one amino acid, e.g., up to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 125, 150, 175, 200, 225, 250, 275, 300, 325, 350, 375, 400, 425, 450, 475, 500, 525, 550, 560 or more amino acids. In embodiments, the "toxin fragment" or "toxin portion" comprises domains 1 and 2, and the core domain III (e.g., as shown in FIG. 2). In embodiments, the "toxin fragment" or "toxin portion" is the mature (i.e., processed) toxin (e.g., Cry toxin).

"Transformation" is a process for introducing a heterologous nucleic acid into a host cell or organism. In particular embodiments, "transformation" means the stable integration of a DNA molecule into the genome of an organism of interest (e.g., a plant cell).

The terms "transformed" and "transgenic" as used herein refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. "Transformed" or "transgenic" cells, tissues, or plants are understood to encompass not only the end product of a transformation process, but also progeny thereof comprising the heterologous nucleic acid molecule. A "non-transformed" or "non-transgenic" host refers to a wild-type organism, e.g., a bacterium or plant, which does not contain the heterologous nucleic acid molecule.

The term "vector" refers to a composition for transferring, delivering or introducing a nucleic acid (or nucleic acids) into a cell. A vector comprises a nucleic acid molecule comprising the nucleotide sequence(s) to be transferred, delivered or introduced.

Chimeric Insecticidal Proteins.

The present invention provides novel chimeric insecticidal proteins comprising at least one region from a first Cry protein (e.g., a BT-0029 protein [SEQ ID NO: 2] and substantially identical variants thereof). In embodiments, the invention provides a chimeric insecticidal protein comprising a region from two or more different Cry proteins. In embodiments, the resulting chimeric insecticidal protein has increased activity against one or more insect pests (e.g., an enhanced activity or activity against a new target pest) and/or a different mode of action against one or more insect pests as compared with one or more (or even all) of the parent proteins. In representative embodiments, the chimeric insecticidal protein is a chimera comprising regions from two different Cry (e.g., Cry1) proteins, and the chimera has increased insecticidal activity against one or more insect pests as compared with both parent proteins.

In embodiments, the chimeric insecticidal proteins of the invention can provide new modes of action against one or more target insect pests. For example, the chimeric insecticidal protein can have insecticidal activity against an insect pest or colony that is generally resistant to the insecticidal activity of another agent (e.g., an insecticidal protein, including without limitation a Bt protein, such as a Cry protein or a Vip protein). In embodiments, the parent proteins themselves are not insecticidally active, or only weakly active, against the resistant insect pest or colony, which may suggest that the chimera has a novel mode of action as compared with the parent proteins. For example, if the parent proteins are active against a target insect pest ("susceptible"), but not against a resistant counterpart, and the chimeric insecticidal protein is active against the resistant insect pest, that is an indication that the chimeric insecticidal protein is toxic to the resistant pest via a novel mode of action.

Accordingly, in embodiments, the invention provides a chimeric insecticidal protein that is toxic to an insect pest (e.g., a lepidopteran insect pest), the chimeric insecticidal protein comprising a region from a BT-0029 protein (SEQ ID NO: 2) or a polypeptide that is substantially identical to the region from a BT-0029 protein. In embodiments, the chimeric insecticidal protein comprises an N-terminal region of a first Cry1 protein, which is optionally a BT-0029 protein (SEQ ID NO: 2) or a polypeptide comprising an amino acid sequence that is substantially identical to the N-terminal region of the BT-0029 protein. In embodiments, the N-terminal region of the first Cry protein is fused to a C-terminal region from a different Cry protein (e.g., a different Cry1 protein) to form a chimeric insecticidal protein (e.g., a chimeric insecticidal Cry protein).

In representative embodiments, the C-terminal region from a different Cry protein can be a C-terminal region from a different Cry1 protein or a polypeptide comprising an amino acid sequence that is substantially identical to the C-terminal region from the different Cry1 protein.

Thus, in a representative embodiment, a chimeric insecticidal protein of the invention comprises, consists essentially of, or consists of, in an N-terminal to a C-terminal direction: (a) an N-terminal region of a first Cry protein (e.g., a Cry1 protein), which is optionally an N-terminal region of a BT-0029 protein or an amino acid sequence that is substantially identical to the N-terminal region of the BT-0029 protein, fused to (b) a C-terminal region of a different Cry protein (e.g., a different Cry1 protein).

In representative embodiments, the different Cry protein (e.g., Cry1 protein) is selected based on an alignment of the C-terminal region from the different Cry protein and the corresponding region from the first Cry protein (e.g., a Cry1 protein), for example, see the exemplary alignments in FIGS. 1A and 1B. In embodiments, the different Cry protein is selected such that the amino acid sequence of the C-terminal region of the different Cry protein is substantially identical to the corresponding region of the first Cry protein. In exemplary embodiments, the amino acid sequence of the C-terminal region of the different Cry protein (e.g., Cry1 protein) is at least about 85%, 86%, 87%, 88%, 89%, 90%, 91%, 92%, 93%, 94%, 95%, 96%, 97%, 98%, 99% or more identical with an amino acid sequence of the corresponding C-terminal region from the first Cry protein. Methods of aligning and determining amino acid sequence identity across an aligned region are well known by those skilled in the art.

In embodiments, the different Cry1 protein includes without limitation a Cry1F protein (e.g., a Cry1Fa or a Cry1Fb protein), a Cry1G protein (e.g., a Cry1Ga, a Cry1Gb, or a Cry1Gc protein), a Cry1I protein (e.g., a Cry1Ia protein, a Cry1Ib protein, a Cry1Ic protein, a Cry1Id protein, a Cry1Ie protein, a Cry1If protein, or a Cry1Ig protein), a Cry1K (e.g., a Cry1Ka protein), or a Cry1C (e.g. a Cry1Ca protein). In embodiments, the different Cry1 protein is a Cry1If protein, optionally a BT-0022 protein (SEQ ID NO: 1). In embodiments, a different Cry1 protein is a Cry1Fa protein (SEQ ID NO: 8). In embodiments, a different Cry1 protein is a Cry1K protein (SEQ ID NO: 12). In embodiments, a different Cry1 protein is a Cry1Ca protein (SEQ ID NO: 17).

The terms "N-terminal region" and a "C-terminal region" do not necessarily indicate that the most N-terminal or C-terminal amino acids (e.g., the N-terminus or C-terminus), respectively, of the full-length protein are included within the region. For example, it is well-known by those skilled in the art that Cry protoxins are processed at both the N-terminus and C-terminus to produce a mature (i.e., processed) toxin. Thus, in embodiments, the "N-terminal region" and/or the "C-terminal region" omit some or all of the processed out portions of the protoxin such that the chimeric insecticidal protein comprises the mature toxin protein (e.g., Cry protein Domains I, II and III), without some or all of the N-terminal peptidyl fragment and/or the C-terminal protoxin tail, or a polypeptide that is substantially identical to the mature toxin protein. In embodiments, the chimeric insecticidal protein comprises the peptidyl fragment and/or protoxin tail. In embodiments, the chimeric insecticidal protein does not comprise the peptidyl fragment or protoxin tail, i.e., corresponds to the mature processed toxin.

In embodiments, the N-terminal region of the first Cry1 protein comprises, consists essentially of, or consists of a polypeptide corresponding to an amino acid sequence from about position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 to about position 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499 or 500 of SEQ ID NO: 2 (full-length BT-0029), and any combination of lower and upper positions as if each such combination were specifically set forth herein.

In embodiments, the N-terminal region of the first Cry1 protein comprises, consists essentially of, or consists of a polypeptide corresponding to an amino acid sequence from about position 1 to about position 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490 or 491 of SEQ ID NO: 2.

In a representative embodiment, the N-terminal region of the first Cry1 protein comprises, consists essentially of, or consists of an amino acid sequence corresponding to an amino acid sequence from about position 1 to about amino acid position 458 of SEQ ID NO: 2.

In representative embodiments, the C-terminal region of the second Cry1 protein comprises, consists essentially of, or consists of a polypeptide corresponding to an amino acid sequence from about position 435, 436, 437, 438, 439, 440, 441, 442, 443, 444, 445, 446, 447, 448, 449, 450, 451, 452, 453, 454, 455, 456, 457, 458, 459, 440, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499 or 500 to about position 580, 581, 582, 583, 584, 585, 586, 587, 588, 589, 590, 591, 592, 593, 594, 595, 596, 587, 598, 599, 600, 601, 602, 603, 604, 605, 606, 607, 608, 609, 610, 611, 612, 613, 614, 615, 616, 617, 618, 619 or 620 of SEQ ID NO: 8 (full-length Cry1Fa), and any combination of lower and upper positions as if each such combination were specifically set forth herein.

In embodiments, the C-terminal region of the second Cry1 protein comprises, consists essentially of, or consists of a polypeptide corresponding to an amino acid sequence from about position 464 to about position 580, 581, 582, 583, 584, 585, 586, 587, 588, 589, 590, 591, 592, 593, 594, 595, 596, 587, 598, 599, 600, 601, 602, 603, 604, 605, 606, 607, 608, 609, 610, 611, 612, 613, 614, 615, 616, 617, 618, 619 or 620 of SEQ ID NO: 8.

In embodiments, the C-terminal region of the second Cry1 protein comprises, consists essentially of, or consists of a polypeptide corresponding to an amino acid sequence from about position 435, 436, 437, 438, 439, 440, 441, 442, 443, 444, 445, 446, 447, 448, 449, 450, 451, 452, 453, 454, 455, 456, 457, 458, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499 or 500 to about position 602 of SEQ ID NO: 8.

In embodiments, the C-terminal region of the second Cry1 protein comprises, consists essentially of, or consists of a polypeptide corresponding to an amino acid sequence from about position 464 to about position 602 of SEQ ID NO: 8.

In representative embodiments, the C-terminal region of the second Cry1 protein comprises, consists essentially of, or consists of a polypeptide corresponding to an amino acid sequence from about position 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, or 535 to about position 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654 or 655 of SEQ ID NO: 1 (full-length BT-0022), and any combination of lower and upper positions as if each such combination were specifically set forth herein.

In embodiments, the C-terminal region of the second Cry1 protein comprises, consists essentially of, or consists of a polypeptide corresponding to an amino acid sequence from about position 498 to about position 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654 or 655 of SEQ ID NO: 1.

In embodiments, the C-terminal region of the second Cry1 protein comprises, consists essentially of, or consists of a polypeptide corresponding to an amino acid sequence from about position 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, or 535 to about position 636 of SEQ ID NO: 1.

In embodiments, the C-terminal region of the second Cry1 protein comprises, consists essentially of, or consists of a polypeptide corresponding to an amino acid sequence from about position 498 to about position 636 of SEQ ID NO: 1.

In representative embodiments, the C-terminal region of the second Cry1 protein comprises, consists essentially of, or consists of a polypeptide corresponding to an amino acid sequence from about position 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536 or 537 to about position 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656 or 657 of SEQ ID NO: 12 (full-length Cry1Ka), and any combination of lower and upper positions as if each such combination were specifically set forth herein.

In embodiments, the C-terminal region of the second Cry1 protein comprises, consists essentially of, or consists of a polypeptide corresponding to an amino acid sequence from about position 500 to about position 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656 or 657 of SEQ ID NO: 12.

In embodiments, the C-terminal region of the second Cry1 protein comprises, consists essentially of, or consists of a polypeptide corresponding to an amino acid sequence from about position 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537 to about position 597 of SEQ ID NO: 12.

In embodiments, the C-terminal region of the second Cry1 protein comprises, consists essentially of, or consists of a polypeptide corresponding to an amino acid sequence from about position 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537 to about position 610 of SEQ ID NO: 12.

In embodiments, the C-terminal region of the second Cry1 protein comprises, consists essentially of, or consists of a polypeptide corresponding to an amino acid sequence from about position 500 to about position 597 of SEQ ID NO: 12.

In embodiments, the C-terminal region of the second Cry1 protein comprises, consists essentially of, or consists of a polypeptide corresponding to an amino acid sequence from about position 500 to about position 610 of SEQ ID NO: 12.

In representative embodiments, the C-terminal region of the second Cry1 protein comprises, consists essentially of, or consists of a polypeptide corresponding to an amino acid sequence from about position 435, 436, 437, 438, 439, 440, 441, 442, 443, 444, 445, 446, 447, 448, 449, 450, 451, 452, 453, 454, 455, 456, 457, 458, 449, 450, 451, 452, 453, 454, 455, 456, 457, 458, 459, 460, 461, 462, 463, 464, 465, 466 or 467 to about position 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616 or 617 of SEQ ID NO: 17 (full-length Cry1Ca), and any combination of lower and upper positions as if each such combination were specifically set forth herein.

In embodiments, the C-terminal region of the second Cry1 protein comprises, consists essentially of, or consists of a polypeptide corresponding to an amino acid sequence from about position 467 to about position 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616 or 617 of SEQ ID NO: 17.

In embodiments, the C-terminal region of the second Cry1 protein comprises, consists essentially of, or consists of a polypeptide corresponding to an amino acid sequence from about position 435, 436, 437, 438, 439, 440, 441, 442, 443, 444, 445, 446, 447, 448, 449, 450, 451, 452, 453, 454, 455, 456, 457, 458, 449, 450, 451, 452, 453, 454, 455, 456, 457, 458, 459, 460, 461, 462, 463, 464, 465, 466 or 467 to about position 617 of SEQ ID NO: 17.

In embodiments, the C-terminal region of the second Cry1 protein comprises, consists essentially of, or consists of a polypeptide corresponding to an amino acid sequence from about position 467 to about position 617 of SEQ ID NO: 17.

As is well known in the art, Cry proteins from Bt have 5 conserved sequence domains (Conserved Block [CB] 1 to 5]) separated by more variable regions (Hofte & Whitely, 1989, Microbiol. Rev. 53:242-255), and three conserved structural domains (Domains I, II and III) (de Maagd et al., 2001, Trends Genetics 17:193-199). FIGS. 1A and 1B show an alignment of the Cry proteins BT-0029, BT-0022, Cry1Fa and Cry1Ka, with CB3 and Domain III indicated. Those skilled in the art can use the well-known sequence and structural information available for Cry proteins to create a chimeric insecticidal Cry protein according to the invention, for example, to select a suitable crossover region(s) between two Cry proteins. In embodiments, a crossover region is located within a conserved block, for example, within CB3. The term "within a conserved block" includes the positions at each end of the conserved block. To illustrate, the term "within CB3" includes the position immediately before (e.g., between the methionine and phenylalanine residues within the sequence VPMFSW in the BT-0029 sequence of FIG. 2A) and immediately after (e.g., between the threonine and asparagine residues within the sequence RRTNVG in the BT-0029 sequence of FIG. 2A) conserved block 3. FIGS. 2A and 2B show exemplary chimeric insecticidal proteins according to the invention with a crossover region within CB3.

With reference to FIG. 2A, in embodiments, a crossover is located in a position corresponding to a position immediately before amino acid residue 1 or immediately following amino acid residue 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or 51, or any combination thereof, in CB3. In embodiments, a crossover is located within a region (including the residues at each end of the region) corresponding to amino acid residue 2 to amino acid residue 7, 8, 9 or 10 of CB3, within a region corresponding to amino acid residue 11 to amino acid residue 14, 15, 16, 17 or 18 of CB3, within a region corresponding to amino acid residue 19 to amino acid residue 27, 28, 29, 30, 31, 32, 33, 34, 35 or 36 of CB3 and/or within a region corresponding to amino acid residue 37, 38 or 39 to amino acid residue 51, and any combination of such regions. In representative embodiments, a crossover is located in a position within a region corresponding to amino acid residue 19 to amino acid residue 51, amino acid residue 19 to amino acid residue 33, amino acid residue 19 to amino acid residue 28, amino acid residue 19 to amino acid residue 27, or amino acid residue 19 to amino acid residue 26 in CB3. In embodiments, a crossover position is located at the specific site in between amino acid residue 18 and amino acid residue 19 in CB3 (e.g., specifically in between the valine and isoleucine in the sequence DPDVITQ in BT-0029, SEQ ID NO: 2).

The chimeric insecticidal proteins can also be defined with respect to the structural domains derived from each of the parent molecules. For example, in embodiments, the N-terminal region of the first Cry protein comprises domain I of the first Cry protein and all or essentially all of domain II. In embodiments, the C-terminal region of the different Cry protein comprises all or essentially all of domain III of the different Cry protein. Those skilled in the art understand that there is some variability in delineating the precise location of the ends of the Cry protein structural domains and the linker regions between the domains, for example, the location of the end of the linker region between domains II and III and the beginning of domain III, although the core of domain III is readily identifiable to those skilled in the art (e.g., corresponding to the location of the core domain III as shown in FIG. 1A and FIG. 2A). In embodiments, the crossover between the N-terminal region of the first Cry protein and the C-terminal region derived from the different Cry protein is located in CB3.

In representative embodiments, the C-terminal region of the different Cry protein (e.g., Cry1 protein) is selected based on an alignment of domain III (e.g., a core domain III as shown in FIG. 1A) from the different Cry protein and the corresponding domain III sequence from the first Cry protein (e.g., a Cry1 protein, such as BT-0029), for example, see the exemplary alignments in FIGS. 1A and 1B, with domain III specifically indicated. In embodiments, the different Cry protein is selected such that the amino acid sequence of domain III of the different Cry protein is substantially identical to the corresponding domain III region of the first Cry protein (e.g., BT-0029). In exemplary embodiments, the amino acid sequence of the domain III region of the different Cry protein (e.g., Cry1 protein) is at least about 85%, 86%, 87%, 88%, 89%, 90%, 91%, 92%, 93%, 94%, 95%, 96%, 97%, 98%, 99% or more identical with an amino acid sequence of the corresponding domain III region from the first Cry protein. Methods of aligning and determining amino acid sequence identity across an aligned region are well known by those skilled in the art.

In particular embodiments, a chimeric insecticidal protein of the invention comprises, consists essentially of, or consists of (a) the amino acid sequence of any one of amino acids 1 to 597 of SEQ ID NO: 3, SEQ ID NO: 9, or SEQ ID NO: 13 or amino acids 1 to 610 of SEQ ID NO: 15, or amino acids 1 to 617 SEQ ID NO: 18, or a toxin fragment of any of SEQ ID Nos: 3, 9, 13, 15, or 18; or (b) an amino acid sequence that is substantially identical to the amino acid sequence of (a).

In particular embodiments, a chimeric insecticidal protein of the invention comprises, consists essentially of, or consists of (a) the amino acid sequence of any one of amino acids 1 to 603 of SEQ ID NO: 3, SEQ ID NO: 9 or SEQ ID NO: 13, or amino acids 1 to 615 of SEQ ID NO:15 or SEQ ID NO:18, or a toxin fragment thereof; or (b) an amino acid sequence that is substantially identical to the amino acid sequence of (a).

In particular embodiments, a chimeric insecticidal protein of the invention comprises, consists essentially of, or consists of (a) the amino acid sequence of any one of amino acids 1 to 607 of SEQ ID NO: 3, SEQ ID NO: 9 or SEQ ID NO: 13, or amino acids 1 to 620 of SEQ ID NO: 15 or SEQ ID NO: 18, or a toxin fragment thereof; or (b) an amino acid sequence that is substantially identical to the amino acid sequence of (a).

In particular embodiments, a chimeric insecticidal protein of the invention comprises, consists essentially of, or consists of (a) the amino acid sequence of any one of amino acids 1 to 610 of SEQ ID NO: 3, SEQ ID NO: 9 or SEQ ID NO: 13, or amino acids 1 to 620 of SEQ ID NO: 15 or SEQ ID NO: 18, or a toxin fragment thereof; or (b) an amino acid sequence that is substantially identical to the amino acid sequence of (a).

As is understood by those skilled in the art, native Cry toxins are expressed as protoxins that are processed to produce a mature processed toxin by cleaving an N-terminal peptidyl fragment and a C-terminal protoxin tail. The N-terminal peptidyl fragment and/or the C-terminal protoxin tail may function to enhance the stability and/or the insecticidal activity of the Cry toxin. In embodiments of the invention, the chimeric insecticidal protein comprises all or a portion of an N-terminal peptidyl fragment and/or a protoxin tail. In embodiments, the chimeric insecticidal protein does not comprise a full N-terminal peptidyl fragment and/or a full protoxin tail. In embodiments, the chimeric insecticidal protein does not comprise an N-terminal peptidyl fragment and/or a protoxin tail, i.e., corresponds to the mature processed toxin.

In embodiments, the N-terminal peptidyl fragment is derived from a Cry protein (e.g., from the first Cry protein, which is optionally a Cry1 protein). In other embodiments, the N-terminal peptidyl fragment is heterologous to the first Cry protein, for example, is not derived from a Cry protein and/or is partially or completely synthetic. In embodiments, the peptidyl fragment comprises at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more amino acids, optionally from the first Cry protein, including without limitation a first Cry1 protein (e.g., BT-0029, SEQ ID NO: 2). In embodiments, the peptidyl fragment comprises amino acids from about amino acid 1 to about amino acid 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 of the first Cry protein, e.g., a Cry1 protein such as BT-0029.

In embodiments, the chimeric insecticidal protein of the invention comprises at the C-terminus a protoxin tail region of a Bt Cry protein, including modifications of native Cry protein protoxin tails that are substantially identical to a native Cry protein protoxin tail. In embodiments, the protoxin tail is from a lepidopteran-active Cry protein. In embodiments, the protoxin tail is not derived from a Cry protein and/or is partially or completely synthetic. In embodiments, the Cry protein is heterologous to the first Cry protein and/or the different Cry protein. In embodiments, the protoxin tail is from a Cry1 protein, e.g., a BT-0029, a BT-0022, a Cry1F (e.g., Cry1Fa), a Cry1I (e.g., a Cry1Ia or a Cry1If), a Cry1K (e.g., a Cry1Ka), or a Cry1C (e.g. Cry1Ca), or is a polypeptide that is substantially identical to a protoxin tail (or fragment thereof) from any of the foregoing. The protoxin tail region may comprise an entire protoxin tail of a Cry protein or any portion thereof. In embodiments, the protoxin tail region comprises at least about 5, 6, 7, 8, 9, 10, 11, 12, 13, 14, 15, 20, 25, 30, 35, 38, 40, 45, 50 or more contiguous amino acids of a Cry protein protoxin tail (e.g., a Cry1 protoxin tail, such as a BT-0029), for example, as shown for the various Cry proteins in FIG. 1A. In embodiments, the protoxin tail comprises at least about 5, 6, 7, 8, 9, 10, 11, 12, 13, 14, 15, 20, 25, 30, 35, 38, 40, 45, 50 or more contiguous amino acids starting with amino acid position 598 of SEQ ID NO: 2 (BT-0029) or the corresponding region from another Cry protein, such as a Cry1 protein (e.g., BT-0022, a Cry1I, a Cry1F, a Cry1K or a Cry1C protein). In embodiments, the protoxin tail comprises amino acids 598 to 1169, or 598 to 652, or 598 to 636, or 598 to 622, or 598 to 610, or 598 to 607, or 598 to 603, or 598 to 600 of SEQ ID NO: 2 (BT-0029) or the corresponding region from another Cry protein (see, e.g., the alignment of BT-0029 with BT-0022, Cry1Fa and Cry1Ka in FIGS. 1A and 1B). In some embodiments, the chimeric insecticidal protein comprises any of SEQ ID Nos:20-25 or SEQ ID Nos:32-35. In other embodiments, the protoxin tail comprises amino acids 637 to 715, or 637 to 691, or 637 to 675, or 637 to 661, or 637 to 649, or 637 to 646, or 637 to 642 of SEQ ID NO: 1 (BT-0022). In still other embodiments, a chimeric insecticidal protein of the invention comprises, consists essentially of, or consists of any of SEQ ID Nos: 26-31.

Accordingly, in embodiments, a chimeric insecticidal protein of the invention comprises, consists essentially of, or consists of (a) the amino acid sequence of any one of SEQ ID NO: 3, SEQ ID NO: 9, SEQ ID NO: 13, SEQ ID NO: 15, SEQ ID NO: 18, SEQ ID Nos:20-35, or a toxin fragment thereof; or (b) an amino acid sequence that is substantially identical to the amino acid sequence of (a). In optional embodiments, the chimeric insecticidal protein of the invention comprises, consists essentially of, or consists of the amino acid sequence of any one of amino acids SEQ ID NO: 3, SEQ ID NO: 9, SEQ ID NO: 13, SEQ ID NO: 15, SEQ ID NO: 18 or SEQ ID Nos: 20-35.

Those skilled in the art will appreciate that the chimeric insecticidal proteins of the invention can further comprise other functional domains and/or peptide tags, for example a peptide tag on the N-terminus and/or C-terminus. For example, it may be useful to express the chimeric insecticidal protein with a peptide tag that can be recognized by a commercially available antibody (e.g., a FLAG motif) or with a peptide tag that facilitates purification (e.g., by addition of a poly-His tag) and/or detection. Alternatively, an epitope can be introduced into the chimeric protein to facilitate the generation of antibodies that specifically recognize the modified chimeric protein to distinguish the modified chimeric protein from the unmodified chimera and/or a parent protein(s). For example, one or more amino acids can be substituted into an antigenic loop of the native sequence to create a new epitope. In one embodiment, the antigenic loop is located in a non-conserved region outside of domain I of the native Cry protein. In embodiments, the antigenic loop is not a loop involved in insect gut receptor recognition by the Cry protein and/or is not involved in the protease activation of the Cry protein. In other embodiments, the chimeric protein can be modified to enhance its stability, for example, by fusing a maltose binding protein (MBP) or glutathione-S-transferase to the polypeptide. As another alternative, the fusion protein can comprise a reporter molecule.

Chimeric insecticidal proteins that are modified by introduction or elimination of a protease processing site at an appropriate position(s) to provide, or eliminate, proteolytic cleavage by an insect, plant and/or microorganism protease are also within the scope of the invention. In embodiments, the modified chimeric insecticidal protein substantially retains insecticidal activity. In embodiments, the stability and/or insecticidal activity of such modified chimeric proteins is increased as compared with the chimeric insecticidal protein that does not contain such modification to introduce/eliminate a protease cleavage site.

Thus, the invention encompasses polypeptides having amino acid sequences that are substantially identical to those specifically disclosed herein, and toxin fragments thereof. It will be understood that the chimeric insecticidal proteins specifically disclosed herein will typically tolerate modifications in the amino acid sequence and substantially retain biological activity (e.g., insecticidal activity). Such modifications include insertions, deletions (including truncations at either terminus), and substitutions of one or more amino acids, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions and/or insertions.

To identify substantially identical polypeptides to the chimeric insecticidal proteins specifically disclosed herein, amino acid substitutions may be based on any characteristic known in the art, including the relative similarity or differences of the amino acid side-chain substituents, for example, their hydrophobicity, hydrophilicity, charge, size, and the like.

For example, in identifying amino acid sequences encoding insecticidal polypeptides other than those specifically disclosed herein, the hydropathic index of amino acids may be considered. The importance of the hydropathic amino acid index in conferring interactive biologic function on a protein is generally understood in the art (see, Kyte and Doolittle, (1982) J. Mol. Biol. 157:105; incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, Id.), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Accordingly, the hydropathic index of the amino acid (or amino acid sequence) may be considered when modifying the chimeric polypeptides specifically disclosed herein.

It is also understood in the art that the substitution of amino acids can be made on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (.+−0.3.0); aspartate (+3.0.+−0.1); glutamate (+3.0.+−0.1); serine (+0.3); asparagine (+0.2); glutamine (+0.2); glycine (0); threonine (−0.4); proline (−0.5+1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Thus, the hydrophilicity of the amino acid (or amino acid sequence) may be considered when identifying additional insecticidal polypeptides beyond those specifically disclosed herein.

The chimeric insecticidal proteins of the invention, including modifications and toxin fragments of the chimeric polypeptide specifically disclosed herein, can be made by any suitable method known in the art, generally by modifying the coding nucleic acid sequences. Methods of manipulating and modifying nucleic acids to achieve a desired modification are well-known in the art. In addition, gene editing techniques can also be used produce a chimeric insecticidal protein of the invention or to make further modifications thereto.

As another approach, the polypeptide to be modified can be expressed in a host cell that exhibits a high rate of base mis-incorporation during DNA replication, such as XL-1 Red (Stratagene, La Jolla, Calif.). After propagation in such strains, one can isolate the DNA (for example, by preparing plasmid DNA or by PCR amplification and cloning of the resulting PCR fragment into a vector), culture the protein mutations in a non-mutagenic strain, and identify mutated genes with insecticidal activity, for example, by performing an assay to test for insecticidal activity. In exemplary methods, the protein is mixed and used in feeding assays. See, for example, Marrone et al. (1985) J. of Economic Entomology 78:290-293. Such assays can include contacting plants with one or more pests and determining the plant's ability to survive or cause the death of the pests. Examples of mutations that result in increased toxicity are found in Schnepf et al. (1998) Microbiol. Mol. Biol. Rev. 62:775-806.

In embodiments, the chimeric insecticidal protein (including substantially similar polypeptides and toxin fragments) of the invention is isolated. In embodiments, the chimeric insecticidal protein (including substantially similar polypeptides and toxin fragments) of the invention is a recombinant protein.

The chimeric insecticidal proteins of the invention have insecticidal activity against a lepidopteran pest. In embodiments, the chimeric insecticidal protein has activity against one or more of the following non-limiting examples of a lepidopteran pest: *Ostrinia* spp. such as *O. nubilalis* (European corn borer) and/or *O. furnacalis* (Asian corn borer); *Plutella* spp. such as *P. xylostella* (diamondback moth); *Spodoptera* spp. such as *S. frugiperda* (fall armyworm), *S. littoralis* (Egyptian cotton leafworm), *S. omithogalli* (yellowstriped armyworm), *S. praefica* (western yellowstriped armyworm), *S. eridania* (southern armyworm) and/or *S. exigua* (beet armyworm); *Agrotis* spp. such as *A. ipsilon* (black cutworm), *A. segetum* (common cutworm), *A. gladiaria* (claybacked cutworm), and/or *A. orthogonia* (pale western cutworm); *Striacosta* spp. such as *S. albicosta* (western bean cutworm); *Helicoverpa* spp. such as *H. zea* (corn earworm), *H. punctigera* (native budworm), and/or *H. armigera* (cotton bollworm); *Heliothis* spp. such as *H. virescens* (tobacco budworm); *Diatraea* spp. such as *D. grandiosella* (southwestern corn borer) and/or *D. saccharalis* (sugarcane borer); *Trichoplusia* spp. such as *T. ni* (cabbage looper); *Sesamia* spp. such as *S. nonagroides* (Mediterranean corn borer) and/or *S. calamistis* (pink stem borer); *Pectinophora* spp. such as *P. gossypiella* (pink bollworm); *Cochylis* spp. such as *C. hospes* (banded sunflower moth); *Manduca* spp. such as *M. sexta* (tobacco hornworm) and/or *M. quinquemaculata* (tomato hornworm); *Elasmopalpus* spp. such as *E. lignosellus* (lesser cornstalk borer); *Pseudoplusia* spp. such as *P. includens* (soybean looper); *Anticarsia* spp. such as *A. gemmatalis* (velvetbean caterpillar); *Plathypena* spp. such as *P. scabra* (green cloverworm); *Pieris* spp. such as *P. brassicae* (cabbage butterfly), *Papaipema* spp. such as *P. nebris* (stalk borer); *Pseudaletia* spp. such as *P. unipuncta* (common armyworm); *Peridroma* spp. such as *P. saucia* (variegated cutworm); *Keiferia* spp. such as *K. lycopersicella* (tomato pinworm); *Artogeia* spp. such as *A. rapae* (imported cabbageworm); *Phthorimaea* spp. such as *P. operculella* (potato tuberworm); *Chrysodeixis* spp. Such as *C. includes* (soybean looper); *Feltia* spp. such as *F. ducens* (dingy cutworm); *Chilo* spp. such as *C. suppressalis*

(striped stem borer), *Cnaphalocrocis* spp. such as *C. medinalis* (rice leaffolder), or any combination of the foregoing.

Optionally, the chimeric insecticidal protein has increased activity against one or more lepidopteran pests as compared with one or more of the parent molecules (e.g., the first Cry protein and the different Cry protein). In embodiments, the chimeric insecticidal protein has increased activity against one or more lepidopteran pests as compared with BT-0029. In embodiments, the chimeric insecticidal protein has increased activity against one or more lepidopteran pests as compared with BT-0022, a Cry1Fa, a Cry1Ia, a Cry1If, a Cry1Ka, or a Cry1C.

In embodiments, the chimeric insecticidal protein has enhanced insecticidal activity against fall armyworm (*Spodoptera frugiperda*) as compared with one or more of the parent molecules (e.g., the first Cry protein and the different Cry protein). In embodiments, the chimeric insecticidal protein has increased activity against fall armyworm as compared with BT-0029. In embodiments, the chimeric insecticidal protein has increased activity against fall armyworm as compared with BT-0022, a Cry1Fa, a Cry1Ia, a Cry1If, a Cry1Ka and/or a Cry1Ca. According to the foregoing embodiments, the chimeric insecticidal protein can optionally have insecticidal activity against a fall armyworm insect pest or colony that has resistance to another insecticidal agent, including another insecticidal protein (such as, e.g., a Bt protein). In embodiments, the chimeric insecticidal protein has insecticidal activity against a fall armyworm colony that is resistant to a Vip3A protein (e.g., a Vip3Aa, including without limitation maize event MIR162) or a Cry1F protein (e.g., Cry1Fa, including without limitation maize event TC1507). In embodiments, the chimeric insecticidal protein has enhanced activity against the resistant fall armyworm colony as compared with one or more of the parent molecules, e.g., BT-0029, BT-0022, a Cry1Fa, a Cry1Ia, a Cry1If, a Cry1Ka and/or a Cry1Ca.

The invention also encompasses antibodies that specifically bind to a chimeric insecticidal protein of the invention. The antibody can optionally be a monoclonal antibody or a polyclonal antisera. In embodiments, the antibody is selective for the chimeric protein and does not bind to one or more of the parent molecules (e.g., BT-0029, BT-0022, Cry1Fa, and the like), and can be used to distinguish the chimeric protein from the parent protein§. Such antibodies may be produced using standard immunological techniques for production of polyclonal antisera and, if desired, immortalizing the antibody-producing cells of the immunized host for sources of monoclonal antibody production. Techniques for producing antibodies to any substance of interest are well known, e.g., as described in Harlow and Lane (1988. Antibodies a laboratory manual. pp. 726. Cold Spring Harbor Laboratory) and as in Goding (Monoclonal Antibodies: Principles & practice. 1986. Academic Press, Inc., Orlando, Fla.). The present invention also encompasses an insecticidal protein that cross-reacts with an antibody, particularly a monoclonal antibody, raised against one or more of the chimeric insecticidal proteins of the present invention.

The antibodies according to the invention are useful, e.g., in immunoassays for determining the amount or presence of a chimeric insecticidal protein of the invention or an antigenically related polypeptide, e.g., in a biological sample. Such assays are also useful in quality-controlled production of compositions containing one or more of the chimeric insecticidal proteins of the invention or an antigenically related polypeptide. In addition, the antibodies can be used to assess the efficacy of recombinant production of one or more of the chimeric proteins of the invention or an antigenically related polypeptide, as well as for screening expression libraries for the presence of a nucleotide sequence encoding one or more of the chimeric proteins of the invention or an antigenically related polypeptide. Antibodies further find use as affinity ligands for purifying or isolating any one or more of the proteins of the invention or an antigenically related polypeptide.

Nucleic acids, Expression Cassettes, and Vectors.

As a further aspect, the invention provides nucleic acids encoding the polypeptides of the invention, including modified polypeptides and toxin fragments as described herein.

According to some embodiments, the invention provides a nucleic acid molecule comprising a nucleotide sequence that comprises, consists essentially of, or consists of: (a) a nucleotide sequence encoding the amino acid sequence of SEQ ID NO: 3, SEQ ID NO: 9, SEQ ID NO: 13, SEQ ID NO: 15, SEQ ID NO: 18, SEQ ID Nos: 20-35, or a toxin fragment thereof; (b) a nucleotide sequence encoding an amino acid sequence that is substantially identical to the amino acid sequence of (a); (c) a nucleotide sequence that anneals under stringent hybridization conditions to the nucleotide sequence of (a) or (b); or (d) a nucleotide sequence that differs from the nucleotide sequences of (a), (b) or (c) due to the degeneracy of the genetic code.

In embodiments, the nucleic acid molecule comprises a nucleotide sequence that comprises, consists essentially of, or consists of: (a) a nucleotide sequence of SEQ ID NO: 4, SEQ ID NO: 5, SEQ ID NO: 6, SEQ ID NO: 7, SEQ ID NO: 10, SEQ ID NO: 11, SEQ ID NO:14, or SEQ ID NO: 16, or a toxin-encoding fragment thereof; (b) a nucleotide sequence that is substantially identical to the nucleotide sequence of (a); (c) a nucleotide sequence that anneals under stringent hybridization conditions to the nucleotide sequence of (a) or (b); or (d) a nucleotide sequence that differs from the nucleotide sequences of (a), (b) or (c) due to the degeneracy of the genetic code. Optionally, the nucleotide sequence comprises, consists essentially of, or consists of the nucleotide sequence of SEQ ID NO: 4, SEQ ID NO: 5, SEQ ID NO: 6, SEQ ID NO: 7, SEQ ID NO: 10, SEQ ID NO: 11, SEQ ID NO: 14 or SEQ ID NO: 16.

In embodiments, the nucleotide sequence is a partially or completely synthetic sequence, e.g., that has codons optimized for expression in a host organism, e.g., in a bacterium host or a plant host (for example, a transgenic monocot plant host or a transgenic dicot plant host). Non-limiting examples nucleotide sequences that are codon-optimized for expression in a maize plant include SEQ ID NO: 5, SEQ ID NO: 6, SEQ ID NO: 7 and SEQ ID NO: 11.

In representative embodiments, for expression in transgenic plants, the nucleotide sequences of the invention are modified and/or optimized. For example, although in many cases genes from microbial organisms can be expressed in plants at high levels without modification, low expression in transgenic plants may result from microbial nucleotide sequences having codons that are not preferred in plants. It is known in the art that living organisms have specific preferences for codon usage, and the codons of the nucleotide sequences described in this invention can be changed to conform with plant preferences, while maintaining the amino acids encoded thereby. Furthermore, it is known in the art that high expression in plants, for example corn plants, can be achieved from coding sequences that have at least about 35% GC content, or at least about 45%, or at least about 50%, or at least about 60%. Microbial nucleotide sequences that have low GC contents may express poorly in plants. Although certain nucleotide sequences can be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, in embodiments, the nucleotide sequence is modified to remove illegitimate splice sites that may cause message truncation. Such modifications to the nucleotide sequences can be made using well known techniques of site directed mutagenesis, PCR, and synthetic gene construction using the methods described, for example, in U.S. Pat. Nos. 5,625,136; 5,500,365 and 6,013,523.

In some embodiments, the invention provides synthetic coding sequences or polynucleotide made according to the procedure disclosed in U.S. Pat. No. 5,625,136. In this procedure, maize preferred codons, i.e., the single codon that most frequently encodes that amino acid in maize, are used. The maize preferred codon for a particular amino acid can be derived, for example, from known gene sequences from maize. For example, maize codon usage for 28 genes from maize plants is found in Murray et al., Nucleic Acids Research 17:477-498 (1989). It is recognized that codons optimized for expression in one plant species will also function in other plant species but possibly not at the same level as the plant species for which the codons were optimized. In this manner, the nucleotide sequences can be optimized for expression in any plant. It is recognized that all or any part of a nucleotide sequence may be optimized or synthetic. That is, a polynucleotide may comprise a nucleotide sequence that is part native sequence and part codon optimized sequence.

In representative embodiments, a polynucleotide of the invention is an isolated polynucleotide. In embodiments, a polynucleotide of the invention is a recombinant polynucleotide.

In embodiments, the invention further provides a nucleic acid molecule comprising a polynucleotide of the operably associated with a promoter (e.g., a heterologous promoter). Promoters can include, for example, constitutive, inducible, temporally regulated, developmentally regulated, chemically regulated, tissue-preferred and/or tissue-specific promoters. In particular aspects, a promoter useful with the invention is a promoter capable of initiating transcription of a nucleotide sequence in a plant cell, e.g., in a cell of a monocot (e.g., maize or rice) or dicot (e.g., soybean, cotton) plant.

In embodiments, a heterologous promoter is a plant-expressible promoter (e.g., monocot expressible or dicot expressible). For example, without limitation, the plant-expressible promoter can be selected from the following promoters: ubiquitin, cestrum yellow virus, corn TrpA, OsMADS 6, maize H3 histone, bacteriophage T3 gene 9 5' UTR, corn sucrose synthetase 1, corn alcohol dehydrogenase 1, corn light harvesting complex, corn heat shock protein, maize mtI, pea small subunit RuBP carboxylase, rice actin, rice cyclophilin, Ti plasmid mannopine synthase, Ti plasmid nopaline synthase, petunia chalcone isomerase, bean glycine rich protein 1, potato patatin, lectin, CaMV 35S and S-E9 small subunit RuBP carboxylase promoter.

Although many promoters from dicotyledons have been shown to be operational in monocotyledons and vice versa, in embodiments, dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

The choice of promoter can vary depending on the temporal and spatial requirements for expression, and also depending on the host cell to be transformed. Thus, for example, expression of the nucleotide sequences of the invention can be in any plant and/or plant part, (e.g., in leaves, in stalks or stems, in ears, in inflorescences (e.g., spikes, panicles, cobs, etc.), in roots, seeds and/or seedlings, and the like). For example, where expression in a specific tissue or organ is desired, a tissue-specific or tissue-preferred promoter can be used (e.g., a root specific/preferred promoter). In contrast, where expression in response to a stimulus is desired a promoter inducible by stimuli or chemicals can be used. Where continuous expression at a relatively constant level is desired throughout the cells of a plant a constitutive promoter can be chosen.

Promoters useful with the invention include, but are not limited to, those that drive expression of a nucleotide sequence constitutively, those that drive expression when induced, and those that drive expression in a tissue- or developmentally-specific manner. These various types of promoters are known in the art.

Suitable constitutive promoters include, for example, CaMV 35S promoter (Odell et al., Nature 313:810-812, 1985); *Arabidopsis* At6669 promoter (see PCT Publication No. W004081173A2); maize Ubi 1 (Christensen et al., Plant Mol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al., Plant J November; 2(6):837-44, 1992); ubiquitin (Christensen et al., Plant Mol. Biol. 18: 675-689, 1992); Rice cyclophilin (Bucholz et al., Plant Mol Biol. 25(5):837-43, 1994); Maize H3 histone (Lepetit et al., Mol. Gen. Genet. 231: 276-285, 1992); Actin 2 (An et al., Plant J. 10(1); 107-121, 1996), constitutive root tip CT2 promoter (SEQ ID NO:1535; see also PCT application No. IL/2005/000627) and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142.

Tissue-specific or tissue-preferential promoters useful for the expression of the polypeptides of the invention in plants, optionally maize, include those that direct expression in root, pith, leaf or pollen. Suitable tissue-specific promoters include, but not limited to, leaf-specific promoters (such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993), seed-preferred promoters (e.g., from seed specific genes; Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson et al., Plant Mol. Biol. 18: 235-245, 1992), legumin (Ellis, et al. Plant Mol. Biol. 10: 203-214, 1988), Glutelin (Takaiwa, et al., Mol. Gen. Genet. 208: 15-22, 1986; Takaiwa, et al., FEBS Letts. 221: 43-47, 1987), Zein (Matzke et al., Plant Mol Biol, 143).323-32 1990), napA (Stalberg, et al., Planta 199: 515-519, 1996), Wheat SPA (Albanietal, Plant Cell, 9: 171-184, 1997), sunflower oleosin (Cummins, et al., Plant Mol. Biol. 19: 873-876, 1992)], endosperm specific promoters (e.g., wheat LMW and HMW, glutenin-1 (Mol Gen Genet 216: 81-90, 1989; NAR 17:461-2), wheat a, b and g gliadins (EMB03:1409-15, 1984), Barley ltr1 promoter, barley B1, C, D hordein (Theor Appl Gen 98:1253-62, 1999; Plant J 4:343-55, 1993; Mol Gen Genet 250:750-60, 1996), Barley DOF (Mena et al., The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al., Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (Plant Mol. Biol 32:1029-35, 1996)], embryo specific promoters (e.g., rice OSH1; Sato et al., Proc. Nati. Acad. Sci. USA, 93: 8117-8122), KNOX (Postma-Haarsma of al, Plant Mol. Biol. 39:257-71, 1999), rice oleosin (Wu et at, J. Biochem., 123:386, 1998)] flower-specific promoters, for example, AtPRP4, chalene synthase (chsA) (Van der Meer, et al., Plant Mol. Biol. 15, 95-109, 1990), LAT52 (Twell et al., Mol. Gen Genet. 217:240-245; 1989), apetala-3, and promoters specific for plant reproductive tissues (e.g., OsMADS promoters; U.S. Patent Publication 2007/0006344).

Examples of promoters suitable for preferential expression in green tissue include many that regulate genes involved in photosynthesis and many of these have been cloned from both monocotyledons and dicotyledons. One such promoter is the maize PEPC promoter from the phosphoenol carboxylase gene (Hudspeth & Grula, Plant Molec. Biol. 12:579-589 (1989)). Another promoter for root specific expression is that described by de Framond (FEBS 290:103-106 (1991) or U.S. Pat. No. 5,466,785). Another promoter useful in the invention is the stem specific promoter described in U.S. Pat. No. 5,625,136, which naturally drives expression of a maize trpA gene.

In addition, promoters functional in plastids can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of a gene in a plant through the application of an exogenous chemical regulator. Regulation of the expression of nucleotide sequences of the invention via promoters that are chemically regulated enables the polypeptides of the invention to be synthesized only when the crop plants are treated with the inducing chemicals. Depending upon the objective, the promoter may be a chemical-inducible promoter, where application of a chemical induces gene expression, or a chemical-repressible promoter, where application of the chemical represses gene expression. Examples of such technology for chemical induction of gene expression is detailed in published application EP 0 332 104 and U.S. Pat. No. 5,614,395.

Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid (e.g., the PR1a system), steroid steroid-responsive promoters (see, e.g., the glucocorticoid-inducible promoter in Schena et al. (1991) Proc. Natl. Acad. Sci. USA 88, 10421-10425 and McNellis et al. (1998) Plant J. 14, 247-257) and tetracycline-inducible and tetracycline-repressible promoters (see, e.g., Gatz et al. (1991) Mol. Gen. Genet. 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) Plant J. 11:605-612), and ecdysone-inducible system promoters.

Other non-limiting examples of inducible promoters include ABA- and turgor-inducible promoters, the auxin-binding protein gene promoter (Schwob et al. (1993) Plant J. 4:423-432), the UDP glucose flavonoid glycosyl-transferase promoter (Ralston et al. (1988) Genetics 119:185-197), the MPI proteinase inhibitor promoter (Cordero et al. (1994) Plant J. 6:141-150), and the glyceraldehyde-3-phosphate dehydrogenase promoter (Kohler et al. (1995) Plant Mol. Biol. 29:1293-1298; Martinez et al. (1989) J. Mol. Biol. 208:551-565; and Quigley et al. (1989) J. Mol. Evol. 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) Current Opinion Biotechnol. 7:168-172 and Gatz (1997) Annu. Rev. Plant Physiol. Plant Mol. Biol. 48:89-108. Other chemically inducible promoters useful for directing the expression of the nucleotide sequences of this invention in plants are disclosed in U.S. Pat. No. 5,614,395. Chemical induction of gene expression is also detailed in EP 0 332 104 (to Ciba-Geigy) and U.S. Pat. No. 5,614,395.

Another category of promoters useful in the invention are wound inducible promoters. Numerous promoters have been described that are expressed at wound sites and also at the sites of phytopathogen infection. Ideally, such a promoter should only be active locally at the sites of insect invasion, and in this way the insecticidal proteins only accumulate in cells that need to synthesize the insecticidal proteins to kill the invading insect pest. Examples of promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

In embodiments a nucleic acid of the invention can comprise, consist essentially of, or consist of an expression cassette, or can be comprised within an expression cassette.

An expression cassette comprising a polynucleotide of interest may be chimeric, meaning that at least one of its components is heterologous with respect to at least one other of its other components. An expression cassette may also be one that is naturally occurring but has been obtained in a recombinant form useful for heterologous expression. Typically, the expression cassette is heterologous with respect to the host, i.e., the particular nucleic acid sequence of the expression cassette does not occur naturally in the host cell and must have been introduced into the host cell or an ancestor of the host cell by a transformation event.

In addition to the promoters operatively associated with the nucleotide sequences of the invention, an expression cassette of this invention can also include other regulatory elements. Regulatory elements include, but are not limited to, enhancers, introns, translation leader sequences, termination signals, and polyadenylation signal sequences. Examples of suitable transcription terminator signals are available and known in the art (e.g., tml from CaMV, E9 from rbcS). Any available terminator known to function in plants can be used in the context of this invention.

Numerous other sequences can be incorporated into expression cassettes described in this invention. These include sequences that have been shown to enhance expression such as intron sequences (e.g., from AdhI and bronzeI) and viral leader sequences (e.g., from TMV, MCMV and AMV).

For more efficient initiation of translation, sequences adjacent to the initiating methionine may be modified. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (while leaving the second amino acid unmodified), or alternatively up to and including the GTC subsequent to the ATG (with the possibility of modifying the second amino acid of the transgene).

In embodiments, it may be desired to target expression of the polypeptides of the present invention to a specific cellular location in the plant cell. In some cases, localization in the cytosol may be desirable, whereas in other cases, localization in some subcellular organelle may be preferred. Any mechanism for targeting gene products, e.g., in plants, can be used to practice this invention, and such mechanisms are known to exist in plants and the sequences controlling the functioning of these mechanisms have been characterized in some detail. Sequences have been characterized which cause the targeting of gene products to other cell compartments. For example, amino terminal sequences can be responsible for targeting a protein of interest to a cell compartment, such as, a vacuole, mitochondrion, peroxisome, protein bodies, endoplasmic reticulum, chloroplast, starch granule, amyloplast, apoplast or cell wall of a plant cell (e.g. Unger et. al. Plant Molec. Biol. 13: 411-418 (1989); Rogers et. al. (1985) Proc. Natl. Acad. Sci. USA 82: 6512-651; U.S. Pat. No. 7,102,057; WO 2005/096704. Optionally, the signal sequence may be an N-terminal signal sequence from waxy, an N-terminal signal sequence from gamma-zein, a starch binding domain, a C-terminal starch binding domain, a chloroplast targeting sequence, which imports the mature protein to the chloroplast (Comai et. al. (1988) J. Biol. Chem. 263: 15104-15109; van den Broeck, et. al. (1985) Nature 313: 358-363; U.S. Pat. No. 5,639,949) or a secretion signal sequence from aleurone cells (Koehler & Ho, Plant Cell 2: 769-783 (1990)). Additionally, amino terminal sequences in conjunction with carboxyl terminal sequences are responsible for vacuolar targeting of gene products and can be used with the present invention (Shinshi et. al. (1990) Plant Molec. Biol. 14: 357-368). In one embodiment, the signal sequence selected includes the known cleavage site, and the fusion constructed takes into account any amino acids after the cleavage site(s), which are required for cleavage. In some cases this requirement may be fulfilled by the addition of a small number of amino acids between the cleavage site and the transgene ATG or, alternatively, replacement of some amino acids within the transgene sequence. These construction techniques are well known in the art and are equally applicable to any cellular compartment.

It will be recognized that the above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

An expression cassette of the invention also can include a nucleotide sequence for a selectable marker, which can be used to select a transformed plant, plant part and/or plant cell. Many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) Mol. Gen. Genet. 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) Biotech. 6:915-922); a nucleotide sequence encoding a nitrilase such as bxn from *Klebsiella ozaenae* that confers resistance to bromoxynil (Stalker et al. (1988) Science 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) J. Biol. Chem. 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; or a nucleotide sequence encoding hph that confers resistance to hygromycin. One of skill in the art is capable of choosing a suitable selectable marker for use in an expression cassette of this invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: Chromosome Structure and Function: Impact of New Concepts, 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) Proc. Natl. Acad. Sci. USA 75:3737-3741); a nucleotide sequence encoding xylE that encodes a catechol dioxygenase (Zukowsky et al. (1983) Proc. Natl. Acad. Sci. USA 80:1101-1105); a nucleotide sequence encoding tyrosinase, an enzyme capable of oxidizing tyrosine to DOPA and dopaquinone, which in turn condenses to form melanin (Katz et al. (1983) J. Gen. Microbiol. 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) Science 234:856-859); a nucleotide sequence encoding aequorin which may be employed in calcium-sensitive bioluminescence detection (Prasher et al. (1985) Biochem. Biophys. Res. Comm. 126:1259-1268); or a nucleotide sequence encoding green fluorescent protein (Niedz et al. (1995) Plant Cell Reports 14:403-406). One of skill in the art can choose a suitable selectable marker for use in an expression cassette of this invention.

In some embodiments, an expression cassette of the invention also can include polynucleotides that encode other desired traits in addition to the chimeric insecticidal proteins of the invention. Examples of such other polynucleotides include that those encode a polypeptide or a dsRNA for the other desired trait(s) of interest. Such expression cassettes comprising the "stacked" traits may be used, e.g., to create plants, plant parts or plant cells having a desired phenotype with the stacked traits (i.e., molecular stacking). Such stacked combinations in plants can also be created by other methods including, but not limited to, cross breeding plants by any conventional methodology (i.e., a breeding stack). If stacked by genetically transforming the plants, the nucleotide sequences of interest can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, or composition of this invention, provided by any combination of expression cassettes. For example, if two nucleotide sequences will be introduced, they can be incorporated in separate cassettes (trans) or can be incorporated on the same cassette (cis). Expression of polynucleotides can be driven by the same promoter or by different promoters. It is further recognized that polynucleotides can be stacked at a desired genomic location using a site-specific recombination system. See, e.g., Int'l Patent Application Publication Nos. WO 99/25821; WO 99/25854; WO 99/25840; WO 99/25855 and WO 99/25853.

In representative embodiments, the expression cassette can also include an additional coding sequence for one or more polypeptides or double stranded RNA molecules (dsRNA) of interest for an agronomic trait (e.g., an agronomic trait that is primarily of benefit to a seed company, grower or grain processor). A polypeptide of interest can be any polypeptide encoded by a nucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, or fungal resistance. See, e.g., U.S. Pat. Nos. 5,569,823; 5,304,730; 5,495,071; 6,329,504; and 6,337,431. In embodiments, the polypeptide of interest can be one that increases plant vigor or yield (including traits that allow a plant to grow at different temperatures, soil conditions and levels of sunlight and precipitation), or one that allows identification of a plant exhibiting a trait of interest (e.g., a selectable marker, seed coat color, etc.). Various polypeptides of interest, as well as methods for introducing these polypeptides into a plant, are described, for example, in U.S. Pat. Nos. 4,761,373; 4,769,061; 4,810, 648; 4,940,835; 4,975,374; 5,013,659; 5,162,602; 5,276, 268; 5,304,730; 5,495,071; 5,554,798; 5,561,236; 5,569, 823; 5,767,366; 5,879,903, 5,928,937; 6,084,155; 6,329,504 and 6,337,431; as well as US Patent Publication No. 2001/ 0016956. See also, on the World Wide Web at lifesci.sussex.ac.uk/home/Neil_Crickmore/Bt/.

Polynucleotides conferring resistance/tolerance to an herbicide that inhibits the growing point or meristem, such as an imidazalinone or a sulfonylurea can also be suitable in some embodiments of the invention. Exemplary polynucleotides in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides encoded by nucleotides sequences conferring resistance to glyphosate are also suitable for the invention. See, e.g., U.S. Pat. Nos. 4,940,835 and 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Polynucleotides coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable polynucleotides include those coding for resistance to herbicides that inhibit photosynthesis, such as a triazine and a benzonitrile (nitrilase). See, U.S. Pat. No. 4,810,648. Additional suitable polynucleotides coding for herbicide resistance include those coding for resistance to 2,2-dichloropropionic acid, sethoxydim, haloxyfop, imidazolinone herbicides, sulfonylurea herbicides, triazolopyrimidine herbicides, s-triazine herbicides and bromoxynil. Also suitable are polynucleotides conferring resistance to a protox enzyme, or that provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Additional suitable polynucleotides include those coding for pesticidal (e.g., insecticidal) polypeptides. These polypeptides may be produced in amounts sufficient to control, for example, insect pests (i.e., insect controlling amounts). In embodiments, the polypeptide is a lepidopteran-active, coleopteran-active, hemipteran-active and/or dipteran-active polypeptide, or any combination thereof. It is recognized that the amount of production of a pesticidal polypeptide in a plant necessary to control insects or other pests may vary depending upon the cultivar, type of pest, environmental factors and the like. Polynucleotides useful for additional insect or pest resistance include, for example, those that encode toxins identified in *Bacillus* organisms. Polynucleotides comprising nucleotide sequences encoding *Bacillus thuringiensis* (Bt) Cry proteins from several subspecies have been cloned and recombinant clones have been found to be toxic to lepidopteran, dipteran and coleopteran insect larvae. Examples of such Bt insecticidal proteins include the Cry proteins such as Cry1Aa, Cry1Ab, Cry1Ac, Cry1B, Cry1C, Cry1D, Cry1Ea, Cry1Fa, Cry3A, Cry9A, Cry9B, Cry9C, and the like, as well as vegetative insecticidal proteins such as Vip1, Vip2, Vip3, and the like, and any combination of the foregoing Bt insecticidal proteins. A full list of Bt-derived proteins can be found on the worldwide web at *Bacillus thuringiensis* Toxin Nomenclature Database maintained by the University of Sussex (see also, Crickmore et al. (1998) Microbiol. Mol. Biol. Rev. 62:807-813).

In embodiments, an additional polypeptide is an insecticidal polypeptide derived from a non-Bt source, including without limitation, an alpha-amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus* spp. (such as *B. laterosporous*) insecticidal protein, a *Lysinibacillus* spp. (such as *L. sphearicus*) insecticidal protein, a *Chromobacterium* spp. (such as *C. subtsugae* or *C. piscinae*) insecticidal protein, a *Yersinia* spp. (such as *Y. entomophaga*) insecticidal protein, a *Paenibacillus* spp. (such as *P. propylaea*) insecticidal protein, a *Clostridium* spp. (such as *C. bifermentans*) insecticidal protein, a *Pseudomonas* spp. (such as *P. fluorescens*) and a lignin.

Polypeptides that are suitable for production in plants further include those that improve or otherwise facilitate the conversion of harvested plants or plant parts into a commercially useful product, including, for example, increased or altered carbohydrate content or distribution, improved fermentation properties, increased oil content, increased protein content, improved digestibility, and increased nutraceutical content, e.g., increased phytosterol content, increased tocopherol content, increased stanol content or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the use of a heterologous cellulase enzyme).

In some embodiments, the polypeptide contributes to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) Foundation for Biotechnical and Industrial Fermentation Research 8:125-135; U.S. Patent Publication No. 2005/0208178; and PCT Publication No. WO 03/16654). In particular, three specific xylanases (XYL-I, XYL-II, and XYL-III) have been identified in *T. reesei* (Tenkanen et al. (1992) Enzyme Microb. Technol. 14:566; Torronen et al. (1992) Bio/Technology 10:1461; and Xu et al. (1998) Appl. Microbiol. Biotechnol. 49:718).

In other embodiments, a polypeptide useful for the invention can be a polysaccharide degrading enzyme. Plants of this invention producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as alpha-amylases (EC 3.2.1.1), glucuronidases (E.C. 3.2.1.131); exo-1,4-alpha-D glucanases such as amyloglucosidases and glucoamylase (EC 3.2.1.3), beta-amylases (EC 3.2.1.2), alpha-glucosidases (EC 3.2.1.20), and other exo-amylases; starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-beta-D-glucanase (EC 3.2.1.39), beta-glucosidase (EC 3.2.1.21); c) L-arabinases, such as endo-1,5-alpha-L-arabinase (EC 3.2.1.99), alpha-arabinosidases (EC 3.2.1.55) and the like; d) galactanases such as endo-1,4-beta-D-galactanase (EC 3.2.1.89), endo-1,3-beta-D-galactanase (EC 3.2.1.90), alpha-galactosidase (EC 3.2.1.22), beta-galactosidase (EC 3.2.1.23) and the like; e) mannanases, such as endo-1,4-beta-D-mannanase (EC 3.2.1.78), beta-mannosidase (EC 3.2.1.25), alpha-mannosidase (EC 3.2.1.24) and the like; f) xylanases, such as endo-1,4-beta-xylanase (EC 3.2.1.8), beta-D-xylosidase (EC 3.2.1.37), 1,3-beta-D-xylanase, and the like; and g) other enzymes such as alpha-L-fucosidase (EC 3.2.1.51), alpha-L-rhamnosidase (EC 3.2.1.40), levanase (EC 3.2.1.65), inulanase (EC 3.2.1.7), and the like. In one embodiment, the alpha-amylase is the synthetic alpha-amylase, Amy797E, described is U.S. Pat. No. 8,093,453.

Further enzymes which may be used with the invention include proteases, such as fungal and bacterial proteases. Fungal proteases include, but are not limited to, those obtained from *Aspergillus, Trichoderma, Mucor* and *Rhizopus*, such as *A. niger, A. awamori, A. oryzae* and *M. miehei*. In some embodiments, the polypeptides of this invention can be cellobiohydrolase (CBH) enzymes (EC 3.2.1.91). In one embodiment, the cellobiohydrolase enzyme can be CBH1 or CBH2.

Other enzymes useful with the invention include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g., E.C. 3.1.1.74).

Double stranded RNA (dsRNA) molecules useful with the invention include, but are not limited to those that suppress target pest (e.g., insect) genes. In embodiments, the dsRNA targets a gene in a lepidopteran, coleopteran, hemipteran or dipteran insect pest, or any combination of the foregoing. As used herein the words "gene suppression", when taken together, are intended to refer to any of the well-known methods for reducing the levels of protein produced as a result of gene transcription to mRNA and subsequent translation of the mRNA. Gene suppression is also intended to mean the reduction of protein expression from a gene or a coding sequence including posttranscriptional gene suppression and transcriptional suppression. Posttranscriptional gene suppression is mediated by the homology between all or a part of a mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA can be in the sense orientation to effect what is called co-suppression, in the anti-sense orientation to effect what is called anti-sense suppression, or in both orientations producing a dsRNA to effect what is called RNA interference (RNAi). Transcriptional suppression is mediated by the presence in the cell of a dsRNA, a gene suppression agent, exhibiting substantial sequence identity to a promoter DNA sequence or the complement thereof to effect what is referred to as promoter trans suppression. Gene suppression may be effective against a native plant gene associated with a trait, e.g., to provide plants with reduced levels of a protein encoded by the native gene or with enhanced or reduced levels of an affected metabolite. Gene suppression can also be effective against target genes in plant pests that may ingest or contact plant material containing gene suppression agents, specifically designed to inhibit or suppress the expression of one or more homologous or complementary sequences in the cells of the pest. Such genes targeted for suppression can encode an essential protein, the predicted function of which is selected from the group consisting of muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, and apoptosis.

In embodiments, the nucleic acids of the invention can further comprise, consist essentially of, or consist of a vector. In embodiments, the polynucleotides and expression cassettes of the invention are comprised within a vector. Vectors for use in transformation of plants and other organisms are well known in the art. Non-limiting examples of general classes of vectors include a plasmid, phage vector, phagemid vector, cosmid vector, fosmid, bacteriophage, artificial chromosome, or a viral vector. In embodiments, the vector is plant vector, e.g., for use in transformation of plants. In embodiments, the vector is a bacterial vector, e.g., for use in transformation of bacteria. Suitable vectors for plants, bacteria and other organisms are known in the art. Transgenic Plants, Plant Parts, Plant Cells, Seed.

The invention also encompasses a transgenic non-human host cell comprising a polynucleotide, a nucleic acid molecule, an expression cassette, a vector, or a polypeptide of the invention. The transgenic non-human host cell can include, but is not limited to, a plant cell (including a monocot cell and/or a dicot cell), a yeast cell, a bacterial cell or an insect cell. Accordingly, in some embodiments, the invention provides a bacterial cell selected from the genera *Bacillus, Brevibacillus, Clostridium, Xenorhabdus, Photorhabdus, Pasteuria, Escherichia, Pseudomonas, Erwinia, Serratia, Klebsiella, Salmonella, Pasteurella, Xanthomonas, Streptomyces, Rhizobium, Rhodopseudomonas, Methylophilius, Agrobacterium, Acetobacter, Lactobacillus, Arthrobacter, Azotobacter, Leuconostoc,* or *Alcaligenes.* Thus, for example, as biological insect control agents, the chimeric insecticidal proteins of the invention can be produced by expression of a polynucleotide encoding the same in a bacterial cell. For example, in some embodiments, a *Bacillus thuringiensis* cell comprising a polynucleotide encoding a chimeric insecticidal protein of the invention is provided.

In embodiments, the transgenic plant cell is a dicot plant cell or a monocot plant cell. In additional embodiments, the dicot plant cell is a soybean cell, sunflower cell, tomato cell, cole crop cell, cotton cell, sugar beet cell or a tobacco cell. In further embodiments, the monocot cell is a barley cell, maize cell, oat cell, rice cell, sorghum cell, sugar cane cell or wheat cell. In embodiments, the invention provides a plurality of dicot cells or monocot cells comprising a polynucleotide expressing a chimeric insecticidal protein of the invention. In embodiments, the plurality of cells are juxtaposed to form an apoplast and are grown in natural sunlight. In embodiments, the transgenic plant cell cannot regenerate a whole plant.

In embodiments of the invention, an insecticidal protein of the invention is expressed in a higher organism, for example, a plant. In this case, transgenic plants expressing effective amounts of the insecticidal protein protect themselves from plant pests such as insect pests. When an insect starts feeding on such a transgenic plant, it ingests the expressed insecticidal protein. This can deter the insect from further biting into the plant tissue or may even harm or kill the insect. In embodiments, a polynucleotide of the invention is inserted into an expression cassette, which is then stably integrated in the genome of the plant. In other embodiments, the polynucleotide is included in a non-pathogenic self-replicating virus.

In some embodiments of the invention, a transgenic plant cell comprising a nucleic acid molecule or polypeptide of the invention is a cell of a plant part, a plant organ or a plant culture (each as described herein) including, but not limited to, a root, a leaf, a seed, a flower, a fruit, a pollen cell, organ or plant culture, and the like, or a callus cell or culture.

A transgenic plant or plant cell in accordance with the invention may be a monocot or dicot plant or plant cell and includes, but is not limited to, corn (maize), soybean, rice, wheat, barley, rye, oat, sorghum, millet, sunflower, safflower, sugar beet, cotton, sugarcane, oilseed rape, alfalfa, tobacco, peanut, vegetable (including, sweet potato, bean, pea, chicory, lettuce, cabbage, cauliflower, broccoli, turnip, carrot, eggplant, cucumber, radish, spinach, potato, tomato, asparagus, onion, garlic, melon, pepper, celery, squash, pumpkin, zucchini, and the like), fruit (including, apple, pear, quince, plum, cherry, peach, nectarine, apricot, strawberry, grape, raspberry, blackberry, pineapple, avocado, papaya, mango, banana, and the like), a specialty plant or plant cell (such as *Arabidopsis*), or a woody plant or plant cell (such as coniferous and/or deciduous trees). In embodiments, a plant or plant cell of the of the invention is a crop plant or plant cell such as maize, sorghum, wheat, sunflower, tomato, a crucifer, pepper, potato, cotton, rice, soybean, sugar beet, sugarcane, tobacco, barley, oilseed rape plant or plant cell, and the like.

The invention further provides a part of a transgenic plant of the invention. Optionally, the plant part comprises a chimeric insecticidal protein of the invention and/or a nucleic acid encoding the same.

The invention further provides a seed of a transgenic plant of the invention or a seed that produces the transgenic plant of the invention. Optionally, the seed comprises a chimeric insecticidal protein of the invention and/or a nucleic acid encoding the same.

Additional embodiments of the invention include harvested products produced from the transgenic plants, plant parts or seed of the invention, as well as a processed product produced from a harvested product. A harvested product can be a whole plant or any plant part, as described herein. Thus, in some embodiments, non-limiting examples of a harvested product include a seed, a fruit, a flower or part thereof (e.g., an anther, a stigma, and the like), a leaf, a stem, and the like. In other embodiments, a processed product includes, but is not limited to, a flour, meal, oil, starch, cereal, and the like produced from a harvested seed or other plant part of the invention. Optionally, the harvested product or the processed product comprises a chimeric insecticidal protein of the invention and/or a nucleic acid encoding the same.

In other embodiments, the invention provides an extract from a transgenic plant, plant part or of the invention, optionally wherein the extract comprises a chimeric insecticidal protein of the invention and/or a nucleic acid encoding the same. Extracts from plants or plant parts can be made according to procedures well known in the art (See, de la Torre et al., Food, Agric. Environ. 2(1):84-89 (2004); Guidet, Nucleic Acids Res. 22(9): 1772-1773 (1994); Lipton et al., Food Agric. Immun. 12:153-164 (2000)).

The chimeric insecticidal protein can function in the plant part, plant cell, plant organ, seed, harvested product, processed product or extract, and the like, as an insect control agent. In other words, the chimeric insecticidal protein can continue to perform the insecticidal function it had in the transgenic plant. The nucleic acid can function to express the chimeric insecticidal protein. As an alternative to encoding the insecticidal protein of the invention, the nucleic acid can function to identify a transgenic plant part, plant cell, plant organ, seed, harvested product, processed product or extract of the invention.

In embodiments, a transgenic plant, plant part, plant cell, plant organ, or seed of the invention is hemizygous for a polynucleotide or expression cassette of the invention. In embodiments, a transgenic plant, plant part, plant cell, plant organ, or seed of the invention is homozygous for a polynucleotide or expression cassette of the invention.

In embodiments, a transgenic plant, plant part, plant cell, plant organ, seed, harvested product, processed product or extract has increased resistance to one or more insect pests (e.g., a lepidopteran pest, such as fall armyworm) as compared with a suitable control that does not comprise a nucleic acid encoding an insecticidal protein of the invention.

Plant Transformation.

Procedures for transforming plants are well known and routine in the art and are described throughout the literature. Non-limiting examples of methods for transformation of plants include transformation via bacterial-mediated nucleic acid delivery (e.g., via *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) or biological mechanism that results in the introduction of nucleic acid into the plant cell, including any combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (Cell. Mol. Biol. Lett. 7:849-858 (2002)).

For *Agrobacterium*-mediated transformation, binary vectors or vectors carrying at least one T-DNA border sequence are generally suitable, whereas for direct gene transfer (e.g., particle bombardment and the like) any vector is suitable and linear DNA containing only the construction of interest can be used. In the case of direct gene transfer, transformation with a single DNA species or co-transformation can be used (Schocher et al., Biotechnology 4:1093-1096 (1986)). For both direct gene transfer and *Agrobacterium*-mediated transfer, transformation is usually (but not necessarily) undertaken with a selectable marker that may be a positive selection (e.g., Phosphomannose Isomerase), provide resistance to an antibiotic (e.g., kanamycin, hygromycin or methotrexate) or a herbicide (e.g., glyphosate or glufosinate). However, the choice of selectable marker is not critical to the invention.

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) Plant Cell 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hofgen & Willmitzer (1988) Nucleic Acids Res. 16:9877).

Dicots as well as monocots may be transformed using *Agrobacterium*. Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* or crop plants such as, by way of example, tobacco plants, for example by immersing bruised leaves or chopped leaves in an *Agrobacterial* solution and then culturing them in suitable media. The transformation of plants by means of *Agrobacterium tumefaciens* is described, for example, by Hagen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

As discussed previously, another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

In other embodiments, a polynucleotide of the invention can be directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Nati. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin or streptomycin can be utilized as selectable markers for transformation (Svab, Z., Hajdukiewicz, P., and Maliga, P. (1990) Proc. Natl. Acad. Sci. USA 87, 8526-8530; Staub, J. M., and Maliga, P. (1992) Plant Cell 4, 39-45). The presence of cloning sites between these markers allows creation of a plastid targeting vector for introduction of foreign genes (Staub, J. M., and Maliga, P. (1993) EMBO J. 12, 601-606). Substantial increases in transformation frequency can be obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In one embodiment, a polynucleotide of the invention can be inserted into a plastid-targeting vector and transformed into the plastid genome of a desired plant host. Thus, plants homoplastic for plastid genomes containing a nucleotide sequence of the invention can be obtained, which are capable of high expression of the polynucleotide.

Methods of selecting for transformed, transgenic plants, plant cells or plant tissue culture are routine in the art and can be employed in the methods of the invention provided herein. For example, a recombinant vector of the invention also can include an expression cassette comprising a nucleotide sequence for a selectable marker, which can be used to select a transformed plant, plant part or plant cell.

Further, as is well known in the art, intact transgenic plants can be regenerated from transformed plant cells, plant tissue culture or cultured protoplasts using any of a variety of known techniques. Plant regeneration from plant cells, plant tissue culture or cultured protoplasts is described, for example, in Evans et al. (Handbook of Plant Cell Cultures, Vol. 1, MacMilan Publishing Co. New York (1983)); and Vasil I. R. (ed.) (Cell Culture and Somatic Cell Genetics of Plants, Acad. Press, Orlando, Vol. I (1984), and Vol. II (1986)).

Additionally, the genetic properties engineered into the transgenic seeds and plants, plant parts, or plant cells of the invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A polynucleotide therefore can be introduced into the plant, plant part or plant cell in any number of ways that are well known in the art, as described above. Therefore, no particular method for introducing one or more polynucleotides into a plant is relied upon, rather any method that allows the one or more polynucleotides to be stably integrated into the genome of the plant can be used. Where more than one polynucleotides is to be introduced, the respective polynucleotides can be assembled as part of a single nucleic acid molecule, or as separate nucleic acid molecules, and can be located on the same or different nucleic acid molecules. Accordingly, the polynucleotides can be introduced into the cell of interest in a single transformation event, in separate transformation events, or, for example, in plants, as part of a breeding protocol.

Once a desired polynucleotide has been transformed into a particular plant species, it may be propagated in that species or moved into other varieties of the same species, particularly including commercial varieties, using traditional breeding techniques.

Insecticidal Compositions.

In some embodiments, the invention provides an insecticidal composition comprising a chimeric insecticidal protein of the invention in an agriculturally acceptable carrier. As used herein an "agriculturally-acceptable carrier" can include natural or synthetic, organic or inorganic material which is combined with the active protein to facilitate its application to or in the plant, or part thereof. Examples of agriculturally acceptable carriers include, without limitation, powders, dusts, pellets, granules, sprays, emulsions, colloids, and solutions. Agriculturally-acceptable carriers further include, but are not limited to, inert components, dispersants, surfactants, adjuvants, tackifiers, stickers, binders, or combinations thereof, that can be used in agricultural formulations. Such compositions can be applied in any manner that brings the pesticidal proteins or other pest control agents in contact with the pests. Accordingly, the compositions can be applied to the surfaces of plants or plant parts, including seeds, leaves, flowers, stems, tubers, roots, and the like. In other embodiments, a plant producing an insecticidal protein of the invention in planta is an agriculturally-acceptable carrier of the expressed insecticidal protein. In embodiments, the compositions and agriculturally-acceptable carriers of the invention exclude transgenic plants.

In further embodiments, the insecticidal composition comprises a bacterial cell or a transgenic bacterial cell of the invention, wherein the bacterial cell or transgenic bacterial cell produces an insecticidal protein of the invention. Such an insecticidal composition can be prepared by desiccation, lyophilization, homogenization, extraction, filtration, centrifugation, sedimentation, or concentration of a culture of *Bacillus thuringiensis* (Bt), including a transgenic Bt culture. In embodiments, a composition of the invention may comprise at least about 1%, at least about 5%, at least about 10%, at least about 20%, at least about 25%, at least about 30%, at least about 35%, at least about 40%, at least about 50%, at least about 60%, at least about 70%, at least about 80%, at least about 90%, at least about 95%, at least about 97%, or at least 99% by weight a polypeptide of the invention. In additional embodiments, the composition comprises from about 1% to about 99% by weight of the insecticidal protein of the invention.

The insecticidal proteins of the invention can be used in combination with other pest control agents to increase pest target spectrum and/or for the prevention or management of insect resistance. Furthermore, the use of the insecticidal proteins of the invention in combination with an insecticidal agent which has a different mode of action or target a different receptor in the insect gut has particular utility for the prevention and/or management of insect resistance.

Therefore, in some embodiments, the invention provides a composition that controls one or more plant pests (e.g., an insect pest such as a lepidopteran insect pest, a coleopteran insect pest, a hemipteran insect pest and/or a dipteran insect pest), wherein the composition comprises a first pest control agent, which is a chimeric insecticidal protein of the invention and at least a second pest control agent that is different from the first pest control agent. In other embodiments, the composition is a formulation for topical application to a plant. In still other embodiments, the composition is a transgenic plant. In further embodiments, the composition is a combination of a formulation topically applied to a transgenic plant. In some embodiments, the formulation comprises the first pest control agent, which is a chimeric insecticidal protein of the invention when the transgenic plant comprises the second pest control agent. In other embodiments, the formulation comprises the second pest control agent when the transgenic plant comprises the first pest control agent, which is a chimeric insecticidal protein of the invention.

In some embodiments, the second pest control agent can be one or more of a chemical pesticide, such as an insecticide, a *Bacillus thuringiensis* (Bt) insecticidal protein, and/or a non-Bt pesticidal agent including without limitation a *Xenorhabdus* insecticidal protein, a *Photorhabdus* insecticidal protein, a *Brevibacillus laterosporus* insecticidal protein, a *Bacillus sphaericus* insecticidal protein, a protease inhibitor (both serine and cysteine types), a lectin, an alpha-amylase, a peroxidase, a cholesterol oxidase, or a double stranded RNA (dsRNA) molecule.

In other embodiments, the second pest control agent is one or more chemical pesticides, which is optionally a seed coating. Non-limiting examples of chemical pesticides include pyrethroids, carbamates, neonicotinoids, neuronal sodium channel blockers, insecticidal macrocyclic lactones, gamma-aminobutyric acid (GABA) antagonists, insecticidal ureas and juvenile hormone mimics. In other embodiments, the chemical pesticide is one or more of abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron, aldicarb, oxamyl, fenamiphos, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad. In still other embodiments, the chemical pesticide is selected from one or more of cypermethrin, cyhalothrin, cyfluthrin and beta-cyfluthrin, esfenvalerate, fenvalerate, tralomethrin, fenothicarb, methomyl, oxamyl, thiodicarb, clothianidin, imidacloprid, thiacloprid, indoxacarb, spinosad, abamectin, avermectin, emamectin, endosulfan, ethiprole, fipronil, flufenoxuron, triflumuron, diofenolan, pyriproxyfen, pymetrozine and amitraz.

In additional embodiments, the second pest control agent can be one or more of any number of *Bacillus thuringiensis* insecticidal proteins including but not limited to a Cry protein, a vegetative insecticidal protein (VIP) and insecticidal chimeras of any of the preceding insecticidal proteins. In other embodiments, the second pest control agent is a Cry protein selected from: Cry1Aa, Cry1Ab, Cry1Ac, Cry1Ad, Cry1Ae, Cry1Af, Cry1Ag, Cry1Ah, Cry1Ai, Cry1Aj, Cry1Ba, Cry1Bb, Cry1Bc, Cry1Bd, Cry1Be, Cry1Bf, Cry1Bg, Cry1Bh, Cry1Bi, Cry1Ca, Cry1Cb, Cry1Da, Cry1Db, Cry1Dc, Cry1Dd, Cry1Ea, Cry1Eb, Cry1Fa, Cry1Fb, Cry1Ga, Cry1Gb, Cry1Gc, Cry1Ha, Cry1Hb, Cry1Hc, Cry1Ia, Cry1Ib, Cry1Ic, Cry1Id, Cry1Ie, Cry1If, Cry1Ig, Cry1Ja, Cry1Jb, Cry1Jc, Cry1Jd, Cry1Ka, Cry1La, Cry1Ma, Cry1Na, Cry1Nb, Cry2Aa, Cry2Ab, Cry2Ac, Cry2Ad, Cry2Ae, Cry2Af, Cry2Ag, Cry2Ah, Cry2Ai, Cry2Aj, Cry2Ak, Cry2Al, Cry2Ba, Cry3Aa, Cry3Ba, Cry3Bb, Cry3Ca, Cry4Aa, Cry4Ba, Cry4Ca, Cry4Cb, Cry4Cc, Cry5Aa, Cry5Ab, Cry5Ac, Cry5Ad, Cry5Ba, Cry5Ca, Cry5 Da, Cry5Ea, Cry6Aa, Cry6Ba, Cry7Aa, Cry7Ab, Cry7Ac, Cry7Ba, Cry7Bb, Cry7Ca, Cry7Cb, Cry7 Da, Cry7Ea, Cry7Fa, Cry7Fb, Cry7Ga, Cry7Gb, Cry7Gc, Cry7Gd, Cry7Ha, Cry71a, Cry7Ja, Cry7Ka, Cry7Kb, Cry7La, Cry8Aa, Cry8Ab, Cry8Ac, Cry8Ad, Cry8Ba, Cry8Bb, Cry8Bc, Cry8Ca, Cry8 Da, Cry8Db, Cry8Ea, Cry8Fa, Cry8Ga, Cry8Ha, Cry8Ia, Cry8Ib, Cry8Ja, Cry8Ka, Cry8Kb, Cry8La, Cry8Ma, Cry8Na, Cry8 Pa, Cry8Qa, Cry8Ra, Cry8Sa, Cry8Ta, Cry9Aa, Cry9Ba, Cry9Bb, Cry9Ca, Cry9 Da, Cry9Db, Cry9Dc, Cry9Ea, Cry9Eb, Cry9Ec, Cry9Ed, Cry9Ee, Cry9Fa, Cry9Ga, Cry10Aa, Cry11Aa, Cry11Ba, Cry11Bb, Cry12Aa, Cry13Aa, Cry14Aa, Cry14Ab, Cry15Aa, Cry16Aa, Cry17Aa, Cry18Aa, Cry18Ba, Cry18Ca, Cry19Aa, Cry19Ba, Cry19Ca, Cry20Aa, Cry20Ba, Cry21Aa, Cry21 Ba, Cry21Ca, Cry21 Da, Cry21 Ea, Cry21 Fa, Cry21Ga, Cry21 Ha, Cry22Aa, Cry22Ab, Cry22Ba, Cry22Bb, Cry23Aa, Cry24Aa, Cry24Ba, Cry24Ca, Cry25Aa, Cry26Aa, Cry27Aa, Cry28Aa, Cry29Aa, Cry29Ba, Cry30Aa, Cry30Ba, Cry30Ca, Cry30 Da, Cry30Db, Cry30Ea, Cry30Fa, Cry30Ga, Cry31Aa, Cry31Ab, Cry31Ac, Cry31Ad, Cry32Aa, Cry32Ab, Cry32Ba, Cry32Ca, Cry32Cb, Cry32 Da, Cry32Ea, Cry32Eb, Cry32Fa, Cry32Ga, Cry32Ha, Cry32Hb, Cry32Ia, Cry32Ja, Cry32Ka, Cry32La, Cry32Ma, Cry32 Mb, Cry32Na, Cry32Ga, Cry32 Pa, Cry32Qa, Cry32Ra, Cry32Sa, Cry32Ta, Cry32Ua, Cry33Aa, Cry34Aa, Cry34Ab, Cry34Ac, Cry34Ba, Cry35Aa, Cry35Ab, Cry35Ac, Cry35Ba, Cry36Aa, Cry37Aa, Cry38Aa, Cry39Aa, Cry40Aa, Cry40Ba, Cry40Ca, Cry40 Da, Cry41Aa, Cry41Ab, Cry41 Ba, Cry42Aa, Cry43Aa, Cry43Ba, Cry43Ca, Cry43Cb, Cry43Cc, Cry44Aa, Cry45Aa, Cry46Aa Cry46Ab, Cry47Aa, Cry48Aa, Cry48Ab, Cry49Aa, Cry49Ab, Cry50Aa, Cry50Ba, Cry51Aa, Cry52Aa, Cry52Ba, Cry53Aa, Cry53Ab, Cry54Aa, Cry54Ab, Cry54Ba, Cry55Aa, Cry56Aa, Cry57Aa, Cry57Ab, Cry58Aa, Cry59Aa, Cry59Ba, Cry60Aa, Cry60Ba, Cry61Aa, Cry62Aa, Cry63Aa, Cry64Aa, Cry65Aa, Cry66Aa, Cry67Aa, Cry68Aa, Cry69Aa, Cry69Ab, Cry70Aa, Cry70Ba, Cry70Bb, Cry71Aa, Cry72Aa, Cry73Aa, or any combination of the foregoing. In embodiments, the Cry protein is a Cry1Fa, for example, as represented by maize event TC1507.

In further embodiments, the second pest control agent is one or more Vip3 vegetative insecticidal proteins selected from Vip3Aa1, Vip3Aa2, Vip3Aa3, Vip3Aa4, Vip3Aa5, Vip3Aa6, Vip3Aa7, Vip3Aa8, Vip3Aa9, Vip3Aa10, Vip3Aa11, Vip3Aa12, Vip3Aa13, Vip3Aa14, Vip3Aa15, Vip3Aa16, Vip3Aa17, Vip3Aa18, Vip3Aa19, Vip3Aa20, Vip3Aa21, Vip3Aa22, Vip3Aa2, Vip3Aa24, Vip3Aa25, Vip3Aa26, Vip3Aa27, Vip3Aa28, Vip3Aa29, Vip3Aa30, Vip3Aa31, Vip3Aa32, Vip3Aa33, Vip3Aa34, Vip3Aa35, Vip3Aa36, Vip3Aa37, Vip3Aa38, Vip3Aa39, Vip3Aa40, Vip3Aa41, Vip3Aa42, Vip3Aa43, Vip3Aa44, Vip3Ab1, Vip3Ab2, Vip3Ac1, Vip3Ad1, Vip3Ad2, Vip3Ae1, Vip3Af1, Vip3Af2, Vip3Af3, Vip3Ag1,Vip3Ag2,Vip3Ag3 HM117633, Vip3Ag4, Vip3Ag5, Vip3Ah1, Vip3Ba1, Vip3Ba2, Vip3Bb1, Vip3Bb2, Vip3Bb3, or any combination of the foregoing. In embodiments, the Vip3 protein is Vip3Aa (U.S. Pat. No. 6,137,033), for example, as represented by corn event MIR162 (U.S. Pat. Nos. 8,232,456; 8,455,720; and 8,618,272).

In embodiments, the second pest control agent may be derived from sources other than *B. thuringiensis*. For example, the second pest control agent can be an alpha-amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus* spp. (such as *B. laterosporous*) insecticidal protein, a *Lysinibacillus* spp. (such as *L. sphaericus*) insecticidal protein, a *Chromobacterium* spp. (such as *C. subtsugae* or *C. piscinae*) insecticidal protein, a *Yersinia* spp. (such as *Y. entomophaga*) insecticidal protein, a *Paenibacillus* spp. (such as *P. propylaea*) insecticidal protein, a *Clostridium* spp. (such as *C. bifermentans*) insecticidal protein, a *Pseudomonas* spp. (such as *P. fluorescens*) and a lignin. In other embodiments, the second agent may be at least one insecticidal protein derived from an insecticidal toxin complex (Tc) from *Photorhabdus, Xenorhabus, Serratia*, or *Yersinia*. In other embodiments. The insecticidal protein may be an ADP-ribosyltransferase derived from an insecticidal bacteria, such as *Photorhabdus* ssp. In other embodiments, the insecticidal protein may be a VIP protein, such as VIP1 and/or VIP2 from *B. cereus*. In still other embodiments, the insecticidal protein may be a binary toxin derived from an insecticidal bacteria, such as ISP1A and ISP2A from *B. laterosporous* or BinA and BinB from *L. sphaericus*. In still other embodiments, the insecticidal protein may be engineered or may be a hybrid or chimera of any of the preceding insecticidal proteins.

In some embodiments, the second pesticidal agent can be non-proteinaceous, for example, an interfering RNA molecule such as a dsRNA, which can be expressed transgenically or applied as part of a composition (e.g., using topical methods). An interfering RNA typically comprises at least a RNA fragment against a target gene, a spacer sequence, and a second RNA fragment which is complementary to the first, so that a double-stranded RNA structure can be formed. RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Interfering RNAs are known in the art to be useful for insect control (see, for example, publication WO2013/192256, incorporated by reference herein). An interfering RNA designed for use in insect control produces a non-naturally occurring double-stranded RNA, which takes advantage of the native RNAi pathways in the insect to trigger down-regulation of target genes that may lead to the cessation of feeding and/or growth and may result in the death of the insect pest. The interfering RNA molecule may confer insect resistance against the same target pest as the protein of the invention, or may target a different pest. The targeted insect plant pest may feed by chewing, sucking, or piercing. Interfering RNAs are known in the art to be useful for insect control. In embodiments, the dsRNA useful for insect control is described in US Patent Application Publication Nos. 20190185526, 20190177736, or 20180200281, filed on Aug. 5, 2016. In embodiments, the dsRNA useful for insect control is described in U.S. Pat. Nos. 92,388,223, 9,340, 797, or 8,946,510. In embodiments, the dsRNA useful for insect control is described in US Patent Application Publication Nos. 20110054007, 20140275208, 20160230185, or 20160230186. In other embodiments, the interfering RNA may confer resistance against a non-insect plant pest, such as a nematode pest or a virus pest.

In still further embodiments, the first insect control agent, which is a chimeric insecticidal protein of the invention and the second pest control agent are co-expressed in a transgenic plant. This co-expression of more than one pesticidal principle in the same transgenic plant can be achieved by genetically engineering a plant to contain and express the nucleic acid sequences encoding the insect control agents. For example, the co-expression of more than one pesticidal agent in the same transgenic plant can be achieved by making a single recombinant vector comprising coding sequences of more than one pesticidal agent in a "molecular stack" and genetically engineering a plant to contain and express all the pesticidal agents in the transgenic plant. Such molecular stacks may be also be made by using minichromosomes as described, for example in U.S. Pat. No. 7,235,716. Alternatively, a plant, Parent 1, can be genetically engineered for the expression of the chimeric insecticidal protein of the invention. A second plant, Parent 2, can be genetically engineered for the expression of a second pest control agent. By crossing Parent 1 with Parent 2, progeny plants are obtained which express both insect control agents from Parents 1 and 2.

In other embodiments, the invention provides a stacked transgenic plant resistant to plant pest infestation comprising a nucleic acid (e.g., DNA) sequence encoding a dsRNA for suppression of an essential gene in a target pest and a nucleic acid e.g., (DNA) sequence encoding a chimeric insecticidal protein of the invention exhibiting insectidical activity against the target pest. It has been reported that dsRNAs are ineffective against certain lepidopteran pests (Rajagopol et al. 2002. J. Biol. Chem. 277:468-494), likely due to the high pH of the midgut which destabilizes the dsRNA. Therefore, in some embodiments where the target pest is a lepidopteran pest, a chimeric insecticidal protein of the invention acts to transiently reduce the midgut pH which serves to stabilize the co-ingested dsRNA rendering the dsRNA effective in silencing the target genes.

Transgenic plants or seed comprising and/or expressing an insecticidal protein of the invention can also be treated with an insecticide or insecticidal seed coating as described in U.S. Pat. Nos. 5,849,320 and 5,876,739. In embodiments, where both the insecticide or insecticidal seed coating and the transgenic plant or seed of the invention are active against the same target insect, for example a lepidopteran pest (e.g., fall armyworm), the combination is useful (i) in a method for further enhancing activity of the composition of the invention against the target insect, and/or (ii) in a method for preventing development of resistance to the composition of the invention by providing yet another mechanism of action against the target insect. Thus, in embodiments, the invention provides a method of enhancing control of a lepidopteran insect population comprising providing a transgenic plant or seed of the invention and applying to the plant or the seed an insecticide or insecticidal seed coating to a transgenic plant or seed of the invention.

Even where the insecticide or insecticidal seed coating is active against a different insect, the insecticide or insecticidal seed coating is useful to expand the range of insect control, for example by adding an insecticide or insecticidal seed coating that has activity against coleopteran insects to a transgenic seed of the invention, which, in some embodiments, has activity against lepidopteran insects, the coated transgenic seed produced controls both lepidopteran and coleopteran insect pests.

Methods of Making and Using the Chimeric Insecticidal Proteins, Nucleic Acids, and Transgenic Plants.

The invention also encompasses methods of producing an insect-resistant (e.g., a lepidopteran insect-resistant) transgenic plant. In representative embodiments, the method comprises: introducing into a plant a polynucleotide, expression cassette or vector of the invention comprising a nucleotide sequence that encodes a chimeric insecticidal protein of the invention (including toxin fragments and modified forms that are substantially identical to the polypeptides specifically disclosed herein), wherein the nucleotide sequence is expressed in the plant to produce the chimeric insecticidal protein of the invention, thereby conferring to the plant resistance to the insect pest, and producing an insect-resistant transgenic plant (e.g., as compared with a suitable control plant, such as a plant that does not comprise the polynucleotide, expression cassette or vector of the invention and/or does not express a polypeptide of the invention).

In embodiments, the method of introducing the polynucleotide, expression cassette or vector of the invention into the plant comprises first transforming a plant cell with the polynucleotide, expression cassette or vector and regenerating a transgenic plant therefrom, where the transgenic plant comprises the polynucleotide, expression cassette or vector and expresses the chimeric insecticidal protein of the invention.

Alternatively, or additionally, the introducing step can comprise crossing a first plant comprising the polynucleotide, expression cassette or vector with a second plant (e.g., a different plant from the first plant, for example, a plant that does not comprise the polynucleotide, expression cassette or vector) and, optionally, producing a progeny plant that comprises the polynucleotide, expression cassette or vector and expresses a chimeric insecticidal protein of the invention, thereby resulting in increased resistance to at least one insect pest. Thus, a transgenic plant of the invention encompasses a plant that is the direct result of a transformation event and the progeny thereof (of any generation) that comprise the polynucleotide, expression cassette or vector and optionally expresses the chimeric insecticidal protein resulting in increased resistance to at least one insect pest.

The invention further provides a method of identifying a transgenic plant of the invention, the method comprising detecting the presence of a polynucleotide, expression cassette, vector or chimeric insecticidal protein of the invention in a plant (or a plant cell, plant part, and the like derived therefrom), and thereby identifying the plant as a transgenic plant of the invention based on the presence of the polynucleotide, expression cassette, vector or chimeric insecticidal protein of the invention.

The invention further provides a method of producing a transgenic plant with increased resistance to at least one insect pest (e.g., a least one lepidopteran pest), the method comprising: planting a seed comprising a polynucleotide, expression cassette or vector of the invention, and growing a transgenic plant from the seed, where the transgenic plant comprises the polynucleotide, expression cassette or vector and produces the chimeric insecticidal protein.

In embodiments, transgenic plants produced by the methods of the invention comprise a polynucleotide, expression cassette or vector of the invention. In embodiments, a transgenic plant produced by the methods of the invention comprise a chimeric insecticidal protein of the invention and, optionally have increased resistance to at least one insect pest.

The methods of producing a transgenic plant described herein optionally comprise a further step of harvesting a seed from the transgenic plant, where the seed comprises the polynucleotide, expression cassette or vector and produces the chimeric insecticidal protein. Optionally, the seed produces a further transgenic plant that comprises the polynucleotide, expression cassette or vector and produces the chimeric insecticidal protein, and thereby has increased resistance to at least one insect pest.

The invention further provides plant parts, plant cells, plant organs, plant cultures, seed, plant extracts, harvested products and processed products of the transgenic plants produced by the methods of the invention.

As a further aspect, the invention also provides a method of producing seed, the method comprising: providing a transgenic plant that comprises a polynucleotide, expression cassette or vector of the invention, and harvesting a seed from the transgenic plant, wherein the seed comprises the polynucleotide, expression cassette, vector and produces the chimeric insecticidal protein. Optionally, the seed produces a further transgenic plant that comprises the polynucleotide, expression cassette or vector and produces the chimeric insecticidal protein, and thereby has increased resistance to at least one insect pest. In representative embodiments, the step of providing the transgenic plant comprises planting a seed that produces the transgenic plant.

The invention further provides a method of producing a hybrid plant seed, the method comprising: crossing a first inbred plant, which is a transgenic plant comprising a polynucleotide, expression cassette or vector of the invention, and optionally expressing a chimeric insecticidal protein of the invention with a different inbred plant (e.g., an inbred plant that does not comprise a polynucleotide, expression cassette or vector of the invention) and allowing hybrid seed to form. Optionally, the method further comprises harvesting a hybrid seed. In embodiments, the hybrid seed comprises the polynucleotide, expression cassette or vector of the invention, and in embodiments may further comprise a chimeric insecticidal protein of the invention and have increased resistance to an insect pest. In embodiments, the hybrid seed produces a transgenic plant that comprises the polynucleotide, expression cassette or vector of the invention, expresses the chimeric insecticidal protein of the invention, and has increased resistance to at least one insect pest.

In some embodiments, a transgenic plant of the invention is resistant to at least one lepidopteran insect pest (as described herein). In embodiments, the transgenic plant controls a fall armyworm insect pest or colony that is resistant to a Vip3A (e.g., a Vip3Aa protein, for example, as expressed in maize event MIR162) and/or Cry1F protein (e.g., a Cry1Fa protein, for example, as expressed in maize event TC1507).

In further embodiments, a method of controlling at least one insect pest (e.g., at least one lepidopteran insect pest, such as fall armyworm) comprises providing a chimeric insecticidal protein of the invention. In embodiments, the method comprises delivering (e.g., orally delivering) to the insect pest or an environment thereof an effective amount of a chimeric insecticidal protein of the invention. Generally, to be effective, the polypeptide is orally ingested by the insect. However, the chimeric insecticidal protein can be delivered to the insect in many recognized ways. The ways to deliver a protein orally to an insect include, but are not limited to, providing the protein (1) in a transgenic plant, wherein the insect eats (ingests) one or more parts of the transgenic plant, thereby ingesting the polypeptide that is expressed in the transgenic plant; (2) in a formulated protein composition(s) that can be applied to or incorporated into, for example, insect growth media; (3) in a protein composition(s) that can be applied to the surface, for example, sprayed, onto the surface of a plant part, which is then ingested by the insect as the insect eats one or more of the sprayed plant parts; (4) a bait matrix; or (5) any other art-recognized protein delivery system. Thus, any method of oral delivery to an insect can be used to deliver the toxic proteins of the invention. In some particular embodiments, the chimeric insecticidal protein of the invention is delivered orally to an insect, for example, where the insect ingests one or more parts of a transgenic plant of the invention.

In other embodiments, the insecticidal protein of the invention is delivered orally to an insect, wherein the insect ingests one or more parts of a plant sprayed with a composition comprising the insecticidal protein of the invention. Delivering the composition of the invention to a plant surface can be done using any method known to those of skill in the art for applying compounds, compositions, formulations and the like to plant surfaces. Some non-limiting examples of delivering to or contacting a plant or part thereof include spraying, dusting, sprinkling, scattering, misting, atomizing, broadcasting, soaking, soil injection, soil incorporation, drenching (e.g., root, soil treatment), dipping, pouring, coating, leaf or stem infiltration, side dressing or seed treatment, and the like, and combinations thereof. These and other procedures for contacting a plant or part thereof with a compound(s), composition(s) or formulation(s) are well-known to those of skill in the art.

In further embodiments, the invention provides a method of controlling a lepidopteran insect pest that is resistant to a Vip3A protein (e.g., a Vip3Aa protein, for example, as expressed by maize event MIR162) and/or a Cry1F protein (e.g. a Cry1Fa protein, for example, as expressed by maize event TC1507) comprising delivering to the lepidopteran insect or an environment thereof an effective amount of a chimeric insecticidal protein or composition of the invention. In representative embodiments, the resistant insect pest is a resistant fall armyworm insect pest or colony.

In other embodiments, the invention provides a method of preventing the development of resistance in a population of a target lepidopteran insect pest to a Vip3A (e.g., a Vip3Aa protein, for example, as expressed by maize event MIR162) and/or Cry1F (e.g. a Cry1Fa protein, for example, as expressed by maize event TC1507) protein expressed in a transgenic plant, the method comprising delivering to the target population a transgenic plant comprising a polynucleotide comprising a nucleotide sequence encoding a Vip3A protein and/or a nucleotide sequence encoding a Cry1F protein; and a polynucleotide expression cassette or vector of the invention expressing a chimeric insecticidal protein of the invention. In some embodiments, the target lepidopteran insect pest is fall army worm. According to foregoing embodiments, the transgenic plant can comprise a breeding stack of two or more of the insecticidal traits, a molecular stack of two or more of the insecticidal traits, or a combination of both.

In some embodiments, the invention encompasses a method of providing a farmer with a means of controlling an insect pest (e.g., a lepidopteran pest, such as fall armyworm), the method comprising supplying or selling to the farmer plant material such as a seed, the plant material comprising a polynucleotide, expression cassette, vector capable of expressing a chimeric insecticidal protein of the invention. In embodiments, the plant material comprises the chimeric insecticidal protein of the invention and, optionally, has increased resistance to at least one insect pest. In embodiments, the plant material is a seed, and a plant grown from the seed comprises the polynucleotide, expression cassette or vector of the invention, expresses a chimeric insecticidal protein of the invention, and has increased resistance to the at least one insect pest.

In addition to providing compositions, the invention provides methods of producing a chimeric insecticidal protein toxic to a lepidopteran pest. Such a method comprises, culturing a transgenic non-human host cell that comprises a polynucleotide, expression cassette or vector of the invention that expresses a chimeric insecticidal protein of the invention under conditions in which the host cell produces the chimeric insecticidal protein that is toxic to the lepidopteran pest. In some embodiments, the transgenic non-human host cell is a plant cell. In some other embodiments, the plant cell is a maize cell. In other embodiments, the conditions under which the plant cell or maize cell are grown include natural sunlight. In other embodiments, the transgenic non-human host cell is a bacterial cell. In still other embodiments, the transgenic non-human host cell is a yeast cell.

In some embodiments, the methods of the invention provide control of at least one lepidopteran insect pest, including without limitation, one or more of the following: Ostrinia spp. such as O. nubilalis (European corn borer) and/or O. furnacalis (Asian corn borer); Plutella spp. such as P. xylostella (diamondback moth); Spodoptera spp. such as S. frugiperda (fall armyworm), S. littoralis (Egyptian cotton leafworm), S. omithogalli (yellowstriped armyworm), S. praefica (western yellowstriped armyworm), S. eridania (southern armyworm) and/or S. exigua (beet armyworm); Agrotis spp. such as A. ipsilon (black cutworm), A. segetum (common cutworm), A. gladiaria (claybacked cutworm), and/or A. orthogonia (pale western cutworm); Striacosta spp. such as S. albicosta (western bean cutworm); Helicoverpa spp. such as H. zea (corn earworm), H. punctigera (native budworm), and/or H. armigera (cotton bollworm); Heliothis spp. such as H. virescens (tobacco budworm); Diatraea spp. such as D. grandiosella (southwestern corn borer) and/or D. saccharalis (sugarcane borer); Trichoplusia spp. such as T. ni (cabbage looper); Sesamia spp. such as S. nonagroides (Mediterranean corn borer) and/or S. calamistis (pink stem borer); Pectinophora spp. such as P. gossypiella (pink bollworm); Cochylis spp. such as C. hospes (banded sunflower moth); Manduca spp. such as M. sexta (tobacco hornworm) and/or M. quinquemaculata (tomato hornworm); Elasmopalpus spp. such as E. lignosellus (lesser cornstalk borer); Pseudoplusia spp. such as P. includens (soybean looper); Anticarsia spp. such as A. gemmatalis (velvetbean caterpillar); Plathypena spp. such as P. scabra (green cloverworm); Pieris spp. such as P. brassicae (cabbage butterfly); Papaipema spp. such as P. nebris (stalk borer); Pseudaletia spp. such as P. unipuncta (common armyworm); Peridroma spp. such as P. saucia (variegated cutworm); Keiferia spp. such as K. lycopersicella (tomato pinworm); Artogeia spp. such as A. rapae (imported cabbageworm); Phthorimaea spp. such as P. operculella (potato tuberworm); Chrysodeixis spp. Such as C. includes (soybean looper); Feltia spp. such as F. ducens (dingy cutworm); Chilo spp. such as C. suppressalis (striped stem borer), Cnaphalocrocis spp. such as C. medinalis (rice leaffolder), or any combination of the foregoing. In embodiments, the methods of the invention provide control of a fall armyworm insect pest or colony that is resistant to a Vip3A (e.g., a Vip3Aa protein, for example, as expressed in maize event MIR162) and/or Cry1F protein (e.g., a Cry1Fa protein, for example, as expressed in maize event TC1507).

The invention also provides for uses of the chimeric insecticidal proteins, nucleic acids, transgenic plants, plant parts, seed and insecticidal compositions of the invention, for example, to control an insect pest, such as a lepidopteran pest (as described herein).

In embodiments, the invention provides a method of using a polynucleotide, expression cassette, vector or host cell of the invention to produce an insecticidal composition for controlling an insect pest (e.g., a lepidopteran insect pest).

In embodiments, the invention provides a method of using a polynucleotide, expression cassette or vector of the invention to produce a transgenic seed, where the transgenic seed grows a transgenic plant with increased resistance to an insect pest.

As another aspect, the invention also contemplates the use of a transgenic plant of the invention to produce a transgenic seed, which is optionally a hybrid seed.

In embodiments, the invention provides a method of using a chimeric insecticidal protein, polynucleotide, expression cassette, vector, transgenic plant or insecticidal composition of the invention to prevent the development of resistance in a population of a target lepidopteran insect pest to a Vip3A protein and/or Cry1F protein (each as described herein).

Statements of the invention include without limitation:

1. A chimeric insecticidal protein that is toxic to a lepidopteran insect pest comprising in an N-terminal to C-terminal direction: (a) an N-terminal region of a first Cry1 protein, which is an N-terminal region of a BT-0029 protein of SEQ ID NO:2 or an amino acid sequence that is at least 90% identical thereto, fused to (b) a C-terminal region of a different Cry1 protein; wherein a crossover position between the first Cry1 protein and the different Cry1 protein is located in conserved block 3.

2. The chimeric insecticidal protein according to statement 1, wherein the different Cry1 protein is a Cry1F, a Cry1G, a Cry1I or a Cry1K protein.

3. The chimeric insecticidal protein according to statement 1, wherein the different Cry1 protein is a Cry1Fa protein.

4. The chimeric insecticidal protein according to statement 1, wherein the different Cry1 protein is a Cry1Ia or a Cry1If protein.

5. The chimeric insecticidal protein according to statement 1, wherein the different Cry1 protein is a BT-0022 protein of SEQ ID NO: 1.

6. The chimeric insecticidal protein according to statement 1, wherein the C-terminal region of the different Cry1 protein comprises an amino acid sequence corresponding to an amino acid sequence from position 464 to 602 of SEQ ID NO: 8 or an amino acid sequence that is at least 80% identical thereto.

7. The chimeric insecticidal protein according to statement 1, wherein the C-terminal region of the different Cry1 protein comprises an amino acid sequence corresponding to an amino acid sequence from position 498 to 636 of SEQ ID NO: 1 or an amino acid sequence that is at least 80% identical thereto.

8. The chimeric insecticidal protein according to any one of statements 1 to 7, wherein the N-terminal region of the first Cry1 protein comprises an amino acid sequence corresponding to an amino acid sequence from position 1 to 458 of SEQ ID NO: 2 or an amino acid sequence that is at least 90% identical thereto.

9. The chimeric insecticidal protein according to any one of statements 1 to 8, wherein the chimeric insecticidal protein further comprises at the N-terminus a peptidyl fragment that is cleaved from the protoxin after ingestion by the lepidopteran insect pest.

10. The chimeric insecticidal protein according to any one of statements 1 to 9, wherein the chimeric insecticidal protein further comprises at the C-terminus a pro-toxin tail from a Cry protein that is cleaved from the protoxin after ingestion by the lepidopteran insect pest.

11. The chimeric insecticidal protein according to any one of statements 1 to 10, wherein the chimeric insecticidal protein comprises: (a) the amino acid sequence from position 1 to 597 of SEQ ID NO: 3 or a toxin fragment thereof; or (b) an amino acid sequence that is at least 80% identical to the amino acid sequence of (a).

12. The chimeric insecticidal protein according to any one of statements 1 to 11, wherein the chimeric insecticidal protein comprises: (a) the amino acid sequence of SEQ ID NO: 3 or a toxin fragment thereof; or (b) an amino acid sequence that is at least 80% identical to the amino acid sequence of (a).

13. The chimeric insecticidal protein according to any one of statements 1 to 10, wherein the chimeric insecticidal protein comprises: (a) the amino acid sequence from positions 1 to 597 of SEQ ID NO: 9 or a toxin fragment thereof; or (b) an amino acid sequence that is at least 80% identical to the amino acid sequence of (a).

14. The chimeric insecticidal protein according to any one of statements 1 to 10 or 13, wherein the chimeric insecticidal protein comprises: (a) the amino acid sequence of SEQ ID NO: 9 or a toxin fragment thereof; or (b) an amino acid sequence that is at least 80% identical to the amino acid sequence of (a).

15. The chimeric insecticidal protein according to any one of statements 1 to 14, wherein the chimeric insecticidal protein comprises the amino acid sequence of SEQ ID NO: 3 or SEQ ID NO: 9.

16. The chimeric insecticidal protein according to any one of statements 1 to 15, wherein the chimeric insecticidal protein has insecticidal activity against one or more of *Spodoptera frugiperda* (fall armyworm), *Chrysodeixis includes* (soybean looper), *Diatraea saccharalis* (sugarcane borer), *Diatraea grandiosella* (southwest corn borer), and *Agrotis ipsilon* (black cutworm).

17. The chimeric insecticidal protein according to any one of statements 1 to 16, wherein the chimeric insecticidal protein has insecticidal activity against a *Spodoptera frugiperda* insect pest or colony with resistance to a Vip3A protein and/or a Cry1F protein.

18. A polynucleotide comprising a nucleotide sequence encoding the chimeric insecticidal protein according to any one of statements 1 to 17.

19. The polynucleotide according to statement 18, wherein the polynucleotide is codon optimized for expression in a plant.

20. The polynucleotide according to statement 18 or statement 19, wherein the polynucleotide comprises a nucleotide sequence that comprises: (a)
a nucleotide sequence of SEQ ID NO: 4, SEQ ID NO: 5, SEQ ID NO: 6, SEQ ID NO: 7, SEQ ID NO: 10, SEQ ID NO: 11 or SEQ ID NO: 14 or a toxin-encoding fragment thereof; (b) a nucleotide sequence that is substantially identical to the nucleotide sequence of (a); or (c) a nucleotide sequence that anneals under stringent hybridization conditions to the nucleotide sequence of (a) or (b); or (d)
a nucleotide sequence that differs from the nucleotide sequence of (a), (b) or (c) due to the degeneracy of the genetic code.

21. The polynucleotide according to statement 18 or statement 19, wherein the nucleotide sequence comprises the nucleotide sequence of SEQ ID NO: 4, SEQ ID NO: 5, SEQ ID NO: 6, SEQ ID NO: 7, SEQ ID NO: 10, SEQ ID NO: 11 or SEQ ID NO: 14.

22. A nucleic acid molecule comprising the polynucleotide according to any one of statements 18 to 21 operably associated with a heterologous promoter.

23. The nucleic acid molecule according to statement 22, wherein the heterologous promoter is a plant expressible promoter.

24. A vector comprising the polynucleotide according to any one of statements 18 to 21 or the nucleic acid molecule according to statement 22 or statement 23.

25. A transgenic cell comprising the polynucleotide according to any one of statements 18 to 21, the nucleic acid molecule according to statement 22 or statement 23, or the vector according to statement 24.

26. The transgenic cell according to statement 25, wherein the cell is a transgenic bacterial cell.

27. The transgenic cell according to statement 25, wherein the cell is a transgenic plant cell.

28. The transgenic plant cell according to statement 27, wherein the plant cell is: (i) a monocot cell, optionally a barley cell, a maize cell, an oat cell, a rice cell, a sorghum cell, a sugarcane cell or a wheat cell; or (ii) a dicot cell, optionally a soybean cell, a sunflower cell, a tomato cell, a cole crop cell, a cotton cell, a sugar beet cell or a tobacco cell.

29. A transgenic plant comprising the transgenic plant cell according to statement 27 or statement 28.

30. The transgenic plant according to statement 29, wherein the plant is: (i) a monocot plant, optionally a barley plant, a maize plant, an oat plant, a rice plant, a sorghum plant, a sugarcane plant or a wheat plant; or (ii) a dicot plant, optionally a soybean plant, a sunflower plant, a tomato plant, a cole crop plant, a cotton plant, a sugar beet plant or a tobacco plant.

31. The transgenic plant according to statement 28 or statement 29, wherein the transgenic plant comprises a further nucleotide sequence encoding a second insect control agent.

32. A transgenic plant part of the transgenic plant according to any one of statements 29 to 31, wherein the transgenic plant part comprises the chimeric insecticidal protein.

33. A transgenic seed of the transgenic plant according to any one of statements 29 to 31.

34. A harvested product derived from the transgenic plant according to any one of statements 29 to 31, the transgenic plant part according to statement 32, or the transgenic seed according to statement 33, wherein the harvested product comprises the chimeric insecticidal protein.

35. A processed product derived from the harvested product according to statement 34, wherein the processed product is a flour, a meal, an oil, a starch, or a product derived from any of the foregoing.

36. An insecticidal composition comprising the chimeric insecticidal protein according to any one of statements 1 to 17 and an agriculturally acceptable carrier.

37. The insecticidal composition according to statement 36, wherein the agriculturally acceptable carrier is a powder, a dust, a pellet, a granule, a spray, an emulsion, a colloid or a solution.

38. The insecticidal composition according to statement 36 or statement 37, wherein the composition is a desiccated, lyophilized, homogenized, extracted, filtrated, centrifuged and/or sedimented composition and/or is a bacterial culture concentrate.

39. The insecticidal composition according to any one of statements 36 to 38, wherein the composition comprises a transgenic bacterial cell that produces the chimeric insecticidal protein.

40. The insecticidal composition according to any one of statements 36 to 39, wherein the composition comprises from about 1% to about 99% by weight of the chimeric insectidical protein.

41. The insecticidal composition according to any one of statements 36 to 40, wherein the composition comprises a second insect control agent.

42. A method of producing a transgenic plant with increased resistance to a lepidopteran insect pest, the method comprising introducing into a plant the polynucleotide of any one of statements 18 to 21, the nucleic acid molecule of statement 22 or statement 23, or the vector of statement 24, wherein the chimeric insecticidal protein is expressed in the plant, thereby producing a transgenic plant with increased resistance to an insect pest.

43. The method according to statement 42, wherein the introducing step comprises: (i) transforming a plant cell with the polynucleotide, nucleic acid molecule or vector and regenerating a transgenic plant; or (ii) crossing a first plant comprising the polynucleotide, nucleic acid molecule or vector with a second plant.

44. The method according to statement 42 or statement 43, wherein the method further comprises obtaining a progeny plant from the transgenic plant, wherein the progeny plant comprises the polynucleotide, the nucleic acid molecule or the vector and has increased resistance to an insect pest.

45. A method of producing a transgenic plant with increased resistance to a lepidopteran insect pest, the method comprising: (a) planting a seed comprising the polynucleotide according to any one of statements 18 to 21, the nucleic acid molecule according to statement 22 or statement 23, or the vector according to statement 24; and (b) growing a transgenic plant from the seed, wherein the transgenic plant comprises the polynucleotide, nucleic acid molecule or vector and produces the chimeric insecticidal protein.

46. The method according to statement 45, wherein the method further comprises: (c) harvesting a seed from the transgenic plant of (b), wherein the harvested seed comprises the chimeric insecticidal protein.

47. A method of producing a seed, the method comprising: (a) providing a transgenic plant that comprises the polynucleotide according to any one of statements 18 to 21, the nucleic acid molecule according to statement 22 or statement 23, or the vector according to statement 24; and (b) harvesting a seed from the transgenic plant of (a), wherein the harvested seed comprises the chimeric insecticidal protein.

48. A method of producing a hybrid plant seed, the method comprising:
(a) crossing a first inbred plant, which is a transgenic plant comprising the polynucleotide according to any one of statements 18 to 21, the nucleic acid molecule according to statement 22 or statement 23, or the vector according to statement 24, with a different inbred plant; and (b) allowing a hybrid seed to form.

49. A method of controlling a lepidopteran insect pest, the method comprising delivering to the insect pest or an environment thereof a composition comprising an effective amount of the chimeric insecticidal protein of any one of statements 1 to 17 or the insecticidal composition of any one of statements 36 to 41.

50. A method of controlling a lepidopteran insect pest resistant to a Vip3A protein and/or a Cry1F protein, the method comprising delivering to the resistant lepidopteran insect pest or an environment thereof the insecticidal protein of any one of statements 1 to 17 or the insecticidal composition of any one of statements 36 to 41.

51. A method of reducing the development of resistance to a Vip3A protein and/or a Cry1F protein in a population of a target lepidopteran insect pest, the method comprising delivering to the target population or an environment thereof a transgenic plant comprising: (i) the polynucleotide according to any one of statements 18 to 21, the nucleic acid molecule according to statement 22 or statement 23, or the vector according to statement 24; and (ii) a polynucleotide comprising a nucleotide sequence encoding a Vip3A protein and/or a nucleotide sequence encoding a Cry1F protein; wherein the chimeric insecticidal protein and the Vip3A protein and/or the Cry1F protein are produced in the transgenic plant.

52. The method according to any one of statements 42 to 51, wherein the lepidopteran insect pest includes one or more of *Spodoptera frugiperda* (fall armyworm), *Chrysodeixis includes* (soybean looper), *Diatraea saccharalis* (sugarcane borer), *Diatraea grandiosella* (southwest corn borer) and *Agrotis ipsilon* (black cutworm).

53. The method according to any one of statements 42 to 52, wherein the lepidopteran insect pest includes a *Spodoptera frugiperda* (fall armyworm) that is resistant to a Vip3A protein and/or a Cry1F protein.

54. The method according to any one of statements 42 to 53, wherein the plant is: (i) a monocot plant, optionally a barley plant, a maize plant, an oat plant, a rice plant, a sorghum plant, a sugarcane plant or a wheat plant; or (ii) a dicot plant, optionally a soybean plant, a sunflower plant, a tomato plant, a cole crop plant, a cotton plant, a sugar beet plant or a tobacco plant.

55. The method according to any one of statements 42 to 54, wherein the plant is a maize plant.

The invention will now be described with reference to the following examples. It will be appreciated by those skilled in the art that these examples do not limit the scope of the claims to the invention, but are rather intended to be exemplary of certain embodiments. Other embodiments of the invention may be practiced without departing from the spirit and the scope of the invention, the scope of which is defined by the disclosure and the appended claims.

EXAMPLES

Example 1. Discovery of a Chimeric BT-0029 Protein, Bt29-Bt22 with Insecticidal Activity Against Fall Armyworm Two lepidopteran-active proteins from *Bacillus thuringiensis* (Bt), BT-0022 (SEQ ID NO: 1; nearest known Cry family member Cry1If) and BT-0029 (SEQ ID NO:2; nearest known Cry family member Cry1Gb), have been disclosed in PCT/US16/038947.

As shown in Table 1 below, the insect spectrum data for BT-0022 and BT-0029 indicate that BT-0022 has no fall armyworm (FAW *Spodoptera frugiperda*) activity, and BT-0029 has only weak FAW activity. Other lepidopteran insect pests tested were: European corn borer (ECB; *Ostrinia nubilalis*), black cutworm (BCW; *Agrotis ipsilon*), corn earworm (CEW; *Helicoverpa zea*), sugarcane borer (SCB; *Diatraea saccharalis*), southwestern corn borer (SWCB; *Diatraea grandiosella*), western bean cutworm (WBCW; *Striacosta albicosta*), soybean looper (SBL; *Pseudoplusia includens*), velvet bean caterpillar (VBC; *Anticarsia gemmatalis*), and tobacco budworm (TBW; *Heliothis virescens*).

TABLE 1

Insecticidal activity of BT-0022 and BT-0029 against various Lepidopteran insects.

| | % Mortality | | | | | | | | | |
|---|---|---|---|---|---|---|---|---|---|---|
| | ECB | BCW | FAW | CEW | SCB | SWCB | WBCW | SBL | VBC | TBW |
| BT-0022 | 100 | 100 | 0 | 20 (M) | 92 | 100 | 0 | 100 | 0 | 42 (S) |
| BT-0029 | 0 | 25 | 25 | 8 | 33 | 17 | ND | 100 | 100 | ND |

M—Medium-sized larvae
S—Small-sized larvae
ND—Not Determined

A protein engineering approach was used in an effort to try to enhance the FAW activity of BT-0029. Using BT-0029 as a template, six engineered proteins were designed by replacing domain III (DIII) of BT-0029 with a domain III from a different Cry protein. Table 2 illustrates six chimeric proteins with their domain composition information. Table 3 provides the sequence information for the full-length proteins.

TABLE 2

Engineered BT-0029 proteins by domain swap

| Name | Domain I | Domain II | Domain III | Protoxin Tail |
|---|---|---|---|---|
| Bt29-1Ab | BT-0029 | BT-0029 | Cry1Ab | BT-0029 |
| Bt29-Bt22 | BT-0029 | BT-0029 | BT-0022 | BT-0029 |
| Bt29-Bt67 | BT-0029 | BT-0029 | BT-0067 | BT-0029 |
| Bt29-Bt51 | BT-0029 | BT-0029 | BT-0051 | BT-0029 |
| Bt29-8D | BT-0029 | BT-0029 | Cry8D | BT-0029 |
| Bt29-3A | BT-0029 | BT-0029 | Cry3A | BT-0029 |

TABLE 3

Full-length protein sequence information.

| Name | Closest Cry Family Member | Sequence |
|---|---|---|
| BT-0029 | Cry1Gb | SEQ ID NO: 2 |
| Cry1Ab | Not applicable | Genbank accession No. AAA22330.1 |
| BT-0022 | Cry1If | SEQ ID NO: 1 |
| Bt-0067 | Cry9Eb | WO2016/094165 |
| Bt-0051 | Cry9Ca | WO2016/094159 |
| Cry8D | Not applicable | Genbank accession No. BAF93483.1 |
| Cry3A | Not applicable | Genbank accession No. AAA22336.1 |
| Cry1Ca | Not applicable | Genbank accession No. AF362020.1 | cDNAs encoding the engineered proteins were synthesized by Genewiz (South Plainfield, N.J.) and cloned into a *Bacillus thuringiensis* (Bt) expression vector containing a Cry1Ac promoter and no terminator. The plasmid DNAs were introduced into Bt strain AB227 via an electroporation-mediated transformation procedure. All six engineered proteins were produced as crystal proteins in Bt. The crystal proteins were purified from the cultures and dissolved in a buffer containing 50 mM $Na_2CO_3$ pH 11.0, 2 mM DTT. Each soluble protein was then evaluated in an insect bioassay.

Briefly, insecticidal activity of the chimeric proteins was examined by an artificial diet based insect bioassay in which the solubilized crystal proteins were overlaid on the surface of artificial insect diet, with a final concentration of 2-3.2 µg/cm2. The buffer (50 mM $Na_2CO_3$ pH 11.0, 2 mM DTT) used for solubilizing the Bt crystal proteins served as the negative control. Full-length Cry1Fa protein (SEQ ID NO: 8) was used as a positive control for FAW activity. Each chimeric protein was tested in duplicate. Insect mortality was assessed on day 7.

The results are shown in Table 4. When the chimeric proteins were tested in the insect bioassay, the Bt29-Bt22 chimera (SEQ ID NO: 3) showed strong insecticidal activity against FAW, whereas two other chimeric proteins (Bt29-Bt67 and Bt29-3A) showed only minor activity to the pest. The Bt29-1Ab chimera did not demonstrate any detectable FAW activity.

For this test, not enough protein of the Bt29-Bt51 and Bt29-8D chimeras were produced to evaluate insecticidal activity.

TABLE 4

Insecticidal Activity against Fall Armyworm

| Treatment | FAW % Mortality | Treatment | FAW % Mortality |
|---|---|---|---|
| Buffer (negative control) | 8 | Bt29-Bt67 | 17 |
| Cry1Fa (full-length; positive control) | 100 | Bt29-3A | 25 |
| Bt29-Bt22 | 100 | Bt29-3A | 33 |
| Bt29-Bt22 | 83 | Bt29-1Ab | 0 |
| Bt29-Bt67 | 8 | Bt29-1Ab | 0 |
| Bt29-Bt67 | 17 | | |

Example 2: Insecticidal Activity of Chimeric BT-0029 Proteins Against Various Lepidopteran Pests Four of the chimeric proteins described in Example 1 (Bt29-3A, Bt29-Bt22, Bt29-1Ab and Bt29-Bt67) were examined for their insecticidal activities against the following lepidopteran pests using art-recognized artificial diet bioassay methods: sugarcane borer (SCB; *Diatraea saccharlis*), southwestern corn borer (SWCB; *Diatraea grandiosella*), soybean looper (SBL; *Pseudoplusia includens*), corn earworm (CEW; *Helicoverpa zea*), tobacco budworm (TBW; *Heliothis virescens*), black cutworm (BCW; *Agrotis ipsilon*) and European corn borer (ECB; *Ostrinia nubilalis*).

As shown in Table 5, all four chimeric proteins tested retained the strong SBL activity of native BT-0029. Bt29-Bt22 and Bt29-Bt67 had weak SCB activity comparable to native BT-0029, whereas Bt29-3A and Bt29-1Ab essentially lost all SCB activity. A slightly increased SWCB activity was observed in Bt29-Bt67 compared to full-length BT-0029. Fairly consistent with the results in Table 1 for native BT-0029, only weak BCW activity was observed for Bt29-3A, Bt29-Bt22 and Bt29-Bt67, and none of the chimeras had CEW, TBW or ECB activity.

TABLE 5

Insecticidal Activity of BT-0029 chimeric proteins against Lepidopteran Pests

| Treatment | % Mortality SCB | SWCB | SBL | CEW | TBW | BCW | ECB |
|---|---|---|---|---|---|---|---|
| Buffer (negative control) | 0 | 17 | 0 | 0 | 0 | 8 | 0 |
| Cry1Fa (full-length; positive control) | 25 | 42 | 100 | 73 | 100 | 42 | 100 |
| Bt29-3A | 0 | 42 | 100 | 0 | 0 | 8 | 0 |
| Bt29-3A | 8 | 25 | 100 | 0 | 0 | 25 | 0 |
| Bt29-Bt22 | 50 | 17 | 100 | 0 | 0 | 17 | 0 |
| Bt29-Bt22 | 33 | 67 | 100 | 0 | 0 | 25 | 0 |
| Bt29-Bt67 | 25 | 58 | 100 | 0 | 0 | 33 | 0 |
| Bt29-Bt67 | 42 | 73 | 100 | 0 | 0 | 8 | 0 |
| Bt29-1Ab | 8 | 0 | 100 | 0 | 0 | 0 | 0 |
| Bt29-1Ab | 0 | 0 | 100 | 0 | 0 | 0 | 0 |
| Bt29-1Fa | 100 | 100 | 100 | 0 | 0 | 0 | 75 |

Example 3: Bt29-1F Possesses Insecticidal Activity Against Fall Armyworm

To examine additional chimeric proteins, a second set of BT-0029 chimeric proteins was designed and tested (Table 6). Bt29-1Fa is a chimeric protein in which domain III of BT-0029 was replaced with domain III of Cry1Fa. The full-length amino acid sequence of Cry1Fa is provided as SEQ ID NO: 8 (see also Genbank accession number AAB00376.1). The amino acid sequence of the Bt29-1Fa chimera is provided as SEQ ID NO: 9, wherein the Cry1Fa sequence is amino acids 459 to 597.

Bt29-1Ka is a chimeric protein in which domain III of BT-0029 was replaced with domain III of Cry1Ka. The full-length amino acid sequence of Cry1Ka is provided as SEQ ID NO: 12 (see also Genbank accession number AAB00376.1). The amino acid sequence of the Bt29-1Ka chimera is also provided as SEQ ID NO: 13, wherein the Cry1Ka sequence is amino acids 459 to 597. A second version of a Bt29-1Ka chimeric protein (designated herein as Bt29-1Kav2) was made by moving the cross-over junction between the Cry1Ka sequence and the BT-0029 sequence in the C-terminus of domain III from amino acid 598 (the cross-over in the first Bt29-1Ka chimera) to amino acid 610. The amino acid sequence of the Bt29-1Kav2 chimera is provided as SEQ ID NO: 15, wherein the Cry1Ka sequence is amino acids 459 to 609.

Bt29-1Ca is a chimeric protein in which domain III of Bt-0029 was replaced with domain III of Cry1Ca. The full-length amino acid sequence of Cry1Ca is provided as SEQ ID NO: 17 (see also Genbank accession number AF362020.1). The amino acid sequence of the Bt29-1Ca chimera is provided as SEQ ID NO: 18, wherein the Cry1Ca sequence is amino acids 467 to 617.

TABLE 6

Engineered BT-0029 proteins by domain III swap

| Name | Domain I | Domain II | Domain III | Protoxin Tail |
|---|---|---|---|---|
| Bt29-1Fa | BT-0029 | BT-0029 | Cry1Fa | BT-0029 |
| Bt29-1Ka | BT-0029 | BT-0029 | Cry1Ka | BT-0029 |
| Bt29-1Ca | BT-0029 | BT-0029 | Cry1Ca | BT-0029 |

Insecticidal activity of the Bt29-1Fa (SEQ ID NO: 9), Bt29-1Ka (SEQ ID NO: 13, Bt29-1Kav2 (SEQ ID NO: 16) and Bt29-1Ca (SEQ ID NO: 18) chimeras were examined by an artificial diet based insect bioassay, in which the solubilized proteins were overlaid on the surface of artificial insect diet, with a final concentration of 2 μg/cm$^2$. The buffer (50 mM Na2CO$_3$ pH 10.5, 2 mM DTT) used for solubilizing the Bt crystal proteins served as the negative control. Full-length Cry1Fa protein (SEQ ID NO: 8) was used as a positive control for FAW activity. Each chimeric protein was tested in triplicate. Insecticidal activity was assessed as effective mortality on day 7 (larvae that have growth inhibition and are moribund are scored as effectively dead).

As shown in Table 7, the chimeric protein designated Bt29-1Fa demonstrated strong activity against FAW.

In this test, insufficient Bt29-1Ka protein was produced to evaluate in the bioassay. Surprisingly, the Bt29-1Kav2 chimera produced protein and was active against fall armyworm (see Table 7).

TABLE 7

Insecticidal Activity of Bt29-1Fa hybrid against Fall Armyworm

| Treatment | FAW % Mortality |
|---|---|
| Bt29-1Fa | 100 |
| Bt29-1Fa | 100 |
| Bt29-1Fa | 100 |
| Bt29-1Ca | 100 |
| Bt29-1Kav2 | 75 |
| Cry1Fa (full length; positive control) | 100 |
| Buffer (negative control) | 8 |

Example 4: Bt29-Bt22 and Bt29-1Fa Possess Insecticidal Activity Against Cry1F-Resistant Fall Armyworm To determine if the toxicity of the BT-0029 chimeric proteins to FAW is through a mode of action (MOA) distinct from Cry1Fa, the two chimeric proteins, Bt29-Bt22 and Bt29-1Fa were produced as described in Example 1, and the crystal proteins were isolated and purified. Purified crystals were dissolved in Buffer 1 (50 mM Na2CO$_3$/NaHCO$_3$, pH 11, 2 mM DTT), and the purity of the dissolved protein preparation was monitored using a Bio-Rad Experion system (BioRad, Hercules, Calif.).

The purified proteins were tested for efficacy against a strain of FAW that is resistant to the insecticidal toxin Cry1Fa. A diet-overlay assay was performed with various doses of each purified toxin (125, 500 and 2000 ng/cm2), essentially as described in Example 1. Vip3A protein (positive control) was dissolved in PBS and the other proteins in Buffer 1 (50 mM Na2CO$_3$/NaHCO$_3$, pH 11, 2 mM DTT). The two negative control treatments were PBS and Buffer 1. A FAW population that is susceptible to either Cry1Fa or Vip3A, i.e. FAW susceptible strain, was also tested. Each protein was tested in duplicates. Insecticidal activity was assessed as effective mortality on day 7 (larvae that have growth inhibition and are moribund are counted as effectively dead).

As shown in Table 8, the susceptible FAW larvae were controlled by Cry1Fa, Vip3A, Bt29-Bt22 and Bt29-1Fa, even at the lowest concentration. In contrast, the Cry1F-resistant FAW strain was not controlled by any dose of Cry1Fa tested, demonstrating the strain is resistant to this toxin (Table 9). Surprisingly, both Bt29-Bt22 and Bt29-1Fa were highly efficacious in controlling the Cry1F-resistant FAW even at a very low dose of 125 ng/cm$^2$ as shown in Table 9, suggesting that the mode of action of these two chimeric proteins against resistant FAW is different from the mode of action of a Cry1Fa protein.

TABLE 8

Insecticidal Activity of Bt29-Bt22 and Bt29-1Fa against susceptible Fall Armyworm at various concentrations

| Treatment | Dose (ng/cm2) | % Mortality |
|---|---|---|
| Vip3Aa | 125 | 100 |
| Vip3Aa | 500 | 100 |
| Vip3Aa | 2000 | 100 |
| Cry1Fa | 125 | 100 |
| Cry1Fa | 500 | 100 |
| Cry1Fa | 2000 | 100 |
| Bt29-Bt22 | 125 | 90 |
| Bt29-Bt22 | 500 | 96 |
| Bt29-Bt22 | 2000 | 100 |
| Bt29-1Fa | 125 | 92 |
| Bt29-1Fa | 500 | 100 |
| Bt29-1Fa | 2000 | 100 |
| Buffer 1 | | 0 |
| PBS | | 0 |

TABLE 9

Insecticidal Activity of Bt29-Bt22 and Bt29-1Fa against Cry1Fa-resistant Fall Armyworm

| Treatment | Dose (ng/cm2) | % Mortality |
|---|---|---|
| Vip3Aa | 125 | 100 |
| Vip3Aa | 500 | 100 |
| Vip3Aa | 2000 | 100 |
| Cry1Fa | 125 | 0 |
| Cry1Fa | 500 | 0 |
| Cry1Fa | 2000 | 0 |
| Bt29-Bt22 | 125 | 100 |
| Bt29-Bt22 | 500 | 100 |
| Bt29-Bt22 | 2000 | 100 |
| Bt29-1Fa | 125 | 100 |
| Bt29-1Fa | 500 | 100 |
| Bt29-1Fa | 2000 | 100 |
| Buffer 1 | | 0 |
| PBS | | 0 |

Example 5: Bt29-Bt22 and Bt29-1Fa Possess Insecticidal Activity Against Vip3A-Resistant Fall Armyworm To determine if the toxicity of the BT-0029 chimeric proteins is through a different MOA from Vip3A protein, the Bt29-Bt22 and Bt29-1Fa proteins were produced as described in Example 1, and the crystal proteins were isolated and purified. Purified crystals were dissolved in Buffer 1 (50 mM Na2CO$_3$/NaHCO$_3$, pH 11, 2 mM DTT), and the purity of the dissolved protein preparation was monitored using a Bio-Rad Experion system (BioRad, Hercules, Calif.).

The purified proteins were tested for efficacy against a strain of FAW that is resistant to the insecticidal toxin Vip3A. A diet-overlay assay was performed with various doses of each purified toxin (125, 500 and 2000 ng/cm$^2$) essentially as described in Example 1. Vip3A protein was dissolved in PBS and the other proteins in Buffer 1 (50 mM Na2CO$_3$/NaHCO$_3$, pH 11, 2 mM DTT). The two negative control treatments were PBS and Buffer 1. Cry1Fa proteins was used as a positive control for the Vip3A-resistant FAW strain. Each protein was tested in duplicate. Insecticidal activity was assessed as effective mortality on day 7 (larvae that have growth inhibition and are moribund are scored as effectively dead).

The Vip3A-resistant FAW strain was not controlled by any dose of Vip3A tested, demonstrating that the strain is resistant to this toxin (Table 10). In contrast, both Bt29-Bt22 and Bt29-1Fa demonstrated a high degree of efficacy against the Vip3A-resistant FAW suggesting that the mode of action of these two chimeric proteins against resistant FAW is different from the mode of action of a Vip3A protein.

TABLE 10

Insecticidal Activity of Bt29-Bt22 and Bt29-1Fa against Vip3A-resistant Fall Armyworm

| Treatment | Dose (ng/cm2) | % Mortality |
|---|---|---|
| Vip3Aa | 125 | 0 |
| Vip3Aa | 500 | 0 |
| Vip3Aa | 2000 | 0 |
| Cry1Fa | 125 | 100 |
| Cry1Fa | 500 | 100 |
| Cry1Fa | 2000 | 100 |
| Bt29-Bt22 | 125 | 100 |
| Bt29-Bt22 | 500 | 100 |
| Bt29-Bt22 | 2000 | 100 |
| Bt29-1Fa | 125 | 100 |
| Bt29-1Fa | 500 | 100 |
| Bt29-1Fa | 2000 | 100 |
| Buffer 1 | | 0 |
| PBS | | 0 |

Example 6. Truncations in Protoxin Tail Region

It is well-known that the protoxin form of Bt Cry proteins is processed at both the N- and C-terminal ends to produce the mature toxin. Six C-terminal truncated forms of the Bt29-Bt22 (SEQ ID NO: 3) chimera, which comprises a BT-0029 protoxin tail region, were made as shown in FIG. 3. In all truncated versions, designated herein as Bt29-Bt22Tr1 (SEQ ID NO: 20), Bt29-Bt22Tr2 (SEQ ID NO: 21), Bt29-Bt22Tr3 (SEQ ID NO: 22), Bt29-Bt22Tr4 (SEQ ID NO: 23), Bt29-Bt22Tr5 (SEQ ID NO: 24), Bt29-Bt22Tr6 (SEQ ID NO: 25), domain III of BT-0022 (ending with PVTA), and at least the first 6 amino acids of the BT-0029 protoxin tail (TFEAEY) were retained. Those skilled in the art will appreciate that the end of domain III and the beginning of the protoxin tail has not been delineated with precision for BT-0029 or the chimeras described herein. The core domain III shown in FIGS. 1A and 1B are based on alignments with other Cry proteins in which the domain III region has been delineated.

The Bt29-Bt22Tr1, -Tr2, -Tr4, and -Tr5 truncated forms all showed FAW activity assessed as growth inhibition (not mortality) in insect bioassays when tested as *E. coli* lysates. The Bt29-Bt22Tr1 and -Tr4 forms were the most promising, demonstrating the highest activity in this assay (67% and 75% growth inhibition, respectively).

A second Bt29-Bt22 full-length chimera was made wherein the protoxin tail region is from BT-0022 (Cry1I) instead of BT-0029 (Cry1G). Six C-terminal truncated forms of this full-length chimera, presented herein as SEQ ID Nos:26-31, were made and tested against fall armyworm and soybean looper. Cry1Fa was used as the positive control. Results are shown in Table 11.

TABLE 11

Insecticidal activity of Bt29-Bt22 with truncated BT-0022 protoxin tail against fall armyworm and soybean looper.

| Chimera | SEQ ID NO: | Effective Mortality (%) FAW | Effective Mortality (%) SBL |
|---|---|---|---|
| BT29BT22-TL22v1 | 26 | 75 | 100 |
| BT29BT22-TL22v2 | 27 | 63 | 100 |
| BT29BT22-TL22v3 | 28 | 50 | 100 |
| BT29BT22-TL22v4 | 29 | 58 | 100 |
| BT29BT22-TL22v5 | 30 | 54 | 100 |
| BT29BT22-TL22v6 | 31 | 83 | 100 |
| Buffer | NA | 0 | 0 |
| Cry1Fa | 8 | 100 | 100 |

Four truncated forms of the Bt29-1Fa (SEQ ID NO: 9), which comprises the BT-0029 protoxin tail region, presented herein as Bt29-1FaTr1 (SEQ ID NO:32), Bt29-1FaTr2 (SEQ ID NO: 33), Bt29-1FaTr3 (SEQ ID NO: 34) and Bt29-1FaTr4 (SEQ ID NO:35), were produced in an *E. coli* expression system and lysates were tested against fall armyworm. Results are shown in Table 12.

TABLE 12

Insecticidal activity of truncated Bt29-1Fa chimeric proteins.

| Chimeric Protein | SEQ ID NO: | % FAW Mortality |
|---|---|---|
| Bt29-1FaTr1 | 32 | 17 |
| Bt29-1FaTr2 | 33 | 8 |
| Bt29-1FaTr3 | 34 | 42 |
| Bt29-1FaTr4 | 35 | 58 |
| Cry11Fa | 8 | 100 |
| Buffer | NA | 0 |
| pET29 | NA | 0 |

Example 7. Expression and Activity of Chimeric Bt29-Bt22 and Bt29-Cry1Fa Proteins in Maize Plants Prior to expression in plants, synthetic polynucleotides comprising a nucleotide sequence encoding a Bt29-Bt22 and a Bt29-1Fa chimera were synthesized on an automated gene synthesis platform (Genscript, Inc., Piscataway, N.J.). For this example, a first and second expression cassette was made comprising a maize ubiquitin promoter (Ubi1) operably linked to either the Bt29-Bt22 or Bt29-1Fa chimeric coding sequence which was operably linked to a maize ubiquitin terminator and a third expression cassette was made comprising a Ubi1 promoter operably linked to a phosphomannose isomerase (PMI) coding sequence which was operably linked to a Ubi terminator. Expression of PMI allows for positive selection of transgenic plants on mannose. For plant transformation, the first and third expression cassettes and the second and third expression cassettes were cloned into a suitable vector for *Agrobacterium*-mediated maize transformation.

Transformation of immature maize embryos is performed essentially as described in Negrotto et al., 2000, Plant Cell Reports 19: 798 803. Briefly, *Agrobacterium* strain LBA4404 (pSB1) comprising an expression vector expressing Bt29-Bt22 or Bt29-Cry1Fa is grown on YEP (yeast extract (5 g/L), peptone (10 g/L), NaCl (5 g/L), 15 g/l agar, pH 6.8) solid medium for 2-4 days at 28° C. Approximately $0.8\times10^9$ *Agrobacterium* cells are suspended in LS-inf media supplemented with 100 μM As. Bacteria are pre-induced in this medium for approximately 30-60 minutes.

Immature embryos from an inbred maize line are excised from 8-12 day old ears into liquid LS-inf+100 μM As. Embryos are rinsed once with fresh infection medium. *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between approximately 20 and 25 embryos per petri plate are transferred to LSDc medium supplemented with cefotaxime (250 mg/l) and silver nitrate (1.6 mg/l) and cultured in the dark at approximately 28° C. for 10 days.

Immature embryos, producing embryogenic callus are transferred to LSD1 M0.5S medium. The cultures are selected on this medium for approximately 6 weeks with a subculture step at about 3 weeks. Surviving calli are transferred to Reg1 medium supplemented with mannose. Following culturing in the light (16 hour light/8 hour dark regiment), green tissues are then transferred to Reg2 medium without growth regulators and incubated for about 1-2 weeks. Plantlets are transferred to Magenta GA-7 boxes (Magenta Corp, Chicago Ill.) containing Reg3 medium and grown in the light. After about 2-3 weeks, plants are tested for the presence of the PMI genes and the chimeric Bt cry gene by PCR. Positive plants from the PCR assay are transferred to a greenhouse for further evaluation.

Transgenic plants were evaluated for copy number (determined by Taqman analysis), protein expression level (determined by ELISA), and efficacy against insect species of interest in leaf excision bioassays. Specifically, plant tissue (leaf or silks) was excised from single copy events (V3-V4 stage) and infested with neonate larvae of a target pest, then incubated at room temperature for 5 days. Leaf disks from transgenic plants expressing each chimeric Bt protein were tested against fall armyworm (*Spodoptera frugiperda*, FAW).

Results confirm that the transgenic plants express the chimeric proteins of the invention and are active against insect pests. Protein expression in the transgenic events for the Bt29-Bt22 chimera ranged from about 25-125 ng/mg total soluble protein (TSP) and for the Bt29-1Fa chimera ranged from about 25-290 ng/mg TSP. About 90% and 92% of the transgenic events expressing the Bt29-Bt22 and Bt29-1Fa chimeras, respectively, produced 100% mortality and larval growth inhibition to fall armyworm.

The above examples clearly illustrate the advantages of the invention. Although the present invention has been described with reference to specific details of certain embodiments thereof, it is not intended that such details should be regarded as limitations upon the scope of the claimed invention except as and to the extent that they are included in the accompanying claims.

SEQUENCE LISTING

<160> NUMBER OF SEQ ID NOS: 35

<210> SEQ ID NO 1
<211> LENGTH: 715
<212> TYPE: PRT
<213> ORGANISM: Artificial Sequence
<220> FEATURE:
<223> OTHER INFORMATION: BT-0022 sequence assembled from Bacillus genome mining.

<400> SEQUENCE: 1

```
Met Lys Ser Lys Asn Gln Asn Met His Gln Ser Leu Ser Asn Asn Ala
1               5                   10                  15

Thr Val Asp Lys Asn Phe Thr Gly Ser Leu Glu Asn Asn Thr Asn Thr
            20                  25                  30

Glu Leu Gln Asn Phe Asn His Glu Gly Ile Glu Pro Phe Val Ser Val
        35                  40                  45

Ser Thr Ile Gln Thr Gly Ile Gly Ile Ala Gly Lys Ile Leu Gly Asn
    50                  55                  60

Leu Gly Val Pro Phe Ala Gly Gln Val Ala Ser Leu Tyr Ser Phe Ile
65                  70                  75                  80

Leu Gly Glu Leu Trp Pro Lys Gly Lys Ser Gln Trp Glu Ile Phe Met
                85                  90                  95

Glu His Val Glu Glu Leu Ile Asn Gln Lys Ile Ser Thr Tyr Ala Arg
            100                 105                 110

Asn Lys Ala Leu Ala Asp Leu Lys Gly Leu Gly Asp Ala Leu Ala Val
        115                 120                 125

Tyr His Glu Ser Leu Glu Ser Trp Ile Lys Asn Arg Asn Asn Thr Arg
    130                 135                 140

Thr Arg Ser Val Val Lys Ser Gln Tyr Ile Thr Leu Glu Leu Met Phe
145                 150                 155                 160

Val Gln Ser Leu Pro Ser Phe Ala Val Ser Gly Glu Glu Val Pro Leu
                165                 170                 175

Leu Pro Ile Tyr Ala Gln Ala Ala Asn Leu His Leu Leu Leu Leu Arg
            180                 185                 190

Asp Ala Ser Ile Phe Gly Lys Glu Trp Gly Leu Ser Asp Ser Glu Ile
        195                 200                 205

Ser Thr Phe Tyr Asn Arg Gln Val Glu Arg Thr Ser Asp Tyr Ser Asp
    210                 215                 220

His Cys Thr Lys Trp Phe Asp Thr Gly Leu Asn Arg Leu Lys Gly Ser
225                 230                 235                 240

Asn Ala Glu Ile Trp Val Lys Tyr Asn Gln Phe Arg Arg Asp Met Thr
                245                 250                 255

Leu Met Val Leu Asp Leu Val Ala Leu Phe Gln Ser Tyr Asp Thr His
            260                 265                 270

Met Tyr Pro Ile Lys Thr Thr Ala Gln Leu Thr Arg Glu Val Tyr Thr
        275                 280                 285

Asn Ala Ile Gly Thr Val His Pro His Pro Ser Phe Thr Ser Thr Thr
    290                 295                 300

Trp Tyr Asn Asn Asn Ala Pro Ser Phe Ser Ala Ile Glu Ala Ala Val
305                 310                 315                 320

Ile Arg Ser Pro His Leu Leu Asp Phe Leu Glu Gln Val Thr Ile Tyr
                325                 330                 335

Ser Leu Leu Ser Arg Trp Ser Asn Thr Gln Tyr Met Asn Met Trp Gly
            340                 345                 350
```

Gly His Lys Leu Glu Phe Arg Thr Ile Gly Gly Thr Leu Asn Thr Ser
355                 360                 365

Thr Gln Gly Ser Thr Asn Thr Ser Ile Asn Pro Val Thr Leu Pro Phe
370                 375                 380

Thr Ser Arg Asp Ile Tyr Arg Thr Glu Ser Leu Ala Gly Leu Asn Leu
385                 390                 395                 400

Phe Leu Thr Gln Pro Val Asn Gly Val Pro Arg Val Asp Phe His Trp
                405                 410                 415

Lys Phe Val Thr His Pro Ile Ala Ser Asp Asn Phe Tyr Tyr Pro Gly
                420                 425                 430

Tyr Ala Gly Ile Gly Thr Gln Leu Gln Asp Ser Glu Asn Glu Leu Pro
            435                 440                 445

Pro Glu Thr Thr Gly Gln Pro Asn Tyr Glu Ser Tyr Ser His Arg Leu
        450                 455                 460

Ser His Ile Gly Leu Ile Ser Ala Ser His Val Lys Ala Leu Val Tyr
465                 470                 475                 480

Ser Trp Thr His Arg Ser Ala Asp Arg Thr Asn Thr Ile His Ser Asp
                485                 490                 495

Ser Ile Thr Gln Ile Pro Leu Val Lys Ala His Thr Leu Gln Ser Gly
                500                 505                 510

Thr Thr Val Val Lys Gly Pro Gly Phe Thr Gly Gly Asp Ile Leu Arg
            515                 520                 525

Arg Thr Ser Gly Gly Pro Phe Ala Phe Ser Asn Val Asn Leu Asp Trp
        530                 535                 540

Asn Leu Ser Gln Arg Tyr Arg Ala Arg Ile Arg Tyr Ala Ser Thr Thr
545                 550                 555                 560

Asn Leu Arg Met Tyr Val Thr Ile Ala Gly Glu Arg Ile Phe Ala Gly
                565                 570                 575

Gln Phe Asn Lys Thr Met Asn Thr Gly Asp Pro Leu Thr Phe Gln Ser
                580                 585                 590

Phe Ser Tyr Ala Thr Ile Asp Thr Ala Phe Thr Phe Pro Thr Lys Ala
            595                 600                 605

Ser Ser Leu Thr Val Gly Ala Asp Thr Phe Ser Ser Gly Asn Glu Val
        610                 615                 620

Tyr Val Asp Arg Phe Glu Leu Ile Pro Val Thr Ala Thr Leu Glu Ala
625                 630                 635                 640

Val Thr Asp Leu Glu Arg Ala Gln Lys Ala Val His Glu Leu Phe Thr
                645                 650                 655

Ser Thr Asn Pro Gly Gly Leu Lys Thr Asp Val Ala Lys Asp His Tyr
                660                 665                 670

Thr Asn Thr Ile Ser Lys Ser Val Gln Ser Val Phe Arg Cys Arg Cys
            675                 680                 685

Ser Glu Arg Thr Arg Ile Tyr Arg Trp Gly Tyr Pro Ser Lys Lys Glu
        690                 695                 700

Tyr Trp Tyr Ile Trp Gly Tyr Thr Ser Lys Tyr
705                 710                 715

<210> SEQ ID NO 2
<211> LENGTH: 1169
<212> TYPE: PRT
<213> ORGANISM: Artificial Sequence
<220> FEATURE:
<223> OTHER INFORMATION: BT-0029 sequence assembled from Bacillus genome mining.

<400> SEQUENCE: 2

-continued

```
Met Glu Ile Asn Asn Gln Asn Gln Cys Val Pro Tyr Asn Cys Leu Asn
 1               5                  10                  15

Asn Pro Glu Ser Glu Ile Leu Asn Val Ala Ile Phe Ser Ser Glu Gln
             20                  25                  30

Val Ala Glu Ile His Leu Lys Ile Thr Arg Leu Ile Leu Glu Asn Phe
         35                  40                  45

Leu Pro Gly Gly Ser Phe Ala Phe Gly Leu Phe Asp Leu Ile Trp Gly
 50                  55                  60

Ile Phe Asn Glu Asp Gln Trp Ser Ala Phe Leu Arg Gln Val Glu Glu
 65                  70                  75                  80

Leu Ile Asn Gln Arg Ile Thr Glu Phe Ala Arg Gly Gln Ala Ile Gln
                 85                  90                  95

Arg Leu Val Gly Phe Gly Arg Ser Tyr Asp Glu Tyr Ile Leu Ala Leu
             100                 105                 110

Lys Glu Trp Glu Asn Asp Pro Asp Asn Pro Ala Ser Lys Glu Arg Val
         115                 120                 125

Arg Thr Arg Phe Arg Thr Thr Asp Ala Leu Leu Thr Gly Val Pro
130                 135                 140

Leu Met Ala Ile Pro Gly Phe Glu Leu Ala Thr Leu Ser Val Tyr Ala
145                 150                 155                 160

Gln Ser Ala Asn Leu His Leu Ala Leu Leu Arg Asp Ala Val Phe Phe
                 165                 170                 175

Gly Glu Arg Trp Gly Leu Thr Gln Thr Asn Ile Asn Asp Leu Tyr Ser
             180                 185                 190

Arg Leu Lys Asn Ser Ile Arg Asp Tyr Thr Asn His Cys Val Arg Phe
         195                 200                 205

Tyr Asn Ile Gly Leu Gly Asn Leu Asn Val Ile Arg Pro Glu Tyr Tyr
210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                 245                 250                 255

Leu Thr Arg Glu Ile Tyr Thr Asp Pro Ile Ile Ser Pro Gly Ala Gln
             260                 265                 270

Ala Gly Tyr Thr Leu Gln Asp Val Leu Arg Glu Pro His Leu Met Asp
         275                 280                 285

Phe Leu Asn Arg Leu Ile Ile Tyr Thr Gly Glu Tyr Arg Gly Ile Arg
290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Thr Ala Glu Pro Thr
                 325                 330                 335

Arg Phe Ile Thr Pro Ser Thr Phe Pro Gly Leu Asn Leu Phe Tyr Arg
             340                 345                 350

Thr Leu Ser Ala Pro Ile Phe Arg Asp Glu Pro Gly Ala Asn Ile Ile
         355                 360                 365

Ile Arg Tyr Arg Thr Ser Leu Val Glu Gly Val Gly Phe Ile Gln Pro
370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                 405                 410                 415
```

-continued

Arg Leu Cys His Val Arg Phe Ala Gln Ser Leu Arg Asn Ala Glu Pro
        420                 425                 430

Leu Asp Tyr Ala Arg Val Pro Met Phe Ser Trp Thr His Arg Ser Ala
        435                 440                 445

Thr Pro Thr Asn Thr Ile Asp Pro Asp Val Ile Thr Gln Ile Pro Leu
        450                 455                 460

Val Lys Ala Phe Asn Leu His Ser Gly Ala Thr Ile Val Lys Gly Pro
465                 470                 475                 480

Gly Phe Thr Gly Gly Asp Ile Leu Arg Arg Thr Asn Val Gly Ser Phe
                485                 490                 495

Gly Asp Met Arg Val Asn Ile Thr Ala Pro Leu Ser Gln Arg Tyr Arg
                500                 505                 510

Val Arg Ile Arg Tyr Ala Ser Thr Thr Asp Leu Gln Phe Tyr Thr Asn
        515                 520                 525

Ile Asn Gly Thr Thr Ile Asn Ile Gly Asn Phe Ser Ser Thr Met Asp
        530                 535                 540

Ser Gly Asp Asp Leu Gln Tyr Gly Arg Phe Arg Val Ala Gly Phe Thr
545                 550                 555                 560

Thr Pro Phe Thr Phe Ser Asp Ala Met Ser Thr Phe Thr Ile Gly Ala
                565                 570                 575

Phe Ser Phe Ser Ser Asn Asn Glu Val Tyr Ile Asp Arg Ile Glu Phe
                580                 585                 590

Val Pro Ala Glu Val Thr Phe Glu Ala Glu Tyr Asp Leu Glu Lys Ala
        595                 600                 605

Gln Lys Ala Val Asn Ala Leu Phe Thr Ser Ser Asn Gln Ile Gly Leu
        610                 615                 620

Lys Thr Asp Val Thr Asp Tyr His Ile Asp Lys Val Ser Asn Leu Val
625                 630                 635                 640

Glu Cys Leu Ser Asp Glu Phe Cys Leu Asp Glu Lys Arg Glu Leu Ser
                645                 650                 655

Glu Lys Val Lys His Ala Lys Arg Leu Cys Asp Glu Arg Asn Leu Leu
                660                 665                 670

Gln Asp Pro Asn Phe Arg Gly Ile Asn Arg Gln Pro Asp Arg Gly Trp
        675                 680                 685

Arg Gly Ser Thr Asp Ile Thr Ile Gln Gly Gly Asp Asp Val Phe Lys
690                 695                 700

Glu Asn Tyr Val Thr Leu Pro Gly Thr Phe Asp Glu Cys Tyr Pro Thr
705                 710                 715                 720

Tyr Leu Tyr Gln Lys Ile Asp Glu Ser Lys Leu Lys Ala Tyr Thr Arg
                725                 730                 735

Tyr Glu Leu Arg Gly Tyr Ile Glu Asp Ser Gln Asp Leu Glu Ile Tyr
        740                 745                 750

Leu Ile Arg Tyr Asn Ala Lys His Glu Thr Val Asn Val Pro Gly Thr
        755                 760                 765

Gly Ser Leu Trp Pro Leu Ser Ala Gln Ser Pro Ile Gly Lys Cys Gly
770                 775                 780

Glu Pro Asn Arg Cys Ala Thr His Leu Glu Trp Asn Pro Asp Leu Asp
785                 790                 795                 800

Cys Ser Cys Arg Asp Gly Glu Lys Cys Ala His His Ser His Phe
                805                 810                 815

Ser Leu Asp Ile Asp Val Gly Cys Thr Asp Leu Asn Glu Asp Leu Gly
        820                 825                 830

Val Trp Val Ile Phe Lys Ile Lys Thr Gln Asp Gly His Ala Arg Leu

-continued

```
            835                 840                 845
Gly Asn Leu Glu Phe Leu Glu Glu Lys Pro Leu Val Gly Glu Ala Leu
    850                 855                 860

Ala Arg Val Lys Arg Ala Glu Lys Lys Trp Arg Asp Lys Arg Glu Lys
865                 870                 875                 880

Leu Glu Leu Glu Thr Asn Ile Val Tyr Lys Ala Lys Lys Ser Val
                885                 890                 895

Asp Ala Leu Phe Val Asn Ser Gln Tyr Asp Arg Leu Gln Ala Asp Thr
            900                 905                 910

Asn Ile Ala Ile Ile His Ala Ala Asp Lys Arg Val His Ser Ile Arg
        915                 920                 925

Glu Ala Tyr Leu Pro Glu Leu Ser Val Ile Pro Gly Val Asn Ala Ala
    930                 935                 940

Ile Phe Glu Glu Leu Glu Gly Arg Ile Phe Thr Ala Tyr Ser Leu Tyr
945                 950                 955                 960

Asp Ala Arg Asn Val Ile Lys Asn Gly Asp Phe Asn Asn Gly Leu Ser
                965                 970                 975

Cys Trp Asn Val Lys Gly His Val Asp Val Glu Glu Gln Asn Asn His
            980                 985                 990

Arg Ser Val Leu Val Pro Glu Trp Glu Ala Glu Val Ser Gln Glu
        995                 1000                1005

Val Arg Val Cys Pro Gly Arg Gly Tyr Ile Leu Arg Val Thr Ala
    1010                1015                1020

Tyr Lys Glu Gly Tyr Gly Glu Gly Cys Val Thr Ile His Glu Ile
    1025                1030                1035

Glu Asp Asn Thr Asp Glu Leu Lys Phe Ser Asn Cys Val Glu Glu
    1040                1045                1050

Glu Ile Tyr Pro Asn Asn Thr Val Thr Cys Asn Asp Tyr Thr Ala
    1055                1060                1065

Thr Gln Glu Glu Tyr Glu Gly Thr Tyr Thr Ser Arg Asn Arg Gly
    1070                1075                1080

Tyr Asp Gly Ala Tyr Glu Ser Asn Ser Ser Val Pro Ala Asp Tyr
    1085                1090                1095

Ala Ser Ala Tyr Glu Glu Lys Ala Tyr Thr Asp Gly Arg Arg Asp
    1100                1105                1110

Asn Thr Cys Glu Ser Asn Arg Gly Tyr Gly Asp Tyr Thr Pro Leu
    1115                1120                1125

Pro Ala Gly Tyr Val Thr Lys Glu Leu Glu Tyr Phe Pro Glu Thr
    1130                1135                1140

Asp Lys Val Trp Ile Glu Ile Gly Glu Thr Glu Gly Thr Phe Ile
    1145                1150                1155

Val Asp Ser Val Glu Leu Leu Leu Met Glu Glu
    1160                1165

<210> SEQ ID NO 3
<211> LENGTH: 1169
<212> TYPE: PRT
<213> ORGANISM: Artificial Sequence
<220> FEATURE:
<223> OTHER INFORMATION: Bt29-Bt22 chimeric protein.

<400> SEQUENCE: 3

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
```

```
            20                  25                  30
Val Ala Glu Ile His Leu Lys Ile Thr Arg Leu Ile Leu Glu Asn Phe
         35                  40                  45
Leu Pro Gly Gly Ser Phe Ala Phe Gly Leu Phe Asp Leu Ile Trp Gly
     50                  55                  60
Ile Phe Asn Glu Asp Gln Trp Ser Ala Phe Leu Arg Gln Val Glu Glu
 65                  70                  75                  80
Leu Ile Asn Gln Arg Ile Thr Glu Phe Ala Arg Gly Gln Ala Ile Gln
                 85                  90                  95
Arg Leu Val Gly Phe Gly Arg Ser Tyr Asp Glu Tyr Ile Leu Ala Leu
                100                 105                 110
Lys Glu Trp Glu Asn Asp Pro Asp Asn Pro Ala Ser Lys Glu Arg Val
                115                 120                 125
Arg Thr Arg Phe Arg Thr Thr Asp Asp Ala Leu Leu Thr Gly Val Pro
                130                 135                 140
Leu Met Ala Ile Pro Gly Phe Glu Leu Ala Thr Leu Ser Val Tyr Ala
145                 150                 155                 160
Gln Ser Ala Asn Leu His Leu Ala Leu Leu Arg Asp Ala Val Phe Phe
                165                 170                 175
Gly Glu Arg Trp Gly Leu Thr Gln Thr Asn Ile Asn Asp Leu Tyr Ser
                180                 185                 190
Arg Leu Lys Asn Ser Ile Arg Asp Tyr Thr Asn His Cys Val Arg Phe
                195                 200                 205
Tyr Asn Ile Gly Leu Gly Asn Leu Asn Val Ile Arg Pro Glu Tyr Tyr
                210                 215                 220
Arg Phe Gln Arg Glu Leu Thr Ile Ser Val Leu Asp Leu Val Ala Leu
225                 230                 235                 240
Phe Pro Asn Tyr Asp Ile Arg Thr Tyr Pro Ile Pro Thr Lys Ser Gln
                245                 250                 255
Leu Thr Arg Glu Ile Tyr Thr Asp Pro Ile Ile Ser Pro Gly Ala Gln
                260                 265                 270
Ala Gly Tyr Thr Leu Gln Asp Val Leu Arg Glu Pro His Leu Met Asp
                275                 280                 285
Phe Leu Asn Arg Leu Ile Ile Tyr Thr Gly Glu Tyr Arg Gly Ile Arg
                290                 295                 300
His Trp Ala Gly His Glu Val Glu Ser Ser Arg Thr Gly Met Met Thr
305                 310                 315                 320
Asn Ile Arg Phe Pro Leu Tyr Gly Thr Ala Thr Ala Glu Pro Thr
                325                 330                 335
Arg Phe Ile Thr Pro Ser Thr Phe Pro Gly Leu Asn Leu Phe Tyr Arg
                340                 345                 350
Thr Leu Ser Ala Pro Ile Phe Arg Asp Glu Pro Gly Ala Asn Ile Ile
                355                 360                 365
Ile Arg Tyr Arg Thr Ser Leu Val Glu Gly Val Gly Phe Ile Gln Pro
                370                 375                 380
Asn Asn Gly Glu Gln Leu Tyr Arg Val Arg Gly Thr Leu Asp Ser Leu
385                 390                 395                 400
Asp Gln Leu Pro Leu Glu Gly Glu Ser Ser Leu Thr Glu Tyr Ser His
                405                 410                 415
Arg Leu Cys His Val Arg Phe Ala Gln Ser Leu Arg Asn Ala Glu Pro
                420                 425                 430
Leu Asp Tyr Ala Arg Val Pro Met Phe Ser Trp Thr His Arg Ser Ala
                435                 440                 445
```

```
Thr Pro Thr Asn Thr Ile Asp Pro Asp Val Ile Thr Gln Ile Pro Leu
    450                 455                 460

Val Lys Ala His Thr Leu Gln Ser Gly Thr Thr Val Val Lys Gly Pro
465                 470                 475                 480

Gly Phe Thr Gly Gly Asp Ile Leu Arg Arg Thr Ser Gly Gly Pro Phe
                485                 490                 495

Ala Phe Ser Asn Val Asn Leu Asp Trp Asn Leu Ser Gln Arg Tyr Arg
            500                 505                 510

Ala Arg Ile Arg Tyr Ala Ser Thr Thr Asn Leu Arg Met Tyr Val Thr
        515                 520                 525

Ile Ala Gly Glu Arg Ile Phe Ala Gly Gln Phe Asn Lys Thr Met Asn
    530                 535                 540

Thr Gly Asp Pro Leu Thr Phe Gln Ser Phe Ser Tyr Ala Thr Ile Asp
545                 550                 555                 560

Thr Ala Phe Thr Phe Pro Thr Lys Ala Ser Ser Leu Thr Val Gly Ala
                565                 570                 575

Asp Thr Phe Ser Ser Gly Asn Glu Val Tyr Val Asp Arg Phe Glu Leu
            580                 585                 590

Ile Pro Val Thr Ala Thr Phe Glu Ala Glu Tyr Asp Leu Glu Lys Ala
        595                 600                 605

Gln Lys Ala Val Asn Ala Leu Phe Thr Ser Ser Asn Gln Ile Gly Leu
    610                 615                 620

Lys Thr Asp Val Thr Asp Tyr His Ile Asp Lys Val Ser Asn Leu Val
625                 630                 635                 640

Glu Cys Leu Ser Asp Glu Phe Cys Leu Asp Lys Arg Glu Leu Ser
                645                 650                 655

Glu Lys Val Lys His Ala Lys Arg Leu Cys Asp Glu Arg Asn Leu Leu
            660                 665                 670

Gln Asp Pro Asn Phe Arg Gly Ile Asn Arg Gln Pro Asp Arg Gly Trp
        675                 680                 685

Arg Gly Ser Thr Asp Ile Thr Ile Gln Gly Gly Asp Asp Val Phe Lys
    690                 695                 700

Glu Asn Tyr Val Thr Leu Pro Gly Thr Phe Asp Glu Cys Tyr Pro Thr
705                 710                 715                 720

Tyr Leu Tyr Gln Lys Ile Asp Glu Ser Lys Leu Lys Ala Tyr Thr Arg
                725                 730                 735

Tyr Glu Leu Arg Gly Tyr Ile Glu Asp Ser Gln Asp Leu Glu Ile Tyr
            740                 745                 750

Leu Ile Arg Tyr Asn Ala Lys His Glu Thr Val Asn Val Pro Gly Thr
        755                 760                 765

Gly Ser Leu Trp Pro Leu Ser Ala Gln Ser Pro Ile Gly Lys Cys Gly
    770                 775                 780

Glu Pro Asn Arg Cys Ala Thr His Leu Glu Trp Asn Pro Asp Leu Asp
785                 790                 795                 800

Cys Ser Cys Arg Asp Gly Glu Lys Cys Ala His His Ser His His Phe
                805                 810                 815

Ser Leu Asp Ile Asp Val Gly Cys Thr Asp Leu Asn Glu Asp Leu Gly
            820                 825                 830

Val Trp Val Ile Phe Lys Ile Lys Thr Gln Asp Gly His Ala Arg Leu
        835                 840                 845

Gly Asn Leu Glu Phe Leu Glu Glu Lys Pro Leu Val Gly Glu Ala Leu
    850                 855                 860
```

```
Ala Arg Val Lys Arg Ala Glu Lys Lys Trp Arg Asp Lys Arg Glu Lys
865                 870                 875                 880

Leu Glu Leu Glu Thr Asn Ile Val Tyr Lys Glu Ala Lys Lys Ser Val
                885                 890                 895

Asp Ala Leu Phe Val Asn Ser Gln Tyr Asp Arg Leu Gln Ala Asp Thr
            900                 905                 910

Asn Ile Ala Ile Ile His Ala Ala Asp Lys Arg Val His Ser Ile Arg
        915                 920                 925

Glu Ala Tyr Leu Pro Glu Leu Ser Val Ile Pro Gly Val Asn Ala Ala
    930                 935                 940

Ile Phe Glu Glu Leu Glu Gly Arg Ile Phe Thr Ala Tyr Ser Leu Tyr
945                 950                 955                 960

Asp Ala Arg Asn Val Ile Lys Asn Gly Asp Phe Asn Asn Gly Leu Ser
                965                 970                 975

Cys Trp Asn Val Lys Gly His Val Asp Val Glu Glu Gln Asn Asn His
            980                 985                 990

Arg Ser Val Leu Val Val Pro Glu  Trp Glu Ala Glu Val  Ser Gln Glu
        995                 1000                1005

Val Arg  Val Cys Pro Gly Arg  Gly Tyr Ile Leu Arg  Val Thr Ala
    1010                 1015                 1020

Tyr Lys  Glu Gly Tyr Gly Glu  Gly Cys Val Thr Ile  His Glu Ile
    1025                 1030                 1035

Glu Asp  Asn Thr Asp Glu Leu  Lys Phe Ser Asn Cys  Val Glu Glu
    1040                 1045                 1050

Glu Ile  Tyr Pro Asn Asn Thr  Val Thr Cys Asn Asp  Tyr Thr Ala
    1055                 1060                 1065

Thr Gln  Glu Glu Tyr Glu Gly  Thr Tyr Thr Ser Arg  Asn Arg Gly
    1070                 1075                 1080

Tyr Asp  Gly Ala Tyr Glu Ser  Asn Ser Ser Val Pro  Ala Asp Tyr
    1085                 1090                 1095

Ala Ser  Ala Tyr Glu Glu Lys  Ala Tyr Thr Asp Gly  Arg Arg Asp
    1100                 1105                 1110

Asn Thr  Cys Glu Ser Asn Arg  Gly Tyr Gly Asp Tyr  Thr Pro Leu
    1115                 1120                 1125

Pro Ala  Gly Tyr Val Thr Lys  Glu Leu Glu Tyr Phe  Pro Glu Thr
    1130                 1135                 1140

Asp Lys  Val Trp Ile Glu Ile  Gly Glu Thr Glu Gly  Thr Phe Ile
    1145                 1150                 1155

Val Asp  Ser Val Glu Leu Leu  Leu Met Glu Glu
    1160                 1165
```

<210> SEQ ID NO 4
<211> LENGTH: 3510
<212> TYPE: DNA
<213> ORGANISM: Artificial Sequence
<220> FEATURE:
<223> OTHER INFORMATION: Coding sequencec for Bt29-Bt22 chimeric protein.

<400> SEQUENCE: 4

```
atggagatta ataatcagaa ccaatgtgtc ccttataatt gtttgaataa tcctgaaagc     60
gagatattaa acgttgcaat ttttagtagc gaacaggtag cagaaattca cttaaagatc    120
acgcgcttaa ttttagagaa ttttttacca ggtgggagtt ttgcattcgg cttatttgat    180
ttaatatggg ggatttttaa tgaagatcaa tggagcgcat ttcttcggca ggtagaagaa    240
```

```
ttaattaatc aaaggataac ggaattcgca agagggcaag caattcagag actagtaggg    300
tttggaagga gttatgatga atatatttta gcactaaaag aatgggaaaa cgatcctgat    360
aacccagctt caaaggaaag agtgcgcact cgatttcgga caactgatga tgccttgcta    420
accggtgttc ctcttatggc aattccaggt tttgaattag ctactttatc tgtttatgct    480
caatcagcca atctacattt agccctatta agagatgctg tattttttgg ggagagatgg    540
ggattgacac aaacaaatat aaatgattta tatagtagat taaaaaactc cattcgtgat    600
tatacaaatc attgtgttcg ttttttataat ataggtttag ggaatttaaa tgttataaga    660
ccagagtatt accgtttcca aagagaatta acaatatctg tcttagatct tgtagctctt    720
tttccaaatt acgatatccg aacatatcca ataccaacta aaagtcaatt aacaagagaa    780
atttatacag atccgattat ttcacctggt gcacaggcag ttatactctt tcaagatgtt    840
ttgagagaac cacaccttat ggactttttta aaccgactta ttatttatac tggtgagtat    900
cgcggaattc gtcactgggc aggacatgaa gtagaatcta gtagaacagg tatgatgact    960
aatataagat ttcctttgta tggaacagcc gcaacagcag aaccaacacg atttataact   1020
cctagtactt ttcctggtct taatttattt tatagaacat tatcagctcc tattttttaga   1080 gatgaaccgg gagctaatat tattattaga tatagaacga gtttggtgga aggagtagga   1140
tttattcaac caaataacgg tgaacagctt tacagagtga gaggaacatt agattctctt   1200
gatcaattac cacttgaggg tgagagtagt ctaactgaat atagtcatcg attatgccat   1260
gttagatttg cgcaatcatt gaggaatgca gaacctttag attatgcaag ggttccgatg   1320
ttttcttgga cacatcgtag tgcaacccct acaaatacaa ttgatccaga tgtcatcacc   1380
caaataccgt tagtaaaagc atataccctt cagtcaggta ctactgttgt aaaagggcca   1440
gggtttacag gtggagatat cctccgacga actagtggag gaccatttgc ttttagtaat   1500
gttaatttag actggaactt gtcacaaaga tatcgtgcta gaatacgcta tgcttctact   1560
actaatctaa gaatgtacgt aacgattgca ggggaacgaa tttttgctgg tcaatttaat   1620
aaaacaatga atactggtga tccattaaca ttccaatctt ttagttacgc aactattgat   1680
acagcattta cattcccaac gaaagcgagc agcttgactg taggtgctga tacttttagc   1740
tcaggtaatg aagtttatgt agatagattt gaattgatcc cagttactgc aacatttgag   1800
gcagaatatg atttagagaa agctcagaaa gcggtgaatg cgctgtttac ttcttccaat   1860
caaatcgggt taaaaacaga tgtgacggac tatcatattg ataaagtatc caatctagtt   1920
gagtgtttat cagatgaatt ttgtctagat gaaaagcgag aattgtccga gaaagtcaaa   1980
catgcgaagc gactctgtga tgagcggaat ttacttcaag atccaaactt cagaggcatc   2040
aatagacaac cagaccgtgg ttggagagga agtacggata ttaccatcca aggaggagat   2100
gacgtattca aagagaatta cgttacgcta ccgggtacct tgatgagtg ctatccaacg    2160 tatttatatc aaaaaatata tgagtcgaaa ttaaaagcct ataccgcta tgaattaaga    2220 gggtatatcg aggatagtca agacttagaa atctatttaa ttcgctacaa tgcaaaacat   2280
gaaacagtaa atgtgccagg tacgggttcc ttatggccgc tttcagccca aagtccaatc   2340
ggaaagtgtg gagaaccgaa tcgatgtgcg acacaccttg aatggaatcc tgacttagat   2400
tgttcgtgta gggatggaga aaagtgtgcc catcattcgc atcatttctc cttagacatt   2460
gatgtaggat gtacagacct aaatgaggac ctaggtgtat gggtgatctt taagattaag   2520
acgcaagatg gtcatgcgag actaggaaat ctagaatttc tcgaagagaa accattagta   2580
ggagaagcgc tagctcgtgt gaagagagcg gagaaaaaat ggagagacaa acgcgaaaaa   2640
```

```
ttggaattgg aaacaaatat tgtttataaa gaggcaaaaa aatctgtaga tgctttattt    2700
gtgaactctc aatatgatag attacaagcg gatacgaata tcgcgataat tcatgcggca    2760
gataaacgcg ttcatagcat tcgagaagca tatcttccag agttgtctgt aattccgggt    2820
gtaaatgcag ctattttgga agaattagag ggacgtattt tcacagccta ctctctatat    2880
gatgcgagaa atgtcattaa aaatggcgat ttcaataatg cttatcatg ctggaacgtg     2940 aaagggcatg tagatgtaga agaacagaac aaccatcgtt cggtccttgt tgttccagaa    3000
tgggaagcag aagtgtcaca agaggttcgt gtctgtccag gtcgtggcta tatccttcgt    3060
gttacagcgt acaagagggg atatggagag ggctgtgtaa cgattcatga gatcgaagac    3120
aatacagacg aactgaaatt cagcaactgt gtagaagagg aaatatatcc aaacaacacg    3180
gtaacgtgta atgattatac tgcgactcaa gaagaatatg agggtacgta cacttctcgt    3240
aatcgaggat atgacggagc ctatgaaagc aattcttctg taccagctga ttatgcatca    3300
gcctatgaag aaaaagcgta tacagatgga agaagagaca atacttgtga atctaacaga    3360
ggatatgggg attacacacc actaccagct ggctatgtga caaaagaatt agagtacttc    3420
ccagaaaccg ataaggtatg gattgagatt ggagaaacgg aaggaacatt tatcgtggac    3480
agcgtggaat tactccttat ggaggaatag                                     3510
```

<210> SEQ ID NO 5
<211> LENGTH: 3510
<212> TYPE: DNA
<213> ORGANISM: Artificial Sequence
<220> FEATURE:
<223> OTHER INFORMATION: Maize optimized coding sequence for Bt29-Bt22
      chimeric protein.

<400> SEQUENCE: 5

```
atggaaatca caaccagaa ccagtgcgtg ccgtacaact gcctcaacaa ccccgagtcc      60
gagatcctga acgtggccat cttctccagc gagcaggtcg cggagatcca cctcaagatc    120
acgcgcctga tcctcgagaa cttcctgccg gcggctcct tcgctttcgg cctgttcgac    180
ctcatctggg gcatcttcaa cgaggaccag tggagcgcgt tcctcaggca ggtggaggag    240
ctgatcaacc agcgcatcac ggagttcgcc aggggccagg ctatccagcg gctggtgggc    300
ttcggcaggt cctacgacga atacatcctg gccctcaagg agtgggagaa cgaccccgac    360
aacccggcca gcaaggagcg cgtgaggacc cgcttcagga ccaccgacga cgctctcctg    420
acgggcgtcc ccctcatggc tatcccgggc ttcgagctgg ccaccctctc ggtgtacgct    480
cagtcggcca acctgcacct cgccctcctg cgggacgctg tgttcttcgg cgagaggtgg    540
ggcctgaccc aaaccaacat caacgacctc tactccaggc tgaagaacag catccgcgac    600
tacacgaacc actgcgtgcg cttctacaac atcggcctgg gcaacctcaa cgtcatcagg    660
ccggaatact accgcttcca gagggagctg accatcagcg tgctggacct cgtcgccctg    720
ttccccaact acgacatccg cacgtacccg atccccacca gtcccagct cacgagggag    780 atctacaccg acccgatcat ctcgccgggc gcccaggccg gctacaccct gcaggacgtc    840
ctgagggagc ccaccctgat ggacttcctg aacaggctca tcatctacac cggcgagtac    900
aggggcatca ggcactgggc gggccacgag gtggagtcca gcaggacggg catgatgacc    960
aacatccgct tccgctcta cggcaccgcg gccacggccg agccaacccg cttcatcacg   1020
ccgtccacct tccccggcct gaacctcttc tacaggaccc tgtcggctcc catcttccgc   1080
gacgagccgg gcgcgaacat catcatccgc tacaggacct ccctcgtgga gggcgtcggc   1140
```

```
ttcatccagc cgaacaacgg cgagcagctg taccgcgtga ggggcacgct ggacagcctg    1200
gaccagctcc cactggaggg cgagtccagc ctcaccgagt actcgcacag gctgtgccac    1260
gtcaggttcg cccagagcct caggaacgcg gagcccctgg actacgccag ggtgcccatg    1320
ttcagctgga cccacaggtc ggctaccccc accaacacca tcgacccaga cgtgatcacg    1380
cagatcccgc tcgtcaaggc ccacaccctg cagtcgggca ccaccgtggt caagggcccc    1440
ggcttcacgg gcggcgacat cctgaggagg acctccggcg gcccattcgc cttcagcaac    1500
gtcaacctcg actggaacct gtcccagcgc tacagggcgc gcatcaggta cgccagcacc    1560
acgaacctgc gcatgtatgt gaccatcgcg ggcgagagga tcttcgccgg ccagttcaac    1620
aagacgatga acaccggcga cccgctcacc ttccagtcct tcagctacgc gacgatcgac    1680
accgccttca cgttccccac gaaggcctcc agcctgaccg tgggcgccga caccttctcc    1740
agcggcaacg aggtctacgt ggaccgcttc gagctgatcc cggtgacggc gaccttcgag    1800
gccgagtacg acctggagaa ggcccagaag gcggtcaacg ccctcttcac ctccagcaac    1860
cagatcggcc tgaagacgga cgtgaccgac taccacatcg acaaggtgtc caacctcgtc    1920
gagtgcctga cgacgagtt ctgcctcgac gagaagaggg agctgtccga gaaggtcaag    1980
cacgccaagc gcctctgcga cgagaggaac ctcctgcagg acccgaactt caggggcatc    2040
aaccgccagc cggacagggg ctggaggggc agcaccgaca tcaccatcca gggcggcgac    2100
gacgtgttca aggagaacta cgtcacgctc ccgggcacct tcgacgagtg ctaccccacg    2160
tacctgtacc agaagatcga cgagtccaag ctcaaggcct acacccgcta cgagctgagg    2220
ggctacatcg aggacagcca ggacctcgag atctacctga tccgctacaa cgcgaagcac    2280
gagacggtga acgtccccgg cacgggctcc ctgtggcccc tctcggctca gtcgccgatc    2340
ggcaagtgcg gcgagcccaa caggtgcgcc acccacctcg agtggaaccc ggacctggac    2400
tgctcctgcc gggacggcga gaagtgcgct caccactccc accacttcag cctggacatc    2460
gacgtgggct gcacggacct caacgaggac ctgggcgtgt gggtcatctt caagatcaag    2520
acgcaggacg ccacgctag gctgggcaac ctcgagttcc tggaggagaa gccgctggtg    2580
ggcgaggctc tggccagggt caagagggcg agaagaagt ggcgcgacaa gagggagaag    2640
ctggagctgg agacgaacat cgtctacaag gaggccaaga agtccgtgga cgcgctcttc    2700
gtcaacagcc agtacgacag gctgcaggcg gacaccaaca tcgccatcat ccacgccgcg    2760
gacaagcgcg tgcactccat cagggaggcc tacctccccg agctgagcgt gatcccgggc    2820
gtcaacgctg ccatcttcga ggagctggag gccgcatct tcaccgccta ctccctgtac    2880
gacgcgagga acgtcatcaa gaacggcgac ttcaacaacg gcctcagctg ctggaacgtg    2940
aagggccacg tggacgtcga ggagcagaac aaccaccgct cggtgctggt ggtccccgag    3000
tgggaggctg aggtcagcca ggaggtgcgc gtctgcccgg gcaggggcta catcctccgc    3060
gtgaccgcgt acaaggaggg ctacggcgag ggctgcgtca cgatccacga gatcgaggac    3120
aacaccgacg agctgaagtt ctccaactgc gtggaggagg agatctaccc gaacaacacg    3180
gtcacctgca cgactacac ggccacccag gaggagtacg agggcacgta cacgtcgagg    3240
aacaggggct acgacggcgc ttacgagtcc aacagctcgg tgccggccga ctacgctagc    3300
gcgtacgagg agaaggccta cacggacggc cgcagggaca cacctgcga gtcgaacagg    3360 ggctacggcg actacacgcc gctcccggcc ggctacgtga ccaaggagct ggagtacttc    3420
ccggagacgg acaaggtctg gatcgagatc ggcgagacgg agggcacctt catcgtggac    3480
```
agcgtcgagc tgctgctcat ggaggagtag                                 3510

<210> SEQ ID NO 6
<211> LENGTH: 3510
<212> TYPE: DNA
<213> ORGANISM: Artificial Sequence
<220> FEATURE:
<223> OTHER INFORMATION: Maize optimized coding sequence for BT29-BT22
      cimeric protein.

<400> SEQUENCE: 6

```
atggaaatca caaccagaa ccagtgcgtg ccgtacaact gccttaacaa ccccgagtcc     60
gagatcctga acgtggccat cttctccagc gagcaggtcg cggagatcca cctcaagatc    120
acgcgcctga tcctcgagaa cttcctgccg gcggctcct tcgctttcgg cctgttcgac    180
ctcatctggg gcatcttcaa cgaggaccag tggagcgcgt tcctcaggca ggtgaggag    240
ctgatcaacc agcgcatcac ggagttcgcc aggggccagg ctatccagcg gctggtgggc    300
ttcggcaggt cctacgacga atacatcctg gccctcaagg agtgggagaa cgaccccgac    360
aacccggcca gcaaggagcg cgtgaggacc cgcttcagga ccaccgacga cgctctcctg    420
acgggcgtcc ccctcatggc tatcccgggc ttcgagctgg ccaccctctc ggtgtacgct    480
cagtcggcca acctgcacct cgccctcctg cgggacgctg tgttcttcgg cgagaggtgg    540
ggcctgaccc aaaccaacat caacgacctc tactccaggc tgaagaacag catccgcgac    600
tacacgaacc actgcgtgcg cttctacaac atcggcctgg caacctcaa cgtcatcagg    660
ccggaatact accgcttcca gagggactg accatcagcg tgctggacct cgtcgccctg    720
ttccccaact acgacatccg cacgtacccg atccccacca gtcccagct cacgagggag    780
atctacaccg accgatcat ctcgccgggc gcccaggccg gctacacct gcaggacgtc    840
ctgagggagc cccacctgat ggacttcctg aacaggctca tcatctacac cggcgagtac    900
agggcgtca ggcactgggc ggccacgag gtggagtcca gcaggacggg catgatgacc    960
aacatcgct tccgctcta cggcaccgcg gccacggcg agccaacccg cttcatcacg    1020
ccgtccacct tccccggcct gaacctcttc tacaggaccc tgtcggctcc catcttccgc    1080
gacgagccgg gcgcgaacat catcatccgc tacaggacct ccctcgtgga gggcgtcggc    1140
ttcatccagc gaacaacgg cgagcagctg taccgcgtga ggggcacgct ggacagcctg    1200
gaccagctcc cactggaggg cgagtccagc ctcaccgagt actcgcacag gctgtgccac    1260
gtcaggttcg cccagagcct caggaacgcg gagcccctgg actacgccag ggtgcccatg    1320
ttcagctgga cccacaggtc ggctaccccc accaacacca tcgacccaga cgtgatcacg    1380
cagatcccgc tcgtcaaggc ccacaccctg cagtcgggca ccaccgtggt caagggcccc    1440
ggcttcacgg gcgcgacat cctgaggagg acctccggcg cccattcgc cttcagcaac    1500
gtcaacctcg actggaacct gtcccagcgc tacagggcgc gcatcaggta cgccagcacc    1560
acgaacctgc gcatgtatgt gaccatcgcg ggcgagagga tcttcgccgg ccagttcaac    1620
aagacgatga acaccggcga cccgctcacc ttccagtcct tcagctacgc gacgatcgac    1680
accgccttca cgttcccac gaaggcctcc agcctgaccg tgggcgccga caccttctcc    1740
agcggcaacg aggtctacgt ggaccgcttc gagctgatcc cggtgacggc gaccttcgag    1800
gccgagtacg acctggagaa ggcccagaag gcggtcaacg ccctcttcac ctccagcaac    1860
cagatcggcc tgaagacgga cgtgaccgac taccacatcg acaaggtgtc caacctcgtc    1920
gagtgcctga cgcgacgagtt ctgcctcgac gagaagaggg agctgtccga aaggtcaag    1980
```

```
cacgccaagc gcctctgcga cgagaggaac ctcctgcagg acccgaactt caggggcatc   2040
aaccgccagc cggacagggg ctggaggggc agcaccgaca tcaccatcca gggcggcgac   2100
gacgtgttca aggagaacta cgtcacgctc ccgggcacct tcgacgagtg ctaccccacg   2160
tacctgtacc agaagatcga cgagtccaag ctcaaggcct acacccgcta cgagctgagg   2220
ggctacatcg aggacagcca ggacctcgag atctacctga tccgctacaa cgcgaagcac   2280
gagacggtga acgtccccgg cacgggctcc ctgtggcccc tctcggctca gtcgccgatc   2340
ggcaagtgcg gcgagcccaa caggtgcgcc acccacctcg agtggaaccc ggacctggac   2400
tgctcctgcc gggacggcga gaagtgcgct caccactccc accacttcag cctggacatc   2460
gacgtgggct gcacggacct caacgaggac ctgggcgtgt gggtcatctt caagatcaag   2520
acgcaggacg gccacgctag gctgggcaac ctcgagttcc tggaggagaa gccgctggtg   2580
ggcgaggctc tggccagggt caagagggcg gagaagaagt ggcgcgacaa gagggagaag   2640
ctggagctgg agacgaacat cgtctacaag gaggccaaga agtccgtgga cgcgctcttc   2700
gtcaacagcc agtacgacag gctgcaggcg gacaccaaca tcgccatcat ccacgccgcg   2760
gacaagcgcg tgcactccat cagggaggcc tacctccccg agctgagcgt gatcccgggc   2820
gtcaacgctg ccatcttcga ggagctggag ggccgcatct tcaccgccta ctccctgtac   2880
gacgcgagga acgtcatcaa gaacggcgac ttcaacaacg gcctcagctg ctggaacgtg   2940
aagggccacg tggacgtcga ggagcagaac aaccaccgct cggtgctggt ggtccccgag   3000
tgggaggctg aggtcagcca ggaggtgcgc gtctgcccgg gcaggggcta catcctccgc   3060
gtgaccgcgt acaaggaggg ctacggcgag ggctgcgtca cgatccacga gatcgaggac   3120
aacaccgacg agctgaagtt ctccaactgc gtggaggagg agatctaccc gaacaacacg   3180
gtcacctgca acgactacac ggccacccag gaggagtacg agggcacgta cacgtcgagg   3240
aacaggggct acgacggcgc ttacgagtcc aacagctcgg tgccggccga ctacgctagc   3300
gcgtacgagg agaaggccta cacggacggc cgcagggaca acacctgcga gtcgaacagg   3360
ggctacggcg actacacgcc gctcccggcc ggctacgtga ccaaggagct ggagtacttc   3420
ccggagacgg acaaggtctg gatcgagatc ggcgagacgg agggcacctt catcgtggac   3480
tcagtcgagc tgctgctcat ggaggagtag                                    3510
```

<210> SEQ ID NO 7
<211> LENGTH: 3510
<212> TYPE: DNA
<213> ORGANISM: Artificial Sequence
<220> FEATURE:
<223> OTHER INFORMATION: Maize optimized coding sequence for Bt29-Bt22 chimeric protein.

<400> SEQUENCE: 7

```
atggagatca acaaccagaa ccagtgcgtg ccgtacaact gccttaacaa ccccgagtcc     60
gagatcctga acgtggccat cttctccagc gagcaggtcg cggagatcca cctcaagatc    120
acgcgcctga tcctcgagaa cttcctgccg ggcggctcct tcgctttcgg cctgttcgac    180
ctcatctggg gcatcttcaa cgaggaccag tggagcgcgt tcctcaggca ggtggaggag    240
ctgatcaacc agcgcatcac ggagttcgcc aggggccagg ctatccagcg gctggtgggc    300
ttcggcaggt cctacgacga gtacatcctg gccctcaagg agtgggagaa cgaccccgac    360
aacccggcca gcaaggagcg cgtgaggacc cgcttcagga ccaccgacga cgctctcctg    420
acgggcgtcc ccctcatggc tatcccgggc ttcgagctgg ccaccctctc ggtgtacgct    480
```

```
cagtcggcca acctgcacct cgccctcctg cgggacgctg tgttcttcgg cgagaggtgg    540
ggcctgaccc agacgaacat caacgacctc tactccaggc tgaagaacag catccgcgac    600
tacacgaacc actgcgtgcg cttctacaac atcggcctgg gcaacctcaa cgtcatcagg    660
ccggagtact accgcttcca gagggagctg accatcagcg tgctggacct cgtcgccctg    720
ttccccaact acgacatccg cacgtacccg atcccaacca gtcccagct cacgagggag     780 atctacaccg acccgatcat ctcgccgggc gcccaggccg ctacaccct gcaggacgtc     840 ctgagggagc cccacctgat ggacttcctg aacaggctca tcatctacac cggcgagtac    900
aggggcatca ggcactgggc gggccacgag gtggagtcca gcaggacggg catgatgacc    960
aacatccgct tcccgctcta cggcaccgcg gccacggccg agccaacccg cttcatcacg   1020
ccgtccacct tccccggcct gaacctcttc tacaggaccc tgtcggctcc catcttccgc   1080
gacgagccgg gcgcgaacat catcatccgc tacaggacct ccctcgtgga gggcgtcggc   1140
ttcatccagc cgaacaacgg cgagcagctg taccgcgtga ggggcacgct ggacagcctg   1200
gaccagctcc cactggaggg cgagtccagc ctcaccgagt actcgcacag gctgtgccac   1260
gtcaggttcg cccagagcct caggaacgcg gagcccctgg actacgccag ggtgcccatg   1320
ttcagctgga cccacaggtc ggctaccccc accaacacca tcgacccaga cgtgatcacg   1380
cagatcccgc tcgtcaaggc ccacaccctg cagtcgggca ccaccgtggt caagggcccc   1440
ggcttcacgg gcgcgacat cctgaggagg acctccggcg gcccattcgc cttcagcaac   1500
gtcaacctcg actggaacct gtcccagcgc tacagggcgc gcatcaggta cgccagcacc   1560
acgaacctgc gcatgtatgt gaccatcgcg ggcgagagga tcttcgccgg ccagttcaac   1620
aagacgatga acaccggcga cccgctcacc ttccagtcct tcagctacgc gacgatcgac   1680
accgccttca cgttccccac gaaggcctcc agcctgaccg tgggcgccga caccttctcc   1740
agcggcaacg aggtctacgt ggaccgcttc gagctgatcc cggtgacggc gaccttcgag   1800
gccgagtacg acctggagaa ggcccagaag gcggtcaacg ccctcttcac ctccagcaac   1860
cagatcggcc tgaagacgga cgtgaccgac taccacatcg acaaggtgtc caacctcgtc   1920
gagtgcctga cgacgagtt ctgcctcgac gagaagaggg agctgtccga aaggtcaag    1980 cacgccaagc gcctctgcga cgagaggaac ctcctgcagg acccgaactt caggggaatc   2040
aaccgccagc cggacagggg ctggaggggc agcaccgaca tcaccatcca gggcggcgac   2100
gacgtgttca aggagaacta cgtcacgctc ccgggcacct cgacgagtg ctaccccacg    2160 tacctgtacc agaagatcga cgagtccaag ctcaaggcct cacccgcta cgagctgagg    2220 ggatacatcg aggacagcca ggacctcgag atctacctga tccgctacaa cgcgaagcac   2280
gagacggtga acgtccccgg cacgggctcc ctgtggcccc tctcggctca gtcgccgatc   2340
ggcaagtgcg gcgagcccaa caggtgcgcc acccacctcg agtggaaccc ggacctggac   2400
tgctcctgcc gggacggcga aagtgcgct caccactccc accacttcag cctggacatc     2460
gacgtgggct gcacggacct caacgaggac ctggcgtgt gggtcatctt caaaatcaag    2520
acgcaggacg ccacgctag gctgggcaac ctcgagttcc tggaggagaa gccgctggtg    2580
ggcgaggctc tggccagggt caagagggcg agaagaagt ggcgcgacaa gagggagaag     2640
ctggagctgg agacgaacat cgtctacaag gaggccaaga agtccgtgga cgcgctcttc    2700
gtcaacagcc agtacgacag gctgcaggcg gacaccaaca tcgccatcat ccacgccgcg   2760
gacaagcgcg tgcactccat cagggaggcc tacctccccg agctgagcgt gatcccgggc   2820
gtcaacgctg ccatcttcga ggagctggag ggccgcatct tcaccgccta ctccctgtac   2880
```

```
gacgcgagga acgtcatcaa gaacggcgac ttcaacaacg gcctcagctg ctggaacgtg    2940
aagggccacg tggacgtcga ggagcagaac aaccaccgct cggtgctggt ggtccccgag    3000
tgggaggctg aggtcagcca ggaggtgcgc gtctgcccgg gcagggggata catcctccgc   3060 gtgaccgcgt acaaggaggg ctacggcgag ggctgcgtca cgatccacga gatcgaggac    3120
aacaccgacg agctgaagtt ctccaactgc gtggaggagg agatctaccc gaacaacacg    3180
gtcacctgca cgactacac ggccacccag gaggagtacg agggcacgta cacgtcgagg     3240
aacaggggct acgacggcgc ttacgagtcc aacagctcgg tgccggccga ctacgctagc    3300
gcgtacgagg agaaggccta cacggacggc cgcagggaca cacctgcga gtcgaacagg     3360 ggctacggcg actacacgcc gctcccggcc ggctacgtga ccaaggagct ggagtacttc    3420
ccggagacgg acaaggtctg gatcgagatc ggcgagacgg agggcacctt catcgtggac    3480
tcagtcgagc tgctgctcat ggaggagtag                                     3510
```

<210> SEQ ID NO 8
<211> LENGTH: 1174
<212> TYPE: PRT
<213> ORGANISM: Bacillus thuringiensis

<400> SEQUENCE: 8

```
Met Glu Asn Asn Ile Gln Asn Gln Cys Val Pro Tyr Asn Cys Leu Asn
1               5                   10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255
```

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
        355                 360                 365

Phe Gly Asn Pro His Tyr Val Leu Gly Leu Arg Gly Val Ala Phe Gln
370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
        435                 440                 445

Thr His Arg Ser Ala Thr Pro Thr Asn Thr Ile Asp Pro Glu Arg Ile
450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
                485                 490                 495

Ser Gly Gly Pro Phe Ala Tyr Thr Ile Val Asn Ile Asn Gly Gln Leu
            500                 505                 510

Pro Gln Arg Tyr Arg Ala Arg Ile Arg Tyr Ala Ser Thr Thr Asn Leu
        515                 520                 525

Arg Ile Tyr Val Thr Val Ala Gly Glu Arg Ile Phe Ala Gly Gln Phe
530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile
            580                 585                 590

Asp Arg Phe Glu Leu Ile Pro Val Thr Ala Thr Phe Glu Ala Glu Tyr
        595                 600                 605

Asp Leu Glu Arg Ala Gln Lys Ala Val Asn Ala Leu Phe Thr Ser Ile
610                 615                 620

Asn Gln Ile Gly Ile Lys Thr Asp Val Thr Asp Tyr His Ile Asp Gln
625                 630                 635                 640

Val Ser Asn Leu Val Asp Cys Leu Ser Asp Glu Phe Cys Leu Asp Glu
                645                 650                 655

Lys Arg Glu Leu Ser Glu Lys Val Lys His Ala Lys Arg Leu Ser Asp
            660                 665                 670

Glu Arg Asn Leu Leu Gln Asp Pro Asn Phe Lys Gly Ile Asn Arg Gln

|         |         |         |         | 675     |         |         |         | 680     |         |         |         | 685     |         |         |
|---------|---------|---------|---------|---------|---------|---------|---------|---------|---------|---------|---------|---------|---------|---------|

Leu Asp Arg Gly Trp Arg Gly Ser Thr Asp Ile Thr Ile Gln Arg Gly
690                   695                   700

Asp Asp Val Phe Lys Glu Asn Tyr Val Thr Leu Pro Gly Thr Phe Asp
705                   710                   715                   720

Glu Cys Tyr Pro Thr Tyr Leu Tyr Gln Lys Ile Asp Glu Ser Lys Leu
                  725                   730                   735

Lys Pro Tyr Thr Arg Tyr Gln Leu Arg Gly Tyr Ile Glu Asp Ser Gln
              740                   745                   750

Asp Leu Glu Ile Tyr Leu Ile Arg Tyr Asn Ala Lys His Glu Thr Val
          755                   760                   765

Asn Val Leu Gly Thr Gly Ser Leu Trp Pro Leu Ser Val Gln Ser Pro
770                   775                   780

Ile Arg Lys Cys Gly Glu Pro Asn Arg Cys Ala Pro His Leu Glu Trp
785                   790                   795                   800

Asn Pro Asp Leu Asp Cys Ser Cys Arg Asp Gly Glu Lys Cys Ala His
                  805                   810                   815

His Ser His His Phe Ser Leu Asp Ile Asp Val Gly Cys Thr Asp Leu
              820                   825                   830

Asn Glu Asp Leu Asp Val Trp Val Ile Phe Lys Ile Lys Thr Gln Asp
          835                   840                   845

Gly His Ala Arg Leu Gly Asn Leu Glu Phe Leu Glu Glu Lys Pro Leu
850                   855                   860

Val Gly Glu Ala Leu Ala Arg Val Lys Arg Ala Glu Lys Lys Trp Arg
865                   870                   875                   880

Asp Lys Arg Glu Lys Leu Glu Leu Glu Thr Asn Ile Val Tyr Lys Glu
                  885                   890                   895

Ala Lys Glu Ser Val Asp Ala Leu Phe Val Asn Ser Gln Tyr Asp Gln
              900                   905                   910

Leu Gln Ala Asp Thr Asn Ile Ala Met Ile His Ala Ala Asp Lys Arg
          915                   920                   925

Val His Arg Ile Arg Glu Ala Tyr Leu Pro Glu Leu Ser Val Ile Pro
930                   935                   940

Gly Val Asn Val Asp Ile Phe Glu Glu Leu Lys Gly Arg Ile Phe Thr
945                   950                   955                   960

Ala Phe Phe Leu Tyr Asp Ala Arg Asn Val Ile Lys Asn Gly Asp Phe
                  965                   970                   975

Asn Asn Gly Leu Ser Cys Trp Asn Val Lys Gly His Val Asp Val Glu
              980                   985                   990

Glu Gln Asn Asn His Arg Ser Val Leu Val Val Pro Glu Trp Glu Ala
          995                   1000                  1005

Glu Val Ser Gln Glu Val Arg Val Cys Pro Gly Arg Gly Tyr Ile
1010                  1015                  1020

Leu Arg Val Thr Ala Tyr Lys Glu Gly Tyr Gly Glu Gly Cys Val
1025                  1030                  1035

Thr Ile His Glu Ile Glu Asn Asn Thr Asp Glu Leu Lys Phe Ser
1040                  1045                  1050

Asn Cys Val Glu Glu Glu Val Tyr Pro Asn Asn Thr Val Thr Cys
1055                  1060                  1065

Asn Asp Tyr Thr Ala Asn Gln Glu Glu Tyr Gly Gly Ala Tyr Thr
1070                  1075                  1080

Ser Arg Asn Arg Gly Tyr Asp Glu Thr Tyr Gly Ser Asn Ser Ser
1085                  1090                  1095

Val Pro Ala Asp Tyr Ala Ser Val Tyr Glu Glu Lys Ser Tyr Thr
    1100                1105                1110

Asp Gly Arg Arg Asp Asn Pro Cys Glu Ser Asn Arg Gly Tyr Gly
    1115                1120                1125

Asp Tyr Thr Pro Leu Pro Ala Gly Tyr Val Thr Lys Glu Leu Glu
    1130                1135                1140

Tyr Phe Pro Glu Thr Asp Lys Val Trp Ile Glu Ile Gly Glu Thr
    1145                1150                1155

Glu Gly Thr Phe Ile Val Asp Ser Val Glu Leu Leu Leu Met Glu
    1160                1165                1170

Glu

<210> SEQ ID NO 9
<211> LENGTH: 1169
<212> TYPE: PRT
<213> ORGANISM: Artificial Sequence
<220> FEATURE:
<223> OTHER INFORMATION: Engineered BT29-Cry1Fa1 chimeric protein.

<400> SEQUENCE: 9

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
            20                  25                  30

Val Ala Glu Ile His Leu Lys Ile Thr Arg Leu Ile Leu Glu Asn Phe
        35                  40                  45

Leu Pro Gly Gly Ser Phe Ala Phe Gly Leu Phe Asp Leu Ile Trp Gly
    50                  55                  60

Ile Phe Asn Glu Asp Gln Trp Ser Ala Phe Leu Arg Gln Val Glu Glu
65                  70                  75                  80

Leu Ile Asn Gln Arg Ile Thr Glu Phe Ala Arg Gly Gln Ala Ile Gln
                85                  90                  95

Arg Leu Val Gly Phe Gly Arg Ser Tyr Asp Glu Tyr Ile Leu Ala Leu
            100                 105                 110

Lys Glu Trp Glu Asn Asp Pro Asp Asn Pro Ala Ser Lys Glu Arg Val
        115                 120                 125

Arg Thr Arg Phe Arg Thr Thr Asp Asp Ala Leu Leu Thr Gly Val Pro
    130                 135                 140

Leu Met Ala Ile Pro Gly Phe Glu Leu Ala Thr Leu Ser Val Tyr Ala
145                 150                 155                 160

Gln Ser Ala Asn Leu His Leu Ala Leu Leu Arg Asp Ala Val Phe Phe
                165                 170                 175

Gly Glu Arg Trp Gly Leu Thr Gln Thr Asn Ile Asn Asp Leu Tyr Ser
            180                 185                 190

Arg Leu Lys Asn Ser Ile Arg Asp Tyr Thr Asn His Cys Val Arg Phe
        195                 200                 205

Tyr Asn Ile Gly Leu Gly Asn Leu Asn Val Ile Arg Pro Glu Tyr Tyr
    210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255

Leu Thr Arg Glu Ile Tyr Thr Asp Pro Ile Ile Ser Pro Gly Ala Gln
            260                 265                 270

-continued

Ala Gly Tyr Thr Leu Gln Asp Val Leu Arg Glu Pro His Leu Met Asp
            275                 280                 285

Phe Leu Asn Arg Leu Ile Ile Tyr Thr Gly Glu Tyr Arg Gly Ile Arg
        290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Thr Ala Glu Pro Thr
                325                 330                 335

Arg Phe Ile Thr Pro Ser Thr Phe Pro Gly Leu Asn Leu Phe Tyr Arg
            340                 345                 350

Thr Leu Ser Ala Pro Ile Phe Arg Asp Glu Pro Gly Ala Asn Ile Ile
        355                 360                 365

Ile Arg Tyr Arg Thr Ser Leu Val Glu Gly Val Gly Phe Ile Gln Pro
    370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                405                 410                 415

Arg Leu Cys His Val Arg Phe Ala Gln Ser Leu Arg Asn Ala Glu Pro
            420                 425                 430

Leu Asp Tyr Ala Arg Val Pro Met Phe Ser Trp Thr His Arg Ser Ala
        435                 440                 445

Thr Pro Thr Asn Thr Ile Asp Pro Asp Val Ile Thr Gln Ile Pro Leu
    450                 455                 460

Val Lys Ala His Thr Leu Gln Ser Gly Thr Thr Val Arg Gly Pro
465                 470                 475                 480

Gly Phe Thr Gly Gly Asp Ile Leu Arg Arg Thr Ser Gly Gly Pro Phe
                485                 490                 495

Ala Tyr Thr Ile Val Asn Ile Asn Gly Gln Leu Pro Gln Arg Tyr Arg
            500                 505                 510

Ala Arg Ile Arg Tyr Ala Ser Thr Thr Asn Leu Arg Ile Tyr Val Thr
        515                 520                 525

Val Ala Gly Glu Arg Ile Phe Ala Gly Gln Phe Asn Lys Thr Met Asp
    530                 535                 540

Thr Gly Asp Pro Leu Thr Phe Gln Ser Phe Ser Tyr Ala Thr Ile Asn
545                 550                 555                 560

Thr Ala Phe Thr Phe Pro Met Ser Gln Ser Ser Phe Thr Val Gly Ala
                565                 570                 575

Asp Thr Phe Ser Ser Gly Asn Glu Val Tyr Ile Asp Arg Phe Glu Leu
            580                 585                 590

Ile Pro Val Thr Ala Thr Phe Glu Ala Glu Tyr Asp Leu Glu Lys Ala
        595                 600                 605

Gln Lys Ala Val Asn Ala Leu Phe Thr Ser Ser Asn Gln Ile Gly Leu
    610                 615                 620

Lys Thr Asp Val Thr Asp Tyr His Ile Asp Lys Val Ser Asn Leu Val
625                 630                 635                 640

Glu Cys Leu Ser Asp Glu Phe Cys Leu Asp Glu Lys Arg Glu Leu Ser
                645                 650                 655

Glu Lys Val Lys His Ala Lys Arg Leu Cys Asp Glu Arg Asn Leu Leu
            660                 665                 670

Gln Asp Pro Asn Phe Arg Gly Ile Asn Arg Gln Pro Asp Arg Gly Trp
        675                 680                 685

Arg Gly Ser Thr Asp Ile Thr Ile Gln Gly Gly Asp Asp Val Phe Lys

-continued

```
            690                 695                 700
Glu Asn Tyr Val Thr Leu Pro Gly Thr Phe Asp Glu Cys Tyr Pro Thr
705                 710                 715                 720

Tyr Leu Tyr Gln Lys Ile Asp Glu Ser Lys Leu Lys Ala Tyr Thr Arg
                725                 730                 735

Tyr Glu Leu Arg Gly Tyr Ile Glu Asp Ser Gln Asp Leu Glu Ile Tyr
                740                 745                 750

Leu Ile Arg Tyr Asn Ala Lys His Glu Thr Val Asn Val Pro Gly Thr
                755                 760                 765

Gly Ser Leu Trp Pro Leu Ser Ala Gln Ser Pro Ile Gly Lys Cys Gly
                770                 775                 780

Glu Pro Asn Arg Cys Ala Thr His Leu Glu Trp Asn Pro Asp Leu Asp
785                 790                 795                 800

Cys Ser Cys Arg Asp Gly Glu Lys Cys Ala His His Ser His His Phe
                805                 810                 815

Ser Leu Asp Ile Asp Val Gly Cys Thr Asp Leu Asn Glu Asp Leu Gly
                820                 825                 830

Val Trp Val Ile Phe Lys Ile Lys Thr Gln Asp Gly His Ala Arg Leu
                835                 840                 845

Gly Asn Leu Glu Phe Leu Glu Glu Lys Pro Leu Val Gly Glu Ala Leu
850                 855                 860

Ala Arg Val Lys Arg Ala Glu Lys Lys Trp Arg Asp Lys Arg Glu Lys
865                 870                 875                 880

Leu Glu Leu Glu Thr Asn Ile Val Tyr Lys Glu Ala Lys Lys Ser Val
                885                 890                 895

Asp Ala Leu Phe Val Asn Ser Gln Tyr Asp Arg Leu Gln Ala Asp Thr
                900                 905                 910

Asn Ile Ala Ile Ile His Ala Ala Asp Lys Arg Val His Ser Ile Arg
                915                 920                 925

Glu Ala Tyr Leu Pro Glu Leu Ser Val Ile Pro Gly Val Asn Ala Ala
                930                 935                 940

Ile Phe Glu Glu Leu Glu Gly Arg Ile Phe Thr Ala Tyr Ser Leu Tyr
945                 950                 955                 960

Asp Ala Arg Asn Val Ile Lys Asn Gly Asp Phe Asn Asn Gly Leu Ser
                965                 970                 975

Cys Trp Asn Val Lys Gly His Val Asp Val Glu Glu Gln Asn Asn His
                980                 985                 990

Arg Ser Val Leu Val Val Pro Glu Trp Glu Ala Glu Val Ser Gln Glu
                995                 1000                1005

Val Arg Val Cys Pro Gly Arg Gly Tyr Ile Leu Arg Val Thr Ala
    1010                1015                1020

Tyr Lys Glu Gly Tyr Gly Glu Gly Cys Val Thr Ile His Glu Ile
    1025                1030                1035

Glu Asp Asn Thr Asp Glu Leu Lys Phe Ser Asn Cys Val Glu Glu
    1040                1045                1050

Glu Ile Tyr Pro Asn Asn Thr Val Thr Cys Asn Asp Tyr Thr Ala
    1055                1060                1065

Thr Gln Glu Glu Tyr Glu Gly Thr Tyr Thr Ser Arg Asn Arg Gly
    1070                1075                1080

Tyr Asp Gly Ala Tyr Glu Ser Asn Ser Ser Val Pro Ala Asp Tyr
    1085                1090                1095

Ala Ser Ala Tyr Glu Glu Lys Ala Tyr Thr Asp Gly Arg Arg Asp
    1100                1105                1110
```

```
Asn Thr Cys Glu Ser Asn Arg Gly Tyr Gly Asp Tyr Thr Pro Leu
    1115            1120                1125

Pro Ala Gly Tyr Val Thr Lys Glu Leu Glu Tyr Phe Pro Glu Thr
    1130            1135                1140

Asp Lys Val Trp Ile Glu Ile Gly Glu Thr Glu Gly Thr Phe Ile
    1145            1150                1155

Val Asp Ser Val Glu Leu Leu Leu Met Glu Glu
    1160            1165
```

<210> SEQ ID NO 10
<211> LENGTH: 3510
<212> TYPE: DNA
<213> ORGANISM: Artificial Sequence
<220> FEATURE:
<223> OTHER INFORMATION: BT29-Cry1Fa1 coding sequence.

<400> SEQUENCE: 10

```
atggagatta taatcagaa ccaatgtgtc ccttataatt gtttgaataa tcctgaaagc      60
gagatattaa acgttgcaat ttttagtagc gaacaggtag cagaaattca cttaaagatc    120
acgcgcttaa ttttagagaa tttttttacca ggtgggagtt ttgcattcgg cttatttgat   180
ttaatatggg ggattttttaa tgaagatcaa tggagcgcat tcttcggca ggtagaagaa    240
ttaattaatc aaaggataac ggaattcgca agagggcaag caattcagag actagtaggg   300
tttggaagga gttatgatga atatatttta gcactaaaag aatgggaaaa cgatcctgat   360
aacccagctt caaggaaag agtgcgcact cgatttcgga caactgatga tgccttgcta   420
accggtgttc ctcttatggc aattccaggt tttgaattag ctactttatc tgtttatgct   480
caatcagcca atctacattt agccctatta gagagatgctg tattttttgg ggagagatgg   540
ggattgacac aaacaaatat aaatgattta tatagtagat taaaaaactc cattcgtgat    600
tatacaaatc attgtgttcg tttttataat ataggtttag ggaatttaaa tgttataaga    660
ccagagtatt accgtttcca aagagaatta acaatatctg tcttagatct tgtagctctt    720
tttccaaatt acgatatccg aacatatcca ataccaacta aagtcaatt aacaagagaa    780
atttatacag atccgattat ttcacctggt gcacaggcag ttatactct tcaagatgtt   840
ttgagagaac cacaccttat ggacttttta aaccgactta ttatttatac tggtgagtat    900
cgcggaattc gtcactgggc aggacatgaa gtagaatcta gtagaacagg tatgatgact    960
aatataagat tccctttgta tggaacagcc gcaacagcag aaccaacacg atttataact   1020
cctagtactt ttcctggtct taatttattt tatagaacat tatcagctcc tatttttaga   1080
gatgaaccgg gagctaatat tattattaga tatagaacga gtttggtgga aggagtagga   1140
tttattcaac caaataacgg tgaacagctt tacagagtga gaggaacatt agattctctt   1200
gatcaattac cacttgaggg tgagagtagt ctaactgaat atagtcatcg attatgccat   1260
gttagatttg cgcaatcatt gaggaatgca gaacctttag attatgcaag ggttccgatg   1320
ttttcttgga cacatcgtag tgcaaccccct acaaatacaa ttgatccaga tgtcatcacc   1380
caaatacccgt tagtaaaagc acatacactt cagtcaggta ctactgttgt aagagggccc   1440
gggtttacgg gaggagatat tcttcgacga caagtggag gaccatttgc ttatactatt   1500
gttaatataa atgggcaatt accccaaagg tatcgtgcaa gaatacgcta tgcctctact   1560
acaaatctaa gaatttacgt aacggttgca ggtgaacgga ttttgctgg tcaatttaac   1620
aaaacaatgg ataccggtga cccattaaca ttccaatctt ttagttacgc aactattaat   1680
```

-continued acagctttta cattcccaat gagccagagt agtttcacag taggtgctga tacttttagt 1740
tcagggaatg aagtttatat agacagattt gaattgattc cagttactgc aacatttgag 1800
gcagaatatg atttagagaa agctcagaaa gcggtgaatg cgctgtttac ttcttccaat 1860
caaatcgggt taaaaacaga tgtgacggac tatcatattg ataaagtatc caatctagtt 1920
gagtgtttat cagatgaatt ttgtctagat gaaaagcgag aattgtccga gaaagtcaaa 1980
catgcgaagc gactctgtga tgagcggaat ttacttcaag atccaaactt cagaggcatc 2040
aatagacaac cagaccgtgg ttggagagga agtacggata ttaccatcca aggaggagat 2100
gacgtattca aagagaatta cgttacgcta ccgggtacct ttgatgagtg ctatccaacg 2160
tatttatatc aaaaaataga tgagtcgaaa ttaaaagcct atacccgcta tgaattaaga 2220
gggtatatcg aggatagtca agacttagaa atctatttaa ttcgctacaa tgcaaaacat 2280
gaaacagtaa atgtgccagg tacgggttcc ttatggccgc tttcagccca aagtccaatc 2340
ggaaagtgtg gagaaccgaa tcgatgtgcg acacaccttg aatggaatcc tgacttagat 2400
tgttcgtgta gggatggaga aaagtgtgcc catcattcgc atcatttctc cttagacatt 2460
gatgtaggat gtacagacct aaatgaggac ctaggtgtat gggtgatctt taagattaag 2520
acgcaagatg gtcatgcgag actaggaaat ctagaatttc tcgaagagaa accattagta 2580
ggagaagcgc tagctcgtgt gaagagagcg gagaaaaaat ggagagacaa acgcgaaaaa 2640
ttggaattgg aaacaaatat tgtttataaa gaggcaaaaa aatctgtaga tgctttattt 2700
gtgaactctc aatatgatag attacaagcg gatacgaata tcgcgataat tcatgcggca 2760
gataaacgcg ttcatagcat tcgagaagca tatcttccag agttgtctgt aattccgggt 2820
gtaaatgcag ctatttttga agaattagag ggacgtattt tcacagccta ctctctatat 2880
gatgcgagaa atgtcattaa aaatggcgat ttcaataatg gcttatcatg ctggaacgtg 2940
aaagggcatg tagatgtaga agaacagaac aaccatcgtt cggtccttgt tgttccagaa 3000
tgggaagcag aagtgtcaca agaggttcgt gtctgtccag gtcgtggcta tatccttcgt 3060
gttacagcgt acaaagaggg atatggagag ggctgtgtaa cgattcatga gatcgaagac 3120
aatacagacg aactgaaatt cagcaactgt gtagaagagg aaatatatcc aaacaacacg 3180
gtaacgtgta atgattatac tgcgactcaa gaagaatatg agggtacgta cacttctcgt 3240
aatcgaggat atgacggagc ctatgaaagc aattcttctg taccagctga ttatgcatca 3300
gcctatgaag aaaaagcgta tacagatgga agaagagaca atacttgtga atctaacaga 3360
ggatatgggg attacacacc actaccagct ggctatgtga caaaagaatt agagtacttc 3420
ccagaaaccg ataaggtatg gattgagatt ggagaaacgg aaggaacatt tatcgtggac 3480
agcgtggaat tactccttat ggaggaatag 3510

<210> SEQ ID NO 11
<211> LENGTH: 3510
<212> TYPE: DNA
<213> ORGANISM: Artificial Sequence
<220> FEATURE:
<223> OTHER INFORMATION: Maize optimized BT29-Cry1Fa1 coding sequence.

<400> SEQUENCE: 11
atggaaatca acaaccagaa ccagtgcgtg ccgtacaact gcctcaacaa ccccgagtcc 60
gagatcctga acgtggccat cttctccagc gagcaggtcg cggagatcca cctcaagatc 120
acgcgcctga tcctcgagaa cttcctgccg ggcggctcct tcgctttcgg cctgttcgac 180
ctcatctggg gcatcttcaa cgaggaccag tggagcgcgt tcctcaggca ggtggaggag 240

```
ctgatcaacc agcgcatcac ggagttcgcc aggggccagg ctatccagcg gctggtgggc      300
ttcggcaggt cctacgacga atacatcctg gccctcaagg agtgggagaa cgaccccgac      360
aacccggcca gcaaggagcg cgtgaggacc cgcttcagga ccaccgacga cgctctcctg      420
acgggcgtcc ccctcatggc tatcccgggc ttcgagctgg ccaccctctc ggtgtacgct      480
cagtcggcca acctgcacct cgccctcctg cgggacgctg tgttcttcgg cgagaggtgg      540
ggcctgaccc aaaccaacat caacgacctc tactccaggc tgaagaacag catccgcgac      600
tacacgaacc actgcgtgcg cttctacaac atcggcctgg gcaacctcaa cgtcatcagg      660
ccggaatact accgcttcca gagggagctg accatcagcg tgctggacct cgtcgccctg      720
ttccccaact acgacatccg cacgtacccg atccccacca agtcccagct cacgagggag      780
atctacaccg acccgatcat ctcgccgggc gcccaggccg gctacaccct gcaggacgtc      840
ctgagggagc cccacctgat ggacttcctg aacaggctca tcatctacac cggcgagtac      900
aggggcatca ggcactgggc gggccacgag gtggagtcca gcaggacggg catgatgacc      960
aacatccgct tcccgctcta cggcaccgcg gccacggccg agccaacccg cttcatcacg     1020
ccgtccacct tccccggcct gaacctcttc tacaggaccc tgtcggctcc catcttccgc     1080
gacgagccgg gcgcgaacat catcatccgc tacaggacct ccctcgtgga gggcgtcggc     1140
ttcatccagc cgaacaacgg cgagcagctg taccgcgtga ggggcacgct ggacagcctg     1200
gaccagctcc cactggaggg cgagtccagc ctcaccgagt actcgcacag gctgtgccac     1260
gtcaggttcg cccagagcct caggaacgcg gagcccctgg actacgccag ggtgcccatg     1320
ttcagctgga cccacaggtc ggctaccccc accaacacca tcgacccaga cgtgatcacg     1380
cagatcccgc tcgtcaaggc ccacaccctg cagtcgggca ccaccgtggt ccgcggccca     1440
ggcttcaccg gcggcgacat cctgaggagg acgagcggcg gccccttcgc ttacaccatc     1500
gtcaacatca cggccagct gccacagagg tacagggcgc gcatcaggta cgcctccacc     1560
acgaacctgc gcatctacgt gaccgtggcg ggcgagagga tcttcgccgg ccagttcaac     1620
aagacgatgg acaccggcga cccgctgacc ttccagtcct tcagctacgc gacgatcaac     1680
accgccttca cgttccccat gagccagtcc agcttcaccg tgggcgccga cacgttctcc     1740
agcggcaacg aggtgtacat cgaccgcttc gagctgatcc cggtgacggc gaccttcgag     1800
gccgagtacg acctggagaa ggcccagaag gcggtcaacg ccctcttcac ctccagcaac     1860
cagatcggcc tgaagacgga cgtgaccgac taccacatcg acaaggtgtc caacctcgtc     1920
gagtgcctga gcgacgagtt ctgcctcgac gagaagaggg agctgtccga aaggtcaag      1980 cacgccaagc gcctctgcga cgagaggaac ctcctgcagg acccgaactt caggggcatc     2040
aaccgccagc cggacagggg ctggaggggc agcaccgaca tcaccatcca gggcggcgac     2100
gacgtgttca aggagaacta cgtcacgctc ccgggcacct tcgacgagtg ctaccccacg     2160
tacctgtacc agaagatcga cgagtccaag ctcaaggcct acacccgcta cgagctgagg     2220
ggctacatcg aggacagcca ggacctcgag atctacctga tccgctacaa cgcgaagcac     2280
gagacggtga acgtccccgg cacgggctcc ctgtggcccc tctcggctca gtcgccgatc     2340
ggcaagtgcg cgagcccaa caggtgcgcc acccacctcg agtggaaccc ggacctggac      2400
tgctcctgcc gggacggcga gaagtgcgct caccactccc accacttcag cctggacatc     2460
gacgtgggct gcacggacct caacgaggac ctgggcgtgt gggtcatctt caagatcaag     2520
acgcaggacg gccacgctag gctgggcaac ctcgagttcc tggaggagaa gccgctggtg     2580
```

```
ggcgaggctc tggccagggt caagagggcg gagaagaagt ggcgcgacaa gagggagaag    2640
ctggagctgg agacgaacat cgtctacaag gaggccaaga agtccgtgga cgcgctcttc    2700
gtcaacagcc agtacgacag gctgcaggcg acaccaaca tcgccatcat ccacgccgcg    2760
gacaagcgcg tgcactccat cagggaggcc tacctccccg agctgagcgt gatcccgggc    2820
gtcaacgctg ccatcttcga ggagctggag ggccgcatct tcaccgccta ctccctgtac    2880
gacgcgagga acgtcatcaa gaacggcgac ttcaacaacg gcctcagctg ctggaacgtg    2940
aagggccacg tggacgtcga ggagcagaac aaccaccgct cggtgctggt ggtccccgag    3000
tgggaggctg aggtcagcca ggaggtgcgc gtctgcccgg gcaggggcta catcctccgc    3060
gtgaccgcgt acaaggaggg ctacggcgag ggctgcgtca cgatccacga gatcgaggac    3120
aacaccgacg agctgaagtt ctccaactgc gtggaggagg agatctaccc gaacaacacg    3180
gtcacctgca cgactacac ggccacccag gaggagtacg agggcacgta cacgtcgagg    3240
aacaggggct acgacggcgc ttacgagtcc aacagctcgg tgccggccga ctacgctagc    3300
gcgtacgagg agaaggccta cacggacggc cgcagggaca cacctgcga gtcgaacagg    3360 ggctacggcg actacacgcc gctcccggcc ggctacgtga ccaaggagct ggagtacttc    3420
ccggagacgg acaaggtctg gatcgagatc ggcgagacgg agggcacctt catcgtggac    3480
agcgtcgagc tgctgctcat ggaggagtag                                    3510
```

<210> SEQ ID NO 12
<211> LENGTH: 1215
<212> TYPE: PRT
<213> ORGANISM: Bacillus thuringiensis

<400> SEQUENCE: 12

```
Met Asn Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Pro Asp
            20                  25                  30

Ala Arg Ile Glu Asp Ser Leu Cys Val Ala Glu Gly Asn Asn Ile Asp
        35                  40                  45

Pro Phe Val Ser Ala Ser Thr Val Gln Thr Gly Ile Ser Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
                85                  90                  95

Trp Glu Ile Phe Met Glu His Val Glu Gln Ile Val Arg Gln Gln Gln
            100                 105                 110

Ile Thr Asp Ser Val Arg Asp Thr Ala Ile Ala Arg Leu Glu Gly Leu
        115                 120                 125

Gly Arg Gly Tyr Arg Ser Tyr Gln Gln Ala Leu Glu Thr Trp Leu Asp
    130                 135                 140

Asn Arg Asn Asp Ala Arg Ser Arg Ser Ile Ile Arg Glu Arg Tyr Ile
145                 150                 155                 160

Ala Leu Glu Leu Asp Ile Thr Thr Ala Ile Pro Leu Phe Ser Ile Arg
                165                 170                 175

Asn Glu Glu Val Pro Leu Leu Met Val Tyr Ala Gln Ala Ala Asn Leu
            180                 185                 190

His Leu Leu Leu Leu Arg Asp Ala Ser Leu Phe Gly Ser Glu Trp Gly
        195                 200                 205
```

-continued

```
Met Ser Ser Ala Asp Val Asn Gln Tyr Tyr Gln Glu Gln Ile Arg Tyr
    210                 215                 220
Thr Glu Glu Tyr Ser Asn His Cys Val Gln Trp Tyr Asn Thr Gly Leu
225                 230                 235                 240
Asn Arg Leu Arg Gly Thr Thr Ala Glu Thr Trp Val Arg Tyr Asn Gln
                245                 250                 255
Phe Arg Arg Asp Leu Thr Leu Gly Val Leu Asp Leu Val Ala Leu Phe
            260                 265                 270
Pro Ser Tyr Asp Thr Arg Thr Tyr Pro Ile Pro Thr Thr Ala Gln Leu
        275                 280                 285
Thr Arg Glu Val Tyr Thr Asp Pro Asn Gly Val Val Ala Gly Pro Asn
290                 295                 300
Asn Ser Trp Phe Arg Asn Gly Ala Ser Phe Ser Ala Ile Glu Asn Ala
305                 310                 315                 320
Ile Ile Arg Gln Pro His Leu Tyr Asp Phe Leu Thr Asn Leu Thr Ile
                325                 330                 335
Tyr Thr Arg Arg Ser Gln Val Gly Thr Thr Ile Met Asn Leu Trp Ala
            340                 345                 350
Gly His Arg Ile Thr Phe Asn Arg Ile Gln Gly Gly Ser Thr Ser Glu
        355                 360                 365
Met Val Tyr Gly Ala Ile Thr Asn Pro Val Ser Val Ser Asp Ile Pro
370                 375                 380
Phe Val Asn Arg Asp Val Tyr Arg Thr Val Ser Leu Ala Gly Gly Leu
385                 390                 395                 400
Gly Ser Leu Ser Gly Ile Arg Tyr Gly Leu Thr Arg Val Asp Phe Asp
                405                 410                 415
Met Ile Phe Arg Asn His Pro Asp Ile Val Thr Gly Leu Phe Tyr His
            420                 425                 430
Pro Gly His Ala Gly Ile Ala Thr Gln Val Lys Asp Ser Asp Thr Glu
        435                 440                 445
Leu Pro Pro Glu Thr Thr Glu Gln Pro Asn Tyr Arg Ala Phe Ser His
450                 455                 460
Leu Leu Ser His Ile Ser Met Gly Pro Thr Thr Gln Asp Val Pro Pro
465                 470                 475                 480
Val Tyr Ser Trp Thr His Gln Ser Ala Asp Arg Thr Asn Thr Ile Asn
                485                 490                 495
Ser Asp Arg Ile Thr Gln Ile Pro Leu Val Lys Ala His Thr Leu Gln
            500                 505                 510
Ser Gly Thr Thr Val Val Lys Gly Pro Gly Phe Thr Gly Gly Asp Ile
        515                 520                 525
Leu Arg Arg Thr Ser Gly Gly Pro Phe Ala Phe Ser Asn Val Asn Leu
530                 535                 540
Asp Phe Asn Leu Ser Gln Arg Tyr Arg Ala Arg Ile Arg Tyr Ala Ser
545                 550                 555                 560
Thr Thr Asn Leu Arg Ile Tyr Val Thr Val Ala Gly Glu Arg Ile Phe
                565                 570                 575
Ala Gly Gln Phe Asp Lys Thr Met Asp Ala Gly Ala Pro Leu Thr Phe
            580                 585                 590
Gln Ser Phe Ser Tyr Ala Thr Ile Asn Thr Ala Phe Thr Phe Pro Glu
        595                 600                 605
Arg Ser Ser Ser Leu Thr Ile Gly Ala Asp Thr Phe Ser Ser Gly Asn
610                 615                 620
Glu Val Tyr Val Asp Arg Phe Glu Leu Ile Gln Val Thr Ala Thr Phe
```

-continued

```
           625                 630                 635                 640
        Glu Ala Glu Ser Asp Leu Glu Arg Ala Arg Lys Ala Val Asn Ala Leu
                        645                 650                 655
        Phe Thr Ser Thr Asn Pro Arg Gly Leu Lys Thr Asp Val Thr Asp Tyr
                        660                 665                 670
        His Ile Asp Gln Val Ser Asn Leu Val Glu Cys Leu Ser Asp Glu Phe
                        675                 680                 685
        Cys Leu Asp Lys Lys Arg Glu Leu Leu Glu Glu Val Lys Tyr Ala Lys
                        690                 695                 700
        Arg Leu Ser Asp Glu Arg Asn Leu Leu Gln Asp Pro Thr Phe Thr Ser
        705                 710                 715                 720
        Ile Ser Gly Gln Thr Asp Arg Gly Trp Ile Gly Ser Thr Gly Ile Ser
                        725                 730                 735
        Ile Gln Gly Gly Asp Asp Ile Phe Lys Glu Asn Tyr Val Arg Leu Pro
                        740                 745                 750
        Gly Thr Val Asp Glu Cys Tyr Pro Thr Tyr Leu Tyr Gln Lys Ile Asp
                        755                 760                 765
        Glu Ser Gln Leu Lys Ser Tyr Thr Arg Tyr Gln Leu Arg Gly Tyr Ile
                        770                 775                 780
        Glu Asp Ser Gln Asp Leu Glu Ile Tyr Leu Ile Arg Tyr Asn Ala Lys
        785                 790                 795                 800
        His Glu Thr Leu Ser Val Pro Gly Thr Glu Ser Pro Trp Pro Ser Ser
                        805                 810                 815
        Gly Val Tyr Pro Ser Gly Arg Cys Gly Glu Pro Asn Arg Cys Ala Pro
                        820                 825                 830
        Arg Ile Glu Trp Asn Pro Asp Leu Asp Cys Ser Cys Arg Tyr Gly Glu
                        835                 840                 845
        Lys Cys Val His His Ser His His Phe Ser Leu Asp Ile Asp Val Gly
                        850                 855                 860
        Cys Thr Asp Leu Asn Glu Asp Leu Gly Val Trp Val Ile Phe Lys Ile
        865                 870                 875                 880
        Lys Thr Gln Asp Gly His Ala Lys Leu Gly Asn Leu Glu Phe Ile Glu
                        885                 890                 895
        Glu Lys Pro Leu Leu Gly Lys Ala Leu Ser Arg Val Lys Arg Ala Glu
                        900                 905                 910
        Lys Lys Trp Arg Asp Lys Tyr Glu Lys Leu Gln Leu Glu Thr Lys Arg
                        915                 920                 925
        Val Tyr Thr Glu Ala Lys Glu Ser Val Asp Ala Leu Phe Val Asp Ser
        930                 935                 940
        Gln Tyr Asp Lys Leu Gln Ala Asn Thr Asn Ile Gly Ile Ile His Gly
        945                 950                 955                 960
        Ala Asp Lys Gln Val His Arg Ile Arg Glu Pro Tyr Leu Ser Glu Leu
                        965                 970                 975
        Pro Val Ile Pro Ser Ile Asn Ala Ala Ile Phe Glu Glu Leu Glu Gly
                        980                 985                 990
        His Ile Phe Lys Ala Tyr Ser Leu Tyr Asp Ala Arg Asn Val Ile Lys
                        995                 1000                1005
        Asn Gly Asp Phe Asn Asn Gly Leu Ser Cys Trp Asn Val Lys Gly
                        1010                1015                1020
        His Val Asp Val Gln Gln Asn His His Arg Ser Val Leu Val Leu
                        1025                1030                1035
        Ser Glu Trp Glu Ala Glu Val Ser Gln Lys Val Arg Val Cys Pro
                        1040                1045                1050
```

Asp Arg Gly Tyr Ile Leu Arg Val Thr Ala Tyr Lys Glu Gly Tyr
1055 1060 1065

Gly Glu Gly Cys Val Thr Ile His Glu Phe Glu Asp Asn Thr Asp
1070 1075 1080

Val Leu Lys Phe Arg Asn Phe Val Glu Glu Glu Val Tyr Pro Asn
1085 1090 1095

Asn Thr Val Thr Cys Asn Asp Tyr Thr Thr Asn Gln Ser Ala Glu
1100 1105 1110

Gly Ser Thr Asp Ala Cys Asn Ser Tyr Asn Arg Gly Tyr Glu Asp
1115 1120 1125

Gly Tyr Glu Asn Arg Tyr Glu Pro Asn Pro Ser Ala Pro Val Asn
1130 1135 1140

Tyr Thr Pro Thr Tyr Glu Glu Gly Met Tyr Thr Asp Thr Gln Gly
1145 1150 1155

Tyr Asn His Cys Val Ser Asp Arg Gly Tyr Arg Asn His Thr Pro
1160 1165 1170

Leu Pro Ala Gly Tyr Val Thr Leu Glu Leu Glu Tyr Phe Pro Glu
1175 1180 1185

Thr Glu Gln Val Trp Ile Glu Ile Gly Glu Thr Glu Gly Thr Phe
1190 1195 1200

Ile Val Gly Ser Val Glu Leu Leu Leu Met Glu Glu
1205 1210 1215

<210> SEQ ID NO 13
<211> LENGTH: 1169
<212> TYPE: PRT
<213> ORGANISM: Artificial Sequence
<220> FEATURE:
<223> OTHER INFORMATION: Engineered BT29-Cry1Ka1 chimeric protein.

<400> SEQUENCE: 13

Met Glu Ile Asn Asn Gln Asn Gln Cys Val Pro Tyr Asn Cys Leu Asn
1 5 10 15

Asn Pro Glu Ser Glu Ile Leu Asn Val Ala Ile Phe Ser Ser Glu Gln
20 25 30

Val Ala Glu Ile His Leu Lys Ile Thr Arg Leu Ile Leu Glu Asn Phe
35 40 45

Leu Pro Gly Gly Ser Phe Ala Phe Gly Leu Phe Asp Leu Ile Trp Gly
50 55 60

Ile Phe Asn Glu Asp Gln Trp Ser Ala Phe Leu Arg Gln Val Glu Glu
65 70 75 80

Leu Ile Asn Gln Arg Ile Thr Glu Phe Ala Arg Gly Gln Ala Ile Gln
85 90 95

Arg Leu Val Gly Phe Gly Arg Ser Tyr Asp Glu Tyr Ile Leu Ala Leu
100 105 110

Lys Glu Trp Glu Asn Asp Pro Asp Asn Pro Ala Ser Lys Glu Arg Val
115 120 125

Arg Thr Arg Phe Arg Thr Thr Asp Asp Ala Leu Leu Thr Gly Val Pro
130 135 140

Leu Met Ala Ile Pro Gly Phe Glu Leu Ala Thr Leu Ser Val Tyr Ala
145 150 155 160

Gln Ser Ala Asn Leu His Leu Ala Leu Leu Arg Asp Ala Val Phe Phe
165 170 175

Gly Glu Arg Trp Gly Leu Thr Gln Thr Asn Ile Asn Asp Leu Tyr Ser
180 185 190

```
Arg Leu Lys Asn Ser Ile Arg Asp Tyr Thr Asn His Cys Val Arg Phe
        195                 200                 205

Tyr Asn Ile Gly Leu Gly Asn Leu Asn Val Ile Arg Pro Glu Tyr Tyr
    210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255

Leu Thr Arg Glu Ile Tyr Thr Asp Pro Ile Ile Ser Pro Gly Ala Gln
            260                 265                 270

Ala Gly Tyr Thr Leu Gln Asp Val Leu Arg Glu Pro His Leu Met Asp
        275                 280                 285

Phe Leu Asn Arg Leu Ile Ile Tyr Thr Gly Glu Tyr Arg Gly Ile Arg
    290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Ala Thr Ala Glu Pro Thr
                325                 330                 335

Arg Phe Ile Thr Pro Ser Thr Phe Pro Gly Leu Asn Leu Phe Tyr Arg
            340                 345                 350

Thr Leu Ser Ala Pro Ile Phe Arg Asp Glu Pro Gly Ala Asn Ile Ile
        355                 360                 365

Ile Arg Tyr Arg Thr Ser Leu Val Glu Gly Val Gly Phe Ile Gln Pro
    370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                405                 410                 415

Arg Leu Cys His Val Arg Phe Ala Gln Ser Leu Arg Asn Ala Glu Pro
            420                 425                 430

Leu Asp Tyr Ala Arg Val Pro Met Phe Ser Trp Thr His Arg Ser Ala
        435                 440                 445

Thr Pro Thr Asn Thr Ile Asp Pro Asp Val Ile Thr Gln Ile Pro Leu
    450                 455                 460

Val Lys Ala His Thr Leu Gln Ser Gly Thr Thr Val Lys Gly Pro
465                 470                 475                 480

Gly Phe Thr Gly Gly Asp Ile Leu Arg Arg Thr Ser Gly Gly Pro Phe
                485                 490                 495

Ala Phe Ser Asn Val Asn Leu Asp Phe Asn Leu Ser Gln Arg Tyr Arg
            500                 505                 510

Ala Arg Ile Arg Tyr Ala Ser Thr Thr Asn Leu Arg Ile Tyr Val Thr
        515                 520                 525

Val Ala Gly Glu Arg Ile Phe Ala Gly Gln Phe Asp Lys Thr Met Asp
    530                 535                 540

Ala Gly Ala Pro Leu Thr Phe Gln Ser Phe Ser Tyr Ala Thr Ile Asn
545                 550                 555                 560

Thr Ala Phe Thr Phe Pro Glu Arg Ser Ser Leu Thr Ile Gly Ala
                565                 570                 575

Asp Thr Phe Ser Ser Gly Asn Glu Val Tyr Val Asp Arg Phe Glu Leu
            580                 585                 590

Ile Gln Val Thr Ala Thr Phe Glu Ala Glu Tyr Asp Leu Glu Lys Ala
        595                 600                 605
```

```
Gln Lys Ala Val Asn Ala Leu Phe Thr Ser Ser Asn Gln Ile Gly Leu
    610                 615                 620

Lys Thr Asp Val Thr Asp Tyr His Ile Asp Lys Val Ser Asn Leu Val
625                 630                 635                 640

Glu Cys Leu Ser Asp Glu Phe Cys Leu Asp Glu Lys Arg Glu Leu Ser
                645                 650                 655

Glu Lys Val Lys His Ala Lys Arg Leu Cys Asp Glu Arg Asn Leu Leu
            660                 665                 670

Gln Asp Pro Asn Phe Arg Gly Ile Asn Arg Gln Pro Asp Arg Gly Trp
        675                 680                 685

Arg Gly Ser Thr Asp Ile Thr Ile Gln Gly Gly Asp Asp Val Phe Lys
690                 695                 700

Glu Asn Tyr Val Thr Leu Pro Gly Thr Phe Asp Glu Cys Tyr Pro Thr
705                 710                 715                 720

Tyr Leu Tyr Gln Lys Ile Asp Glu Ser Lys Leu Lys Ala Tyr Thr Arg
                725                 730                 735

Tyr Glu Leu Arg Gly Tyr Ile Glu Asp Ser Gln Asp Leu Glu Ile Tyr
            740                 745                 750

Leu Ile Arg Tyr Asn Ala Lys His Glu Thr Val Asn Val Pro Gly Thr
        755                 760                 765

Gly Ser Leu Trp Pro Leu Ser Ala Gln Ser Pro Ile Gly Lys Cys Gly
770                 775                 780

Glu Pro Asn Arg Cys Ala Thr His Leu Glu Trp Asn Pro Asp Leu Asp
785                 790                 795                 800

Cys Ser Cys Arg Asp Gly Glu Lys Cys Ala His His Ser His His Phe
                805                 810                 815

Ser Leu Asp Ile Asp Val Gly Cys Thr Asp Leu Asn Glu Asp Leu Gly
            820                 825                 830

Val Trp Val Ile Phe Lys Ile Lys Thr Gln Asp Gly His Ala Arg Leu
        835                 840                 845

Gly Asn Leu Glu Phe Leu Glu Glu Lys Pro Leu Val Gly Glu Ala Leu
850                 855                 860

Ala Arg Val Lys Arg Ala Glu Lys Lys Trp Arg Asp Lys Arg Glu Lys
865                 870                 875                 880

Leu Glu Leu Glu Thr Asn Ile Val Tyr Lys Glu Ala Lys Lys Ser Val
                885                 890                 895

Asp Ala Leu Phe Val Asn Ser Gln Tyr Asp Arg Leu Gln Ala Asp Thr
            900                 905                 910

Asn Ile Ala Ile Ile His Ala Ala Asp Lys Arg Val His Ser Ile Arg
        915                 920                 925

Glu Ala Tyr Leu Pro Glu Leu Ser Val Ile Pro Gly Val Asn Ala Ala
930                 935                 940

Ile Phe Glu Glu Leu Glu Gly Arg Ile Phe Thr Ala Tyr Ser Leu Tyr
945                 950                 955                 960

Asp Ala Arg Asn Val Ile Lys Asn Gly Asp Phe Asn Asn Gly Leu Ser
                965                 970                 975

Cys Trp Asn Val Lys Gly His Val Asp Val Glu Glu Gln Asn Asn His
            980                 985                 990

Arg Ser Val Leu Val Val Pro Glu Trp Glu Ala Glu Val Ser Gln Glu
        995                 1000                1005

Val Arg Val Cys Pro Gly Arg Gly Tyr Ile Leu Arg Val Thr Ala
        1010                1015                1020

Tyr Lys Glu Gly Tyr Gly Glu Gly Cys Val Thr Ile His Glu Ile
```

Glu Asp Asn Thr Asp Glu Leu Lys Phe Ser Asn Cys Val Glu Glu
    1040                1045                1050

Glu Ile Tyr Pro Asn Asn Thr Val Thr Cys Asn Asp Tyr Thr Ala
    1055                1060                1065

Thr Gln Glu Glu Tyr Glu Gly Thr Tyr Thr Ser Arg Asn Arg Gly
    1070                1075                1080

Tyr Asp Gly Ala Tyr Glu Ser Asn Ser Ser Val Pro Ala Asp Tyr
    1085                1090                1095

Ala Ser Ala Tyr Glu Glu Lys Ala Tyr Thr Asp Gly Arg Arg Asp
    1100                1105                1110

Asn Thr Cys Glu Ser Asn Arg Gly Tyr Gly Asp Tyr Thr Pro Leu
    1115                1120                1125

Pro Ala Gly Tyr Val Thr Lys Glu Leu Glu Tyr Phe Pro Glu Thr
    1130                1135                1140

Asp Lys Val Trp Ile Glu Ile Gly Glu Thr Glu Gly Thr Phe Ile
    1145                1150                1155

Val Asp Ser Val Glu Leu Leu Leu Met Glu Glu
    1160                1165

<210> SEQ ID NO 14
<211> LENGTH: 3510
<212> TYPE: DNA
<213> ORGANISM: Artificial Sequence
<220> FEATURE:
<223> OTHER INFORMATION: BT29-Cry1Ka1 coding sequence.

<400> SEQUENCE: 14
atggagatta taatcagaa ccaatgtgtc ccttataatt gtttgaataa tcctgaaagc    60
gagatattaa acgttgcaat ttttagtagc gaacaggtag cagaaattca cttaaagatc   120
acgcgcttaa ttttagagaa tttttttacca ggtgggagtt ttgcattcgg cttatttgat   180
ttaatatggg ggattttaa tgaagatcaa tggagcgcat tcttcggca ggtagaagaa    240 ttaattaatc aaaggataac ggaattcgca gagggcaag caattcagag actagtaggg    300
tttggaagga gttatgatga atatattta gcactaaaag aatgggaaaa cgatcctgat    360
aacccagctt caaggaaag agtgcgcact cgatttcgga caactgatga tgccttgcta    420
accggtgttc ctcttatggc aattccaggt tttgaattag ctactttatc tgtttatgct    480
caatcagcca atctacattt agccctatta agagatgctg tatttttgg ggagagatgg    540 ggattgcac aaacaaatat aaatgattta tatagtagat taaaaaactc cattcgtgat    600
tatacaaatc attgtgttcg tttttataat ataggtttag ggaatttaaa tgttataaga    660
ccagagtatt accgtttcca aagagaatta acaatatctg tcttagatct tgtagctctt    720
tttccaaatt acgatatccg aacatatcca ataccaacta aaagtcaatt aacaagagaa    780
atttatacag atccgattat ttcacctggt gcacaggcag ttatactct tcaagatgtt    840 ttgagagaac acaccttat ggacttttta aaccgactta ttatttatac tggtgagtat    900
cgcggaattc gtcactgggc aggacatgaa gtagaatcta gtagaacagg tatgatgact    960
aatataagat ttccttgta tggaacagcc gcaacagcag aaccaacacg atttataact   1020
cctagtactt ttcctggtct taatttattt tatagaacat tatcagctcc tatttttaga   1080
gatgaaccgg gagctaatat tattattaga tatagaacga gtttggtgga aggagtagga   1140
tttattcaac caaataacgg tgaacagctt tacagagtga gaggaacatt agattctctt   1200

```
gatcaattac cacttgaggg tgagagtagt ctaactgaat atagtcatcg attatgccat    1260
gttagatttg cgcaatcatt gaggaatgca gaacctttag attatgcaag ggttccgatg    1320
ttttcttgga cacatcgtag tgcaacccct acaaatacaa ttgatccaga tgtcatcacc    1380
caaataccgt tagtaaaggc gcatacccctc caatcgggta caactgtagt aaaagggcca    1440
gggtttacag gaggggatat cctccgtcga acaagtggag gaccatttgc ttttagtaat    1500
gttaatctag attttaactt gtcacaaagg tatcgtgcta gaattcgtta tgcctctact    1560
actaacctaa gaatttacgt aacggttgca ggtgaacgaa tttttgctgg tcaatttgac    1620
aaaacgatgg atgctggtgc cccattaaca ttccaatctt ttagttacgc aactattaat    1680
acagctttta cattcccaga aagatcgagc agcttgacta taggtgccga tacgtttagt    1740
tcaggtaatg aagtttatgt agatagattt gaattaatcc aagttactgc aacatttgag    1800
gcagaatatg atttagagaa agctcagaaa gcggtgaatg cgctgtttac ttcttccaat    1860
caaatcgggt taaaaacaga tgtgacggac tatcatattg ataaagtatc caatctagtt    1920
gagtgtttat cagatgaatt ttgtctagat gaaaagcgag aattgtccga gaaagtcaaa    1980
catgcgaagc gactctgtga tgagcggaat ttacttcaag atccaaactt cagaggcatc    2040
aatagacaac cagaccgtgg ttggagagga agtacggata ttaccatcca aggaggagat    2100
gacgtattca aagagaatta cgttacgcta ccgggtacct ttgatgagtg ctatccaacg    2160
tatttatatc aaaaaataga tgagtcgaaa ttaaaagcct atacccgcta tgaattaaga    2220
gggtatatcg aggatagtca agacttagaa atctatttaa ttcgctacaa tgcaaaacat    2280
gaaacagtaa atgtgccagg tacgggttcc ttatggccgc tttcagccca aagtccaatc    2340
ggaaagtgtg gagaaccgaa tcgatgtgcg acacaccttg aatggaatcc tgacttagat    2400
tgttcgtgta gggatggaga aaagtgtgcc catcattcgc atcatttctc cttagacatt    2460
gatgtaggat gtacagacct aaatgaggac ctaggtgtat gggtgatctt taagattaag    2520
acgcaagatg gtcatgcgag actaggaaat ctagaatttc tcgaagagaa accattagta    2580
ggagaagcgc tagctcgtgt gaagagagcg gagaaaaaat ggagagacaa acgcgaaaaa    2640
ttggaattgg aaacaaatat tgtttataaa gaggcaaaaa aatctgtaga tgctttattt    2700
gtgaactctc aatatgatag attacaagcg gatacgaata tcgcgataat tcatgcggca    2760
gataaacgcg ttcatagcat tcgagaagca tatcttccag agttgtctgt aattccgggt    2820
gtaaatgcag ctattttga agaattagag ggacgtattt tcacagccta ctctctatat    2880
gatgcgagaa atgtcattaa aaatggcgat ttcaataatg gcttatcatg ctggaacgtg    2940
aaagggcatg tagatgtaga agaacagaac aaccatcgtt cggtccttgt tgttccagaa    3000
tgggaagcag aagtgtcaca agaggttcgt gtctgtccag gtcgtggcta tatccttcgt    3060
gttacagcgt acaaagaggg atatggagag ggctgtgtaa cgattcatga gatcgaagac    3120
aatacagacg aactgaaatt cagcaactgt gtagaagagg aaatatatcc aaacaacacg    3180
gtaacgtgta atgattatac tgcgactcaa gaagaatatg agggtacgta cacttctcgt    3240
aatcgaggat atgacggagc ctatgaaagc aattcttctg taccagctga ttatgcatca    3300
gcctatgaag aaaaagcgta tacagatgga agaagagaca atacttgtga atctaacaga    3360
ggatatgggg attacacacc actaccagct ggctatgtga caaaagaatt agagtacttc    3420
ccagaaaccg ataaggtatg gattgagatt ggagaaacgg aaggaacatt tatcgtggac    3480
agcgtggaat tactcccttat ggaggaatag                                    3510
```

```
<210> SEQ ID NO 15
<211> LENGTH: 1169
<212> TYPE: PRT
<213> ORGANISM: Artificial Sequence
<220> FEATURE:
<223> OTHER INFORMATION: Bt29-1Kav2 chimeric protein

<400> SEQUENCE: 15

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
            20                  25                  30

Val Ala Glu Ile His Leu Lys Ile Thr Arg Leu Ile Leu Glu Asn Phe
        35                  40                  45

Leu Pro Gly Gly Ser Phe Ala Phe Gly Leu Phe Asp Leu Ile Trp Gly
    50                  55                  60

Ile Phe Asn Glu Asp Gln Trp Ser Ala Phe Leu Arg Gln Val Glu Glu
65                  70                  75                  80

Leu Ile Asn Gln Arg Ile Thr Glu Phe Ala Arg Gly Gln Ala Ile Gln
                85                  90                  95

Arg Leu Val Gly Phe Gly Arg Ser Tyr Asp Glu Tyr Ile Leu Ala Leu
            100                 105                 110

Lys Glu Trp Glu Asn Asp Pro Asp Asn Pro Ala Ser Lys Glu Arg Val
        115                 120                 125

Arg Thr Arg Phe Arg Thr Thr Asp Asp Ala Leu Leu Thr Gly Val Pro
    130                 135                 140

Leu Met Ala Ile Pro Gly Phe Glu Leu Ala Thr Leu Ser Val Tyr Ala
145                 150                 155                 160

Gln Ser Ala Asn Leu His Leu Ala Leu Leu Arg Asp Ala Val Phe Phe
                165                 170                 175

Gly Glu Arg Trp Gly Leu Thr Gln Thr Asn Ile Asn Asp Leu Tyr Ser
            180                 185                 190

Arg Leu Lys Asn Ser Ile Arg Asp Tyr Thr Asn His Cys Val Arg Phe
        195                 200                 205

Tyr Asn Ile Gly Leu Gly Asn Leu Asn Val Ile Arg Pro Glu Tyr Tyr
    210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255

Leu Thr Arg Glu Ile Tyr Thr Asp Pro Ile Ile Ser Pro Gly Ala Gln
            260                 265                 270

Ala Gly Tyr Thr Leu Gln Asp Val Leu Arg Glu Pro His Leu Met Asp
        275                 280                 285

Phe Leu Asn Arg Leu Ile Ile Tyr Thr Gly Glu Tyr Arg Gly Ile Arg
    290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Ala Thr Ala Glu Pro Thr
                325                 330                 335

Arg Phe Ile Thr Pro Ser Thr Phe Pro Gly Leu Asn Leu Phe Tyr Arg
            340                 345                 350

Thr Leu Ser Ala Pro Ile Phe Arg Asp Glu Pro Gly Ala Asn Ile Ile
        355                 360                 365

Ile Arg Tyr Arg Thr Ser Leu Val Glu Gly Val Gly Phe Ile Gln Pro
```

```
            370                 375                 380
Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                405                 410                 415

Arg Leu Cys His Val Arg Phe Ala Gln Ser Leu Arg Asn Ala Glu Pro
                420                 425                 430

Leu Asp Tyr Ala Arg Val Pro Met Phe Ser Trp Thr His Arg Ser Ala
            435                 440                 445

Thr Pro Thr Asn Thr Ile Asp Pro Asp Val Ile Thr Gln Ile Pro Leu
        450                 455                 460

Val Lys Ala His Thr Leu Gln Ser Gly Thr Thr Val Val Lys Gly Pro
465                 470                 475                 480

Gly Phe Thr Gly Gly Asp Ile Leu Arg Arg Thr Ser Gly Gly Pro Phe
                485                 490                 495

Ala Phe Ser Asn Val Asn Leu Asp Phe Asn Leu Ser Gln Arg Tyr Arg
                500                 505                 510

Ala Arg Ile Arg Tyr Ala Ser Thr Thr Asn Leu Arg Ile Tyr Val Thr
            515                 520                 525

Val Ala Gly Glu Arg Ile Phe Ala Gly Gln Phe Asp Lys Thr Met Asp
530                 535                 540

Ala Gly Ala Pro Leu Thr Phe Gln Ser Phe Ser Tyr Ala Thr Ile Asn
545                 550                 555                 560

Thr Ala Phe Thr Phe Pro Glu Arg Ser Ser Leu Thr Ile Gly Ala
                565                 570                 575

Asp Thr Phe Ser Ser Gly Asn Glu Val Tyr Val Asp Arg Phe Glu Leu
            580                 585                 590

Ile Gln Val Thr Ala Thr Phe Glu Ala Glu Ser Asp Leu Glu Arg Ala
            595                 600                 605

Arg Lys Ala Val Asn Ala Leu Phe Thr Ser Ser Asn Gln Ile Gly Leu
        610                 615                 620

Lys Thr Asp Val Thr Asp Tyr His Ile Asp Lys Val Ser Asn Leu Val
625                 630                 635                 640

Glu Cys Leu Ser Asp Glu Phe Cys Leu Asp Glu Lys Arg Glu Leu Ser
                645                 650                 655

Glu Lys Val Lys His Ala Lys Arg Leu Cys Asp Glu Arg Asn Leu Leu
                660                 665                 670

Gln Asp Pro Asn Phe Arg Gly Ile Asn Arg Gln Pro Asp Arg Gly Trp
            675                 680                 685

Arg Gly Ser Thr Asp Ile Thr Ile Gln Gly Gly Asp Asp Val Phe Lys
        690                 695                 700

Glu Asn Tyr Val Thr Leu Pro Gly Thr Phe Asp Glu Cys Tyr Pro Thr
705                 710                 715                 720

Tyr Leu Tyr Gln Lys Ile Asp Glu Ser Lys Leu Lys Ala Tyr Thr Arg
                725                 730                 735

Tyr Glu Leu Arg Gly Tyr Ile Glu Asp Ser Gln Asp Leu Glu Ile Tyr
                740                 745                 750

Leu Ile Arg Tyr Asn Ala Lys His Glu Thr Val Asn Val Pro Gly Thr
            755                 760                 765

Gly Ser Leu Trp Pro Leu Ser Ala Gln Ser Pro Ile Gly Lys Cys Gly
        770                 775                 780

Glu Pro Asn Arg Cys Ala Thr His Leu Glu Trp Asn Pro Asp Leu Asp
785                 790                 795                 800
```

Cys Ser Cys Arg Asp Gly Glu Lys Cys Ala His His Ser His His Phe
                805                 810                 815

Ser Leu Asp Ile Asp Val Gly Cys Thr Asp Leu Asn Glu Asp Leu Gly
            820                 825                 830

Val Trp Val Ile Phe Lys Ile Lys Thr Gln Asp Gly His Ala Arg Leu
            835                 840                 845

Gly Asn Leu Glu Phe Leu Glu Glu Lys Pro Leu Val Gly Glu Ala Leu
        850                 855                 860

Ala Arg Val Lys Arg Ala Glu Lys Lys Trp Arg Asp Lys Arg Glu Lys
865                 870                 875                 880

Leu Glu Leu Glu Thr Asn Ile Val Tyr Lys Ala Lys Lys Ser Val
                885                 890                 895

Asp Ala Leu Phe Val Asn Ser Gln Tyr Asp Arg Leu Gln Ala Asp Thr
            900                 905                 910

Asn Ile Ala Ile Ile His Ala Ala Asp Lys Arg Val His Ser Ile Arg
        915                 920                 925

Glu Ala Tyr Leu Pro Glu Leu Ser Val Ile Pro Gly Val Asn Ala Ala
        930                 935                 940

Ile Phe Glu Glu Leu Glu Gly Arg Ile Phe Thr Ala Tyr Ser Leu Tyr
945                 950                 955                 960

Asp Ala Arg Asn Val Ile Lys Asn Gly Asp Phe Asn Asn Gly Leu Ser
                965                 970                 975

Cys Trp Asn Val Lys Gly His Val Asp Val Glu Glu Gln Asn Asn His
            980                 985                 990

Arg Ser Val Leu Val Val Pro Glu Trp Glu Ala Glu Val Ser Gln Glu
        995                 1000                1005

Val Arg Val Cys Pro Gly Arg Gly Tyr Ile Leu Arg Val Thr Ala
    1010                1015                1020

Tyr Lys Glu Gly Tyr Gly Glu Gly Cys Val Thr Ile His Glu Ile
    1025                1030                1035

Glu Asp Asn Thr Asp Glu Leu Lys Phe Ser Asn Cys Val Glu Glu
    1040                1045                1050

Glu Ile Tyr Pro Asn Asn Thr Val Thr Cys Asn Asp Tyr Thr Ala
    1055                1060                1065

Thr Gln Glu Glu Tyr Glu Gly Thr Tyr Thr Ser Arg Asn Arg Gly
    1070                1075                1080

Tyr Asp Gly Ala Tyr Glu Ser Asn Ser Ser Val Pro Ala Asp Tyr
    1085                1090                1095

Ala Ser Ala Tyr Glu Glu Lys Ala Tyr Thr Asp Gly Arg Arg Asp
    1100                1105                1110

Asn Thr Cys Glu Ser Asn Arg Gly Tyr Gly Asp Tyr Thr Pro Leu
    1115                1120                1125

Pro Ala Gly Tyr Val Thr Lys Glu Leu Glu Tyr Phe Pro Glu Thr
    1130                1135                1140

Asp Lys Val Trp Ile Glu Ile Gly Glu Thr Glu Gly Thr Phe Ile
    1145                1150                1155

Val Asp Ser Val Glu Leu Leu Leu Met Glu Glu
    1160                1165

<210> SEQ ID NO 16
<211> LENGTH: 3510
<212> TYPE: DNA
<213> ORGANISM: Artificial Sequence
<220> FEATURE:

<223> OTHER INFORMATION: Bt29-1Ka chimera

<400> SEQUENCE: 16

```
atggagatta ataatcagaa ccaatgtgtc ccttataatt gtttgaataa tcctgaaagc     60
gagatattaa acgttgcaat ttttagtagc gaacaggtag cagaaattca cttaaagatc    120
acgcgcttaa ttttagagaa ttttttacca ggtgggagtt ttgcattcgg cttatttgat    180
ttaatatggg ggatttttaa tgaagatcaa tggagcgcat ttcttcggca ggtagaagaa    240
ttaattaatc aaaggataac ggaattcgca agagggcaag caattcagag actagtaggg    300
tttggaagga gttatgatga atatatttta gcactaaaag aatgggaaaa cgatcctgat    360
aacccagctt caaaggaaag agtgcgcact cgatttcgga caactgatga tgccttgcta    420
accggtgttc ctcttatggc aattccaggt tttgaattag ctactttatc tgtttatgct    480
caatcagcca atctacattt agccctatta agagatgctg tatttttgg ggagagatgg     540
ggattgacac aaacaaatat aaatgattta tatagtagat taaaaaactc cattcgtgat    600
tatacaaatc attgtgttcg tttttataat ataggtttag ggaatttaaa tgttataaga    660
ccagagtatt accgtttcca aagagaatta acaatatctg tcttagatct tgtagctctt    720
tttccaaatt acgatatccg aacatatcca ataccaacta aaagtcaatt aacaagagaa    780
atttatacag atccgattat ttcacctggt gcacaggcag gttatactct tcaagatgtt    840
ttgagagaac cacaccttat ggacttttta aaccgactta ttatttatac tggtgagtat    900
cgcggaattc gtcactgggc aggacatgaa gtagaatcta gtagaacagg tatgatgact    960
aatataagat ttcctttgta tggaacagcc gcaacagcag aaccaacacg atttataact   1020
cctagtactt ttcctggtct taatttattt tatagaacat tatcagctcc tatttttaga   1080
gatgaaccgg gagctaatat tattattaga tatagaacga gtttggtgga aggagtagga   1140
tttattcaac caaataacgg tgaacagctt tacagagtga gaggaacatt agattctctt   1200
gatcaattac cacttgaggg tgagagtagt ctaactgaat atagtcatcg attatgccat   1260
gttagatttg cgcaatcatt gaggaatgca gaacctttag attatgcaag ggttccgatg   1320
ttttcttgga cacatcgtag tgcaacccct acaaatacaa ttgatccaga tgtcatcacc   1380
caaataccgt tagtaaaagc acataccctt cagtcaggta ctactgttgt aaaagggcca   1440
gggtttacag gtggagatat cctccgacga actagtggag gaccatttgc ttttagtaat   1500
gttaatttag actttaactt gtcacaaaga tatcgtgcta gaatacgcta tgcttctact   1560
actaatctaa gaatttacgt aacggtagca ggggaacgaa tttttgctgg tcaatttgat   1620
aaaacaatgg atgcaggtgc accattaaca ttccaatctt ttagttacgc aactattaat   1680
acagcattta cattcccaga aagaagtagc agcttgacta ttggtgctga tacttttagc   1740
tcaggtaatg aagtttatgt agatagattt gaattgatcc aggttactgc aacatttgag   1800
gcagaatcag atttagagag agcacgaaaa gcggtgaatg cgctgtttac ttcttccaat   1860
caaatcgggt taaaaacaga tgtgacggac tatcatattg ataaagtatc caatctagtt   1920
gagtgtttat cagatgaatt ttgtctagat gaaaagcgag aattgtccga gaaagtcaaa   1980
catgcgaagc gactctgtga tgagcggaat ttacttcaag atccaaactt cagaggcatc   2040
aatagacaac cagaccgtgg ttggagagga agtacggata ttaccatcca aggaggagat   2100
gacgtattca aagagaatta cgttacgcta ccgggtacct ttgatgagtg ctatccaacg   2160
tatttatatc aaaaaataga tgagtcgaaa ttaaaagcct atacccgcta tgaattaaga   2220
gggtatatcg aggatagtca agacttagaa atctatttaa ttcgctacaa tgcaaaacat   2280
```

```
gaaacagtaa atgtgccagg tacgggttcc ttatggccgc tttcagccca aagtccaatc    2340
ggaaagtgtg gagaaccgaa tcgatgtgcg acacaccttg aatggaatcc tgacttagat    2400
tgttcgtgta gggatggaga aaagtgtgcc catcattcgc atcatttctc cttagacatt    2460
gatgtaggat gtacagacct aaatgaggac ctaggtgtat gggtgatctt aagattaag     2520 acgcaagatg gtcatgcgag actaggaaat ctagaatttc tcgaagagaa accattagta    2580
ggagaagcgc tagctcgtgt gaagagagcg gagaaaaaat ggagagacaa cgcgaaaaa     2640 ttggaattgg aaacaaatat tgtttataaa gaggcaaaaa atctgtaga tgctttattt     2700 gtgaactctc aatatgatag attacaagcg gatacgaata tcgcgataat tcatgcggca    2760
gataaacgcg ttcatagcat tcgagaagca tatcttccag agttgtctgt aattccgggt    2820
gtaaatgcag ctattttga agaattagag ggacgtattt tcacagccta ctctctatat     2880
gatgcgagaa atgtcattaa aaatggcgat ttcaataatg gcttatcatg ctggaacgtg    2940
aaagggcatg tagatgtaga agaacagaac aaccatcgtt cggtccttgt tgttccagaa    3000
tgggaagcag aagtgtcaca agaggttcgt gtctgtccag gtcgtggcta tatccttcgt    3060
gttacagcgt acaaagaggg atatggagag ggctgtgtaa cgattcatga gatcgaagac    3120
aatacagacg aactgaaatt cagcaactgt gtagaagagg aaatatatcc aaacaacacg    3180
gtaacgtgta atgattatac tgcgactcaa gaagaatatg agggtacgta cacttctcgt    3240
aatcgaggat atgacggagc ctatgaaagc aattcttctg taccagctga ttatgcatca    3300
gcctatgaag aaaaagcgta tacagatgga agaagagaca atacttgtga atctaacaga    3360
ggatatgggg attacacacc actaccagct ggctatgtga caaaagaatt agagtacttc    3420
ccagaaaccg ataaggtatg gattgagatt ggagaaacgg aaggaacatt tatcgtggac    3480
agcgtggaat tactccttat ggaggaatag                                     3510
```

<210> SEQ ID NO 17
<211> LENGTH: 1189
<212> TYPE: PRT
<213> ORGANISM: Bacillus thuringiensis

<400> SEQUENCE: 17

```
Met Glu Glu Asn Asn Gln Asn Gln Cys Ile Pro Tyr Asn Cys Leu Ser
1               5                   10                  15

Asn Pro Glu Glu Val Leu Leu Asp Gly Glu Arg Ile Ser Thr Gly Asn
                20                  25                  30

Ser Ser Ile Asp Ile Ser Leu Ser Leu Val Gln Phe Leu Val Ser Asn
            35                  40                  45

Phe Val Pro Gly Gly Gly Phe Leu Val Gly Leu Ile Asp Phe Val Trp
        50                  55                  60

Gly Ile Val Gly Pro Ser Gln Trp Asp Ala Phe Leu Val Gln Ile Glu
65                  70                  75                  80

Gln Leu Ile Asn Glu Arg Ile Ala Glu Phe Ala Arg Asn Ala Ala Ile
                85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Ala Thr Arg Thr Arg
        115                 120                 125

Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
```

```
              145                 150                 155                 160
         Ala Gln Ala Ala Asn Leu His Leu Ala Ile Leu Arg Asp Ser Val Ile
                         165                 170                 175
         Phe Gly Glu Arg Trp Gly Leu Thr Thr Ile Asn Val Asn Glu Asn Tyr
                         180                 185                 190
         Asn Arg Leu Ile Arg His Ile Asp Glu Tyr Ala Asp His Cys Ala Asn
                         195                 200                 205
         Thr Tyr Asn Arg Gly Leu Asn Asn Leu Pro Lys Ser Thr Tyr Gln Asp
                 210                 215                 220
         Trp Ile Thr Tyr Asn Arg Leu Arg Arg Asp Leu Thr Leu Thr Val Leu
         225                 230                 235                 240
         Asp Ile Ala Ala Phe Phe Pro Asn Tyr Asp Asn Arg Arg Tyr Pro Ile
                             245                 250                 255
         Gln Pro Val Gly Gln Leu Thr Arg Glu Val Tyr Thr Asp Pro Leu Ile
                         260                 265                 270
         Asn Phe Asn Pro Gln Leu Gln Ser Val Ala Gln Leu Pro Thr Phe Asn
                         275                 280                 285
         Val Met Glu Ser Ser Ala Ile Arg Asn Pro His Leu Phe Asp Ile Leu
                 290                 295                 300
         Asn Asn Leu Thr Ile Phe Thr Asp Trp Phe Ser Val Gly Arg Asn Phe
         305                 310                 315                 320
         Tyr Trp Gly Gly His Arg Val Ile Ser Ser Leu Ile Gly Gly Gly Asn
                             325                 330                 335
         Ile Thr Ser Pro Ile Tyr Gly Arg Glu Ala Asn Gln Glu Pro Pro Arg
                         340                 345                 350
         Ser Phe Thr Phe Asn Gly Pro Val Phe Arg Thr Leu Ser Asn Pro Thr
                         355                 360                 365
         Leu Arg Leu Leu Gln Gln Pro Trp Pro Ala Pro Pro Phe Asn Leu Arg
                 370                 375                 380
         Gly Val Glu Gly Val Glu Phe Ser Thr Pro Thr Asn Ser Phe Thr Tyr
         385                 390                 395                 400
         Arg Gly Arg Gly Thr Val Asp Ser Leu Thr Glu Leu Pro Pro Glu Asp
                             405                 410                 415
         Asn Ser Val Pro Pro Arg Glu Gly Tyr Ser His Arg Leu Cys His Ala
                         420                 425                 430
         Thr Phe Val Gln Arg Ser Gly Thr Pro Phe Leu Thr Thr Gly Val Val
                         435                 440                 445
         Phe Ser Trp Thr His Arg Ser Ala Thr Leu Thr Asn Thr Ile Asp Pro
                 450                 455                 460
         Glu Arg Ile Asn Gln Ile Pro Leu Val Lys Gly Phe Arg Val Trp Gly
         465                 470                 475                 480
         Gly Thr Ser Val Ile Thr Gly Pro Gly Phe Thr Gly Gly Asp Ile Leu
                             485                 490                 495
         Arg Arg Asn Thr Phe Gly Asp Phe Val Ser Leu Gln Val Asn Ile Asn
                         500                 505                 510
         Ser Pro Ile Thr Gln Arg Tyr Arg Leu Arg Phe Arg Tyr Ala Ser Ser
                         515                 520                 525
         Arg Asp Ala Arg Val Ile Val Leu Thr Gly Ala Ala Ser Thr Gly Val
                 530                 535                 540
         Gly Gly Gln Val Ser Val Asn Met Pro Leu Gln Lys Thr Met Glu Ile
         545                 550                 555                 560
         Gly Glu Asn Leu Thr Ser Arg Thr Phe Arg Tyr Thr Asp Phe Ser Asn
                             565                 570                 575
```

-continued

```
Pro Phe Ser Phe Arg Ala Asn Pro Asp Ile Gly Ile Ser Glu Gln
            580                 585                 590

Pro Leu Phe Gly Ala Gly Ser Ile Ser Ser Gly Glu Leu Tyr Ile Asp
        595                 600                 605

Lys Ile Glu Ile Ile Leu Ala Asp Ala Thr Phe Glu Ala Glu Ser Asp
    610                 615                 620

Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Gln Val
                645                 650                 655

Ser Asn Leu Val Asp Cys Leu Ser Asp Glu Phe Cys Leu Asp Glu Lys
            660                 665                 670

Arg Glu Leu Ser Glu Lys Val Lys His Ala Lys Arg Leu Ser Asp Glu
        675                 680                 685

Arg Asn Leu Leu Gln Asp Pro Asn Phe Arg Gly Ile Asn Arg Gln Pro
    690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Pro Gly Thr Val Asp Glu
                725                 730                 735

Cys Tyr Pro Thr Tyr Leu Tyr Gln Lys Ile Asp Glu Ser Lys Leu Lys
            740                 745                 750

Ala Tyr Thr Arg Tyr Glu Leu Arg Gly Tyr Ile Glu Asp Ser Gln Asp
        755                 760                 765

Leu Glu Ile Tyr Leu Ile Arg Tyr Asn Ala Lys His Glu Ile Val Asn
    770                 775                 780

Val Pro Gly Thr Gly Ser Leu Trp Pro Leu Ser Ala Gln Ser Pro Ile
785                 790                 795                 800

Gly Lys Cys Gly Glu Pro Asn Arg Cys Ala Pro His Leu Glu Trp Asn
                805                 810                 815

Pro Asp Leu Asp Cys Ser Cys Arg Asp Gly Glu Lys Cys Ala His His
            820                 825                 830

Ser His His Phe Thr Leu Asp Ile Asp Val Gly Cys Thr Asp Leu Asn
        835                 840                 845

Glu Asp Leu Gly Val Trp Val Ile Phe Lys Ile Lys Thr Gln Asp Gly
    850                 855                 860

His Ala Arg Leu Gly Asn Leu Glu Phe Leu Glu Glu Lys Pro Leu Leu
865                 870                 875                 880

Gly Glu Ala Leu Ala Arg Val Lys Arg Ala Glu Lys Lys Trp Arg Asp
                885                 890                 895

Lys Arg Glu Lys Leu Gln Leu Glu Thr Asn Ile Val Tyr Lys Glu Ala
            900                 905                 910

Lys Glu Ser Val Asp Ala Leu Phe Val Asn Ser Gln Tyr Asp Arg Leu
        915                 920                 925

Gln Val Asp Thr Asn Ile Ala Met Ile His Ala Ala Asp Lys Arg Val
    930                 935                 940

His Arg Ile Arg Glu Ala Tyr Leu Pro Glu Leu Ser Val Ile Pro Gly
945                 950                 955                 960

Val Asn Ala Ala Ile Phe Glu Glu Leu Glu Gly Arg Ile Phe Thr Ala
                965                 970                 975

Tyr Ser Leu Tyr Asp Ala Arg Asn Val Ile Lys Asn Gly Asp Phe Asn
            980                 985                 990
```

```
Asn Gly Leu Leu Cys Trp Asn Val  Lys Gly His Val Asp  Val Glu Glu
        995                 1000                 1005

Gln Asn  Asn His Arg Ser Val  Leu Val Ile Pro Glu  Trp Glu Ala
    1010                 1015                 1020

Glu Val  Ser Gln Glu Val Arg  Val Cys Pro Gly Arg  Gly Tyr Ile
    1025                 1030                 1035

Leu Arg  Val Thr Ala Tyr Lys  Glu Gly Tyr Gly Glu  Gly Cys Val
    1040                 1045                 1050

Thr Ile  His Glu Ile Glu Asp  Asn Thr Asp Glu Leu  Lys Phe Ser
    1055                 1060                 1065

Asn Cys  Val Glu Glu Glu Val  Tyr Pro Asn Asn Thr  Val Thr Cys
    1070                 1075                 1080

Asn Asn  Tyr Thr Gly Thr Gln  Glu Glu Tyr Glu Gly  Thr Tyr Thr
    1085                 1090                 1095

Ser Arg  Asn Gln Gly Tyr Asp  Glu Ala Tyr Gly Asn  Asn Pro Ser
    1100                 1105                 1110

Val Pro  Ala Asp Tyr Ala Ser  Val Tyr Glu Glu Lys  Ser Tyr Thr
    1115                 1120                 1125

Asp Gly  Arg Arg Glu Asn Pro  Cys Glu Ser Asn Arg  Gly Tyr Gly
    1130                 1135                 1140

Asp Tyr  Thr Pro Leu Pro Ala  Gly Tyr Val Thr Lys  Asp Leu Glu
    1145                 1150                 1155

Tyr Phe  Pro Glu Thr Asp Lys  Val Trp Ile Glu Ile  Gly Glu Thr
    1160                 1165                 1170

Glu Gly  Thr Phe Ile Val Asp  Ser Val Glu Leu Leu  Leu Met Glu
    1175                 1180                 1185

Glu

<210> SEQ ID NO 18
<211> LENGTH: 1181
<212> TYPE: PRT
<213> ORGANISM: Artificial Sequence
<220> FEATURE:
<223> OTHER INFORMATION: Engineered Bt29-1Ca chimeric protein.

<400> SEQUENCE: 18

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
            20                  25                  30

Val Ala Glu Ile His Leu Lys Ile Thr Arg Leu Ile Leu Glu Asn Phe
        35                  40                  45

Leu Pro Gly Gly Ser Phe Ala Phe Gly Leu Phe Asp Leu Ile Trp Gly
    50                  55                  60

Ile Phe Asn Glu Asp Gln Trp Ser Ala Phe Leu Arg Gln Val Glu Glu
65                  70                  75                  80

Leu Ile Asn Gln Arg Ile Thr Glu Phe Ala Arg Gly Gln Ala Ile Gln
                85                  90                  95

Arg Leu Val Gly Phe Gly Arg Ser Tyr Asp Glu Tyr Ile Leu Ala Leu
            100                 105                 110

Lys Glu Trp Glu Asn Asp Pro Asp Asn Pro Ala Ser Lys Glu Arg Val
        115                 120                 125

Arg Thr Arg Phe Arg Thr Thr Asp Asp Ala Leu Leu Thr Gly Val Pro
    130                 135                 140

Leu Met Ala Ile Pro Gly Phe Glu Leu Ala Thr Leu Ser Val Tyr Ala
```

```
            145                 150                 155                 160
        Gln Ser Ala Asn Leu His Leu Ala Leu Leu Arg Asp Ala Val Phe Phe
                        165                 170                 175
        Gly Glu Arg Trp Gly Leu Thr Gln Thr Asn Ile Asn Asp Leu Tyr Ser
                        180                 185                 190
        Arg Leu Lys Asn Ser Ile Arg Asp Tyr Thr Asn His Cys Val Arg Phe
                        195                 200                 205
        Tyr Asn Ile Gly Leu Gly Asn Leu Asn Val Ile Arg Pro Glu Tyr Tyr
                        210                 215                 220
        Arg Phe Gln Arg Glu Leu Thr Ile Ser Val Leu Asp Leu Val Ala Leu
        225                 230                 235                 240
        Phe Pro Asn Tyr Asp Ile Arg Thr Tyr Pro Ile Pro Thr Lys Ser Gln
                        245                 250                 255
        Leu Thr Arg Glu Ile Tyr Thr Asp Pro Ile Ile Ser Pro Gly Ala Gln
                        260                 265                 270
        Ala Gly Tyr Thr Leu Gln Asp Val Leu Arg Glu Pro His Leu Met Asp
                        275                 280                 285
        Phe Leu Asn Arg Leu Ile Ile Tyr Thr Gly Glu Tyr Arg Gly Ile Arg
                        290                 295                 300
        His Trp Ala Gly His Glu Val Glu Ser Ser Arg Thr Gly Met Met Thr
        305                 310                 315                 320
        Asn Ile Arg Phe Pro Leu Tyr Gly Thr Ala Ala Thr Ala Glu Pro Thr
                        325                 330                 335
        Arg Phe Ile Thr Pro Ser Thr Phe Pro Gly Leu Asn Leu Phe Tyr Arg
                        340                 345                 350
        Thr Leu Ser Ala Pro Ile Phe Arg Asp Glu Pro Gly Ala Asn Ile Ile
                        355                 360                 365
        Ile Arg Tyr Arg Thr Ser Leu Val Glu Gly Val Gly Phe Ile Gln Pro
                        370                 375                 380
        Asn Asn Gly Glu Gln Leu Tyr Arg Val Arg Gly Thr Leu Asp Ser Leu
        385                 390                 395                 400
        Asp Gln Leu Pro Leu Glu Gly Glu Ser Ser Leu Thr Glu Tyr Ser His
                        405                 410                 415
        Arg Leu Cys His Val Arg Phe Ala Gln Ser Leu Arg Asn Ala Glu Pro
                        420                 425                 430
        Leu Asp Tyr Ala Arg Val Pro Met Phe Ser Trp Thr His Arg Ser Ala
                        435                 440                 445
        Thr Pro Thr Asn Thr Ile Asp Pro Asp Val Ile Thr Gln Ile Pro Leu
                        450                 455                 460
        Val Lys Gly Phe Arg Val Trp Gly Gly Thr Ser Val Ile Thr Gly Pro
        465                 470                 475                 480
        Gly Phe Thr Gly Gly Asp Ile Leu Arg Arg Asn Thr Phe Gly Asp Phe
                        485                 490                 495
        Val Ser Leu Gln Val Asn Ile Asn Ser Pro Ile Thr Gln Arg Tyr Arg
                        500                 505                 510
        Leu Arg Phe Arg Tyr Ala Ser Ser Arg Asp Ala Arg Val Ile Val Leu
                        515                 520                 525
        Thr Gly Ala Ala Ser Thr Gly Val Gly Gly Gln Val Ser Val Asn Met
                        530                 535                 540
        Pro Leu Gln Lys Thr Met Glu Ile Gly Glu Asn Leu Thr Ser Arg Thr
        545                 550                 555                 560
        Phe Arg Tyr Thr Asp Phe Ser Asn Pro Phe Ser Phe Arg Ala Asn Pro
                        565                 570                 575
```

-continued

```
Asp Ile Ile Gly Ile Ser Glu Gln Pro Leu Phe Gly Ala Gly Ser Ile
            580                 585                 590

Ser Ser Gly Glu Leu Tyr Ile Asp Lys Ile Glu Ile Ile Leu Ala Asp
        595                 600                 605

Ala Thr Phe Glu Ala Glu Tyr Asp Leu Glu Lys Ala Gln Lys Ala Val
610                 615                 620

Asn Ala Leu Phe Thr Ser Ser Asn Gln Ile Gly Leu Lys Thr Asp Val
625                 630                 635                 640

Thr Asp Tyr His Ile Asp Lys Val Ser Asn Leu Val Glu Cys Leu Ser
                645                 650                 655

Asp Glu Phe Cys Leu Asp Glu Lys Arg Glu Leu Ser Glu Lys Val Lys
            660                 665                 670

His Ala Lys Arg Leu Cys Asp Glu Arg Asn Leu Leu Gln Asp Pro Asn
        675                 680                 685

Phe Arg Gly Ile Asn Arg Gln Pro Asp Arg Gly Trp Arg Gly Ser Thr
690                 695                 700

Asp Ile Thr Ile Gln Gly Gly Asp Asp Val Phe Lys Glu Asn Tyr Val
705                 710                 715                 720

Thr Leu Pro Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Glu Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
770                 775                 780

Pro Leu Ser Ala Gln Ser Pro Ile Gly Lys Cys Gly Glu Pro Asn Arg
785                 790                 795                 800

Cys Ala Thr His Leu Glu Trp Asn Pro Asp Leu Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Arg Leu Gly Asn Leu Glu
850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Leu Glu
                885                 890                 895

Thr Asn Ile Val Tyr Lys Glu Ala Lys Lys Ser Val Asp Ala Leu Phe
            900                 905                 910

Val Asn Ser Gln Tyr Asp Arg Leu Gln Ala Asp Thr Asn Ile Ala Ile
        915                 920                 925

Ile His Ala Ala Asp Lys Arg Val His Ser Ile Arg Glu Ala Tyr Leu
930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Tyr Ser Leu Tyr Asp Ala Arg Asn
                965                 970                 975

Val Ile Lys Asn Gly Asp Phe Asn Asn Gly Leu Ser Cys Trp Asn Val
            980                 985                 990
```

```
Lys Gly His Val Asp Val Glu Glu  Gln Asn Asn His Arg  Ser Val Leu
        995                 1000                      1005

Val Val Pro Glu Trp Glu Ala  Glu Val Ser Gln Glu  Val Arg Val
    1010                1015                 1020

Cys Pro Gly Arg Gly Tyr Ile  Leu Arg Val Thr Ala  Tyr Lys Glu
    1025                1030                 1035

Gly Tyr Gly Glu Gly Cys Val  Thr Ile His Glu Ile  Glu Asp Asn
    1040                1045                 1050

Thr Asp Glu Leu Lys Phe Ser  Asn Cys Val Glu Glu  Glu Ile Tyr
    1055                1060                 1065

Pro Asn Asn Thr Val Thr Cys  Asn Asp Tyr Thr Ala  Thr Gln Glu
    1070                1075                 1080

Glu Tyr Glu Gly Thr Tyr Thr  Ser Arg Asn Arg Gly  Tyr Asp Gly
    1085                1090                 1095

Ala Tyr Glu Ser Asn Ser Ser  Val Pro Ala Asp Tyr  Ala Ser Ala
    1100                1105                 1110

Tyr Glu Glu Lys Ala Tyr Thr  Asp Gly Arg Arg Asp  Asn Thr Cys
    1115                1120                 1125

Glu Ser Asn Arg Gly Tyr Gly  Asp Tyr Thr Pro Leu  Pro Ala Gly
    1130                1135                 1140

Tyr Val Thr Lys Glu Leu Glu  Tyr Phe Pro Glu Thr  Asp Lys Val
    1145                1150                 1155

Trp Ile Glu Ile Gly Glu Thr  Glu Gly Thr Phe Ile  Val Asp Ser
    1160                1165                 1170

Val Glu Leu Leu Leu Met Glu  Glu
    1175                1180

<210> SEQ ID NO 19
<211> LENGTH: 3546
<212> TYPE: DNA
<213> ORGANISM: Artificial Sequence
<220> FEATURE:
<223> OTHER INFORMATION: Bt29-1Ca chimera

<400> SEQUENCE: 19
atggagatta taatcagaa ccaatgtgtc ccttataatt gtttgaataa tcctgaaagc      60
gagatattaa acgttgcaat ttttagtagc gaacaggtag cagaaattca cttaaagatc     120
acgcgcttaa ttttagagaa ttttttacca ggtgggagtt ttgcattcgg cttatttgat     180
ttaatatggg ggattttta tgaagatcaa tggagcgcat tcttcggca ggtagaagaa       240 ttaattaatc aaaggataac ggaattcgca agagggcaag caattcagag actagtaggg    300
tttggaagga gttatgatga atatatttta gcactaaaag aatgggaaaa cgatcctgat    360
aacccagctt caaggaaag agtgcgcact cgatttcgga caactgatga tgccttgcta    420
accggtgttc ctcttatggc aattccaggt tttgaattag ctactttatc tgtttatgct    480
caatcagcca atctacattt agccctatta agagatgctg tattttttgg ggagagatgg    540
ggattgacac aaacaaatat aaatgattta tatagtagat taaaaactc cattcgtgat    600 tatacaaatc attgtgttcg ttttataat ataggtttag ggaatttaaa tgttataaga    660
ccagagtatt accgtttcca agagaatta acaatatctg tcttagatct tgtagctctt    720
tttccaaatt acgatatccg aacatatcca ataccaacta aagtcaatt aacaagagaa    780 atttatacag atcgattat ttcacctggt gcacaggcag ttatactct tcaagatgtt    840 ttgagagaac cacaccttat ggacttttta aaccgactta ttatttatac tggtgagtat    900
```

```
cgcggaattc gtcactgggc aggacatgaa gtagaatcta gtagaacagg tatgatgact    960
aatataagat ttcctttgta tggaacagcc gcaacagcag aaccaacacg atttataact   1020
cctagtactt ttcctggtct taatttattt tatagaacat tatcagctcc tatttttaga   1080
gatgaaccgg gagctaatat tattattaga tatagaacga gtttggtgga aggagtagga   1140
tttattcaac caaataacgg tgaacagctt tacagagtga gaggaacatt agattctctt   1200
gatcaattac cacttgaggg tgagagtagt ctaactgaat atagtcatcg attatgccat   1260
gttagatttg cgcaatcatt gaggaatgca gaacctttag attatgcaag ggttccgatg   1320
tttctcttgga cacatcgtag tgcaacccct acaaatacaa ttgatccaga tgtcatcacc   1380
caaataccgc tggtgaaagg ctttcgcgtg tggggcggca ccagcgtgat taccggcccg   1440
ggctttaccg gcggcgatat tctgcgccgc aacacctttg gcgattttgt gagcctgcag   1500
gtgaacatta acagcccgat tacccagcgc tatcgcctgc gctttcgcta tgcgagcagc   1560
cgcgatgcgc gcgtgattgt gctgaccggc gcggcgagca ccggcgtggg cggccaggtg   1620
agcgtgaaca tgccgctgca gaaaaccatg gaaattggcg aaaacctgac cagccgcacc   1680
tttcgctata ccgatttag caacccgttt agctttcgcg cgaacccgga tattattggc   1740
attagcgaac agccgctgtt tggcgcgggc agcattagca gcggcgaact gtatattgat   1800
aaaattgaaa ttattctggc ggatgcgaca tttgaggcag aatatgattt agagaaagct   1860
cagaaagcgg tgaatgcgct gtttacttct tccaatcaaa tcgggttaaa aacagatgtg   1920
acggactatc atattgataa agtatccaat ctagttgagt gtttatcaga tgaattttgt   1980
ctagatgaaa agcgagaatt gtccgagaaa gtcaaacatg cgaagcgact ctgtgatgag   2040
cggaatttac ttcaagatcc aaacttcaga ggcatcaata gacaaccaga ccgtggttgg   2100
agaggaagta cggatattac catccaagga ggagatgacg tattcaaaga gaattacgtt   2160
acgctaccgg gtacctttga tgagtgctat ccaacgtatt tatatcaaaa aatagatgag   2220
tcgaaattaa aagcctatac ccgctatgaa ttaagagggt atatcgagga tagtcaagac   2280
ttagaaatct atttaattcg ctacaatgca aaacatgaaa cagtaaatgt gccaggtacg   2340
ggttccttat ggccgctttc agcccaaagt ccaatcggaa agtgtggaga accgaatcga   2400
tgtgcgacac accttgaatg gaatcctgac ttagattgtt cgtgtaggga tggagaaaag   2460
tgtgcccatc attcgcatca tttctcctta gacattgatg taggatgtac agacctaaat   2520
gaggacctag gtgtatgggt gatctttaag attaagacgc aagatggtca tgcgagacta   2580
ggaaatctag aatttctcga agagaaacca ttagtaggag aagcgctagc tcgtgtgaag   2640
agagcggaga aaaatggag agacaaacgc gaaaaattgg aattggaaac aaatattgtt   2700
tataagagg caaaaaaatc tgtagatgct ttatttgtga actctcaata tgatagatta   2760
caagcggata cgaatatcgc gataattcat gcggcagata acgcgttca tagcattcga   2820
gaagcatatc ttccagagtt gtctgtaatt ccggtgtaa atgcagctat ttttgaagaa   2880
ttagagggac gtattttcac agcctactct ctatatgatg cgagaaatgt cattaaaaat   2940
ggcgatttca ataatggctt atcatgctgg aacgtgaaag gcatgtaga tgtagaagaa   3000
cagaacaacc atcgttcggt ccttgttgtt ccagaatggg aagcagaagt gtcacaagag   3060
gttcgtgtct gtccaggtcg tggctatatc cttcgtgtta cagcgtacaa agagggatat   3120
ggagagggct gtgtaacgat tcatgagatc gaagacaata cagacgaact gaaattcagc   3180
aactgtgtag aagaggaaat atatccaaac aacacggtaa cgtgtaatga ttatactgcg   3240
actcaagaag aatatgaggg tacgtacact tctcgtaatc gaggatatga cggagcctat   3300
```

```
gaaagcaatt cttctgtacc agctgattat gcatcagcct atgaagaaaa agcgtataca    3360
gatggaagaa gagacaatac ttgtgaatct aacagaggat atggggatta cacaccacta    3420
ccagctggct atgtgacaaa agaattagag tacttcccag aaaccgataa ggtatggatt    3480
gagattggag aaacggaagg aacatttatc gtggacagcg tggaattact ccttatggag    3540
gaatag                                                               3546
```

<210> SEQ ID NO 20
<211> LENGTH: 652
<212> TYPE: PRT
<213> ORGANISM: Artificial Sequence
<220> FEATURE:
<223> OTHER INFORMATION: Bt29-Bt22Tr1

<400> SEQUENCE: 20

```
Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
            20                  25                  30

Val Ala Glu Ile His Leu Lys Ile Thr Arg Leu Ile Leu Glu Asn Phe
        35                  40                  45

Leu Pro Gly Gly Ser Phe Ala Phe Gly Leu Phe Asp Leu Ile Trp Gly
    50                  55                  60

Ile Phe Asn Glu Asp Gln Trp Ser Ala Phe Leu Arg Gln Val Glu Glu
65                  70                  75                  80

Leu Ile Asn Gln Arg Ile Thr Glu Phe Ala Arg Gly Gln Ala Ile Gln
                85                  90                  95

Arg Leu Val Gly Phe Gly Arg Ser Tyr Asp Glu Tyr Ile Leu Ala Leu
            100                 105                 110

Lys Glu Trp Glu Asn Asp Pro Asp Asn Pro Ala Ser Lys Glu Arg Val
        115                 120                 125

Arg Thr Arg Phe Arg Thr Thr Asp Asp Ala Leu Leu Thr Gly Val Pro
    130                 135                 140

Leu Met Ala Ile Pro Gly Phe Glu Leu Ala Thr Leu Ser Val Tyr Ala
145                 150                 155                 160

Gln Ser Ala Asn Leu His Leu Ala Leu Leu Arg Asp Ala Val Phe Phe
                165                 170                 175

Gly Glu Arg Trp Gly Leu Thr Gln Thr Asn Ile Asn Asp Leu Tyr Ser
            180                 185                 190

Arg Leu Lys Asn Ser Ile Arg Asp Tyr Thr Asn His Cys Val Arg Phe
        195                 200                 205

Tyr Asn Ile Gly Leu Gly Asn Leu Asn Val Ile Arg Pro Glu Tyr Tyr
    210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255

Leu Thr Arg Glu Ile Tyr Thr Asp Pro Ile Ile Ser Pro Gly Ala Gln
            260                 265                 270

Ala Gly Tyr Thr Leu Gln Asp Val Leu Arg Glu Pro His Leu Met Asp
        275                 280                 285

Phe Leu Asn Arg Leu Ile Ile Tyr Thr Gly Tyr Arg Gly Ile Arg
    290                 295                 300

His Trp Ala Gly His Glu Val Glu Ser Ser Arg Thr Gly Met Met Thr
```

```
            305                 310                 315                 320
Asn Ile Arg Phe Pro Leu Tyr Gly Thr Ala Ala Thr Ala Glu Pro Thr
                325                 330                 335

Arg Phe Ile Thr Pro Ser Thr Phe Pro Gly Leu Asn Leu Phe Tyr Arg
                340                 345                 350

Thr Leu Ser Ala Pro Ile Phe Arg Asp Glu Pro Gly Ala Asn Ile Ile
                355                 360                 365

Ile Arg Tyr Arg Thr Ser Leu Val Glu Gly Val Gly Phe Ile Gln Pro
                370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                405                 410                 415

Arg Leu Cys His Val Arg Phe Ala Gln Ser Leu Arg Asn Ala Glu Pro
                420                 425                 430

Leu Asp Tyr Ala Arg Val Pro Met Phe Ser Trp Thr His Arg Ser Ala
                435                 440                 445

Thr Pro Thr Asn Thr Ile Asp Pro Asp Val Ile Thr Gln Ile Pro Leu
                450                 455                 460

Val Lys Ala His Thr Leu Gln Ser Gly Thr Thr Val Lys Gly Pro
465                 470                 475                 480

Gly Phe Thr Gly Gly Asp Ile Leu Arg Arg Thr Ser Gly Gly Pro Phe
                485                 490                 495

Ala Phe Ser Asn Val Asn Leu Asp Trp Asn Leu Ser Gln Arg Tyr Arg
                500                 505                 510

Ala Arg Ile Arg Tyr Ala Ser Thr Thr Asn Leu Arg Met Tyr Val Thr
                515                 520                 525

Ile Ala Gly Glu Arg Ile Phe Ala Gly Gln Phe Asn Lys Thr Met Asn
                530                 535                 540

Thr Gly Asp Pro Leu Thr Phe Gln Ser Phe Ser Tyr Ala Thr Ile Asp
545                 550                 555                 560

Thr Ala Phe Thr Phe Pro Thr Lys Ala Ser Ser Leu Thr Val Gly Ala
                565                 570                 575

Asp Thr Phe Ser Ser Gly Asn Glu Val Tyr Val Asp Arg Phe Glu Leu
                580                 585                 590

Ile Pro Val Thr Ala Thr Phe Glu Ala Glu Tyr Asp Leu Glu Lys Ala
                595                 600                 605

Gln Lys Ala Val Asn Ala Leu Phe Thr Ser Ser Asn Gln Ile Gly Leu
                610                 615                 620

Lys Thr Asp Val Thr Asp Tyr His Ile Asp Lys Val Ser Asn Leu Val
625                 630                 635                 640

Glu Cys Leu Ser Asp Glu Phe Cys Leu Asp Glu Lys
                645                 650

<210> SEQ ID NO 21
<211> LENGTH: 636
<212> TYPE: PRT
<213> ORGANISM: Artificial Sequence
<220> FEATURE:
<223> OTHER INFORMATION: Bt29-Bt22Tr2

<400> SEQUENCE: 21

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
```

-continued

```
                20                  25                  30
Val Ala Glu Ile His Leu Lys Ile Thr Arg Leu Ile Leu Glu Asn Phe
             35                  40                  45
Leu Pro Gly Ser Phe Ala Phe Gly Leu Phe Asp Leu Ile Trp Gly
 50                  55                  60
Ile Phe Asn Glu Asp Gln Trp Ser Ala Phe Leu Arg Gln Val Glu Glu
 65                  70                  75                  80
Leu Ile Asn Gln Arg Ile Thr Glu Phe Ala Arg Gly Gln Ala Ile Gln
                 85                  90                  95
Arg Leu Val Gly Phe Gly Arg Ser Tyr Asp Glu Tyr Ile Leu Ala Leu
            100                 105                 110
Lys Glu Trp Glu Asn Asp Pro Asp Asn Pro Ala Ser Lys Glu Arg Val
            115                 120                 125
Arg Thr Arg Phe Arg Thr Thr Asp Asp Ala Leu Leu Thr Gly Val Pro
            130                 135                 140
Leu Met Ala Ile Pro Gly Phe Glu Leu Ala Thr Leu Ser Val Tyr Ala
145                 150                 155                 160
Gln Ser Ala Asn Leu His Leu Ala Leu Leu Arg Asp Ala Val Phe Phe
                165                 170                 175
Gly Glu Arg Trp Gly Leu Thr Gln Thr Asn Ile Asn Asp Leu Tyr Ser
            180                 185                 190
Arg Leu Lys Asn Ser Ile Arg Asp Tyr Thr Asn His Cys Val Arg Phe
            195                 200                 205
Tyr Asn Ile Gly Leu Gly Asn Leu Asn Val Ile Arg Pro Glu Tyr Tyr
            210                 215                 220
Arg Phe Gln Arg Glu Leu Thr Ile Ser Val Leu Asp Leu Val Ala Leu
225                 230                 235                 240
Phe Pro Asn Tyr Asp Ile Arg Thr Tyr Pro Ile Pro Thr Lys Ser Gln
                245                 250                 255
Leu Thr Arg Glu Ile Tyr Thr Asp Pro Ile Ile Ser Pro Gly Ala Gln
            260                 265                 270
Ala Gly Tyr Thr Leu Gln Asp Val Leu Arg Glu Pro His Leu Met Asp
            275                 280                 285
Phe Leu Asn Arg Leu Ile Ile Tyr Thr Gly Glu Tyr Arg Gly Ile Arg
            290                 295                 300
His Trp Ala Gly His Glu Val Glu Ser Ser Arg Thr Gly Met Met Thr
305                 310                 315                 320
Asn Ile Arg Phe Pro Leu Tyr Gly Thr Ala Ala Thr Ala Glu Pro Thr
                325                 330                 335
Arg Phe Ile Thr Pro Ser Thr Phe Pro Gly Leu Asn Leu Phe Tyr Arg
            340                 345                 350
Thr Leu Ser Ala Pro Ile Phe Arg Asp Glu Pro Gly Ala Asn Ile Ile
            355                 360                 365
Ile Arg Tyr Arg Thr Ser Leu Val Glu Gly Val Gly Phe Ile Gln Pro
            370                 375                 380
Asn Asn Gly Glu Gln Leu Tyr Arg Val Arg Gly Thr Leu Asp Ser Leu
385                 390                 395                 400
Asp Gln Leu Pro Leu Glu Gly Glu Ser Ser Leu Thr Glu Tyr Ser His
                405                 410                 415
Arg Leu Cys His Val Arg Phe Ala Gln Ser Leu Arg Asn Ala Glu Pro
            420                 425                 430
Leu Asp Tyr Ala Arg Val Pro Met Phe Ser Trp Thr His Arg Ser Ala
            435                 440                 445
```

```
Thr Pro Thr Asn Thr Ile Asp Pro Asp Val Ile Thr Gln Ile Pro Leu
    450                 455                 460

Val Lys Ala His Thr Leu Gln Ser Gly Thr Thr Val Lys Gly Pro
465                 470                 475                 480

Gly Phe Thr Gly Gly Asp Ile Leu Arg Arg Thr Ser Gly Gly Pro Phe
                485                 490                 495

Ala Phe Ser Asn Val Asn Leu Asp Trp Asn Leu Ser Gln Arg Tyr Arg
                500                 505                 510

Ala Arg Ile Arg Tyr Ala Ser Thr Thr Asn Leu Arg Met Tyr Val Thr
            515                 520                 525

Ile Ala Gly Glu Arg Ile Phe Ala Gly Gln Phe Asn Lys Thr Met Asn
            530                 535                 540

Thr Gly Asp Pro Leu Thr Phe Gln Ser Phe Ser Tyr Ala Thr Ile Asp
545                 550                 555                 560

Thr Ala Phe Thr Phe Pro Thr Lys Ala Ser Ser Leu Thr Val Gly Ala
                565                 570                 575

Asp Thr Phe Ser Ser Gly Asn Glu Val Tyr Val Asp Arg Phe Glu Leu
            580                 585                 590

Ile Pro Val Thr Ala Thr Phe Glu Ala Glu Tyr Asp Leu Glu Lys Ala
            595                 600                 605

Gln Lys Ala Val Asn Ala Leu Phe Thr Ser Ser Asn Gln Ile Gly Leu
    610                 615                 620

Lys Thr Asp Val Thr Asp Tyr His Ile Asp Lys Val
625                 630                 635

<210> SEQ ID NO 22
<211> LENGTH: 622
<212> TYPE: PRT
<213> ORGANISM: Artificial Sequence
<220> FEATURE:
<223> OTHER INFORMATION: Bt29-Bt22Tr3

<400> SEQUENCE: 22

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
            20                  25                  30

Val Ala Glu Ile His Leu Lys Ile Thr Arg Leu Ile Leu Glu Asn Phe
        35                  40                  45

Leu Pro Gly Gly Ser Phe Ala Phe Gly Leu Phe Asp Leu Ile Trp Gly
    50                  55                  60

Ile Phe Asn Glu Asp Gln Trp Ser Ala Phe Leu Arg Gln Val Glu Glu
65                  70                  75                  80

Leu Ile Asn Gln Arg Ile Thr Glu Phe Ala Arg Gly Gln Ala Ile Gln
                85                  90                  95

Arg Leu Val Gly Phe Gly Arg Ser Tyr Asp Glu Tyr Ile Leu Ala Leu
            100                 105                 110

Lys Glu Trp Glu Asn Asp Pro Asp Asn Pro Ala Ser Lys Glu Arg Val
        115                 120                 125

Arg Thr Arg Phe Arg Thr Thr Asp Ala Leu Leu Thr Gly Val Pro
    130                 135                 140

Leu Met Ala Ile Pro Gly Phe Glu Leu Ala Thr Leu Ser Val Tyr Ala
145                 150                 155                 160

Gln Ser Ala Asn Leu His Leu Ala Leu Leu Arg Asp Ala Val Phe Phe
                165                 170                 175
```

```
Gly Glu Arg Trp Gly Leu Thr Gln Thr Asn Ile Asn Asp Leu Tyr Ser
                180                 185                 190

Arg Leu Lys Asn Ser Ile Arg Asp Tyr Thr Asn His Cys Val Arg Phe
            195                 200                 205

Tyr Asn Ile Gly Leu Gly Asn Leu Asn Val Ile Arg Pro Glu Tyr Tyr
        210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255

Leu Thr Arg Glu Ile Tyr Thr Asp Pro Ile Ile Ser Pro Gly Ala Gln
            260                 265                 270

Ala Gly Tyr Thr Leu Gln Asp Val Leu Arg Glu Pro His Leu Met Asp
        275                 280                 285

Phe Leu Asn Arg Leu Ile Ile Tyr Thr Gly Glu Tyr Arg Gly Ile Arg
        290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Ala Thr Ala Glu Pro Thr
                325                 330                 335

Arg Phe Ile Thr Pro Ser Thr Phe Pro Gly Leu Asn Leu Phe Tyr Arg
            340                 345                 350

Thr Leu Ser Ala Pro Ile Phe Arg Asp Glu Pro Gly Ala Asn Ile Ile
        355                 360                 365

Ile Arg Tyr Arg Thr Ser Leu Val Glu Gly Val Gly Phe Ile Gln Pro
370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                405                 410                 415

Arg Leu Cys His Val Arg Phe Ala Gln Ser Leu Arg Asn Ala Glu Pro
            420                 425                 430

Leu Asp Tyr Ala Arg Val Pro Met Phe Ser Trp Thr His Arg Ser Ala
        435                 440                 445

Thr Pro Thr Asn Thr Ile Asp Pro Asp Val Ile Thr Gln Ile Pro Leu
        450                 455                 460

Val Lys Ala His Thr Leu Gln Ser Gly Thr Thr Val Lys Gly Pro
465                 470                 475                 480

Gly Phe Thr Gly Gly Asp Ile Leu Arg Arg Thr Ser Gly Gly Pro Phe
                485                 490                 495

Ala Phe Ser Asn Val Asn Leu Asp Trp Asn Leu Ser Gln Arg Tyr Arg
            500                 505                 510

Ala Arg Ile Arg Tyr Ala Ser Thr Thr Asn Leu Arg Met Tyr Val Thr
        515                 520                 525

Ile Ala Gly Glu Arg Ile Phe Ala Gly Gln Phe Asn Lys Thr Met Asn
        530                 535                 540

Thr Gly Asp Pro Leu Thr Phe Gln Ser Phe Ser Tyr Ala Thr Ile Asp
545                 550                 555                 560

Thr Ala Phe Thr Phe Pro Thr Lys Ala Ser Ser Leu Thr Val Gly Ala
                565                 570                 575

Asp Thr Phe Ser Ser Gly Asn Glu Val Tyr Val Asp Arg Phe Glu Leu
            580                 585                 590
```

Ile Pro Val Thr Ala Thr Phe Glu Ala Glu Tyr Asp Leu Glu Lys Ala
                595                 600                 605

Gln Lys Ala Val Asn Ala Leu Phe Thr Ser Ser Asn Gln Ile
            610                 615                 620

<210> SEQ ID NO 23
<211> LENGTH: 610
<212> TYPE: PRT
<213> ORGANISM: Artificial Sequence
<220> FEATURE:
<223> OTHER INFORMATION: Bt29-Bt22Tr4

<400> SEQUENCE: 23

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
            20                  25                  30

Val Ala Glu Ile His Leu Lys Ile Thr Arg Leu Ile Leu Glu Asn Phe
        35                  40                  45

Leu Pro Gly Gly Ser Phe Ala Phe Gly Leu Phe Asp Leu Ile Trp Gly
    50                  55                  60

Ile Phe Asn Glu Asp Gln Trp Ser Ala Phe Leu Arg Gln Val Glu Glu
65                  70                  75                  80

Leu Ile Asn Gln Arg Ile Thr Glu Phe Ala Arg Gly Gln Ala Ile Gln
                85                  90                  95

Arg Leu Val Gly Phe Gly Arg Ser Tyr Asp Glu Tyr Ile Leu Ala Leu
            100                 105                 110

Lys Glu Trp Glu Asn Asp Pro Asp Asn Pro Ala Ser Lys Glu Arg Val
        115                 120                 125

Arg Thr Arg Phe Arg Thr Thr Asp Asp Ala Leu Leu Thr Gly Val Pro
    130                 135                 140

Leu Met Ala Ile Pro Gly Phe Glu Leu Ala Thr Leu Ser Val Tyr Ala
145                 150                 155                 160

Gln Ser Ala Asn Leu His Leu Ala Leu Leu Arg Asp Ala Val Phe Phe
                165                 170                 175

Gly Glu Arg Trp Gly Leu Thr Gln Thr Asn Ile Asn Asp Leu Tyr Ser
            180                 185                 190

Arg Leu Lys Asn Ser Ile Arg Asp Tyr Thr Asn His Cys Val Arg Phe
        195                 200                 205

Tyr Asn Ile Gly Leu Gly Asn Leu Asn Val Ile Arg Pro Glu Tyr Tyr
    210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255

Leu Thr Arg Glu Ile Tyr Thr Asp Pro Ile Ile Ser Pro Gly Ala Gln
            260                 265                 270

Ala Gly Tyr Thr Leu Gln Asp Val Leu Arg Glu Pro His Leu Met Asp
        275                 280                 285

Phe Leu Asn Arg Leu Ile Ile Tyr Thr Gly Tyr Arg Gly Ile Arg
    290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Ala Thr Ala Glu Pro Thr
                325                 330                 335

```
Arg Phe Ile Thr Pro Ser Thr Phe Pro Gly Leu Asn Leu Phe Tyr Arg
                340                 345                 350

Thr Leu Ser Ala Pro Ile Phe Arg Asp Glu Pro Gly Ala Asn Ile Ile
            355                 360                 365

Ile Arg Tyr Arg Thr Ser Leu Val Glu Gly Val Gly Phe Ile Gln Pro
        370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Leu Thr Glu Tyr Ser His
                405                 410                 415

Arg Leu Cys His Val Arg Phe Ala Gln Ser Leu Arg Asn Ala Glu Pro
            420                 425                 430

Leu Asp Tyr Ala Arg Val Pro Met Phe Ser Trp Thr His Arg Ser Ala
        435                 440                 445

Thr Pro Thr Asn Thr Ile Asp Pro Asp Val Ile Thr Gln Ile Pro Leu
    450                 455                 460

Val Lys Ala His Thr Leu Gln Ser Gly Thr Thr Val Val Lys Gly Pro
465                 470                 475                 480

Gly Phe Thr Gly Gly Asp Ile Leu Arg Arg Thr Ser Gly Gly Pro Phe
                485                 490                 495

Ala Phe Ser Asn Val Asn Leu Asp Trp Asn Leu Ser Gln Arg Tyr Arg
            500                 505                 510

Ala Arg Ile Arg Tyr Ala Ser Thr Thr Asn Leu Arg Met Tyr Val Thr
        515                 520                 525

Ile Ala Gly Glu Arg Ile Phe Ala Gly Gln Phe Asn Lys Thr Met Asn
    530                 535                 540

Thr Gly Asp Pro Leu Thr Phe Gln Ser Phe Ser Tyr Ala Thr Ile Asp
545                 550                 555                 560

Thr Ala Phe Thr Phe Pro Thr Lys Ala Ser Ser Leu Thr Val Gly Ala
                565                 570                 575

Asp Thr Phe Ser Ser Gly Asn Glu Val Tyr Val Asp Arg Phe Glu Leu
            580                 585                 590

Ile Pro Val Thr Ala Thr Phe Glu Ala Glu Tyr Asp Leu Glu Lys Ala
        595                 600                 605

Gln Lys
    610

<210> SEQ ID NO 24
<211> LENGTH: 607
<212> TYPE: PRT
<213> ORGANISM: Artificial Sequence
<220> FEATURE:
<223> OTHER INFORMATION: Bt29-Bt22Tr5

<400> SEQUENCE: 24

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
                20                  25

-continued

```
Leu Ile Asn Gln Arg Ile Thr Glu Phe Ala Arg Gly Gln Ala Ile Gln
                85                  90                  95
Arg Leu Val Gly Phe Gly Arg Ser Tyr Asp Glu Tyr Ile Leu Ala Leu
            100                 105                 110
Lys Glu Trp Glu Asn Asp Pro Asp Asn Pro Ala Ser Lys Glu Arg Val
        115                 120                 125
Arg Thr Arg Phe Arg Thr Thr Asp Asp Ala Leu Leu Thr Gly Val Pro
    130                 135                 140
Leu Met Ala Ile Pro Gly Phe Glu Leu Ala Thr Leu Ser Val Tyr Ala
145                 150                 155                 160
Gln Ser Ala Asn Leu His Leu Ala Leu Leu Arg Asp Ala Val Phe Phe
                165                 170                 175
Gly Glu Arg Trp Gly Leu Thr Gln Thr Asn Ile Asn Asp Leu Tyr Ser
            180                 185                 190
Arg Leu Lys Asn Ser Ile Arg Asp Tyr Thr Asn His Cys Val Arg Phe
        195                 200                 205
Tyr Asn Ile Gly Leu Gly Asn Leu Asn Val Ile Arg Pro Glu Tyr Tyr
    210                 215                 220
Arg Phe Gln Arg Glu Leu Thr Ile Ser Val Leu Asp Leu Val Ala Leu
225                 230                 235                 240
Phe Pro Asn Tyr Asp Ile Arg Thr Tyr Pro Ile Pro Thr Lys Ser Gln
                245                 250                 255
Leu Thr Arg Glu Ile Tyr Thr Asp Pro Ile Ile Ser Pro Gly Ala Gln
            260                 265                 270
Ala Gly Tyr Thr Leu Gln Asp Val Leu Arg Glu Pro His Leu Met Asp
        275                 280                 285
Phe Leu Asn Arg Leu Ile Ile Tyr Thr Gly Glu Tyr Arg Gly Ile Arg
    290                 295                 300
His Trp Ala Gly His Glu Val Glu Ser Ser Arg Thr Gly Met Met Thr
305                 310                 315                 320
Asn Ile Arg Phe Pro Leu Tyr Gly Thr Ala Ala Thr Ala Glu Pro Thr
                325                 330                 335
Arg Phe Ile Thr Pro Ser Thr Phe Pro Gly Leu Asn Leu Phe Tyr Arg
            340                 345                 350
Thr Leu Ser Ala Pro Ile Phe Arg Asp Glu Pro Gly Ala Asn Ile Ile
        355                 360                 365
Ile Arg Tyr Arg Thr Ser Leu Val Glu Gly Val Gly Phe Ile Gln Pro
    370                 375                 380
Asn Asn Gly Glu Gln Leu Tyr Arg Val Arg Gly Thr Leu Asp Ser Leu
385                 390                 395                 400
Asp Gln Leu Pro Leu Glu Gly Glu Ser Ser Leu Thr Glu Tyr Ser His
                405                 410                 415
Arg Leu Cys His Val Arg Phe Ala Gln Ser Leu Arg Asn Ala Glu Pro
            420                 425                 430
Leu Asp Tyr Ala Arg Val Pro Met Phe Ser Trp Thr His Arg Ser Ala
        435                 440                 445
Thr Pro Thr Asn Thr Ile Asp Pro Asp Val Ile Thr Gln Ile Pro Leu
    450                 455                 460
Val Lys Ala His Thr Leu Gln Ser Gly Thr Thr Val Val Lys Gly Pro
465                 470                 475                 480
Gly Phe Thr Gly Gly Asp Ile Leu Arg Arg Thr Ser Gly Gly Pro Phe
                485                 490                 495
Ala Phe Ser Asn Val Asn Leu Asp Trp Asn Leu Ser Gln Arg Tyr Arg
```

```
                500                 505                 510
Ala Arg Ile Arg Tyr Ala Ser Thr Thr Asn Leu Arg Met Tyr Val Thr
            515                 520                 525
Ile Ala Gly Glu Arg Ile Phe Ala Gly Gln Phe Asn Lys Thr Met Asn
            530                 535                 540
Thr Gly Asp Pro Leu Thr Phe Gln Ser Phe Ser Tyr Ala Thr Ile Asp
545                 550                 555                 560
Thr Ala Phe Thr Phe Pro Thr Lys Ala Ser Ser Leu Thr Val Gly Ala
                565                 570                 575
Asp Thr Phe Ser Ser Gly Asn Glu Val Tyr Val Asp Arg Phe Glu Leu
            580                 585                 590
Ile Pro Val Thr Ala Thr Phe Glu Ala Glu Tyr Asp Leu Glu Lys
            595                 600                 605

<210> SEQ ID NO 25
<211> LENGTH: 603
<212> TYPE: PRT
<213> ORGANISM: Artificial Sequence
<220> FEATURE:
<223> OTHER INFORMATION: Bt29-Bt22Tr6

<400> SEQUENCE: 25

Met Glu Ile Asn Asn Gln Asn Gln Cys Val Pro Tyr Asn Cys Leu Asn
1               5                   10                  15
Asn Pro Glu Ser Glu Ile Leu Asn Val Ala Ile Phe Ser Glu Gln
            20                  25                  30
Val Ala Glu Ile His Leu Lys Ile Thr Arg Leu Ile Leu Glu Asn Phe
            35                  40                  45
Leu Pro Gly Gly Ser Phe Ala Phe Gly Leu Phe Asp Leu Ile Trp Gly
    50                  55                  60
Ile Phe Asn Glu Asp Gln Trp Ser Ala Phe Leu Arg Gln Val Glu Glu
65                  70                  75                  80
Leu Ile Asn Gln Arg Ile Thr Glu Phe Ala Arg Gly Gln Ala Ile Gln
                85                  90                  95
Arg Leu Val Gly Phe Gly Arg Ser Tyr Asp Glu Tyr Ile Leu Ala Leu
            100                 105                 110
Lys Glu Trp Glu Asn Asp Pro Asp Asn Pro Ala Ser Lys Glu Arg Val
            115                 120                 125
Arg Thr Arg Phe Arg Thr Thr Asp Ala Leu Leu Thr Gly Val Pro
            130                 135                 140
Leu Met Ala Ile Pro Gly Phe Glu Leu Ala Thr Leu Ser Val Tyr Ala
145                 150                 155                 160
Gln Ser Ala Asn Leu His Leu Ala Leu Leu Arg Asp Ala Val Phe Phe
                165                 170                 175
Gly Glu Arg Trp Gly Leu Thr Gln Thr Asn Ile Asn Asp Leu Tyr Ser
            180                 185                 190
Arg Leu Lys Asn Ser Ile Arg Asp Tyr Thr Asn His Cys Val Arg Phe
            195                 200                 205
Tyr Asn Ile Gly Leu Gly Asn Leu Asn Val Ile Arg Pro Glu Tyr Tyr
            210                 215                 220
Arg Phe Gln Arg Glu Leu Thr Ile Ser Val Leu Asp Leu Val Ala Leu
225                 230                 235                 240
Phe Pro Asn Tyr Asp Ile Arg Thr Tyr Pro Ile Pro Thr Lys Ser Gln
                245                 250                 255
Leu Thr Arg Glu Ile Tyr Thr Asp Pro Ile Ile Ser Pro Gly Ala Gln
```

-continued

```
                260                 265                 270
Ala Gly Tyr Thr Leu Gln Asp Val Leu Arg Glu Pro His Leu Met Asp
            275                 280                 285

Phe Leu Asn Arg Leu Ile Ile Tyr Thr Gly Glu Tyr Arg Gly Ile Arg
        290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Thr Ala Glu Pro Thr
            325                 330                 335

Arg Phe Ile Thr Pro Ser Thr Phe Pro Gly Leu Asn Leu Phe Tyr Arg
        340                 345                 350

Thr Leu Ser Ala Pro Ile Phe Arg Asp Glu Pro Gly Ala Asn Ile Ile
        355                 360                 365

Ile Arg Tyr Arg Thr Ser Leu Val Glu Gly Val Gly Phe Ile Gln Pro
        370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
            405                 410                 415

Arg Leu Cys His Val Arg Phe Ala Gln Ser Leu Arg Asn Ala Glu Pro
        420                 425                 430

Leu Asp Tyr Ala Arg Val Pro Met Phe Ser Trp Thr His Arg Ser Ala
        435                 440                 445

Thr Pro Thr Asn Thr Ile Asp Pro Asp Val Ile Thr Gln Ile Pro Leu
        450                 455                 460

Val Lys Ala His Thr Leu Gln Ser Gly Thr Thr Val Val Lys Gly Pro
465                 470                 475                 480

Gly Phe Thr Gly Gly Asp Ile Leu Arg Arg Thr Ser Gly Gly Pro Phe
            485                 490                 495

Ala Phe Ser Asn Val Asn Leu Asp Trp Asn Leu Ser Gln Arg Tyr Arg
        500                 505                 510

Ala Arg Ile Arg Tyr Ala Ser Thr Thr Asn Leu Arg Met Tyr Val Thr
        515                 520                 525

Ile Ala Gly Glu Arg Ile Phe Ala Gly Gln Phe Asn Lys Thr Met Asn
        530                 535                 540

Thr Gly Asp Pro Leu Thr Phe Gln Ser Phe Ser Tyr Ala Thr Ile Asp
545                 550                 555                 560

Thr Ala Phe Thr Phe Pro Thr Lys Ala Ser Ser Leu Thr Val Gly Ala
            565                 570                 575

Asp Thr Phe Ser Ser Gly Asn Glu Val Tyr Val Asp Arg Phe Glu Leu
        580                 585                 590

Ile Pro Val Thr Ala Thr Phe Glu Ala Glu Tyr
        595                 600
```

<210> SEQ ID NO 26
<211> LENGTH: 676
<212> TYPE: PRT
<213> ORGANISM: Artificial Sequence
<220> FEATURE:
<223> OTHER INFORMATION: BT29BT22-TL22v1

<400> SEQUENCE: 26

```
Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
```

```
            20                  25                  30
Val Ala Glu Ile His Leu Lys Ile Thr Arg Leu Ile Leu Glu Asn Phe
    35                  40                  45
Leu Pro Gly Gly Ser Phe Ala Phe Gly Leu Phe Asp Leu Ile Trp Gly
50                  55                  60
Ile Phe Asn Glu Asp Gln Trp Ser Ala Phe Leu Arg Gln Val Glu Glu
65                  70                  75                  80
Leu Ile Asn Gln Arg Ile Thr Glu Phe Ala Arg Gly Gln Ala Ile Gln
                85                  90                  95
Arg Leu Val Gly Phe Gly Arg Ser Tyr Asp Glu Tyr Ile Leu Ala Leu
                100                 105                 110
Lys Glu Trp Glu Asn Asp Pro Asp Asn Pro Ala Ser Lys Glu Arg Val
                115                 120                 125
Arg Thr Arg Phe Arg Thr Thr Asp Asp Ala Leu Leu Thr Gly Val Pro
                130                 135                 140
Leu Met Ala Ile Pro Gly Phe Glu Leu Ala Thr Leu Ser Val Tyr Ala
145                 150                 155                 160
Gln Ser Ala Asn Leu His Leu Ala Leu Leu Arg Asp Ala Val Phe Phe
                165                 170                 175
Gly Glu Arg Trp Gly Leu Thr Gln Thr Asn Ile Asn Asp Leu Tyr Ser
                180                 185                 190
Arg Leu Lys Asn Ser Ile Arg Asp Tyr Thr Asn His Cys Val Arg Phe
                195                 200                 205
Tyr Asn Ile Gly Leu Gly Asn Leu Asn Val Ile Arg Pro Glu Tyr Tyr
                210                 215                 220
Arg Phe Gln Arg Glu Leu Thr Ile Ser Val Leu Asp Leu Val Ala Leu
225                 230                 235                 240
Phe Pro Asn Tyr Asp Ile Arg Thr Tyr Pro Ile Pro Thr Lys Ser Gln
                245                 250                 255
Leu Thr Arg Glu Ile Tyr Thr Asp Pro Ile Ile Ser Pro Gly Ala Gln
                260                 265                 270
Ala Gly Tyr Thr Leu Gln Asp Val Leu Arg Glu Pro His Leu Met Asp
                275                 280                 285
Phe Leu Asn Arg Leu Ile Ile Tyr Thr Gly Glu Tyr Arg Gly Ile Arg
                290                 295                 300
His Trp Ala Gly His Glu Val Glu Ser Ser Arg Thr Gly Met Met Thr
305                 310                 315                 320
Asn Ile Arg Phe Pro Leu Tyr Gly Thr Ala Thr Ala Glu Pro Thr
                325                 330                 335
Arg Phe Ile Thr Pro Ser Thr Phe Pro Gly Leu Asn Leu Phe Tyr Arg
                340                 345                 350
Thr Leu Ser Ala Pro Ile Phe Arg Asp Glu Pro Gly Ala Asn Ile Ile
                355                 360                 365
Ile Arg Tyr Arg Thr Ser Leu Val Glu Gly Val Gly Phe Ile Gln Pro
                370                 375                 380
Asn Asn Gly Glu Gln Leu Tyr Arg Val Arg Gly Thr Leu Asp Ser Leu
385                 390                 395                 400
Asp Gln Leu Pro Leu Glu Gly Glu Ser Ser Leu Thr Glu Tyr Ser His
                405                 410                 415
Arg Leu Cys His Val Arg Phe Ala Gln Ser Leu Arg Asn Ala Glu Pro
                420                 425                 430
Leu Asp Tyr Ala Arg Val Pro Met Phe Ser Trp Thr His Arg Ser Ala
                435                 440                 445
```

```
Thr Pro Thr Asn Thr Ile Asp Pro Asp Val Ile Thr Gln Ile Pro Leu
    450                 455                 460

Val Lys Ala His Thr Leu Gln Ser Gly Thr Thr Val Val Lys Gly Pro
465                 470                 475                 480

Gly Phe Thr Gly Gly Asp Ile Leu Arg Arg Thr Ser Gly Gly Pro Phe
                485                 490                 495

Ala Phe Ser Asn Val Asn Leu Asp Trp Asn Leu Ser Gln Arg Tyr Arg
            500                 505                 510

Ala Arg Ile Arg Tyr Ala Ser Thr Thr Asn Leu Arg Met Tyr Val Thr
        515                 520                 525

Ile Ala Gly Glu Arg Ile Phe Ala Gly Gln Phe Asn Lys Thr Met Asn
    530                 535                 540

Thr Gly Asp Pro Leu Thr Phe Gln Ser Phe Ser Tyr Ala Thr Ile Asp
545                 550                 555                 560

Thr Ala Phe Thr Phe Pro Thr Lys Ala Ser Ser Leu Thr Val Gly Ala
                565                 570                 575

Asp Thr Phe Ser Ser Gly Asn Glu Val Tyr Val Asp Arg Phe Glu Leu
            580                 585                 590

Ile Pro Val Thr Ala Thr Leu Glu Ala Val Thr Asp Leu Glu Arg Ala
        595                 600                 605

Gln Lys Ala Val His Glu Leu Phe Thr Ser Thr Asn Pro Gly Gly Leu
    610                 615                 620

Lys Thr Asp Val Ala Lys Asp His Tyr Thr Asn Thr Ile Ser Lys Ser
625                 630                 635                 640

Val Gln Ser Val Phe Arg Cys Arg Cys Ser Glu Arg Thr Arg Ile Tyr
                645                 650                 655

Arg Trp Gly Tyr Pro Ser Lys Lys Glu Tyr Trp Tyr Ile Trp Gly Tyr
            660                 665                 670

Thr Ser Lys Tyr
        675

<210> SEQ ID NO 27
<211> LENGTH: 644
<212> TYPE: PRT
<213> ORGANISM: Artificial Sequence
<220> FEATURE:
<223> OTHER INFORMATION: BT29BT22-TL22v2

<400> SEQUENCE: 27

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
            20                  25                  30

Val Ala Glu Ile His Leu Lys Ile Thr Arg Leu Ile Leu Glu Asn Phe
        35                  40                  45

Leu Pro Gly Gly Ser Phe Ala Phe Gly Leu Phe Asp Leu Ile Trp Gly
    50                  55                  60

Ile Phe Asn Glu Asp Gln Trp Ser Ala Phe Leu Arg Gln Val Glu Glu
65                  70                  75                  80

Leu Ile Asn Gln Arg Ile Thr Glu Phe Ala Arg Gly Gln Ala Ile Gln
                85                  90                  95

Arg Leu Val Gly Phe Gly Arg Ser Tyr Asp Glu Tyr Ile Leu Ala Leu
            100                 105                 110

Lys Glu Trp Glu Asn Asp Pro Asp Asn Pro Ala Ser Lys Glu Arg Val
        115                 120                 125
```

```
Arg Thr Arg Phe Arg Thr Thr Asp Asp Ala Leu Leu Thr Gly Val Pro
    130                 135                 140

Leu Met Ala Ile Pro Gly Phe Glu Leu Ala Thr Leu Ser Val Tyr Ala
145                 150                 155                 160

Gln Ser Ala Asn Leu His Leu Ala Leu Leu Arg Asp Ala Val Phe Phe
                165                 170                 175

Gly Glu Arg Trp Gly Leu Thr Gln Thr Asn Ile Asn Asp Leu Tyr Ser
            180                 185                 190

Arg Leu Lys Asn Ser Ile Arg Asp Tyr Thr Asn His Cys Val Arg Phe
        195                 200                 205

Tyr Asn Ile Gly Leu Gly Asn Leu Asn Val Ile Arg Pro Glu Tyr Tyr
    210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255

Leu Thr Arg Glu Ile Tyr Thr Asp Pro Ile Ile Ser Pro Gly Ala Gln
            260                 265                 270

Ala Gly Tyr Thr Leu Gln Asp Val Leu Arg Glu Pro His Leu Met Asp
        275                 280                 285

Phe Leu Asn Arg Leu Ile Ile Tyr Thr Gly Glu Tyr Arg Gly Ile Arg
    290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Ala Thr Ala Glu Pro Thr
                325                 330                 335

Arg Phe Ile Thr Pro Ser Thr Phe Pro Gly Leu Asn Leu Phe Tyr Arg
            340                 345                 350

Thr Leu Ser Ala Pro Ile Phe Arg Asp Glu Pro Gly Ala Asn Ile Ile
        355                 360                 365

Ile Arg Tyr Arg Thr Ser Leu Val Glu Gly Val Gly Phe Ile Gln Pro
    370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                405                 410                 415

Arg Leu Cys His Val Arg Phe Ala Gln Ser Leu Arg Asn Ala Glu Pro
            420                 425                 430

Leu Asp Tyr Ala Arg Val Pro Met Phe Ser Trp Thr His Arg Ser Ala
        435                 440                 445

Thr Pro Thr Asn Thr Ile Asp Pro Asp Val Ile Thr Gln Ile Pro Leu
    450                 455                 460

Val Lys Ala His Thr Leu Gln Ser Gly Thr Thr Val Val Lys Gly Pro
465                 470                 475                 480

Gly Phe Thr Gly Gly Asp Ile Leu Arg Arg Thr Ser Gly Gly Pro Phe
                485                 490                 495

Ala Phe Ser Asn Val Asn Leu Asp Trp Asn Leu Ser Gln Arg Tyr Arg
            500                 505                 510

Ala Arg Ile Arg Tyr Ala Ser Thr Thr Asn Leu Arg Met Tyr Val Thr
        515                 520                 525

Ile Ala Gly Glu Arg Ile Phe Ala Gly Gln Phe Asn Lys Thr Met Asn
    530                 535                 540
```

```
Thr Gly Asp Pro Leu Thr Phe Gln Ser Phe Ser Tyr Ala Thr Ile Asp
545                 550                 555                 560

Thr Ala Phe Thr Phe Pro Thr Lys Ala Ser Ser Leu Thr Val Gly Ala
                565                 570                 575

Asp Thr Phe Ser Ser Gly Asn Glu Val Tyr Val Asp Arg Phe Glu Leu
            580                 585                 590

Ile Pro Val Thr Ala Thr Leu Glu Ala Val Thr Asp Leu Glu Arg Ala
        595                 600                 605

Gln Lys Ala Val His Glu Leu Phe Thr Ser Thr Asn Pro Gly Gly Leu
    610                 615                 620

Lys Thr Asp Val Ala Lys Asp His Tyr Thr Asn Thr Ile Ser Lys Ser
625                 630                 635                 640

Val Gln Ser Val
```

<210> SEQ ID NO 28
<211> LENGTH: 634
<212> TYPE: PRT
<213> ORGANISM: Artificial Sequence
<220> FEATURE:
<223> OTHER INFORMATION: BT29BT22-TL22v3

<400> SEQUENCE: 28

```
Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
            20                  25                  30

Val Ala Glu Ile His Leu Lys Ile Thr Arg Leu Ile Leu Glu Asn Phe
        35                  40                  45

Leu Pro Gly Gly Ser Phe Ala Phe Gly Leu Phe Asp Leu Ile Trp Gly
    50                  55                  60

Ile Phe Asn Glu Asp Gln Trp Ser Ala Phe Leu Arg Gln Val Glu Glu
65                  70                  75                  80

Leu Ile Asn Gln Arg Ile Thr Glu Phe Ala Arg Gly Gln Ala Ile Gln
                85                  90                  95

Arg Leu Val Gly Phe Gly Arg Ser Tyr Asp Glu Tyr Ile Leu Ala Leu
            100                 105                 110

Lys Glu Trp Glu Asn Asp Pro Asn Pro Ala Ser Lys Glu Arg Val
        115                 120                 125

Arg Thr Arg Phe Arg Thr Thr Asp Ala Leu Leu Thr Gly Val Pro
    130                 135                 140

Leu Met Ala Ile Pro Gly Phe Glu Leu Ala Thr Leu Ser Val Tyr Ala
145                 150                 155                 160

Gln Ser Ala Asn Leu His Leu Ala Leu Leu Arg Asp Ala Val Phe Phe
                165                 170                 175

Gly Glu Arg Trp Gly Leu Thr Gln Thr Asn Ile Asn Asp Leu Tyr Ser
            180                 185                 190

Arg Leu Lys Asn Ser Ile Arg Asp Tyr Thr Asn His Cys Val Arg Phe
        195                 200                 205

Tyr Asn Ile Gly Leu Gly Asn Leu Asn Val Ile Arg Pro Glu Tyr Tyr
    210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255

Leu Thr Arg Glu Ile Tyr Thr Asp Pro Ile Ile Ser Pro Gly Ala Gln
```

```
                    260                 265                 270
Ala Gly Tyr Thr Leu Gln Asp Val Leu Arg Glu Pro His Leu Met Asp
            275                 280                 285

Phe Leu Asn Arg Leu Ile Ile Tyr Thr Gly Glu Tyr Arg Gly Ile Arg
            290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Ala Thr Ala Glu Pro Thr
            325                 330                 335

Arg Phe Ile Thr Pro Ser Thr Phe Pro Gly Leu Asn Leu Phe Tyr Arg
            340                 345                 350

Thr Leu Ser Ala Pro Ile Phe Arg Asp Glu Pro Gly Ala Asn Ile Ile
            355                 360                 365

Ile Arg Tyr Arg Thr Ser Leu Val Glu Gly Val Gly Phe Ile Gln Pro
            370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
            405                 410                 415

Arg Leu Cys His Val Arg Phe Ala Gln Ser Leu Arg Asn Ala Glu Pro
            420                 425                 430

Leu Asp Tyr Ala Arg Val Pro Met Phe Ser Trp Thr His Arg Ser Ala
            435                 440                 445

Thr Pro Thr Asn Thr Ile Asp Pro Asp Val Ile Thr Gln Ile Pro Leu
            450                 455                 460

Val Lys Ala His Thr Leu Gln Ser Gly Thr Thr Val Val Lys Gly Pro
465                 470                 475                 480

Gly Phe Thr Gly Gly Asp Ile Leu Arg Arg Thr Ser Gly Gly Pro Phe
            485                 490                 495

Ala Phe Ser Asn Val Asn Leu Asp Trp Asn Leu Ser Gln Arg Tyr Arg
            500                 505                 510

Ala Arg Ile Arg Tyr Ala Ser Thr Thr Asn Leu Arg Met Tyr Val Thr
            515                 520                 525

Ile Ala Gly Glu Arg Ile Phe Ala Gly Gln Phe Asn Lys Thr Met Asn
            530                 535                 540

Thr Gly Asp Pro Leu Thr Phe Gln Ser Phe Ser Tyr Ala Thr Ile Asp
545                 550                 555                 560

Thr Ala Phe Thr Phe Pro Thr Lys Ala Ser Ser Leu Thr Val Gly Ala
                    565                 570                 575

Asp Thr Phe Ser Ser Gly Asn Glu Val Tyr Val Asp Arg Phe Glu Leu
            580                 585                 590

Ile Pro Val Thr Ala Thr Leu Glu Ala Val Thr Asp Leu Glu Arg Ala
            595                 600                 605

Gln Lys Ala Val His Glu Leu Phe Thr Ser Thr Asn Pro Gly Gly Leu
            610                 615                 620

Lys Thr Asp Val Ala Lys Asp His Tyr Thr
625                 630

<210> SEQ ID NO 29
<211> LENGTH: 622
<212> TYPE: PRT
<213> ORGANISM: Artificial Sequence
<220> FEATURE:
<223> OTHER INFORMATION: BT29BT22-TL22v4
```

```
<400> SEQUENCE: 29

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
            20                  25                  30

Val Ala Glu Ile His Leu Lys Ile Thr Arg Leu Ile Leu Glu Asn Phe
        35                  40                  45

Leu Pro Gly Gly Ser Phe Ala Phe Gly Leu Phe Asp Leu Ile Trp Gly
    50                  55                  60

Ile Phe Asn Glu Asp Gln Trp Ser Ala Phe Leu Arg Gln Val Glu Glu
65                  70                  75                  80

Leu Ile Asn Gln Arg Ile Thr Glu Phe Ala Arg Gly Gln Ala Ile Gln
                85                  90                  95

Arg Leu Val Gly Phe Gly Arg Ser Tyr Asp Glu Tyr Ile Leu Ala Leu
            100                 105                 110

Lys Glu Trp Glu Asn Asp Pro Asp Asn Pro Ala Ser Lys Glu Arg Val
        115                 120                 125

Arg Thr Arg Phe Arg Thr Thr Asp Asp Ala Leu Leu Thr Gly Val Pro
130                 135                 140

Leu Met Ala Ile Pro Gly Phe Glu Leu Ala Thr Leu Ser Val Tyr Ala
145                 150                 155                 160

Gln Ser Ala Asn Leu His Leu Ala Leu Leu Arg Asp Ala Val Phe Phe
                165                 170                 175

Gly Glu Arg Trp Gly Leu Thr Gln Thr Asn Ile Asn Asp Leu Tyr Ser
            180                 185                 190

Arg Leu Lys Asn Ser Ile Arg Asp Tyr Thr Asn His Cys Val Arg Phe
        195                 200                 205

Tyr Asn Ile Gly Leu Gly Asn Leu Asn Val Ile Arg Pro Glu Tyr Tyr
210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255

Leu Thr Arg Glu Ile Tyr Thr Asp Pro Ile Ile Ser Pro Gly Ala Gln
            260                 265                 270

Ala Gly Tyr Thr Leu Gln Asp Val Leu Arg Glu Pro His Leu Met Asp
        275                 280                 285

Phe Leu Asn Arg Leu Ile Ile Tyr Thr Gly Glu Tyr Arg Gly Ile Arg
290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Ala Thr Ala Glu Pro Thr
                325                 330                 335

Arg Phe Ile Thr Pro Ser Thr Phe Pro Gly Leu Asn Leu Phe Tyr Arg
            340                 345                 350

Thr Leu Ser Ala Pro Ile Phe Arg Asp Glu Pro Gly Ala Asn Ile Ile
        355                 360                 365

Ile Arg Tyr Arg Thr Ser Leu Val Glu Gly Val Gly Phe Ile Gln Pro
370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                405                 410                 415
```

```
Arg Leu Cys His Val Arg Phe Ala Gln Ser Leu Arg Asn Ala Glu Pro
            420                 425                 430

Leu Asp Tyr Ala Arg Val Pro Met Phe Ser Trp Thr His Arg Ser Ala
        435                 440                 445

Thr Pro Thr Asn Thr Ile Asp Pro Asp Val Ile Thr Gln Ile Pro Leu
    450                 455                 460

Val Lys Ala His Thr Leu Gln Ser Gly Thr Thr Val Lys Gly Pro
465                 470                 475                 480

Gly Phe Thr Gly Gly Asp Ile Leu Arg Arg Thr Ser Gly Pro Phe
                485                 490                 495

Ala Phe Ser Asn Val Asn Leu Asp Trp Asn Leu Ser Gln Arg Tyr Arg
                500                 505                 510

Ala Arg Ile Arg Tyr Ala Ser Thr Thr Asn Leu Arg Met Tyr Val Thr
            515                 520                 525

Ile Ala Gly Glu Arg Ile Phe Ala Gly Gln Phe Asn Lys Thr Met Asn
        530                 535                 540

Thr Gly Asp Pro Leu Thr Phe Gln Ser Phe Ser Tyr Ala Thr Ile Asp
545                 550                 555                 560

Thr Ala Phe Thr Phe Pro Thr Lys Ala Ser Ser Leu Thr Val Gly Ala
                565                 570                 575

Asp Thr Phe Ser Ser Gly Asn Glu Val Tyr Val Asp Arg Phe Glu Leu
                580                 585                 590

Ile Pro Val Thr Ala Thr Leu Glu Ala Val Thr Asp Leu Glu Arg Ala
            595                 600                 605

Gln Lys Ala Val His Glu Leu Phe Thr Ser Thr Asn Pro Gly
        610                 615                 620

<210> SEQ ID NO 30
<211> LENGTH: 610
<212> TYPE: PRT
<213> ORGANISM: Artificial Sequence
<220> FEATURE:
<223> OTHER INFORMATION: BT29BT22-TL22v5

<400> SEQUENCE: 30

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
            20                  25                  30

Val Ala Glu Ile His Leu Lys Ile Thr Arg Leu Ile Leu Glu Asn Phe
        35                  40                  45

Leu Pro Gly Gly Ser Phe Ala Phe Gly Leu Phe Asp Leu Ile Trp Gly
    50                  55                  60

Ile Phe Asn Glu Asp Gln Trp Ser Ala Phe Leu Arg Gln Val Glu Glu
65                  70                  75                  80

Leu Ile Asn Gln Arg Ile Thr Glu Phe Ala Arg Gly Gln Ala Ile Gln
            85                  90                  95

Arg Leu Val Gly Phe Gly Arg Ser Tyr Asp Glu Tyr Ile Leu Ala Leu
            100                 105                 110

Lys Glu Trp Glu Asn Asp Pro Asp Asn Pro Ala Ser Lys Glu Arg Val
        115                 120                 125

Arg Thr Arg Phe Arg Thr Thr Asp Asp Ala Leu Leu Thr Gly Val Pro
    130                 135                 140

Leu Met Ala Ile Pro Gly Phe Glu Leu Ala Thr Leu Ser Val Tyr Ala
145                 150                 155                 160
```

```
Gln Ser Ala Asn Leu His Leu Ala Leu Leu Arg Asp Ala Val Phe Phe
                165                 170                 175

Gly Glu Arg Trp Gly Leu Thr Gln Thr Asn Ile Asn Asp Leu Tyr Ser
            180                 185                 190

Arg Leu Lys Asn Ser Ile Arg Asp Tyr Thr Asn His Cys Val Arg Phe
            195                 200                 205

Tyr Asn Ile Gly Leu Gly Asn Leu Asn Val Ile Arg Pro Glu Tyr Tyr
        210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255

Leu Thr Arg Glu Ile Tyr Thr Asp Pro Ile Ile Ser Pro Gly Ala Gln
            260                 265                 270

Ala Gly Tyr Thr Leu Gln Asp Val Leu Arg Glu Pro His Leu Met Asp
            275                 280                 285

Phe Leu Asn Arg Leu Ile Ile Tyr Thr Gly Glu Tyr Arg Gly Ile Arg
        290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Thr Ala Glu Pro Thr
                325                 330                 335

Arg Phe Ile Thr Pro Ser Thr Phe Pro Gly Leu Asn Leu Phe Tyr Arg
            340                 345                 350

Thr Leu Ser Ala Pro Ile Phe Arg Asp Glu Pro Gly Ala Asn Ile Ile
            355                 360                 365

Ile Arg Tyr Arg Thr Ser Leu Val Glu Gly Val Gly Phe Ile Gln Pro
        370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                405                 410                 415

Arg Leu Cys His Val Arg Phe Ala Gln Ser Leu Arg Asn Ala Glu Pro
            420                 425                 430

Leu Asp Tyr Ala Arg Val Pro Met Phe Ser Trp Thr His Arg Ser Ala
            435                 440                 445

Thr Pro Thr Asn Thr Ile Asp Pro Asp Val Ile Thr Gln Ile Pro Leu
        450                 455                 460

Val Lys Ala His Thr Leu Gln Ser Gly Thr Thr Val Val Lys Gly Pro
465                 470                 475                 480

Gly Phe Thr Gly Gly Asp Ile Leu Arg Arg Thr Ser Gly Gly Pro Phe
                485                 490                 495

Ala Phe Ser Asn Val Asn Leu Asp Trp Asn Leu Ser Gln Arg Tyr Arg
            500                 505                 510

Ala Arg Ile Arg Tyr Ala Ser Thr Thr Asn Leu Arg Met Tyr Val Thr
            515                 520                 525

Ile Ala Gly Glu Arg Ile Phe Ala Gly Gln Phe Asn Lys Thr Met Asn
        530                 535                 540

Thr Gly Asp Pro Leu Thr Phe Gln Ser Phe Ser Tyr Ala Thr Ile Asp
545                 550                 555                 560

Thr Ala Phe Thr Phe Pro Thr Lys Ala Ser Ser Leu Thr Val Gly Ala
                565                 570                 575
```

```
Asp Thr Phe Ser Ser Gly Asn Glu Val Tyr Val Asp Arg Phe Glu Leu
            580                 585                 590

Ile Pro Val Thr Ala Thr Leu Glu Ala Val Thr Asp Leu Glu Arg Ala
            595                 600                 605

Gln Lys
    610

<210> SEQ ID NO 31
<211> LENGTH: 600
<212> TYPE: PRT
<213> ORGANISM: Artificial Sequence
<220> FEATURE:
<223> OTHER INFORMATION: BT29BT22-TL22v6

<400> SEQUENCE: 31

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
            20                  25                  30

Val Ala Glu Ile His Leu Lys Ile Thr Arg Leu Ile Leu Glu Asn Phe
        35                  40                  45

Leu Pro Gly Gly Ser Phe Ala Phe Gly Leu Phe Asp Leu Ile Trp Gly
    50                  55                  60

Ile Phe Asn Glu Asp Gln Trp Ser Ala Phe Leu Arg Gln Val Glu Glu
65                  70                  75                  80

Leu Ile Asn Gln Arg Ile Thr Glu Phe Ala Arg Gly Gln Ala Ile Gln
                85                  90                  95

Arg Leu Val Gly Phe Gly Arg Ser Tyr Asp Glu Tyr Ile Leu Ala Leu
            100                 105                 110

Lys Glu Trp Glu Asn Asp Pro Asp Asn Pro Ala Ser Lys Glu Arg Val
        115                 120                 125

Arg Thr Arg Phe Arg Thr Thr Asp Asp Ala Leu Leu Thr Gly Val Pro
    130                 135                 140

Leu Met Ala Ile Pro Gly Phe Glu Leu Ala Thr Leu Ser Val Tyr Ala
145                 150                 155                 160

Gln Ser Ala Asn Leu His Leu Ala Leu Leu Arg Asp Ala Val Phe Phe
                165                 170                 175

Gly Glu Arg Trp Gly Leu Thr Gln Thr Asn Ile Asn Asp Leu Tyr Ser
            180                 185                 190

Arg Leu Lys Asn Ser Ile Arg Asp Tyr Thr Asn His Cys Val Arg Phe
        195                 200                 205

Tyr Asn Ile Gly Leu Gly Asn Leu Asn Val Ile Arg Pro Glu Tyr Tyr
    210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255

Leu Thr Arg Glu Ile Tyr Thr Asp Pro Ile Ile Ser Pro Gly Ala Gln
            260                 265                 270

Ala Gly Tyr Thr Leu Gln Asp Val Leu Arg Glu Pro His Leu Met Asp
        275                 280                 285

Phe Leu Asn Arg Leu Ile Ile Tyr Thr Gly Glu Tyr Arg Gly Ile Arg
    290                 295                 300

His Trp Ala Gly His Glu Val Glu Ser Ser Arg Thr Gly Met Met Thr
305                 310                 315                 320
```

```
Asn Ile Arg Phe Pro Leu Tyr Gly Thr Ala Thr Ala Glu Pro Thr
                325                 330                 335

Arg Phe Ile Thr Pro Ser Thr Phe Pro Gly Leu Asn Leu Phe Tyr Arg
            340                 345                 350

Thr Leu Ser Ala Pro Ile Phe Arg Asp Glu Pro Gly Ala Asn Ile Ile
            355                 360                 365

Ile Arg Tyr Arg Thr Ser Leu Val Glu Gly Val Gly Phe Ile Gln Pro
    370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                405                 410                 415

Arg Leu Cys His Val Arg Phe Ala Gln Ser Leu Arg Asn Ala Glu Pro
            420                 425                 430

Leu Asp Tyr Ala Arg Val Pro Met Phe Ser Trp Thr His Arg Ser Ala
        435                 440                 445

Thr Pro Thr Asn Thr Ile Asp Pro Asp Val Ile Thr Gln Ile Pro Leu
    450                 455                 460

Val Lys Ala His Thr Leu Gln Ser Gly Thr Thr Val Lys Gly Pro
465                 470                 475                 480

Gly Phe Thr Gly Gly Asp Ile Leu Arg Arg Thr Ser Gly Gly Pro Phe
                485                 490                 495

Ala Phe Ser Asn Val Asn Leu Asp Trp Asn Leu Ser Gln Arg Tyr Arg
            500                 505                 510

Ala Arg Ile Arg Tyr Ala Ser Thr Thr Asn Leu Arg Met Tyr Val Thr
        515                 520                 525

Ile Ala Gly Glu Arg Ile Phe Ala Gly Gln Phe Asn Lys Thr Met Asn
    530                 535                 540

Thr Gly Asp Pro Leu Thr Phe Gln Ser Phe Ser Tyr Ala Thr Ile Asp
545                 550                 555                 560

Thr Ala Phe Thr Phe Pro Thr Lys Ala Ser Ser Leu Thr Val Gly Ala
                565                 570                 575

Asp Thr Phe Ser Ser Gly Asn Glu Val Tyr Val Asp Arg Phe Glu Leu
            580                 585                 590

Ile Pro Val Thr Ala Thr Leu Glu
        595                 600

<210> SEQ ID NO 32
<211> LENGTH: 610
<212> TYPE: PRT
<213> ORGANISM: Artificial Sequence
<220> FEATURE:
<223> OTHER INFORMATION: Bt29-1FaTr1

<400> SEQUENCE: 32

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
                20                  25                  30

Val Ala Glu Ile His Leu L

Leu Ile Asn Gln Arg Ile Thr Glu Phe Ala Arg Gly Gln Ala Ile Gln
            85                  90                  95

Arg Leu Val Gly Phe Gly Arg Ser Tyr Asp Glu Tyr Ile Leu Ala Leu
            100                 105                 110

Lys Glu Trp Glu Asn Asp Pro Asp Asn Pro Ala Ser Lys Glu Arg Val
            115                 120                 125

Arg Thr Arg Phe Arg Thr Thr Asp Asp Ala Leu Leu Thr Gly Val Pro
            130                 135                 140

Leu Met Ala Ile Pro Gly Phe Glu Leu Ala Thr Leu Ser Val Tyr Ala
145                 150                 155                 160

Gln Ser Ala Asn Leu His Leu Ala Leu Leu Arg Asp Ala Val Phe Phe
                165                 170                 175

Gly Glu Arg Trp Gly Leu Thr Gln Thr Asn Ile Asn Asp Leu Tyr Ser
            180                 185                 190

Arg Leu Lys Asn Ser Ile Arg Asp Tyr Thr Asn His Cys Val Arg Phe
            195                 200                 205

Tyr Asn Ile Gly Leu Gly Asn Leu Asn Val Ile Arg Pro Glu Tyr Tyr
            210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255

Leu Thr Arg Glu Ile Tyr Thr Asp Pro Ile Ile Ser Pro Gly Ala Gln
            260                 265                 270

Ala Gly Tyr Thr Leu Gln Asp Val Leu Arg Glu Pro His Leu Met Asp
            275                 280                 285

Phe Leu Asn Arg Leu Ile Ile Tyr Thr Gly Glu Tyr Arg Gly Ile Arg
290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Ala Thr Ala Glu Pro Thr
                325                 330                 335

Arg Phe Ile Thr Pro Ser Thr Phe Pro Gly Leu Asn Leu Phe Tyr Arg
            340                 345                 350

Thr Leu Ser Ala Pro Ile Phe Arg Asp Glu Pro Gly Ala Asn Ile Ile
            355                 360                 365

Ile Arg Tyr Arg Thr Ser Leu Val Glu Gly Val Gly Phe Ile Gln Pro
            370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                405                 410                 415

Arg Leu Cys His Val Arg Phe Ala Gln Ser Leu Arg Asn Ala Glu Pro
            420                 425                 430

Leu Asp Tyr Ala Arg Val Pro Met Phe Ser Trp Thr His Arg Ser Ala
            435                 440                 445

Thr Pro Thr Asn Thr Ile Asp Pro Asp Val Ile Thr Gln Ile Pro Leu
450                 455                 460

Val Lys Ala His Thr Leu Gln Ser Gly Thr Thr Val Val Arg Gly Pro
465                 470                 475                 480

Gly Phe Thr Gly Gly Asp Ile Leu Arg Arg Thr Ser Gly Gly Pro Phe
                485                 490                 495

Ala Tyr Thr Ile Val Asn Ile Asn Gly Gln Leu Pro Gln Arg Tyr Arg

```
                500                 505                 510
Ala Arg Ile Arg Tyr Ala Ser Thr Thr Asn Leu Arg Ile Tyr Val Thr
            515                 520                 525
Val Ala Gly Glu Arg Ile Phe Ala Gly Gln Phe Asn Lys Thr Met Asp
            530                 535                 540
Thr Gly Asp Pro Leu Thr Phe Gln Ser Phe Ser Tyr Ala Thr Ile Asn
545                 550                 555                 560
Thr Ala Phe Thr Phe Pro Met Ser Gln Ser Ser Phe Thr Val Gly Ala
                565                 570                 575
Asp Thr Phe Ser Ser Gly Asn Glu Val Tyr Ile Asp Arg Phe Glu Leu
            580                 585                 590
Ile Pro Val Thr Ala Thr Phe Glu Ala Glu Tyr Asp Leu Glu Arg Ala
            595                 600                 605
Gln Lys
    610

<210> SEQ ID NO 33
<211> LENGTH: 607
<212> TYPE: PRT
<213> ORGANISM: Artificial Sequence
<220> FEATURE:
<223> OTHER INFORMATION: Bt29-1FaTr2

<400> SEQUENCE: 33

Met Glu Ile Asn Asn Gln Asn Gln Cys Val Pro Tyr Asn Cys Leu Asn
1               5                   10                  15
Asn Pro Glu Ser Glu Ile Leu Asn Val Ala Ile Phe Ser Ser Glu Gln
            20                  25                  30
Val Ala Glu Ile His Leu Lys Ile Thr Arg Leu Ile Leu Glu Asn Phe
        35                  40                  45
Leu Pro Gly Gly Ser Phe Ala Phe Gly Leu Phe Asp Leu Ile Trp Gly
    50                  55                  60
Ile Phe Asn Glu Asp Gln Trp Ser Ala Phe Leu Arg Gln Val Glu Glu
65                  70                  75                  80
Leu Ile Asn Gln Arg Ile Thr Glu Phe Ala Arg Gly Gln Ala Ile Gln
                85                  90                  95
Arg Leu Val Gly Phe Gly Arg Ser Tyr Asp Glu Tyr Ile Leu Ala Leu
            100                 105                 110
Lys Glu Trp Glu Asn Asp Pro Asp Asn Pro Ala Ser Lys Glu Arg Val
        115                 120                 125
Arg Thr Arg Phe Arg Thr Thr Asp Asp Ala Leu Leu Thr Gly Val Pro
    130                 135                 140
Leu Met Ala Ile Pro Gly Phe Glu Leu Ala Thr Leu Ser Val Tyr Ala
145                 150                 155                 160
Gln Ser Ala Asn Leu His Leu Ala Leu Leu Arg Asp Ala Val Phe Phe
                165                 170                 175
Gly Glu Arg Trp Gly Leu Thr Gln Thr Asn Ile Asn Asp Leu Tyr Ser
            180                 185                 190
Arg Leu Lys Asn Ser Ile Arg Asp Tyr Thr Asn His Cys Val Arg Phe
        195                 200                 205
Tyr Asn Ile Gly Leu Gly Asn Leu Asn Val Ile Arg Pro Glu Tyr Tyr
    210                 215                 220
Arg Phe Gln Arg Glu Leu Thr Ile Ser Val Leu Asp Leu Val Ala Leu
225                 230                 235                 240
Phe Pro Asn Tyr Asp Ile Arg Thr Tyr Pro Ile Pro Thr Lys Ser Gln
```

```
            245                 250                 255
Leu Thr Arg Glu Ile Tyr Thr Asp Pro Ile Ser Pro Gly Ala Gln
            260                 265                 270

Ala Gly Tyr Thr Leu Gln Asp Val Leu Arg Glu Pro His Leu Met Asp
            275                 280                 285

Phe Leu Asn Arg Leu Ile Ile Tyr Thr Gly Glu Tyr Arg Gly Ile Arg
            290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Thr Ala Glu Pro Thr
                325                 330                 335

Arg Phe Ile Thr Pro Ser Thr Phe Pro Gly Leu Asn Leu Phe Tyr Arg
                340                 345                 350

Thr Leu Ser Ala Pro Ile Phe Arg Asp Glu Pro Gly Ala Asn Ile Ile
                355                 360                 365

Ile Arg Tyr Arg Thr Ser Leu Val Glu Gly Val Gly Phe Ile Gln Pro
        370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                    405                 410                 415

Arg Leu Cys His Val Arg Phe Ala Gln Ser Leu Arg Asn Ala Glu Pro
                420                 425                 430

Leu Asp Tyr Ala Arg Val Pro Met Phe Ser Trp Thr His Arg Ser Ala
                435                 440                 445

Thr Pro Thr Asn Thr Ile Asp Pro Asp Val Ile Thr Gln Ile Pro Leu
    450                 455                 460

Val Lys Ala His Thr Leu Gln Ser Gly Thr Thr Val Arg Gly Pro
465                 470                 475                 480

Gly Phe Thr Gly Gly Asp Ile Leu Arg Arg Thr Ser Gly Gly Pro Phe
                    485                 490                 495

Ala Tyr Thr Ile Val Asn Ile Asn Gly Gln Leu Pro Gln Arg Tyr Arg
                500                 505                 510

Ala Arg Ile Arg Tyr Ala Ser Thr Thr Asn Leu Arg Ile Tyr Val Thr
            515                 520                 525

Val Ala Gly Glu Arg Ile Phe Ala Gly Gln Phe Asn Lys Thr Met Asp
            530                 535                 540

Thr Gly Asp Pro Leu Thr Phe Gln Ser Phe Ser Tyr Ala Thr Ile Asn
545                 550                 555                 560

Thr Ala Phe Thr Phe Pro Met Ser Gln Ser Ser Phe Thr Val Gly Ala
                565                 570                 575

Asp Thr Phe Ser Ser Gly Asn Glu Val Tyr Ile Asp Arg Phe Glu Leu
                580                 585                 590

Ile Pro Val Thr Ala Thr Phe Glu Ala Glu Tyr Asp Leu Glu Arg
            595                 600                 605
```

<210> SEQ ID NO 34
<211> LENGTH: 603
<212> TYPE: PRT
<213> ORGANISM: Artificial Sequence
<220> FEATURE:
<223> OTHER INFORMATION: Bt29-1FaTr3

<400> SEQUENCE: 34

Met Glu Ile Asn Asn Gln Asn Gln Cys Val Pro Tyr Asn Cys Leu Asn

-continued

```
1               5                   10                  15
Asn Pro Glu Ser Glu Ile Leu Asn Val Ala Ile Phe Ser Ser Glu Gln
                20                  25                  30
Val Ala Glu Ile His Leu Lys Ile Thr Arg Leu Ile Leu Glu Asn Phe
                35                  40                  45
Leu Pro Gly Gly Ser Phe Ala Phe Gly Leu Phe Asp Leu Ile Trp Gly
                50                  55                  60
Ile Phe Asn Glu Asp Gln Trp Ser Ala Phe Leu Arg Gln Val Glu Glu
65                  70                  75                  80
Leu Ile Asn Gln Arg Ile Thr Glu Phe Ala Arg Gly Gln Ala Ile Gln
                85                  90                  95
Arg Leu Val Gly Phe Gly Arg Ser Tyr Asp Glu Tyr Ile Leu Ala Leu
                100                 105                 110
Lys Glu Trp Glu Asn Asp Pro Asn Pro Ala Ser Lys Glu Arg Val
                115                 120                 125
Arg Thr Arg Phe Arg Thr Thr Asp Asp Ala Leu Leu Thr Gly Val Pro
                130                 135                 140
Leu Met Ala Ile Pro Gly Phe Glu Leu Ala Thr Leu Ser Val Tyr Ala
145                 150                 155                 160
Gln Ser Ala Asn Leu His Leu Ala Leu Leu Arg Asp Ala Val Phe Phe
                165                 170                 175
Gly Glu Arg Trp Gly Leu Thr Gln Thr Asn Ile Asn Asp Leu Tyr Ser
                180                 185                 190
Arg Leu Lys Asn Ser Ile Arg Asp Tyr Thr Asn His Cys Val Arg Phe
                195                 200                 205
Tyr Asn Ile Gly Leu Gly Asn Leu Asn Val Ile Arg Pro Glu Tyr Tyr
                210                 215                 220
Arg Phe Gln Arg Glu Leu Thr Ile Ser Val Leu Asp Leu Val Ala Leu
225                 230                 235                 240
Phe Pro Asn Tyr Asp Ile Arg Thr Tyr Pro Ile Pro Thr Lys Ser Gln
                245                 250                 255
Leu Thr Arg Glu Ile Tyr Thr Asp Pro Ile Ile Ser Pro Gly Ala Gln
                260                 265                 270
Ala Gly Tyr Thr Leu Gln Asp Val Leu Arg Glu Pro His Leu Met Asp
                275                 280                 285
Phe Leu Asn Arg Leu Ile Ile Tyr Thr Gly Glu Tyr Arg Gly Ile Arg
                290                 295                 300
His Trp Ala Gly His Glu Val Glu Ser Ser Arg Thr Gly Met Met Thr
305                 310                 315                 320
Asn Ile Arg Phe Pro Leu Tyr Gly Thr Ala Ala Thr Ala Glu Pro Thr
                325                 330                 335
Arg Phe Ile Thr Pro Ser Thr Phe Pro Gly Leu Asn Leu Phe Tyr Arg
                340                 345                 350
Thr Leu Ser Ala Pro Ile Phe Arg Asp Glu Pro Gly Ala Asn Ile Ile
                355                 360                 365
Ile Arg Tyr Arg Thr Ser Leu Val Glu Gly Val Gly Phe Ile Gln Pro
                370                 375                 380
Asn Asn Gly Glu Gln Leu Tyr Arg Val Arg Gly Thr Leu Asp Ser Leu
385                 390                 395                 400
Asp Gln Leu Pro Leu Glu Gly Glu Ser Ser Leu Thr Glu Tyr Ser His
                405                 410                 415
Arg Leu Cys His Val Arg Phe Ala Gln Ser Leu Arg Asn Ala Glu Pro
                420                 425                 430
```

```
Leu Asp Tyr Ala Arg Val Pro Met Phe Ser Trp Thr His Arg Ser Ala
        435                 440                 445

Thr Pro Thr Asn Thr Ile Asp Pro Asp Val Ile Thr Gln Ile Pro Leu
    450                 455                 460

Val Lys Ala His Thr Leu Gln Ser Gly Thr Thr Val Arg Gly Pro
465                 470                 475                 480

Gly Phe Thr Gly Gly Asp Ile Leu Arg Arg Thr Ser Gly Gly Pro Phe
                485                 490                 495

Ala Tyr Thr Ile Val Asn Ile Asn Gly Gln Leu Pro Gln Arg Tyr Arg
                500                 505                 510

Ala Arg Ile Arg Tyr Ala Ser Thr Thr Asn Leu Arg Ile Tyr Val Thr
                515                 520                 525

Val Ala Gly Glu Arg Ile Phe Ala Gly Gln Phe Asn Lys Thr Met Asp
            530                 535                 540

Thr Gly Asp Pro Leu Thr Phe Gln Ser Phe Ser Tyr Ala Thr Ile Asn
545                 550                 555                 560

Thr Ala Phe Thr Phe Pro Met Ser Gln Ser Ser Phe Thr Val Gly Ala
                565                 570                 575

Asp Thr Phe Ser Ser Gly Asn Glu Val Tyr Ile Asp Arg Phe Glu Leu
                580                 585                 590

Ile Pro Val Thr Ala Thr Phe Glu Ala Glu Tyr
            595                 600

<210> SEQ ID NO 35
<211> LENGTH: 600
<212> TYPE: PRT
<213> ORGANISM: Artificial Sequence
<220> FEATURE:
<223> OTHER INFORMATION: Bt29-1FaTr4

<400> SEQUENCE: 35

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
            20                  25                  30

Val Ala Glu Ile His Leu Lys Ile Thr Arg Le

```
Arg Leu Lys Asn Ser Ile Arg Asp Tyr Thr Asn His Cys Val Arg Phe
            195                 200                 205

Tyr Asn Ile Gly Leu Gly Asn Leu Asn Val Ile Arg Pro Glu Tyr Tyr
210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255

Leu Thr Arg Glu Ile Tyr Thr Asp Pro Ile Ile Ser Pro Gly Ala Gln
            260                 265                 270

Ala Gly Tyr Thr Leu Gln Asp Val Leu Arg Glu Pro His Leu Met Asp
        275                 280                 285

Phe Leu Asn Arg Leu Ile Ile Tyr Thr Gly Glu Tyr Arg Gly Ile Arg
290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Thr Ala Glu Pro Thr
                325                 330                 335

Arg Phe Ile Thr Pro Ser Thr Phe Pro Gly Leu Asn Leu Phe Tyr Arg
            340                 345                 350

Thr Leu Ser Ala Pro Ile Phe Arg Asp Glu Pro Gly Ala Asn Ile Ile
            355                 360                 365

Ile Arg Tyr Arg Thr Ser Leu Val Glu Gly Val Gly Phe Ile Gln Pro
370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                405                 410                 415

Arg Leu Cys His Val Arg Phe Ala Gln Ser Leu Arg Asn Ala Glu Pro
            420                 425                 430

Leu Asp Tyr Ala Arg Val Pro Met Phe Ser Trp Thr His Arg Ser Ala
        435                 440                 445

Thr Pro Thr Asn Thr Ile Asp Pro Asp Val Ile Thr Gln Ile Pro Leu
450                 455                 460

Val Lys Ala His Thr Leu Gln Ser Gly Thr Thr Val Val Arg Gly Pro
465                 470                 475                 480

Gly Phe Thr Gly Gly Asp Ile Leu Arg Arg Thr Ser Gly Gly Pro Phe
                485                 490                 495

Ala Tyr Thr Ile Val Asn Ile Asn Gly Gln Leu Pro Gln Arg Tyr Arg
            500                 505                 510

Ala Arg Ile Arg Tyr Ala Ser Thr Thr Asn Leu Arg Ile Tyr Val Thr
        515                 520                 525

Val Ala Gly Glu Arg Ile Phe Ala Gly Gln Phe Asn Lys Thr Met Asp
530                 535                 540

Thr Gly Asp Pro Leu Thr Phe Gln Ser Phe Ser Tyr Ala Thr Ile Asn
545                 550                 555                 560

Thr Ala Phe Thr Phe Pro Met Ser Gln Ser Ser Phe Thr Val Gly Ala
                565                 570                 575

Asp Thr Phe Ser Ser Gly Asn Glu Val Tyr Ile Asp Arg Phe Glu Leu
            580                 585                 590

Ile Pro Val Thr Ala Thr Phe Glu
            595                 600
```

What is claimed is:

1. A chimeric insecticidal protein that is toxic to a lepidopteran insect pest comprising SEQ ID NO: 3.

2. The chimeric insecticidal protein according claim 1, wherein the chimeric insecticidal protein has insecticidal activity against a *Spodoptera frugiperda* insect pest with resistance to a Vip3A protein or a Cry1F protein.

3. A method of controlling a lepidopteran insect pest, the method comprising delivering to the insect pest or an environment thereof a composition comprising an effective amount of the chimeric insecticidal protein of claim 1.

* * * * *